United States Patent
Otte et al.

(10) Patent No.: US 9,228,004 B2
(45) Date of Patent: Jan. 5, 2016

(54) SELECTION OF HOST CELLS EXPRESSING PROTEIN AT HIGH LEVELS

(71) Applicant: ChromaGenics B.V., Leiden (NL)

(72) Inventors: Arie Pieter Otte, Amersfoort (NL); Henricus J.M. van Blokland, Wijdewormer (NL); Theodorus Hendrikus Jacobus Kwaks, Amsterdam (NL); Richard George Antonius Bernardus Sewalt, Arnhem (NL)

(73) Assignee: ChromaGenics B.V., Leiden (NL)

(*) Notice: Subject to any disclaimer, the term of this patent is extended or adjusted under 35 U.S.C. 154(b) by 0 days.

(21) Appl. No.: 14/081,938

(22) Filed: Nov. 15, 2013

(65) Prior Publication Data

US 2014/0106401 A1 Apr. 17, 2014

Related U.S. Application Data

(60) Division of application No. 13/135,966, filed on Jul. 18, 2011, now abandoned, which is a continuation of application No. 11/416,490, filed on May 2, 2006, now abandoned, which is a continuation-in-part of application No. 11/269,525, filed on Nov. 7, 2005, now abandoned, said application No. 13/135,966 is a continuation-in-part of application No. 11/359,953, filed on Feb. 21, 2006, which is a continuation-in-part of application No. 11/269,525, filed on Nov. 7, 2005, now abandoned, said application No. 13/135,966 is a continuation of application No. 12/226,706, filed as application No. PCT/EP2007/053984 on Apr. 24, 2007, now Pat. No. 8,039,230.

(60) Provisional application No. 60/626,301, filed on Nov. 8, 2004, provisional application No. 60/696,610, filed on Jul. 5, 2005.

(30) Foreign Application Priority Data

Nov. 8, 2004 (EP) .................................... 04105593
May 2, 2006 (EP) .................................... 06113354

(51) Int. Cl.

| | |
|---|---|
| C12P 21/06 | (2006.01) |
| C07K 14/505 | (2006.01) |
| C12N 15/85 | (2006.01) |
| C12N 9/12 | (2006.01) |
| C12P 21/04 | (2006.01) |
| C12N 1/00 | (2006.01) |
| C12N 5/02 | (2006.01) |
| C12N 15/00 | (2006.01) |
| C12N 15/74 | (2006.01) |
| C12N 15/82 | (2006.01) |
| C12N 15/86 | (2006.01) |
| C07H 21/00 | (2006.01) |
| C07H 21/04 | (2006.01) |

(52) U.S. Cl.
CPC ............ *C07K 14/505* (2013.01); *C12N 9/1205* (2013.01); *C12N 15/85* (2013.01); *C12Y 207/01095* (2013.01); *C12N 2840/203* (2013.01); *C12N 2840/50* (2013.01)

(58) Field of Classification Search
None
See application file for complete search history.

(56) References Cited

U.S. PATENT DOCUMENTS

| | | | |
|---|---|---|---|
| 4,965,196 A | 10/1990 | Levinson et al. | |
| 5,021,344 A | 6/1991 | Armau et al. | |
| 5,118,620 A | 6/1992 | Armau et al. | |
| 5,527,701 A | 6/1996 | Yamaguchi et al. | |
| 5,561,053 A | 10/1996 | Crowley | |
| 5,610,053 A | 3/1997 | Chung et al. | |
| 5,627,033 A | 5/1997 | Smith et al. | |
| 5,648,267 A | 7/1997 | Reff | |
| 5,658,763 A | 8/1997 | Dorai et al. | |
| 5,733,779 A | 3/1998 | Reff | |

(Continued)

FOREIGN PATENT DOCUMENTS

| | | |
|---|---|---|
| EP | 0 724 639 | 1/2001 |
| EP | 1 273 666 | 1/2003 |

(Continued)

OTHER PUBLICATIONS

Aranda et al., Definition of Transcriptional Pause Elements in Fission Yeast, Molecular and Cellular Biology, Feb. 1999, pp. 1251-1261, vol. 19, No. 2.

(Continued)

*Primary Examiner* — Nancy J Leith
(74) *Attorney, Agent, or Firm* — TraskBritt, P.C.

(57) ABSTRACT

Described is a DNA molecule comprising an open reading frame sequence encoding a selectable marker polypeptide, wherein the DNA molecule in the coding strand comprises a translation start sequence for the selectable marker polypeptide having a GTG or TTG start codon, and wherein the ORF sequence that encodes the selectable marker protein has been mutated to replace at least half of its CpG dinucleotides as compared to the native ORF sequence that encodes the selectable marker protein. Further provided are such DNA molecules wherein the ORF sequence that encodes a selectable marker polypeptide is part of a multicistronic transcription unit that further comprises an open reading frame sequence encoding a polypeptide of interest. Also described are methods for obtaining host cells expressing a polypeptide of interest, wherein the host cells comprise the DNA molecules described herein. Further provided is the production of polypeptides of interest, comprising culturing host cells comprising the DNA molecules described herein.

12 Claims, 45 Drawing Sheets

(56) References Cited

U.S. PATENT DOCUMENTS

| | | |
|---|---|---|
| 5,773,695 A | 6/1998 | Thompson et al. |
| 5,888,809 A | 3/1999 | Allison |
| 5,972,605 A | 10/1999 | Villepornteau et al. |
| 5,994,128 A | 11/1999 | Fallaux et al. |
| 6,060,273 A | 5/2000 | Dirks et al. |
| 6,107,477 A | 8/2000 | Whitney et al. |
| 6,319,707 B1 | 11/2001 | Adam et al. |
| 6,395,549 B1 | 5/2002 | Tuan et al. |
| 6,413,744 B1 | 7/2002 | Morris et al. |
| 6,521,419 B1 | 2/2003 | Koduri et al. |
| 6,558,948 B1 | 5/2003 | Kochanek et al. |
| 6,586,205 B1 | 7/2003 | Glucksmann et al. |
| 6,800,457 B2 | 10/2004 | Koduri et al. |
| 6,872,524 B1 | 3/2005 | Otte |
| 7,001,772 B2 | 2/2006 | Roessler et al. |
| 7,109,029 B2 | 9/2006 | Clarke et al. |
| 7,192,741 B2 | 3/2007 | Otte et al. |
| 7,244,609 B2 | 7/2007 | Drocourt et al. |
| 7,267,965 B2 | 9/2007 | Otte et al. |
| 7,364,878 B2 | 4/2008 | Otte et al. |
| 7,442,787 B2 | 10/2008 | Antoniou et al. |
| 7,655,441 B2 | 2/2010 | Otte et al. |
| 7,659,094 B2 | 2/2010 | Otte et al. |
| 7,662,591 B2 | 2/2010 | Otte et al. |
| 7,736,868 B2 | 6/2010 | Otte et al. |
| 7,736,869 B2 | 6/2010 | Otte et al. |
| 7,736,870 B2 | 6/2010 | Otte et al. |
| 7,749,733 B2 | 7/2010 | Otte et al. |
| 7,794,977 B2 | 9/2010 | Otte et al. |
| 8,039,230 B2 | 10/2011 | Otte et al. |
| 2002/0155540 A1 | 10/2002 | Padidam |
| 2003/0138908 A1 | 7/2003 | Koduri et al. |
| 2003/0166042 A1 | 9/2003 | Glucksmann et al. |
| 2003/0199468 A1 | 10/2003 | Otte et al. |
| 2004/0219677 A1 | 11/2004 | Drocourt et al. |
| 2005/0106580 A1 | 5/2005 | Enenkel et al. |
| 2005/0106609 A1 | 5/2005 | Otte et al. |
| 2005/0191723 A1 | 9/2005 | Otte et al. |
| 2006/0003416 A1 | 1/2006 | Otte et al. |
| 2006/0010506 A1 | 1/2006 | Otte et al. |
| 2006/0141577 A1 | 6/2006 | Otte et al. |
| 2006/0172382 A1 | 8/2006 | Otte et al. |
| 2006/0195935 A1 | 8/2006 | Otte et al. |
| 2006/0263882 A1 | 11/2006 | Fazio et al. |
| 2007/0026498 A1 | 2/2007 | Otte et al. |
| 2007/0026499 A1 | 2/2007 | Otte et al. |
| 2007/0031933 A1 | 2/2007 | Otte et al. |
| 2007/0031934 A1 | 2/2007 | Otte et al. |
| 2007/0031935 A1 | 2/2007 | Otte et al. |
| 2007/0031936 A1 | 2/2007 | Otte et al. |
| 2007/0037256 A1 | 2/2007 | Otte et al. |
| 2007/0128717 A1 | 6/2007 | Otte et al. |
| 2007/0212755 A1 | 9/2007 | Otte et al. |
| 2008/0085537 A1 | 4/2008 | Otte et al. |
| 2008/0206813 A1 | 8/2008 | Otte et al. |
| 2009/0011468 A1 | 1/2009 | Otte et al. |
| 2009/0098601 A1 | 4/2009 | Otte et al. |
| 2010/0136616 A1 | 6/2010 | Otte et al. |
| 2010/0190207 A1 | 7/2010 | Otte et al. |
| 2011/0014655 A1 | 1/2011 | Otte et al. |

FOREIGN PATENT DOCUMENTS

| | | |
|---|---|---|
| JP | 5501054 | 3/1993 |
| JP | 2004533262 | 11/2004 |
| WO | 91/01374 | 2/1991 |
| WO | 94/23046 | 10/1994 |
| WO | 96/04390 | 2/1996 |
| WO | 96/12008 | 4/1996 |
| WO | 97/27207 | 7/1997 |
| WO | 98/11207 | 3/1998 |
| WO | 98/39411 | 9/1998 |
| WO | 98/49289 | 11/1998 |
| WO | 00/05393 | 2/2000 |
| WO | 00/09749 | 2/2000 |
| WO | 00/17337 | 3/2000 |
| WO | 00/23606 | 4/2000 |
| WO | 01/02553 | 1/2001 |
| WO | 01/32901 | 5/2001 |
| WO | 01/57188 | 8/2001 |
| WO | 01/59117 | 8/2001 |
| WO | 01/59118 | 8/2001 |
| WO | 02/24930 A2 | 3/2002 |
| WO | 02/072846 | 9/2002 |
| WO | 02/074969 | 9/2002 |
| WO | 02/099070 | 12/2002 |
| WO | 02/099089 | 12/2002 |
| WO | 03/004704 | 1/2003 |
| WO | 03/083077 | 10/2003 |
| WO | 03/106684 | 12/2003 |
| WO | 2004/027072 | 4/2004 |
| WO | 2004/055215 A1 | 7/2004 |
| WO | 2004/056986 A2 | 7/2004 |
| WO | 2005/040377 | 5/2005 |
| WO | 2006/005718 | 1/2006 |
| WO | 2006/048459 | 5/2006 |
| WO | 2007/096399 | 8/2007 |

OTHER PUBLICATIONS

Auten et al., "Effect of Scaffold Attachment Region on Transgene Expression in Retrovirus Vector-Transduced Primary T cells and Macrophages," Human Gene Therapy, May 20, 1999, pp. 1389-1399, vol. 10, No. 8.

Bell et al., Insulators and Boundaries: Versatile Regulatory Elements in the Eukaryotic Genome, Science, pp. 447-450, vol. 291, No. 5503, 2001.

Bird, et al. Methylation-Induced Repression—Belts, Braces and Chromatin, Cell, Nov. 24, 1999, pp. 451-454, vol. 99.

Burgess-Beusse et al., The insulation of genes from external enhancers and silencing chromatin, PNAS, Dec. 10, 2002, pp. 16433-16437, vol. 99, Suppl. 4.

Carroll et al., Translation of Equine Infectious Anemia Virus Bicistronic tat-rev mRNA Requires Leaky Ribosome Scanning of the tat CTG Initiation Codon, J. Virol., 1993, pp. 1433-1440, vol. 67 No. 3, American Society for Microbiology.

Chan et al., p300-CBP proteins: HATs for transcriptional bridges and scaffolds, Journal of Cell Science, 2001, pp. 2363-2373, vol. 114.

Chang et al., Baculovirus gp64 Gene Expression: Negative Regulation by Minicistron, Journal of Virology, Oct. 1997, pp. 7448-7460, vol. 71, No. 10/.

Chung et al., A 5' Element of the Chicken Beta-Globin Domain Serves as an Insulator in Human Erythroid Cells and Protects against Position Effect in Drosophila, Aug. 13, 1993, Cell, pp. 505-514, vol. 74.

Database EMBL 'Online! Dec. 15, 1999, "*Homo sapiens* BAC clone RP11-572N21 from 2, complete sequence," XP002359988 retrieved from EBI accession No. EM_PRO:AC018470, database accession No. AC018470, for SEQ ID No. 17.

Database EMBL 'Online! Mar. 15, 1999, "*Homo sapiens* chromosome UNK clone CTA-435J10, working draft sequence, 1 unordered pieces," XP002359997 retrieved from EBI accession No. EM_PRO:AC007044, database accession No. AC007044 for SEQ ID No. 61.

Database EMBL 'Online! Mar. 19, 1998, CIT-HSP-2172C8.TF CIT-HSP *Homo sapiens* genomic clone 2172C8, genomic survey sequence, XP002359995 retrieved from EBI accession No. EM_PRO:B92131, database accession No. B92131 for SEQ ID No. 44.

Database EMBL 'Online! Dec. 23, 1999, "Human DNA sequence from clone RP11-54H19 on chromosome 1 Contains the 3' end of the LMNA gene for lamin A/C, the gene for a novel protein similar to semaphorins (FLJ12287), a novel gene (KIAA0446), the PMF1 gene for polyamine-modulated factor 1, the BGLAP gene for bone gamma-carboxyglutamate (gla) p," XP002359989, retrieved from EBI accession No. EM_PRO:AL135927, database accession No. AL135927 for SEQ ID No. 27.

Database EMBL 'Online! Sep. 24, 2000, "*Homo sapiens* chromosome 4 clone RP11-680I18, working draft sequence, 25 unordered

(56) References Cited

OTHER PUBLICATIONS pieces," XP002359987 retrieved from EBI accession No. EM_PRO:AC080087, database accession No. AC080087 for SEQ ID No. 9.
Database EMBL 'Online! Jan. 25, 2001, "QV2-NN0045-081200-535-c10 NN0045 *Homo sapiens* cDNA, mRNA sequence." XP002359993 retrieved from EBI accession No. EM_PRO:BF960930, database accession No. BF960930 for SEQ ID No. 43.
Database EMBL 'Online! Apr. 26, 2001, "RST28606 Athersys RAGE Library *Homo sapiens* cDNA, mRNA sequence," XP002359990 retrieved from EBI accession No. EM_PRO:BG209092, database accession No. BG209092 for SEQ ID No. 40.
Database EMBL 'Online! Oct. 28, 1998, "*Homo sapiens* neurexin III-alpha gene, partial cds," XP002359992, retrieved from EBI accession No. EM_PRO:AF099810, database accession No. AF099810 for SEQ ID No. 43.
Database EMBL 'Online! Sep. 29, 1999, "*Homo sapiens* genomic DNA, chromosome 22q11.2, Cat Eye Syndrome region, clone:N64E9," XP002359991, retrieved from EBI accession No. EM_PRO:AP000526, database accession No. AP000526 for SEQ ID No. 40.
Database EMBL 'Online! Sep. 29, 1999, *Homo sapiens* genomic DNA, chromosome 22q11.2, Cat Eye Syndrome region, clone:N14H11, XP002359994 retrieved from EBI accession No. EM_PRO:AP000525, database accession No. AP000525 for SEQ ID No. 44.
Database EMBL 'Online! Sep. 29, 1999, "*Homo sapiens* genomic DNA, chromosome 22q11.2, Cat Eye Syndrome region, clone:c91G6," XP002359996 retrieved from EBI accession No. EM_PRO:AP000528, database accession No. AP000528 for SEQ ID No. 45.
Database EMBL 'Online! Feb. 3, 2004, "Sequence 33099 from Patent W002068579," XP002359986 retrieved from EBI accession No. EM_PRO:CQ747165, database accession No. CQ747165 for SEQ ID No. 9.
Database EMBL 'Online! Aug. 4, 1999, "*Homo sapiens* chromosome 19 clone CTD-2540B15, complete sequence," XP002359985 retrieved from EBI accession No. EM_PRO:AC008738, database accession No. AC008738 for SEQ ID No. 7.
Database EMBL 'Online!, Jul. 8, 1992, *H. sapiens* HOX4B gene upstream sequence XP002348163 retrieved from EBI, Database accession No. X67079, Abstract.
Database EMBL, Jun. 19, 2002, accession No. AL773524, Human DNA sequence from clone RP11-250K24 on chromosome 9 Contains a calponin 2 (CNN2) pseudogene and a novel pseudogene.
Database EMBL, Aug. 2, 2003, accession No. AC146157, Pantroglodytes BAC clone RP43-2A11 from 7, complete sequence.
Database EMBL, May 26, 2000, accession No. AC069285, *Homo sapiens* BAC clone RP11-196D18 from 7, complete sequence.
Database EMBL, Aug. 9, 2002, accession No. AL845331, Human DNA sequence from clone RP11-407P15 on chromosome 9.
De Boer, et al., Portable Shine-Dalgarno regions; nucleotides between the Shine-Dalgarno sequence and the start codon affect the translation efficiency, Gene Amplification and Analysis, 1983, pp. 103-116, vol. 3.
Dummitt, et al., N-Terminal Methionine Removal and Methionine Removal and Methionine Metabolism in Saccharomyces cerevisiae, Journal of Cellular Biology, 2003, pp. 964-974, vol. 89.
Eggermont et al., Poly(A) signals and transcriptional pause sites combine to prevent interference between RNA polymerase II promoters, The EMBO Journal, 1993, pp. 2539-2548, vol. 12, No. 6.
Emery et al., A chromatin insulator protects retrovirus vectors from chromosomal position effects, Proceedings of the National Academy of Sciences of USA, Aug. 1, 2000, pp. 9150-9155, vol. 97, No. 16.
European Search Report for EP 04 10 5593 dated Jun. 21, 2005.
European Search Report for EP 05 07 6209 dated Dec. 22, 2005.

Farrell et al., Conserved CTCF Insulator Elements Flank the Mouse and Human Beta-Globin Loci, Molecular and Cellular Biology, Jun. 2002, pp. 3820-3831, vol. 22. No. 11.
Frengen, et al., Modular bacterial artificial chromosome vectors for transfer of large inserts into mammalian cells, Genomics, vol. 68, No. 2, pp. 118-126, Sep. 2000.
GenBank Accession AY237385.1 (AAO89266, GI:37933202), accessed on Jul. 23, 2008.
GenBank Accession No. AC007689.13, GI: 8573011, Jun. 25, 2000.
GenBank Accession No. AL021960, GI: 4584387, publicly available Apr. 1999, last visited Sep. 26, 2011.
GenBank Accession No. AL096766.12, GI: 5738627, Aug. 17, 1999.
GenBank Accession No. AL449105, GI: 14268199, publicly available Jun. 2001, printed as pp. 1-47.
GenBank Accession No. AL449105, GI: 46559322, publicly available Jan. 2009, printed as pp. 1-63.
Glucksmann et al., Database accession No. AAH76193, Oct. 29, 2001.
Han et al., "Matrix attachment regions (MARs) enhance transformation frequency and transgene expression in poplar," Transgenic Research, 1997, pp. 415-420, vol. 6.
Hellen, et al., Internal ribosome entry sites in eukaryotic mRNA molecules, Genes and Development, 2001, pp. 1593-1612, vol. 15, Nol. 13, Cold Spring Harbor Laboratory Press.
Hennecke et al., Composition and arrangement of genes define the strength of IRES-driven translation in bicistronic mRNAs, Nucleic Acids Res., 2001, pp. 3327-3334, vol. 29, No. 16, Oxford University Press.
Izumi, et al. Homgeneous Tetracycline-Regulatable Gene Expression in Mammalian Fibroblasts; Journal of Cellular Biochemistry 76; 1999; pp. 280-289.
Johnson et al., Requirements for utilization of CREB binding protein by hypersensitive site two of the Beta-globin locus control region, Nucleic Acids Research 2002, pp. 1522-1530, vol. 30, No. 7.
Kaufman, et al., Improved vectors for stable expression of foreign genes in mammalian cells by use of the untranslated leader sequence from EMC virus, Nucleic Acids Research, 1991, pp. 4485-4490, vol. 19, No. 16.
Kellum et al., A Group of scs Elements Function as Domain Boundaries in an Enhancer-Blocking Assay, Molecular and Cellular Biology, May 1992, pp. 2424-2431, vol. 12, No. 5.
Kim, et al., Poly(A)-dependent Transcription Termination; The Journal of Biological Chemistry; vol. 278, No. 43; Oct. 24, 2003; pp. 41691-41701.
Kozak, Downstream secondary structure facilitates recognition of initiator codons by eukaryotic ribosomes, PNAS, 1990, pp. 8301-8305, vol. 87, No. 21.
Kozak, Initiation of translation in prokaryotes and eukaryotes, Gene, 1999, pp. 187-208, Vo. 234.
Kozak, M., An analysis of 5'-noncoding sequences from 699 vertebrate messenger RNAs, Nucleic Acids Res., 1987, pp. 8125-8148, vol. 15, No. 20.
Kozak, M., Context Effects and Inefficient Initiation at Non-AUG Codons in Eucaryotic Cell-Free Translation Systems, Molecular and Cellular biology, Nov. 1989, pp. 5073-5080, vol. 9, No. 11.
Kozak, M., Point Mutations Define a Sequence Flanking the AUG Initiator Codon That Modulates Translation by Eukaryotic Ribosomes, Cell, Jan. 31, 1986, pp. 283-292, vol. 44.
Kozak, M., Recognition of AUG and alternative initiator codons in augmented by G in position +4 but is not generally affected by the nucleotides in positions +5 and +6, The EMBO Journal, 1997, pp. 2482-2492, vol. 16, No. 9.
Kozak, Pushing the limits of the scanning mechanism for initiation of translation, Gene, 2002, pp. 1-34, vol. 299.
Kuhn, et al., Functional Analysis of the Internal Translation Initiation Site of Foot-and-Mouth Disease Virus, Journal of Virology, Oct. 1990, pp. 4625-4631, vol. 64, No. 10.
Kwaks et al., Identification of anti-repressor elements that confer high stable protein in production in mammalian cells, Nature Biotechnology, May 20, 2003, pp. 553-558, vol. 21, No. 5.
Kwaks, et al., Employing epigenetics to augment the expression of the therapeutic proteins in mammalian cells, Trends in Biotechnology, Mar. 2006, pp. 137-142, vol. 24, No. 3.

(56) References Cited

OTHER PUBLICATIONS

Kwaks, et al., Targeting of histone acetyltranscerase domain to a promoter enhances protein expression levels in mammalian cells, Journal of Biotechnology, 2005, pp. 35-46, vol. 115.

Lee, et al., Engineering Chinese hamster ovary (CHO) cells to achieve an inverse growth-associated production of a foreign protein, β-galactosidase, Cytotechnology, 1998, pp. 73-80, vol. 28.

Liu, et al., Construction of Discistronic expression vector in mammalian cell with IRES and dhfr; Bull Acad Mil Med Sci, Mar. 2000; vol. 24, No. 1; pp. 9-11.

Lopez De Quinto, et al., Parameters influencing translation efficiency in aphthovirus IRES-based bicistronic expression vectors, Gene, 1998, pp. 51-56, vol. 217.

Maniatis et al., Recognition Sequences of Repressor and Polymerase in the Operators of Bacteriophage Lambda, Cell, Jun. 1975, pp. 109-113, vol. 5.

Martinez-Balbas et al., The acetyltransferase activity of CBP stimulates transcription, The EMBO Journal, 1998, pp. 2886-2893, vol. 17, No. 10.

Mielke et al., "Stabilized, long-term expression of heterodimeric proteins from tricistronic mRNA," Gene, Aug. 22, 2000, pp. 1-8, vol. 254, No. 1-2.

Migliaccio et al., "Stable and unstable transgene integration sites in the human genome: extinction of the Green Fluorescent Protein transgene in K562 cells," Gene, Oct. 3, 2000, pp. 197-214, vol. 256, No. 1-2.

Moser et al., An Update of pTRIDENT Multicistronic Expression Vectors: pTRIDENTs Containing Novel Streptogramin-Responsive Promoters, Biotechnol. Prog., 2000, pp. 724-735, vol. 16, Zurich, Switzerland.

Otte, et al. Various Expression-Augmenting DNA Elements Benefit from STAR-Select, a Novel High Stringency Selection System from Protein Expression, Biotechnol. Prog., 2007, pp. 801-807, vol. 23.

Parola et al., The Peptide Product of a 5' Leader Cistron in the beta 2 Adrenergic Receptor mRNA Inhibits Receptor Synthesis, The Journal of Biol. Chem., 1994, pp. 4497-4505, vol. 269, No. 6.

Partial European Search Report, EP 05 07 6209, dated Oct. 7, 2005.

PCT International Preliminary Examination Report, PCT/NL03/00850, dated Mar. 24, 2005.

PCT International Preliminary Report of Patentability, PCT/EP2005/055794, dated Jan. 26, 2007.

PCT International Preliminary Report of Patentability, PCT/EP2007/053984, dated Jul. 25, 2008.

PCT International Search Report for Application PCT/EP2007/052664, dated May 25, 2007.

PCT International Search Report PCT/EP2007/053984, dated Apr. 24, 2007.

PCT International Search Report, PCT/EP2007/051696, dated Mar. 5, 2008.

PCT International Search Report, PCT/NL02/00390, dated Jul. 29, 2003.

PCT International Search Report, PCT/NL03/00432, dated Jan. 9, 2004.

PCT International Search Report, PCT/NL03/00850, dated Jun. 9, 2004.

PCT Written Opinion of the International Searching Authority for Application PCT/EP2007/052664 dated May 25, 2007.

PCT Written Opinion, PCT/EP2007/051696 dated Mar. 5, 2008.

Pile et al., GAGA Factor-dependent Transcription and Establishment of DNase Hypersensitivity Are Independent and Unrelated Events In Vivo, J. of Biological Chemistry, Jan. 14, 2000, pp. 1398-1404, vol. 275, No. 2.

Razin, CpG methylation, chromatin structure and gene silencing—a three-way connection, The EMBO Journal, 1998, pp. 4905-4908, vol. 17, No. 17.

Reik et al., Biotechnologies and therapeutics: Chromatin as a target, Current Opinion in Genetics & Development, 2002, pp. 233-242, vol. 12.

Rees et al., Bicistronic Vector for the Creation of Stable Mammalian Cell Lines that Predisposes All Antibiotic-Resistant Cells to Express Recombinant Protein, Biotechniques, 1996, pp. 102-110, vol. 20, No. 1, Middlesex, UK.

Seum et al., A GAL4-HP1 fusion protein targeted near heterochromatin promotes gene silencing, Chromosoma, 2000, pp. 453-459, vol. 109.

Shizuya, et al., Cloning and stable maintenance of 300-kilbase-pair fragments of human DNA in *Escherichia coli* using an F-factor-based-vector. Proc Natl Acad Sci USA. vol. 89, No. 18, pp. 8794-8797, Sep. 1992.

Sigrist et al., Chromatin Insulator Elements Block the Silencing of a Target Gene by the Drosophila Polycomb Response Element (PRE) but Allow trans Interactions Between PREs on Different Chromosomes, Genetics, Sep. 1997, pp. 209-211, vol. 147, No. 1.

Son et al., Excision of the First Intron from the Gonadotropin-releasing Hormone (GnRH) Transcript Serves as a Key Regulatory Step for GnR Biosynthesis, The Journal of Biological Chemistry, 2003, pp. 18037-18044, vol. 278, No. 20.

Spyrou et al., Molecular analysis of the proviral DNA of equine infectious anemia virus in mules in Greece; taken from http://www.ncbi.nlm.nih.gov/entrez/viewer.fcgi?db=-protein&id=37933202; accessed on Jul. 23, 2008.

Tang et al., A transformation system for the nonuniversal $CUG^{Ser}$ codon usage species *Candida rugosa*, J. Microbiol. Methods, 2003, pp. 231-238, vol. 52.

Tomita et al., Translational properties of the human papillomavirus type-6 L1-coding mRNA, Gene, Nov. 15, 1993, pp. 223-225, vol. 133, No. 2.

Van Blokland, et al., A novel, high stringency selection system allows screening of few clones for high protein expression, Journal of Biotechnology, 2007, pp. 237-245, vol. 128.

Van Der Vlag et al., Transcription Repression Mediated by Polycomb Group Proteins and Other Chromatin-associated Repressors Is Selectively Blocked by Insulators, Journal of Biological Chemistry, Jan. 7, 2000, pp. 697-704, vol. 275, No. 1.

Wells, et al., Codon optimization, genetic insulation, and an rtTA reporter improve performance of the tetracycline switch**, Transgenic Research 8; 1999; pp. 371-381.

West et al., Insulators: many functions, many mechanisms, Genes and Development, Feb. 1, 2002, pp. 271-288, vol. 16, No. 3.

Williams, et al., CpG-island fragments from the HNRPA2B1/CVX3 genomics locus reduce silencing and enhance transgene expression from the hCMV promoter/enhancer in mammalian cells, published Jun. 3, 2005, http://www.biomedcentral.com/1472-6750/5/17.

Yew et al., CpG-Depleted Plasmid DNA Vectors with Enhanced Safety and Long-Term Gene Expression *in Vivo*, Molecular Therapy, 2002, pp. 731-738, vol. 5, The American Society of Gene Therapy.

Youn, et al.; An Intronic Silencer of the Mouse Perforin Gene, Mol. Cells., 2001, pp. 61-68, vol. 33, No. 1.

Zeocin™, Instruction Manual, Version J, Aug. 22, 2002.

USPTO STIC Sequence search of SEQ ID No. 128 (2011, pp. 1-4).

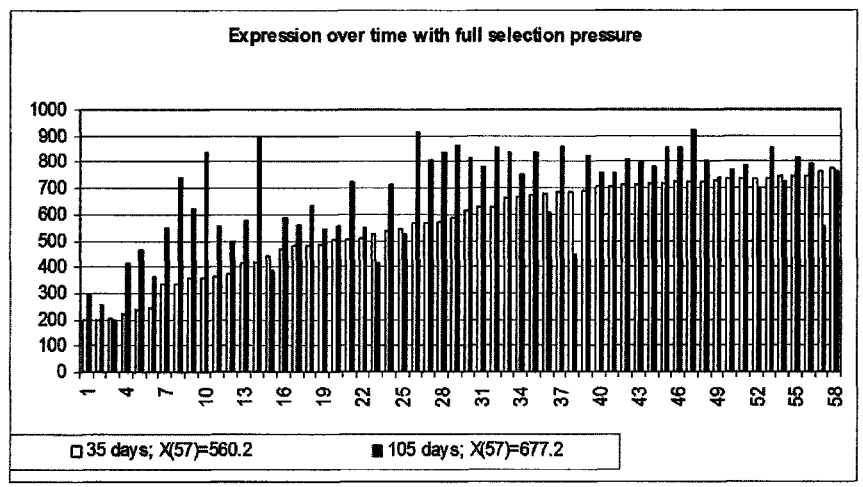
FIG. 6

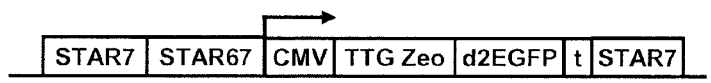
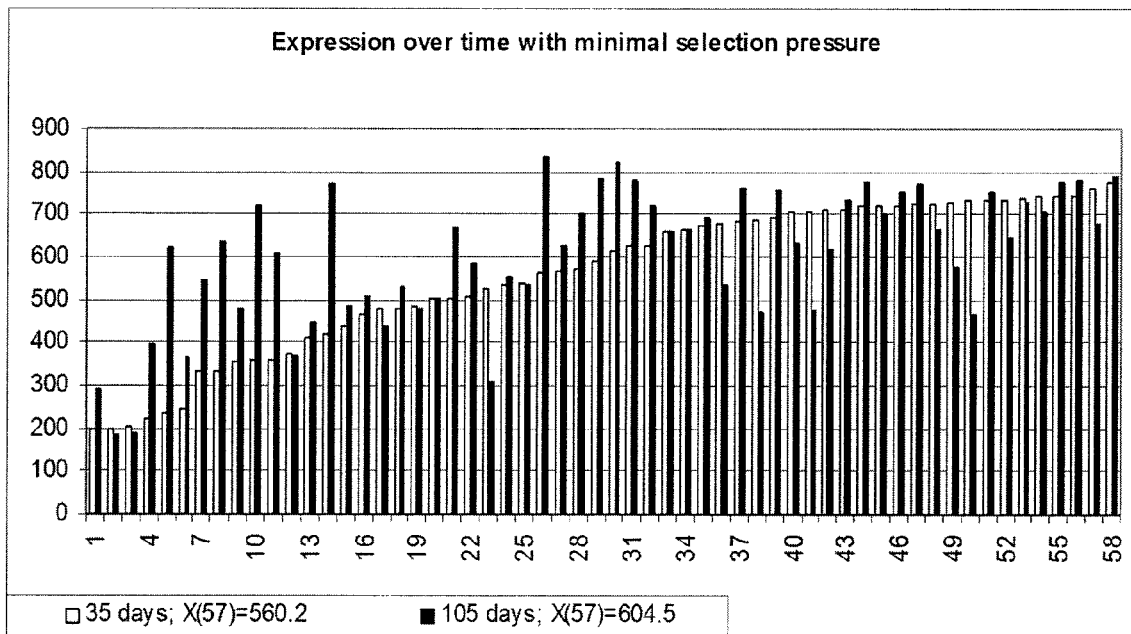
FIG. 7

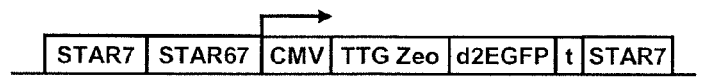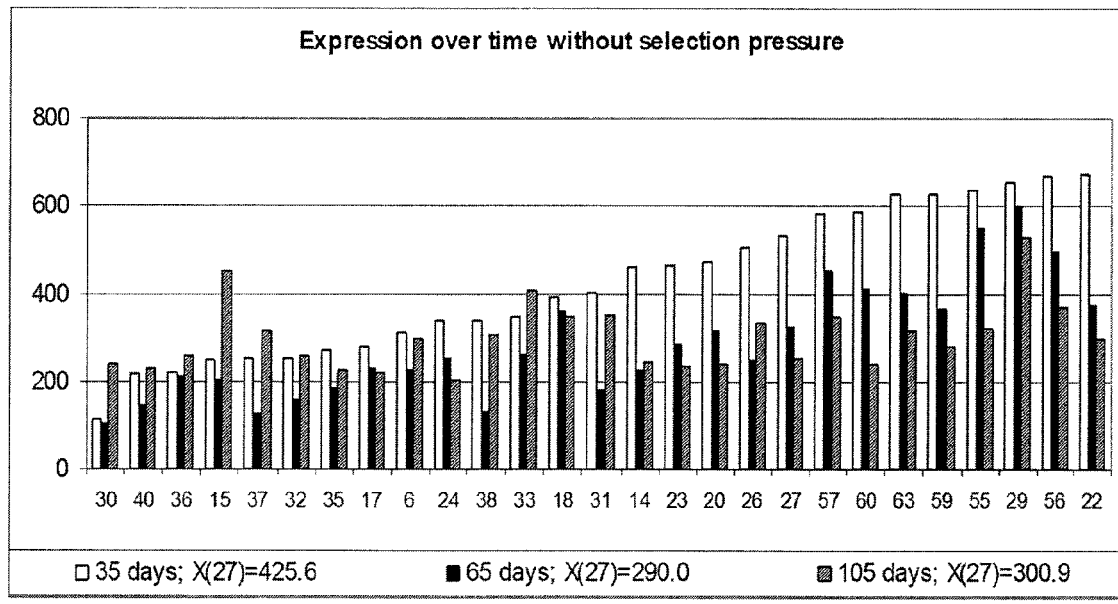
FIG. 8

ATGGCCAAGTTGACCAGTGCCGTTCCGGTGCTCACCGCGCGAC
GTCGCCGGAGCGGTCGAGTTCTGGACCGACCGGCTCGGGTTCTCC
CGGGACTTCGTGGAGGACGACTTCGCCGGTGTGGTCCGGGACGAC
GTGACCCTGTTCATCAGCGCGGTCCAGGACCAGGTGGTGCCGGAC
AACACCCTGGCCTGGGTGTGGGTGCGCGGCCTGGACGAGCTGTAC
GCCGAGTGGTCGGAGGTCGTGTCCACGAACTTCCGGGACGCCTCC
GGGCCGGCCATGACCGAGATCGGCGAGCAGCCGTGGGGCGGGAG
TTCGCCCTGCGCGACCCGGCCGGCAACTGCGTGCACTTCGTGGCC
GAGGAGCAGGACTGA

FIG. 15

ATGGCCAAGCCTTTGTCTCAAGAAGAATCCACCCTCATTGAAAGAGCAACGG
CTACAATCAACAGCATCCCCATCTCTGAAGACTACAGCGTCGCCAGCGCAGC
TCTCTCTAGCGACGGCCGCATCTTCACTGGTGTCAATGTATATCATTTTACT
GGGGGACCTTGTGCAGAACTCGTGGTGCTGGGCACTGCTGCTGCTGCGGCAG
CTGGCAACCTGACTTGTATCGTCGCGATCGGAAATGAGAACAGGGGCATCTT
GAGCCCCTGCGGACGGTGCCGACAGGTGCTTCTCGATCTGCATCCTGGGATC
AAAGCCATAGTGAAGGACAGTGATGGACAGCCGACGGCAGTTGGGATTCGTG
AATTGCTGCCCTCTGGTTATGTGTGGGAGGCTAA

FIG. 16

ATGACCGAGTACAAGCCCACGGTGCGCCTCGCCACCCGCGACGACGTCCCC
AGGGCCGTACGCACCCTCGCCGCCGCGTTCGCCGACTACCCCGCCACGCGC
CACACCGTCGATCCGGACCGCCACATCGAGCGGGTCACCGAGCTGCAAGAA
CTCTTCCTCACGCGCGTCGGGCTCGACATCGGCAAGGTGTGGGTCGCGGAC
GACGGCGCCGCGGTGGCGGTCTGGACCACGCCGGAGAGCGTCGAAGCGGGG
GCGGTGTTCGCCGAGATCGGCCCGCGATGGCCGAGTTGAGCGGTTCCCGG
CTGGCCGCGCAGCAACAGATGGAAGGCCTCCTGGCGCCGCACCGGCCCAAG
GAGCCCGCGTGGTTCCTGGCCACCGTCGGCGTCTCGCCCGACCACCAGGGC
AAGGGTCTGGGCAGCGCCGTCGTGCTCCCCGGAGTGGAGGCGGCCGAGCGC
GCCGGGGTGCCCGCCTTCCTGGAGACCTCCGCGCCCCGCAACCTCCCCTTC
TACGAGCGGCTCGGCTTCACCGTCACCGCCGACGTCGAGTGCCCGAAGGAC
CGCGCGACCTGGTGCATGACCCGCAAGCCCGGTGCCTGA

FIG. 17

ATGGTTCGACCATTGAACTGCATCGTCGCCGTGTCCCAAAATATGGGGAT
TGGCAAGAACGGAGACCTACCCTGGCCTCCGCTCAGGAACGAGTTCAAGT
ACTTCCAAAGAATGACCACAACCTCTTCAGTGGAAGGTAAACAGAATCTG
GTGATTATGGGTAGGAAAACCTGGTTCTCCATTCCTGAGAAGAATCGACC
TTTAAAGGACAGAATTAATATAGTTCTCAGTAGAGAACTCAAAGAACCAC
CACGAGGAGCTCATTTTCTTGCCAAAAGTTTGG<u>ATGATG</u>CCTTAAGACTT
ATTGAACAACCGGAATTGGCAAGTAAAGTAGACATGGTTTGGATAGTCGG
AGGCAGTTCTGTTTACCAGGAAGCCATGAATCAACCAGGCCACCTCAGAC
TCTTTGTGACAAGGATCATGCAGGAATTTGAAAGTGACACGTTTTTCCCA
GAAATTGATTTGGGGAAATATAAACTTCTCCAGAATACCCAGGCGTCCT
CTCTGAGGTCCAGGAGGAAAAGGCATCAAGTATAAGTTTGAAGTCTACG
AGAAGAAAGACTAA

FIG. 18

ATGAAAAAGCCTGAACTCACCGCGACGTCTGTCGAGAAGTTTCTGATCGA
AAAGTTCGACAGCGTCTCCGACCTGATGCAGCTCTCGGAGGGCGAAGAAT
CTCGTGCTTTCAGCTTCGATGTAGGAGGGCGTGGATATGTCCTGCGGGTA
AATAGCTGCGCCGATGGTTTCTACAAAGATCGTTATGTTTATCGGCACTT
TGCATCGGCCGCGCTCCCGATTCCGGAAGTGCTTGACATTGGGGAATTCA
GCGAGAGCCTGACCTATTGCATCTCCGCCGTGCACAGGGTGTCACGTTG
CAAGACCTGCCTGAAACCGAACTGCCCGCTGTTCTGCAGCCGGTCGCGGA
GGCCATGGATGCGATCGCTGCGGCCGATCTTAGCCAGACGAGCGGGTTCG
GCCCATTCGGACCGCAAGGAATCGGTCAATACACTACATGGCGTGATTTC
ATATGCGCGATTGCTGATCCCCATGTGTATCACTGGCAAACTGTATGGA
CGACACCGTCAGTGCGTCCGTCGCGCAGGCTCTCGATGAGCTGATGCTTT
GGGCCGAGGACTGCCCCGAAGTCCGGCACCTCGTGCACGCGGATTTCGGC
TCCAACAATGTCCTGACGGACAATGGCCGCATAACAGCGGTCATTGACTG
GAGCGAGGCGATGTTCGGGGATTCCCAATACGAGGTCGCCAACATCTTCT
TCTGGAGGCCGTGGTTGGCTTGTATGGAGCAGCAGACGCGCTACTTCGAG
CGGAGGCATCCGGAGCTTGCAGGATCGCCGCGGCTCCGGGCGTATATGCT
CCGCATTGGTCTTGACCAACTCTATCAGAGCTTGGTTGACGGCAATTTCG
ATGATGCAGCTTGGGCGCAGGGTCGATGCGACGCAATCGTCCGATCCGGA
GCCGGGACTGTCGGGCGTACACAAATCGCCCGCAGAAGCGCGGCCGTCTG
GACCGATGGCTGTGTAGAAGTACTCGCCGATAGTGGAAACCGACGCCCCA
GCACTCGTCCGGAGGCAAAGGAATTCGGGAGATGGGGGAGGCTAACTGAA
ACACGGAAGGAGACAATACCGGAAGGAACCCGCGCTATGACGGCAATAAA
AAGACAGAATAAAACGCACGGGTGTTGGGTCGTTTGTTCATAA

FIG. 19

ATGGGATCGGCCATTGAACAAGATGGATTGCACGCAGGTTCTCCGGCCGC
TTGGGTGGAGAGGCTATTCGGCTATGACTGGGCACAACAGACAATCGGCT
GCTCTGATGCCGCCGTGTTCCGGCTGTCAGCGCAGGGGCGCCCGGTTCTT
TTTGTCAAGACCGACCTGTCCGGTGCCCTGAATGAACTGCAGGACGAGGC
AGCGCGGCTATCGTGGCTGGCCACGACGGGCGTTCCTTGCGCAGCTGTGC
TCGACGTTGTCACTGAAGCGGGAAGGACTGGCTGCTATTGGGCGAAGTG
CCGGGGCAGGATCTCCTGTCATCTCACCTTGCTCCTGCCGAGAAAGTATC
CATCATGGCTGATGCAATGCGGCGGCTGCATACGCTTGATCCGGCTACCT
GCCCATTCGACCACCAAGCGAAACATCGCATCGAGCGAGCACGTACTCGG
ATGGAAGCCGGTCTTGTCGATCAGGATGATCTGGACGAAGAGCATCAGGG
GCTCGCGCCAGCCGAACTGTTCGCCAGGCTCAAGGCGCGCATGCCCACG
GCGATGATCTCGTCGTGACCCATGGCGATGCCTGCTTGCCGAATATCATG
GTGGAAAATGGCCGCTTTTCTGGATTCATCGACTGTGGCCGGCTGGGTGT
GGCGGACCGCTATCAGGACATAGCGTTGGCTACCCGTGATATTGCTGAAG
AGCTTGGCGGCGAATGGGCTGACCGCTTCCTCGTGCTTTACGGTATCGCC
GCTCCCGATTCGCAGCGCATCGCCTTCTATCGCCTTCTTGACGAGTTCTT
CTGA

FIG. 20

ATGACCACCTCAGCAAGTTCCCACTTAAATAAAGGCATCAAGCAGGTGTA
CATGTCCCTGCCTCAGGGTGAGAAAGTCCAGGCCATGTATATCTGGATCG
ATGGTACTGGAGAAGGACTGCGCTGCAAGACCCGGACCCTGGACAGTGAG
CCCAAGTGTGTGGAAGAGTTGCCTGAGTGGAATTTCGATGGCTCCAGTAC
TTTACAGTCTGAGGGTTCCAACAGTGACATGTATCTCGTGCCTGCTGCC**A
TG**TTTCGGGACCCCTTCCGTAAGGACCCTAACAAGCTGGTGTTATGTGAA
GTTTTCAAGTACAATCGAAGGCCTGCAGAGACCAATTTGAGGCACACCTG
TAAACGGATAATGGACATGGTGAGCAACCAGCACCCCTGGTTTGGCATGG
AGCAGGAGTATACCCTCATGGGGACAGATGGGCACCCCTTTGGTTGGCCT
TCCAACGGCTTCCCAGGGCCCCAGGGTCCATATTACTGTGGTGTGGGAGC
AGACAGAGCCTATGGCAGGACATCGTGGAGGCCCATTACCGGGCCTGCT
TGTATGCTGGAGTCAAGATTGCGGGACTAATGCCGAGGTATGCCTGCC
CAGTGGGAATTTCAGATTGGACCTTGTGAAGGAATCAGCATGGGAGATCA
TCTCTGGGTGGCCCGTTTCATCTTGCATCGTGTGTGTGAAGACTTTGGAG
TGATAGCAACCTTTGATCCTAAGCCCATTCCTGGGAACTGGAATGGTGCA
GGCTGCCATACCAACTTCAGCACCAAGGCCATGCGGGAGGAGAATGGTCT
GAAGTACATCGAGGAGGCCATTGAGAAACTAAGCAAGCGGCACCAGTACC
ACATCCGTGCCTATGATCCCAAGGGAGGCCTGGACAATGCCCGACGTCTA
ACTGGATTCCATGAAACCTCCAACATCAACGACTTTTCTGGTGGTGTAGC
CAATCGTAGCGCCAGCATACGCATTCCCCGGACTGTTGGCCAGGAGAAGA
AGGGTTACTTTGAAGATCGTCGCCCCTCTGCCAACTGCGACCCCTTTTCG
GTGACAGAAGCCCTCATCCGCACGTGTCTTCTCAATGAAACCGGCGATGA
GCCCTTCCAGTACAAAAATTA

FIG. 21

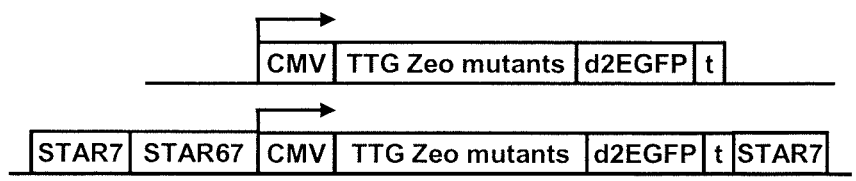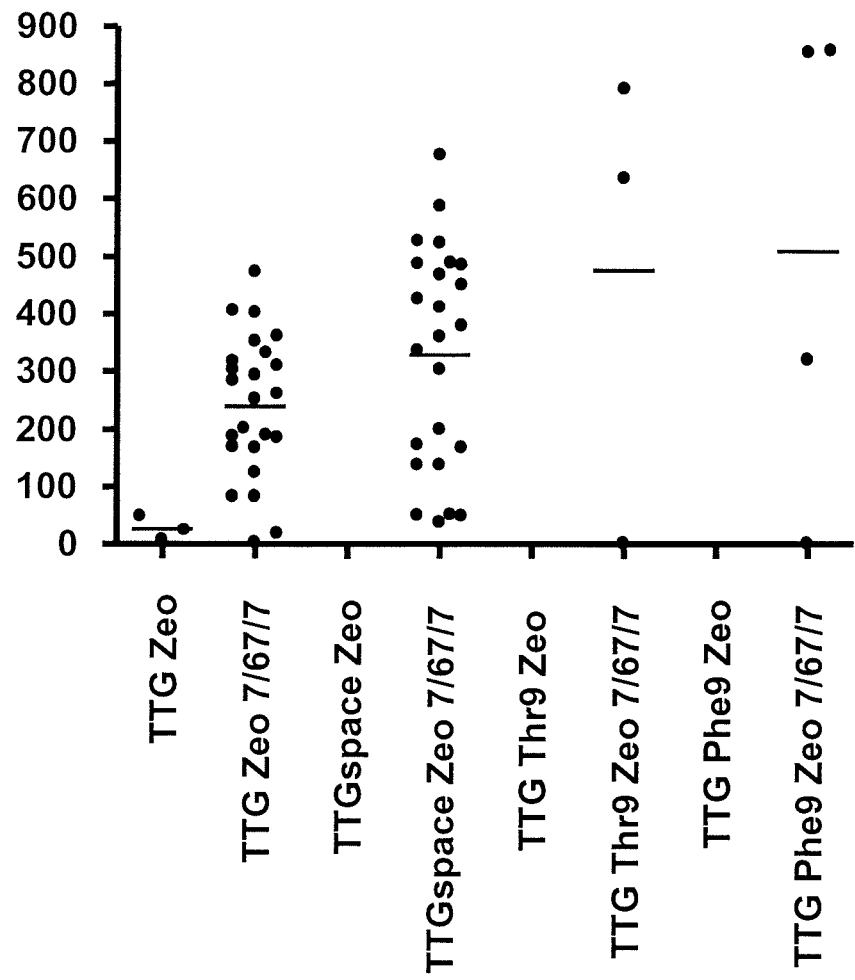
FIG. 25

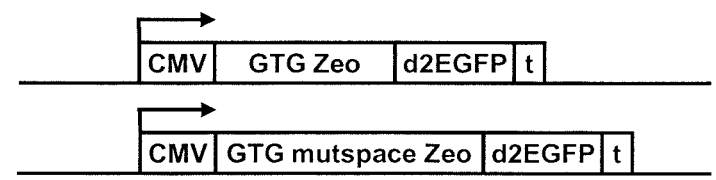
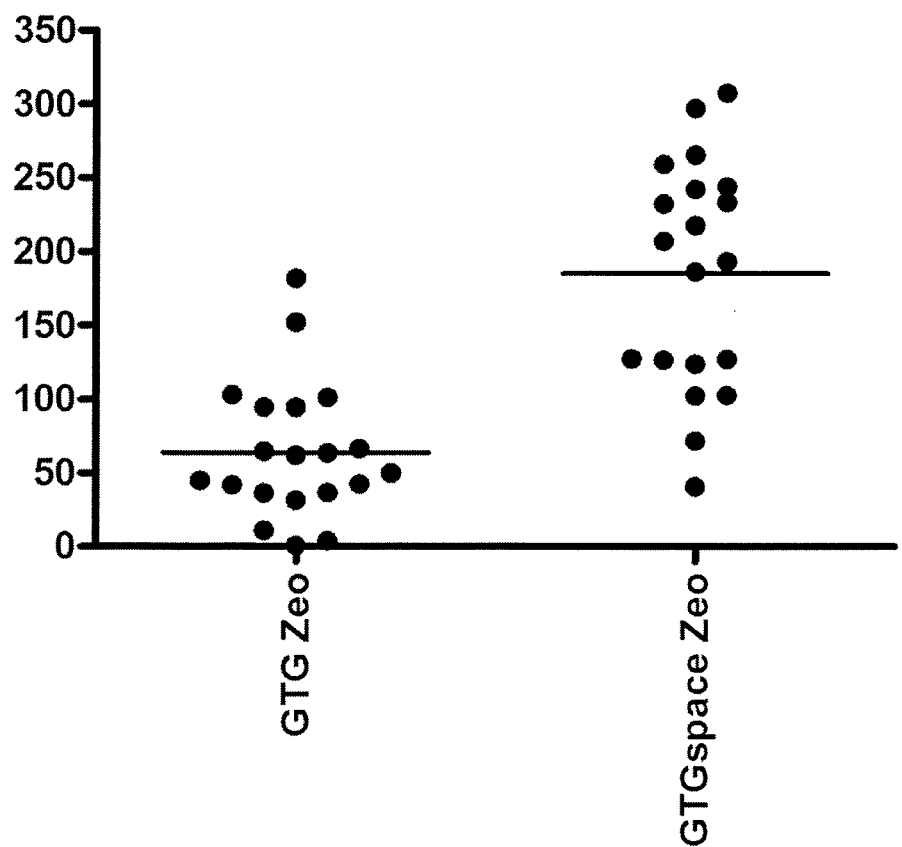
FIG. 30

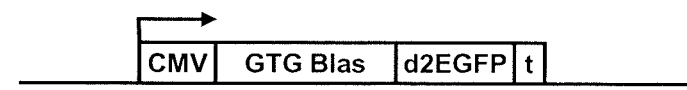
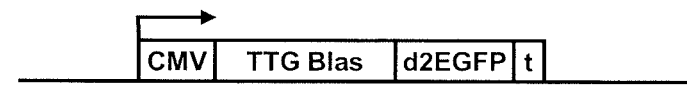
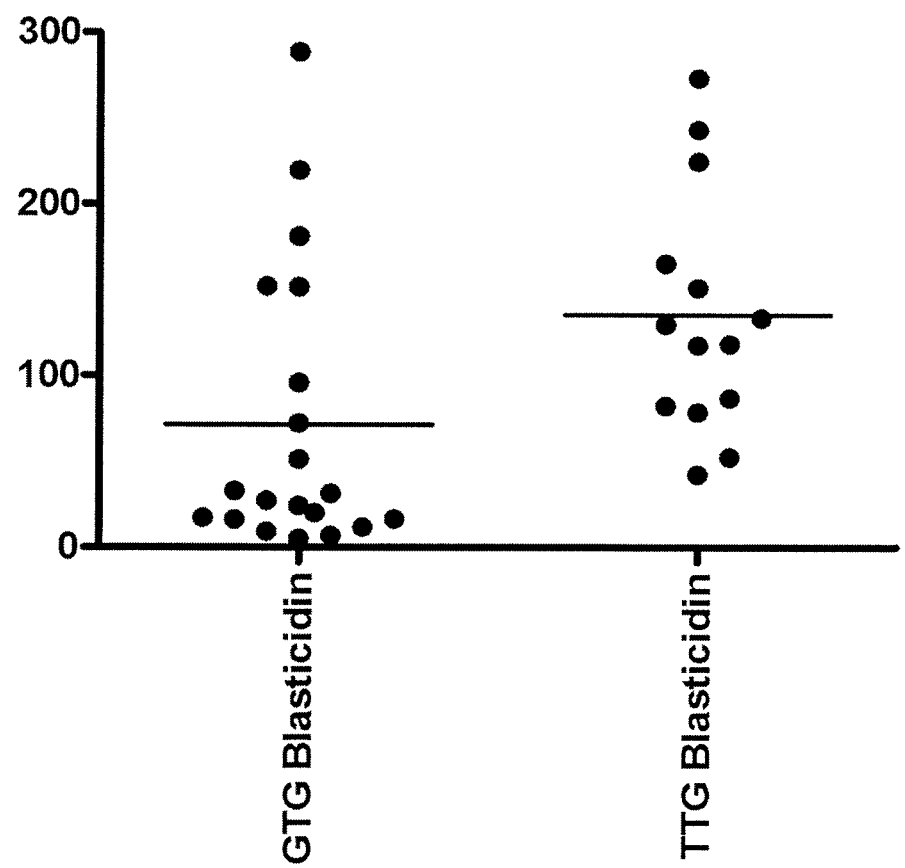
FIG. 31

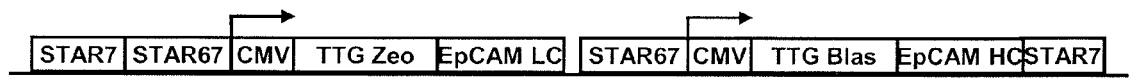
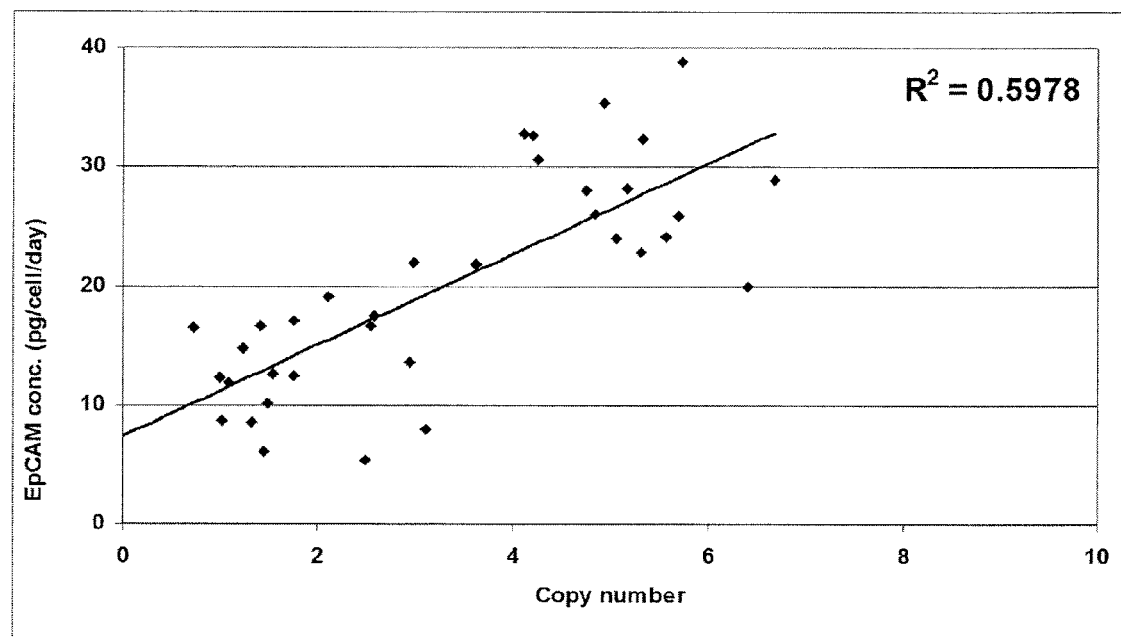
FIG. 33

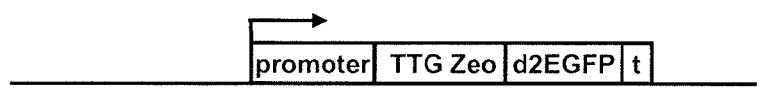
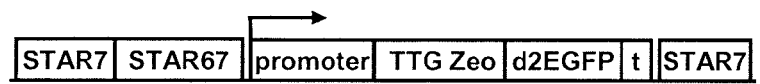
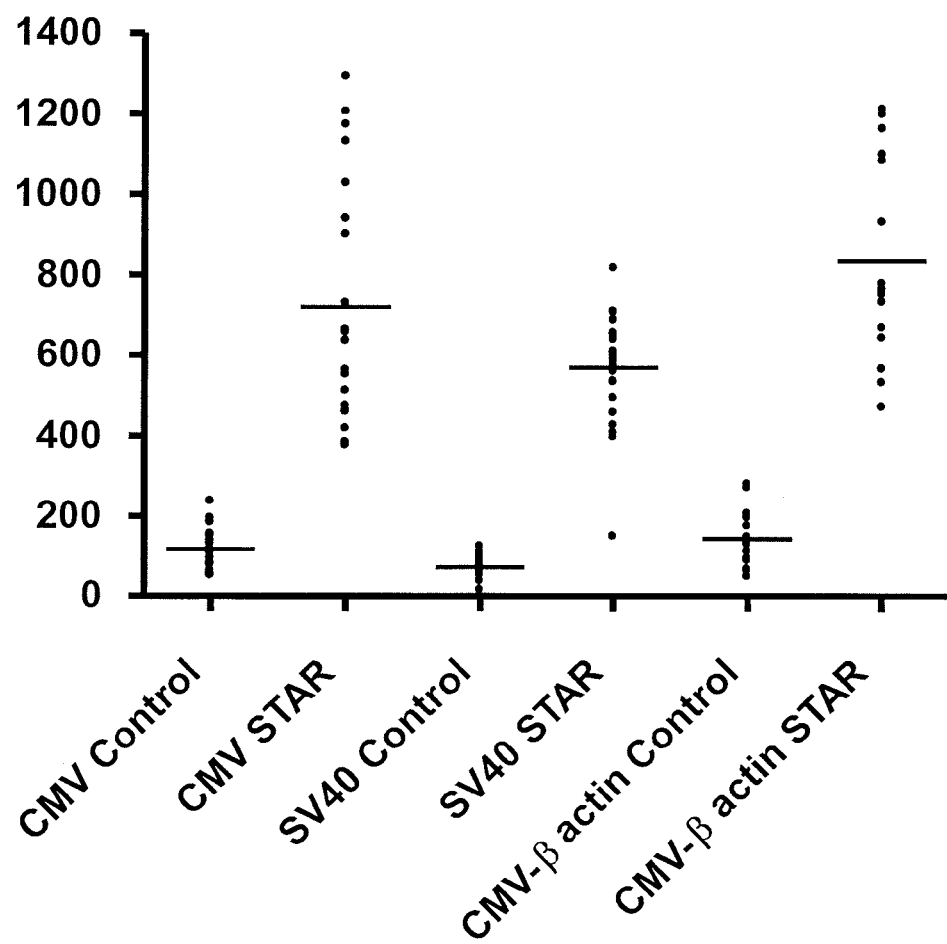
FIG. 35

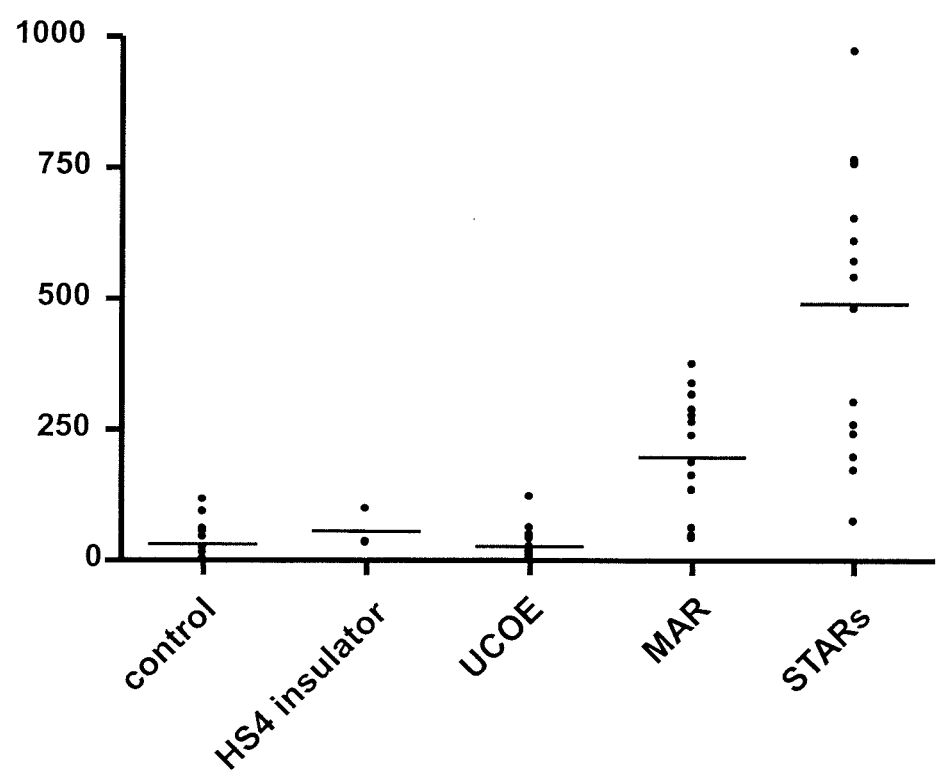
FIG. 37

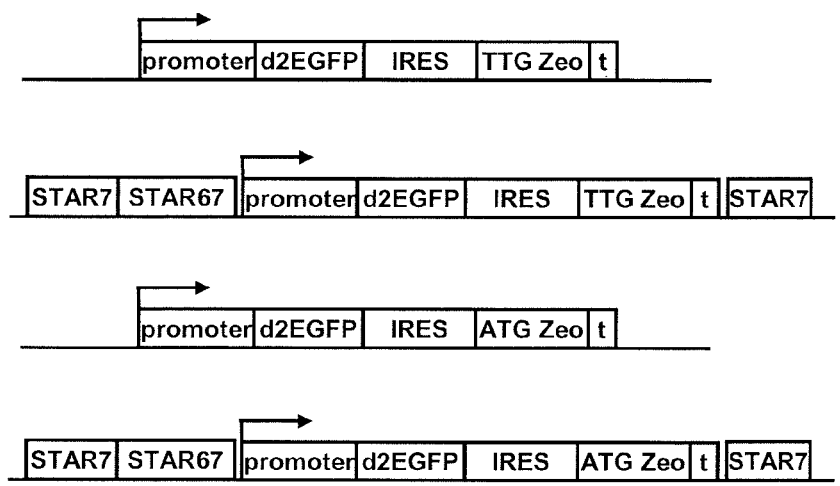
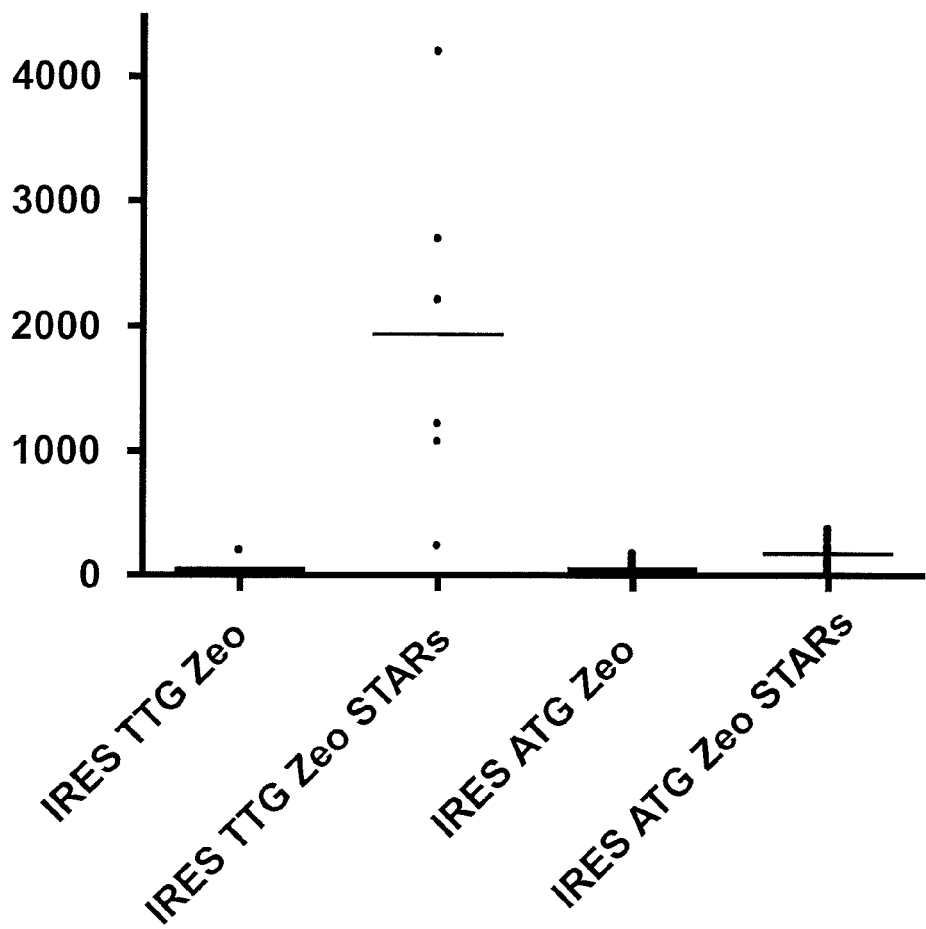
FIG. 38

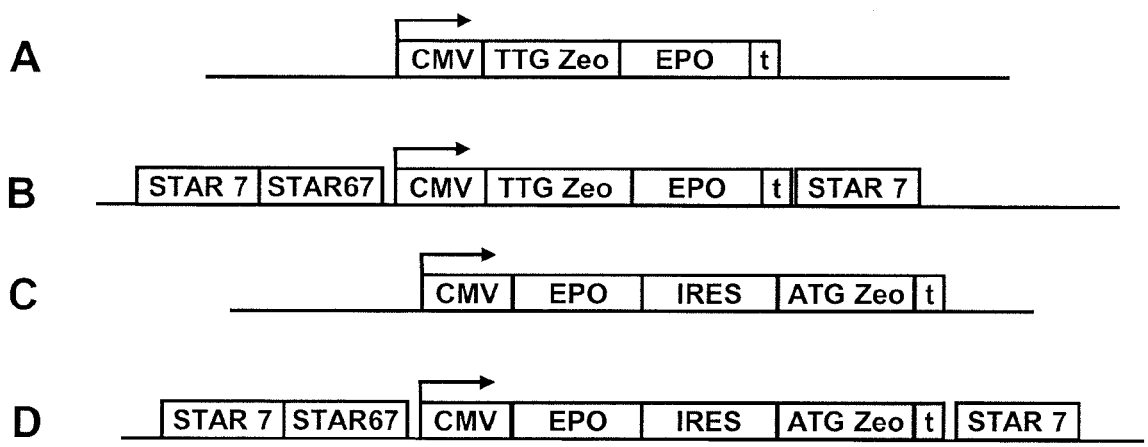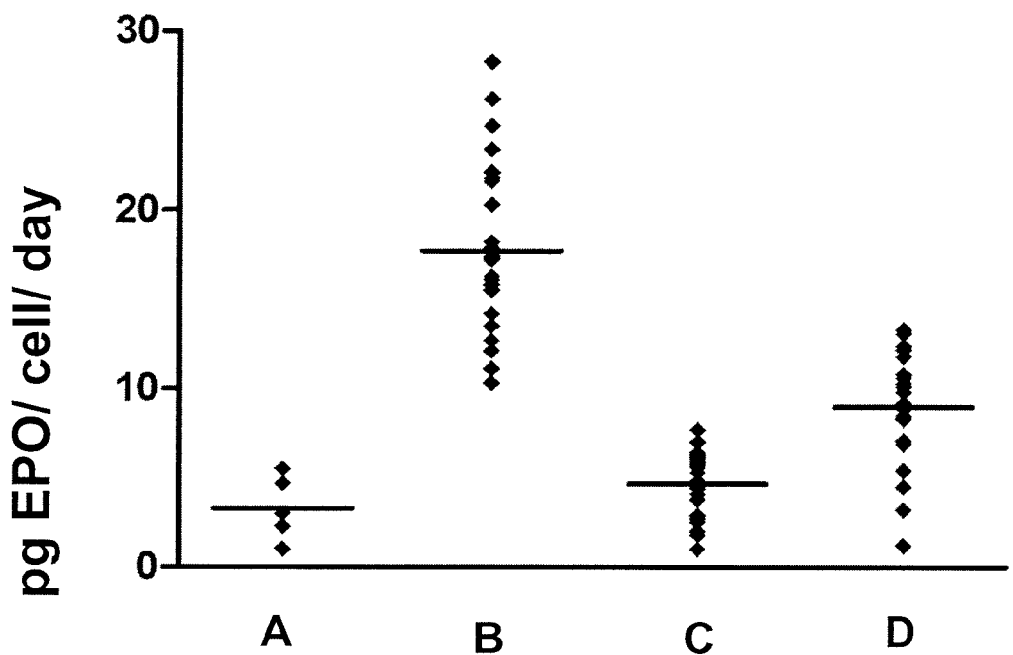
FIG. 39

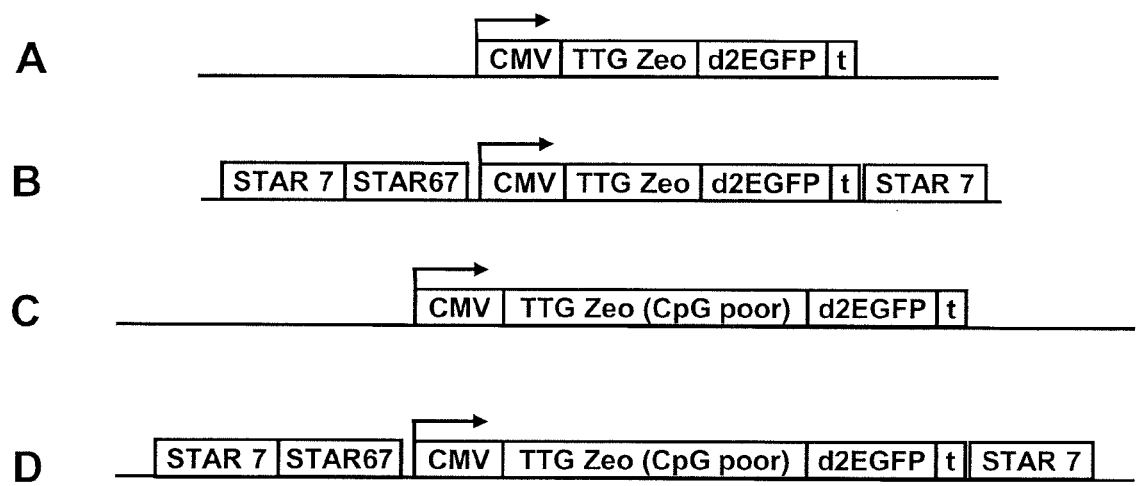
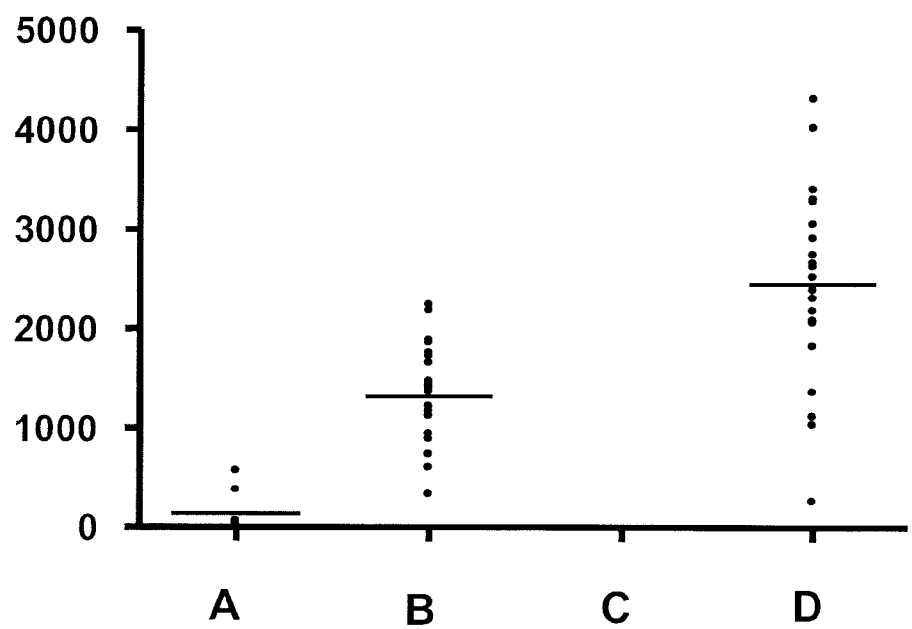
FIG. 41

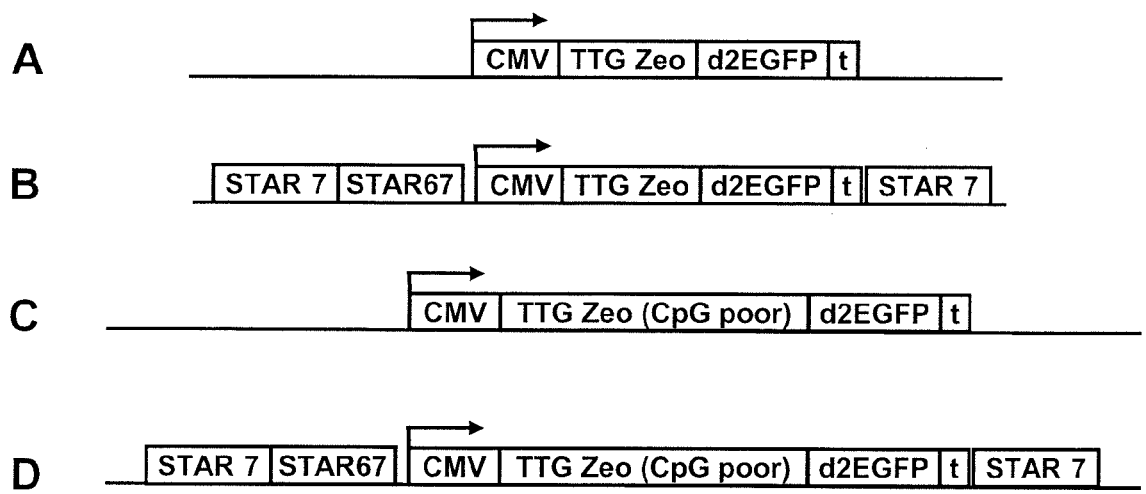
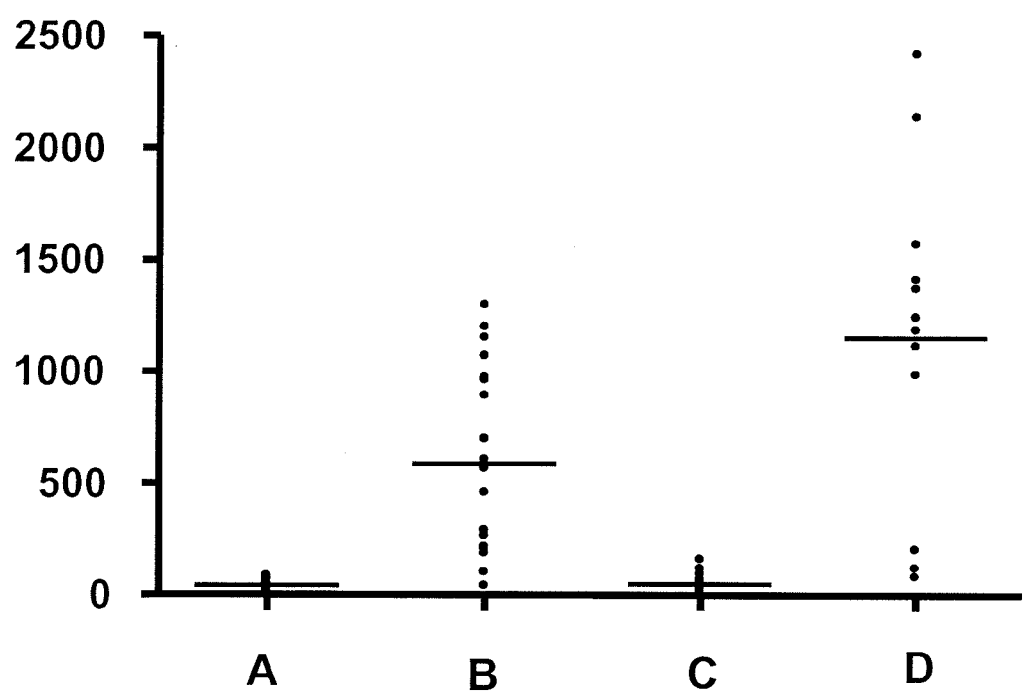
FIG. 42

A
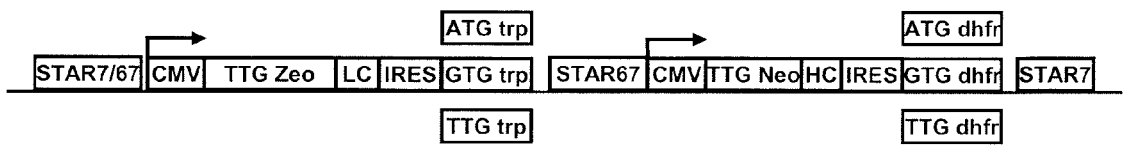
B
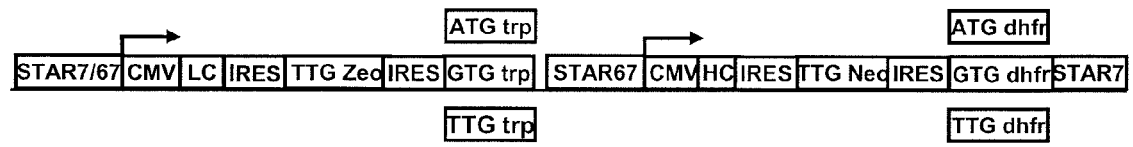
FIG. 47

SELECTION OF HOST CELLS EXPRESSING PROTEIN AT HIGH LEVELS

CROSS-REFERENCE TO RELATED APPLICATIONS

This application is a divisional of U.S. patent application Ser. No. 13/135,966, filed Jul. 18, 2011, which application is a continuation of U.S. patent application Ser. No. 11/416,490, filed May 2, 2006, which is a continuation-in-part of U.S. patent application Ser. No. 11/269,525, filed Nov. 7, 2005, which application claims the benefit under 35 U.S.C. §119(e) of U.S. Provisional Patent Application Ser. No. 60/626,301, filed Nov. 8, 2004, and U.S. Provisional Patent Application Ser. No. 60/696,610, filed Jul. 5, 2005. U.S. patent application Ser. No. 11/269,525 also claims the benefit of EP 04105593.0, filed Nov. 8, 2004. This application is related to U.S. patent application Ser. No. 11/359,953, filed Feb. 21, 2006, and which itself is a continuation-in-part of the aforementioned U.S. patent application Ser. No. 11/269,525, filed Nov. 7, 2005. This application is also related to U.S. patent application Ser. No. 12/226,706, filed Oct. 24, 2008, now U.S. Pat. No. 8,039,230, issued Oct. 18, 2011, which is the national stage of PCT International Patent Application No. PCT/EP2007/053984, filed on Apr. 24, 2007, designating the United States of America, and published, in English, as PCT International Publication No. WO 2007/128685 A1 on Nov. 15, 2007, and claims priority to U.S. patent application Ser. No. 11/416,490, filed May 2, 2006, and EP 06113354.2, also filed on May 2, 2006. The entirety of the disclosure of each of the preceding applications is hereby incorporated herein in its entirety by this reference.

STATEMENT ACCORDING TO 37 C.F.R. §1.821(C) OR (E)—SEQUENCE LISTING SUBMITTED AS PDF FILE WITH A REQUEST TO TRANSFER CRF FROM PARENT APPLICATION

Pursuant to 37 C.F.R. §1.821(c) or (e), a file containing a PDF version of the Sequence Listing has been submitted concomitant with this application, the contents of which are hereby incorporated by reference. The transmittal documents of this application include a Request to Transfer CRF from the parent application.

TECHNICAL FIELD

The disclosure relates to the field of molecular biology and biotechnology. More specifically the disclosure relates to means and methods for improving the selection of host cells that express proteins at high levels.

BACKGROUND

Proteins can be produced in various host cells for a wide range of applications in biology and biotechnology, for instance as biopharmaceuticals. Eukaryotic and particularly mammalian host cells are preferred for this purpose for expression of many proteins, for instance when such proteins have certain posttranslational modifications such as glycosylation. Methods for such production are well established, and generally entail the expression in a host cell of a nucleic acid (also referred to as "transgene") encoding the protein of interest. In general, the transgene together with a selectable marker gene is introduced into a precursor cell, cells are selected for the expression of the selectable marker gene, and one or more clones that express the protein of interest at high levels are identified, and used for the expression of the protein of interest.

One problem associated with the expression of transgenes is that it is unpredictable, stemming from the high likelihood that the transgene will become inactive due to gene silencing (McBurney et al., 2002), and therefore many host cell clones have to be tested for high expression of the transgene.

Methods of selecting recombinant host cells expressing relatively high levels of desired proteins are known.

One method describes the use of selectable marker proteins with mutations in their coding sequence that diminish, but do not destroy the function of the marker (e.g., WO 01/32901). The rationale is that higher levels of the mutant marker expression are required when selection conditions are employed and therefore selection for high expression of the marker is achieved, therewith concomitantly selecting host cells that also express the gene of interest at high levels.

Another method makes use of a selection marker gene under control of a promoter sequence that has been mutated such that the promoter has an activity level substantially below that of its corresponding wild type (U.S. Pat. No. 5,627,033).

Another method describes the use of an impaired dominant selectable marker sequence, such as neomycin phosphotransferase with an impaired consensus Kozak sequence, to decrease the number of colonies to be screened and to increase the expression levels of a gene of interest that is co-linked to the dominant selectable marker (U.S. Pat. Nos. 5,648,267 and 5,733,779). In certain embodiments thereof, the gene of interest is placed within an (artificial) intron in the dominant selectable marker. The gene of interest and the dominant selectable marker are in different transcriptional cassettes and each contains its own eukaryotic promoter in this method (U.S. Pat. Nos. 5,648,267 and 5,733,779).

Another method uses the principle of a selectable marker gene containing an intron that does not naturally occur within the selectable gene, wherein the intron is capable of being spliced in a host cell to provide mRNA encoding a selectable protein and wherein the intron in the selectable gene reduces the level of selectable protein produced from the selectable gene in the host cell (European Patent 0724639 B1).

In yet another method, DNA constructs are used comprising a selectable gene positioned within an intron defined by a 5' splice donor site comprising an efficient splice donor sequence such that the efficiency of splicing an mRNA having the splice donor site is between about 80-99%, and a 3' splice acceptor site, and a product gene encoding a product of interest downstream of 3' splice acceptor site, the selectable gene and the product gene being controlled by the same transcriptional regulatory region (U.S. Pat. No. 5,561,053).

In certain methods, use is made of polycistronic expression vector constructs. An early report of use of this principle describes a polycistronic expression vector, containing sequences coding for both the desired protein and a selectable protein, which coding sequences are governed by the same promoter and separated by a translational stop and start signal codons (U.S. Pat. No. 4,965,196). In certain embodiments in U.S. Pat. No. 4,965,196, the selectable marker is the amplifiable DHFR gene. In a particularly preferred embodiment of the system described in U.S. Pat. No. 4,965,196, the sequence coding for the selectable marker is downstream from that coding for the desired polypeptide, such that procedures designed to select for the cells transformed by the selectable marker will also select for particularly enhanced production of the desired protein.

In further improvements based on the concept of multicistronic expression vectors, bicistronic vectors have been described for the rapid and efficient creation of stable mammalian cell lines that express recombinant protein. These vectors contain an internal ribosome entry site (IRES) between the upstream coding sequence for the protein of interest and the downstream coding sequence of the selection marker (Rees et al., 1996). Such vectors are commercially available, for instance the pIRES1 vectors from Clontech (CLONTECHniques, October 1996). Using such vectors for introduction into host cells, selection of sufficient expression of the downstream marker protein then automatically selects for high transcription levels of the multicistronic mRNA, and hence a strongly increased probability of high expression of the protein of interest is envisaged using such vectors.

Preferably in such methods, the IRES used is an IRES which gives a relatively low level of translation of the selection marker gene, to further improve the chances of selecting for host cells with a high expression level of the protein of interest by selecting for expression of the selection marker protein (see, e.g., PCT International Publication WO 03/106684).

DISCLOSURE

This instant disclosure aims at providing improved means and methods for selecting host cells expressing high levels of proteins of interest.

U.S. patent application Ser. No. 11/269,525 (hereinafter "the incorporated '525 application") and International Patent Application No. PCT/EP2005/055794, both incorporated in their entirety by reference herein, disclose a concept for selecting host cells expressing high levels of polypeptides of interest, the concept referred to therein as "reciprocal interdependent translation." In that concept, a multicistronic transcription unit is used wherein a sequence encoding a selectable marker polypeptide is upstream of a sequence encoding a polypeptide of interest, and wherein the translation of the selectable marker polypeptide is impaired by mutations therein, whereas translation of the polypeptide of interest is very high (see, e.g., FIG. 2 herein for a schematic view).

U.S. patent application Ser. No. 11/359,953 (hereinafter "the incorporated '953 application"), incorporated in its entirety by reference herein, discloses alternative means and methods for selecting host cells expressing high levels of polypeptide. The incorporated '953 application is based on a similar principle as the incorporated '525 application, this principle also using multicistronic transcription units and impairment of the translation initiation of the selectable marker polypeptide by mutation of the start codon thereof. The main difference between the means and methods disclosed in the incorporated '525 application and the incorporated '953 application is in the order of the sequences encoding the selectable marker polypeptide and the sequence encoding the polypeptide of interest in the multicistronic transcription units.

Both the incorporated '525 and '953 patent applications thus provide means and methods for selecting host cells with very high expression levels of a polypeptide of interest. Provided herein are further advantageous embodiments and improvements to the means and methods disclosed in the incorporated '525 and '953 applications.

Also provided is a DNA molecule comprising an open reading frame ("ORF") sequence that encodes a selectable marker polypeptide, wherein the DNA molecule in the coding strand comprises a translation start sequence for the selectable marker polypeptide chosen from the group consisting of: a) a GTG start codon; and b) a TTG start codon; and wherein the ORF sequence that encodes the selectable marker protein has been mutated to replace at least 10% of its CpG dinucleotides as compared to the native ORF sequence that encodes the selectable marker protein.

The translation start sequence in the coding strand for the selectable marker polypeptide may comprise a GTG or TTG start codon, most preferably a TTG start codon, flanked by sequences providing for relatively good recognition of the non-ATG sequences as start codons, such that at least some ribosomes start translation from these start codons, i.e., the translation start sequence may comprise the sequence ACC [GTG or TTG start codon]G or GCC[GTG or TTG start codon]G.

In certain embodiments, the selectable marker protein provides resistance against lethal and/or growth-inhibitory effects of a selection agent, such as an antibiotic. In certain embodiments, the selectable marker polypeptide provides resistance against ZEOCIN® antibiotic or against neomycin.

In certain embodiments, the DNA molecule comprises comprising an ORF sequence that encodes a polypeptide that provides resistance against neomycin, wherein the DNA molecule comprises a sequence chosen from the group consisting of: a) SEQ ID NO:128, with the proviso that at least half of the CpG dinucleotides has been replaced without mutating the peptide that is encoded, and with the further proviso that the start codon is either GTG or TTG; and b) SEQ ID NO:118, with the proviso that at least half of the CpG dinucleotides of the coding strand has been replaced without mutating the peptide that is encoded, and with the further proviso that the start codon is either GTG or TTG; and c) SEQ ID NO:128 or SEQ ID NO:118, with the proviso that it contains a mutation to encode either of the following polypeptide variants as compared to the polypeptide encoded by the native sequences: (i) substitution valine at position 201 into glycine (201V>G), or (ii) substitution of glutamic acid at position 185 into aspartic acid (185E>D), or (iii) a combination of both mutations (i) and (ii) (185E>D and 201V>G), with the further proviso that at least half of the CpG dinucleotides of the coding strand has been replaced without further mutating the amino acid sequence that is encoded beyond the mutation indicated under (i)-(iii), and with the further proviso that the start codon is either GTG or TTG. In one advantageous embodiment hereof, the DNA molecule comprises SEQ ID NO:130, with the proviso that nucleotide A at position 555 is replaced by C to encode the encode the 185E>D mutation, and that nucleotide T at position 602 is replaced by G and that nucleotide G at position 603 is replaced by T to encode the 201V>G mutation, and with the further proviso that the start codon is either GTG or TTG.

In certain embodiments, the DNA molecule comprises an ORF sequence that encodes a polypeptide that provides resistance against ZEOCIN®, wherein the DNA molecule comprises a sequence chosen from the group consisting of: a) SEQ ID NO:92, with the proviso that at least half of the CpG dinucleotides has been replaced without mutating the amino acid sequence that is encoded, and with the further proviso that the start codon is either GTG or TTG; and b) SEQ ID NO:92 wherein nucleotide A at position 280 is replaced by T, and with the proviso that at least half of the CpG dinucleotides has been replaced without mutating the amino acid sequence that is encoded, and with the further proviso that the start codon is either GTG or TTG. In one advantageous embodiment hereof, the DNA sequence comprises SEQ ID NO:132.

In another aspect, provided is a DNA molecule comprising an ORF sequence that encodes a selectable marker polypeptide, wherein the selectable marker polypeptide is chosen from the group consisting of: (i) tryptophan synthesizing enzyme (trp); (ii) histidine synthesizing enzyme (his); and (iii) 5,6,7,8 tetrahydrofolate synthesizing enzyme (dhfr); and wherein the DNA molecule in the coding strand comprises a translation start sequence for the selectable marker polypeptide chosen from the group consisting of: a) a GTG start codon; and b) a TTG start codon.

In certain embodiments, the DNA molecule comprises an ORF sequence that encodes trp, wherein the DNA molecule comprises a sequence chosen from the group consisting of SEQ ID NO:134 and SEQ ID NO:136, with the proviso that the first three nucleotides (the start codon) are either GTG or TTG.

In certain embodiments, the DNA molecule comprises an ORF sequence that encodes his, wherein the DNA molecule comprises a sequence chosen from the group consisting of SEQ ID NO:138 and SEQ ID NO:140, with the proviso that the first three nucleotides (the start codon) are either GTG or TTG.

In certain embodiments, the DNA molecule comprises an ORF sequence that encodes dhfr, wherein the DNA molecule comprises a sequence chosen from the group consisting of SEQ ID NO:98 and SEQ ID NO:122, with the proviso that the first three nucleotides (the start codon) are either GTG or TTG.

The coding sequence of the polypeptide of interest may comprises an optimal translation start sequence.

In certain embodiments, the ORF sequence that encodes the selectable marker polypeptide has no ATG sequence in the coding strand.

In certain embodiments, the ORF sequence that encodes a selectable marker polypeptide is part of a multicistronic transcription unit that further comprises an ORF sequence encoding a polypeptide of interest.

In certain embodiments thereof, the ORF that encodes the selectable marker polypeptide is upstream of the ORF encoding the polypeptide of interest, and the ORF that encodes the selectable marker polypeptide has no ATG sequence in the coding strand. In alternative embodiments, the ORF that encodes the polypeptide of interest is upstream of the ORF that encodes the selectable marker polypeptide, and the ORF that encodes the selectable marker polypeptide is operably linked to an internal ribosome entry site (IRES).

Further provided are expression cassettes comprising a DNA molecule hereof, which expression cassettes further comprise a promoter upstream of the multicistronic expression unit and being functional in a eukaryotic host cell for initiation transcription of the multicistronic expression unit, and the expression cassettes further comprising a transcription termination sequence downstream of the multicistronic expression unit.

In certain embodiments thereof, such expression cassettes further comprise at least one chromatin control element chosen from the group consisting of a matrix or scaffold attachment region (MAR/SAR), an insulator sequence, a ubiquitous chromatin opener element (UCOE), and an anti-repressor sequence. Anti-repressor sequences are most preferred in this aspect, and in certain embodiments, the anti-repressor sequences are chosen from the group consisting of: a) any one SEQ ID NO:1 through SEQ ID NO:66; b) fragments of any one of SEQ ID NO:1 through SEQ ID NO:66, wherein the fragments have anti-repressor activity; c) sequences that are at least 70% identical in nucleotide sequence to a) or b) wherein the sequences have anti-repressor activity; and d) the complement to any one of a) to c). In certain certain embodiments, the anti-repressor sequences are chosen from the group consisting of: STAR67 (SEQ ID NO:66), START (SEQ ID NO:7), STAR9 (SEQ ID NO:9), STAR17 (SEQ ID NO:17), STAR27 (SEQ ID NO:27), STAR29 (SEQ ID NO:29), STAR43 (SEQ ID NO:43), STAR44 (SEQ ID NO:44), STAR45 (SEQ ID NO:45), STAR47 (SEQ ID NO:47), STAR61 (SEQ ID NO:61), and functional fragments or derivatives of these STAR sequences. In certain embodiments, the expression cassette comprises STAR67, or a functional fragment or derivative thereof, positioned upstream of the promoter driving expression of the multicistronic gene. In certain embodiments, the multicistronic gene is flanked on both sides by at least one anti-repressor sequence. In certain embodiments, expression cassettes are provided herein, comprising in 5' to 3' order: anti-repressor sequence A—anti-repressor sequence B—[promoter—multicistronic transcription unit hereof (encoding the functional selectable marker protein {from a sequence with a GTG or TTG start codon} and upstream or downstream thereof the polypeptide of interest)—transcription termination sequence]—anti-repressor sequence C, wherein A, B and C may be the same or different.

In certain embodiments, the polypeptide of interest is a part of a multimeric protein, for example a heavy or light chain of an immunoglobulin.

Also provided are host cells comprising DNA molecules hereof.

Further provided are methods for generating host cells expressing a polypeptide of interest, comprising: introducing into a plurality of precursor host cells an expression cassette hereof, culturing the cells under conditions selecting for expression of the selectable marker polypeptide, and selecting at least one host cell producing the polypeptide of interest.

Further provided are methods for producing a polypeptide of interest, the methods comprising culturing a host cell, the host cell comprising an expression cassette hereof, and expressing the polypeptide of interest from the expression cassette. In certain embodiments, the polypeptide of interest is harvested from the host cells and/or from the host cell culture medium.

In certain embodiments, if the selectable marker polypeptide is trp, the host cell in advantageous embodiments is cultured in a culture medium that contains indole and which culture medium is essentially devoid of tryptophan. In other embodiments, if the selectable marker polypeptide is his, the host cell in advantageous embodiments is cultured in a culture medium that contains histidinol and which culture medium is essentially devoid of histidine. In other embodiments, if the selectable marker polypeptide is dhfr, the host cell in advantageous embodiments is cultured in a culture medium that contains folate and which culture medium is essentially devoid of glycine, hypoxanthine and thymidine.

In further aspects, provided is RNA molecules having the sequence of a transcription product of a DNA molecule hereof. Further, provided is selectable marker polypeptides that are the translation product of a DNA molecule hereof.

In another aspect, further provided is a DNA molecule comprising an expression cassette comprising a multicistronic transcription unit, the multicistronic transcription unit comprising a sequence coding for a polypeptide of interest, a sequence coding for a first selectable marker polypeptide, and a sequence coding for a second selectable marker polypeptide, wherein the sequence encoding the first selectable marker polypeptide in the coding strand comprises a translation start sequence chosen from the group consisting of a GTG start codon and a TTG start codon, and wherein the second selectable marker polypeptide is chosen from the group consisting of: (i) tryptophan synthesizing enzyme (trp); (ii) histidine synthesizing enzyme (his); and (iii) 5,6,7,8 tetrahydrofolate synthesizing enzyme (dhfr), and wherein the expression cassette further comprises a promoter upstream of the multicistronic expression unit and a transcription termination sequence downstream of the multicistronic expression unit, wherein the expression cassette is functional in a eukaryotic host cell for initiating transcription of the multicistronic expression unit, and wherein the DNA molecule further comprises at least one chromatin control element selected from the group consisting of matrix attachment regions (MAR), and anti-repressor (STAR) sequences.

In one embodiment thereof, the sequence encoding the first selectable marker polypeptide is upstream of the sequence encoding the polypeptide of interest and the sequence encoding the first selectable marker polypeptide in the coding strand is devoid of the sequence ATG, and the sequence encoding the second selectable marker polypeptide is downstream of the polypeptide of interest and is operably linked to an IRES.

In another embodiment, the sequence encoding the polypeptide of interest is upstream of the sequences encoding the first and second selectable marker polypeptide, and the sequence encoding the first selectable marker polypeptide is operably linked to an IRES, and the sequence encoding the second selectable marker polypeptide is operably linked to an IRES.

In certain embodiments, the first selectable marker polypeptide confers resistance against lethal or growth-inhibitory effects of a selection agent chosen from the group consisting of ZEOCIN® and neomycin antibiotics.

In certain embodiments, a chromatin control element is an anti-repressor sequence chosen from the group consisting of any one of SEQ ID NO:1 through SEQ ID NO:66, and the complement of any of these.

Further provided is host cells comprising such DNA molecules.

Further provided is a method for expressing a polypeptide of interest, comprising culturing a host cell that comprises a DNA molecule hereof, and expressing the polypeptide of interest form the expression cassette, and wherein: a) if the second selectable marker polypeptide is trp, the host cell is cultured in a culture medium that contains indole and which culture medium is essentially devoid of tryptophan; b) if the second selectable marker polypeptide is his, the host cell is cultured in a culture medium that contains histidinol and which culture medium is essentially devoid of histidine; c) if the second selectable marker polypeptide is dhfr, the host cell is cultured in a culture medium that contains folate and which culture medium is essentially devoid of glycine, hypoxanthine and thymidine. In certain embodiments, the method further comprises harvesting the polypeptide of interest, from the host cell, from the culture medium, or from both the host cell and the culture medium.

BRIEF DESCRIPTION OF THE DRAWINGS

FIG. 6. Stability of expression of several clones with a multicistronic transcription unit hereof (including a ZEOCIN® with TTG start codon) of the incorporated '525 application. Selection pressure (100 µg/ml zeocin) was present during the complete experiment. d2EGFP signal for independent colonies is shown on the vertical axis. See, Example 5 for details.

FIG. 7. As FIG. 6, but ZEOCIN® antibiotic concentration was lowered to 20 µg/ml after establishment of clones.

FIG. 8. As FIG. 6, but ZEOCIN® antibiotic was absent from culture medium after establishment of clones.

FIG. 15. Coding sequence of the wild-type ZEOCIN®-resistance gene (SEQ ID NO:92). Bold ATGs code for methione. The first bold ATG is the start codon.

FIG. 16. Coding sequence of the wild-type blasticidin resistance gene (SEQ ID NO:94). Bold ATGs code for methione. The first bold ATG is the start codon. Other ATGs in the sequence are underlined: these internal ATGs do not code for methionine, because they are not in frame.

FIG. 17. Coding sequence of the wild-type puromycin resistance gene (SEQ ID NO:96). Bold ATGs code for methione. The first bold ATG is the start codon.

FIG. 18. Coding sequence of the wild-type mouse DHFR gene (SEQ ID NO:98). Bold ATGs code for methione. The first bold ATG is the start codon. Other ATGs in the sequence are underlined: these internal ATGs do not code for methionine, because they are not in frame.

FIG. 19. Coding sequence of the wild-type hygromycin resistance gene (SEQ ID NO:100). Bold ATGs code for methione. The first bold ATG is the start codon. Other ATGs in the sequence are underlined: these internal ATGs do not code for methionine, because they are not in frame.

FIG. 20. Coding sequence of the wild-type neomycin-resistance gene (SEQ ID NO:102). Bold ATGs code for methione. The first bold ATG is the start codon. Other ATGs in the sequence are underlined: these internal ATGs do not code for methionine, because they are not in frame.

FIG. 21. Coding sequence of the wild-type human glutamine synthase (GS) gene (SEQ ID NO:104). Bold ATGs code for methione. The first bold ATG is the start codon. Other ATGs in the sequence are underlined: these internal ATGs do not code for methionine, because they are not in frame.

FIG. 25. Results with expression systems containing the further modified ZEOCIN®-resistance selection marker genes. See, Example 8 for details. Dots indicate individual data points; lines indicate the average expression levels; used constructs are indicated on the horizontal axis, and schematically depicted above the graph; vertical axis indicates d2EGFP signal.

FIG. 30. Results with expression constructs (ZEOCIN®-selectable marker) of the incorporated '525 application in PER.C6® cells. See, Example 12 for details. Dots indicate individual data points; lines indicate the average expression levels; used constructs are indicated on the horizontal axis, and schematically depicted above the graph; vertical axis indicates d2EGFP signal.

FIG. 31. Results with expression constructs (blasticidin selectable marker) of the incorporated '525 application in PER.C6® cells. See, Example 12 for details. Dots indicate individual data points; lines indicate the average expression levels; used constructs are indicated on the horizontal axis, and schematically depicted above the graph; vertical axis indicates d2EGFP signal.

FIG. 33. Copy-number dependency of expression of an antibody using transcription units of the incorporated '525 application. See, Example 14 for details.

FIG. 35. Results with different promoters. See, Example 16 for details. Dots indicate individual data points; lines indicate the average expression levels; used constructs are indicated on the horizontal axis, and schematically depicted above the graph; vertical axis indicates d2EGFP signal.

FIG. 37. Results with other chromatin control elements. See, Example 18 for details. Dots indicate individual data points; lines indicate the average expression levels; used constructs are indicated on the horizontal axis, and schematically depicted above the graph (black triangles indicate different tested chromatin control elements); vertical axis indicates d2EGFP signal.

FIG. 38. Results with expression constructs of the incorporated '953 application. The expression construct contains the sequence encoding the polypeptide of interest (exemplified here by d2EGFP) upstream of an IRES, which is upstream of the sequence encoding the selectable marker hereof (exemplified here by the ZEOCIN®-resistance gene, with a TTG start codon (TTG Zeo) (or in controls with its normal ATG start codon (ATG Zeo)). See, Example 19 for details. Dots indicate individual data points; lines indicate the average expression levels; used constructs are indicated on the horizontal axis, and schematically depicted above the graph; vertical axis indicates d2EGFP signal.

FIG. 39. EPO expression with expression constructs hereof. See, Example 20 for details.

FIG. 41. Results with a ZEOCIN®-resistance marker with reduced CpG content in CHO-K1 cells. Dots indicate individual data points; lines indicate the average expression levels; vertical axis indicates d2EGFP signal. See, Example 22 for details.

FIG. 42. As in FIG. 41, but now in CHO-DG44 cells. See, Example 22 for details.

FIGS. 47A-47B. Schematic drawing of constructs having multicistronic transcription units with two selectable marker polypeptides and one polypeptide of interest (HC: heavy chain; LC: light chain), the first selectable marker polypeptide providing resistance to an antibiotic and having a TTG (or GTG, not shown) start codon in the coding sequence and the second selectable marker polypeptide being trp or dhfr and being under control of an IRES. See, Example 27 for details.

DETAILED DESCRIPTION

Figure 1:
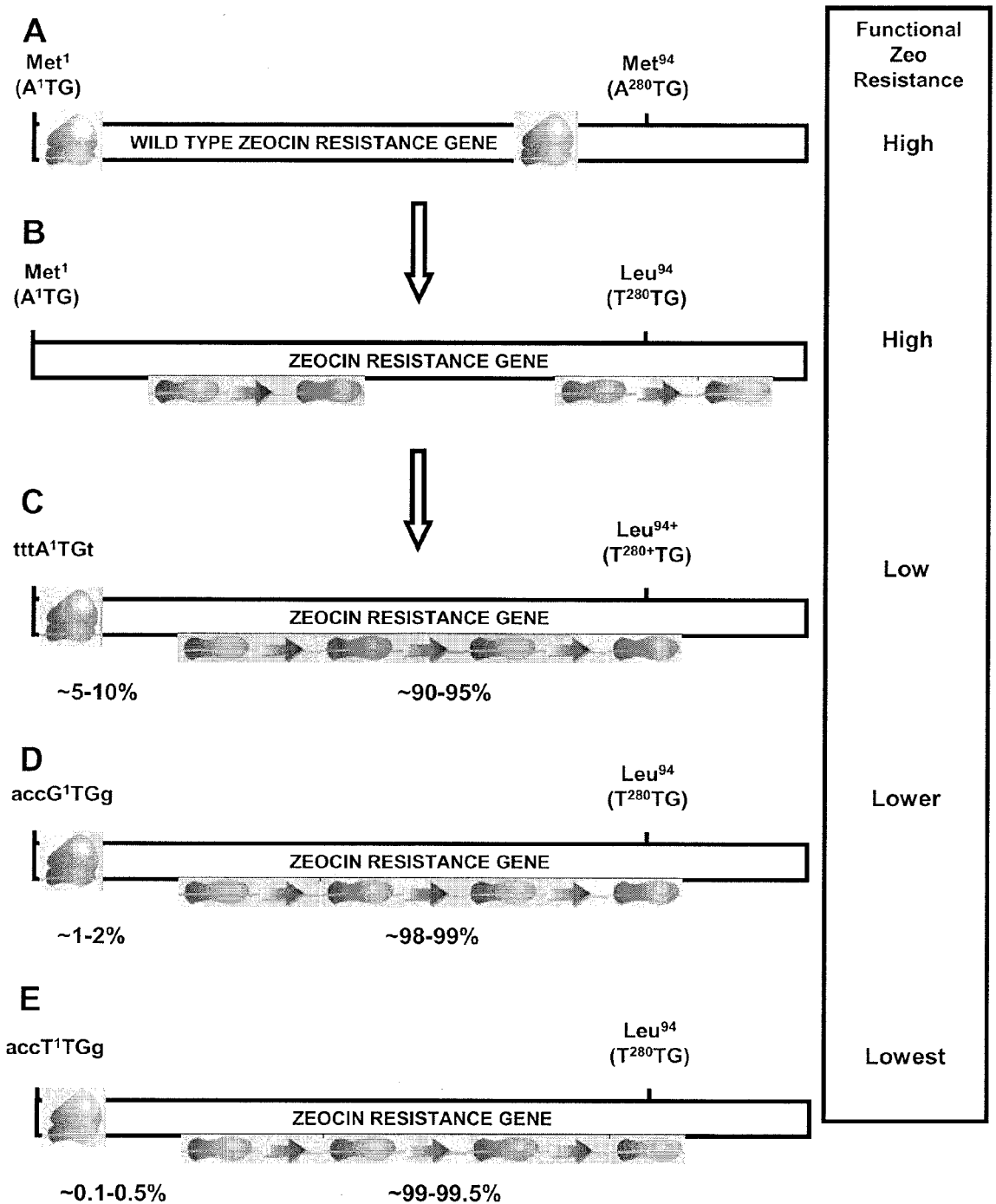
FIG. 1. Schematic representation of the use of a selection marker gene (ZEOCIN®-resistance gene) of the incorporated '525 application. A. wild-type ZEOCIN®-resistance gene, having its normal translation initiation site (ATG start codon) and one internal ATG codon, which codes for methionine. B. mutant ZEOCIN®-resistance gene, wherein the internal ATG has been mutated into a codon for leucine; this mutant is a functional ZEOCIN®-resistance gene. C. same as B, but comprising a mutated translation initiation site, wherein the context of the ATG start codon has been mutated to decrease the translation initiation. D. same as B, but comprising a mutated start codon (GTG). E. same as B, but with a TTG start codon. The numbers under the Figures C-E schematically indicate a relative amount of initiation frequency (under the start codon) and "scan-through" frequency (under the coding sequence) by the ribosomes, but only in a semi-quantitative manner, i.e., they indicate the efficiency of translation initiation compared to each other, but the qualitative numbers may differ completely: the numbers only serve to explain the disclosure. See, Example 1 for details.

In one aspect, provided is a DNA molecule comprising an ORF sequence that encodes a selectable marker polypeptide, wherein the DNA molecule in the coding strand comprises a translation start sequence for the selectable marker polypeptide chosen from the group consisting of: a) a GTG start codon; and b) a TTG start codon; and wherein the ORF sequence that encodes the selectable marker protein has been mutated to replace at least 10% of its CpG dinucleotides (any "CG" in the sequence) as compared to the native ORF sequence that encodes the selectable marker protein. Such a DNA molecule can be used hereof for obtaining eukaryotic host cells expressing high levels of the polypeptide of interest, by selecting for the expression of the selectable marker polypeptide. Subsequently or simultaneously, one or more host cell(s) expressing the polypeptide of interest can be identified, and further used for expression of high levels of the polypeptide of interest.

It is shown herein that the reduction of the CpG content of the selectable marker gene hereof, i.e., having a TTG or GTG start codon, can lead to improved expression of a polypeptide of interest that is translated from a multicistronic transcription unit from which also the selectable marker polypeptide is translated. Without wishing to be bound by theory, it is believed that reduction of the CpG content may reduce the possibility for silencing of transcription, because CpG dinucleotides can be methylated and silenced in eukaryotes. Selectable marker polypeptides that are encoded by genes with a relatively high CpG content, often derived from bacterial sequences, for instance, ZEOCIN® antibiotic and neomycin, may benefit from the reduction of the CpG content. In certain embodiments, CpG dinucleotides are removed from a sequence encoding a selectable marker polypeptide without changing the encoded amino acid sequence. This can be done by taking advantage of the redundancy of the genetic code, as is well known and routine to the person skilled in the art of molecular biology.

In certain embodiments, in particular when the selectable marker polypeptide coding sequence is to be used upstream of the coding sequence of a polypeptide of interest in a multicistronic transcription unit described herein, the coding sequence of the selectable marker polypeptide is devoid of ATG sequences.

It is expected that a positive effect of removing CpG dinucleotides will be apparent when at least 10% of the CpG dinucleotides in the coding sequence of the selectable marker gene have been replaced. It is expected that removal of more CpG dinucleotides will increase the effect, and hence in certain embodiments, at least 20%, at least 30%, at least 40%, at least 50%, at least 60%, at least 70% or at least 80% of the CpG dinucleotides are mutated compared to the native ORF sequence that encodes the selectable marker protein. In certain advantageous embodiments, at least half of the CpG dinucleotides of the ORF sequence that encodes the selectable marker polypeptide have been replaced as compared to the native ORF sequence that encodes the selectable marker polypeptide.

A native ORF sequence that encodes the selectable marker polypeptide that provides resistance to neomycin is given as SEQ ID NO:128 (containing internal ATGs) and as SEQ ID NO:118 (lacking internal ATGs). In advantageous embodiments, these sequences may contain one or more further mutations so that the encoded polypeptide has a mutation of valine at position 201 to glycine (201V>G), of glutamic acid at position 185 to aspartic acid (185E>D), or both (185E>D, 201V>G).

A native ORF sequence that encodes the selectable marker polypeptide that provides resistance to ZEOCIN® antibiotic is given as SEQ ID NO:92 (containing internal ATGs), and mutation of A at position 280 into T in this sequence gives a sequence lacking internal ATGs, and wherein the internally encoded methionine at position 94 is replaced by leucine. For the DNA sequences hereof, the start codon (first three nucleotides of the DNA sequences) is mutated into a GTG or into a TTG start codon.

In certain advantageous embodiments, the selectable marker polypeptide provides resistance against ZEOCIN® antibiotic. In certain embodiments thereof, the DNA molecule comprises SEQ ID NO:92, wherein at least half of the CpG dinucleotides has been replaced without mutating the amino acid sequence that is encoded, with the proviso that the start codon (first three nucleotides in the sequence) is replaced by a start codon chosen from GTG or TTG. In an alternative embodiment, the DNA molecule comprises SEQ ID NO:92 wherein nucleotide A at position 280 is replaced by T, such that encoded amino acid 94 (methionine) is replaced by leucine, and wherein at least half of the CpG dinucleotides has been replaced without further mutating the amino acid sequence that is encoded, with the proviso that the start codon (first three nucleotides in the sequence) is replaced by a start codon chosen from GTG or TTG. This embodiment lacks ATG sequences in the coding sequence for the ZEOCIN® antibiotic-resistance gene, and is therefore suitable in the multicistronic transcription units hereof wherein the coding sequence for the selectable marker polypeptide is upstream of the coding sequence for the polypeptide of interest. In one preferred embodiment hereof, the DNA molecule comprises SEQ ID NO:132.

In other advantageous embodiments, the selectable marker polypeptide provides resistance against neomycin. In certain embodiments thereof, the DNA molecule comprises a sequence chosen from the group consisting of any one of: a) SEQ ID NO:128, with the proviso that at least half of the CpG dinucleotides has been replaced without mutating the amino acid sequence that is encoded, and with the further proviso that the start codon (the first ATG sequence) is replaced by either GTG or TTG; b) SEQ ID NO:118, with the proviso that at least half of the CpG dinucleotides has been replaced without mutating the amino acid sequence that is encoded, and with the further proviso that the start codon (the first ATG sequence) is replaced by either GTG or TTG; and c) SEQ ID NO:128 or SEQ ID NO:118, containing a mutation to encode a neomycin-resistance protein variant as compared to the sequences encoded by the indicated sequences, the variant having glycine at position 201 in the encoded protein (201G variant), or aspartic acid at position 185 (185D variant), or both glycine at position 201 and aspartic acid at position 185 (185D, 201G variant), with the proviso that at least half of the CpG dinucleotides in the given DNA sequence has been replaced without further mutating the amino acid sequence that is encoded, and with the further proviso that the start codon (the first ATG sequence) is replaced by either GTG or TTG. The 185D variant is for instance obtained by replacing the codon from position 553-555 in the provided nucleic acid sequences with the sequence GAC, and the 201G variant is for instance obtained by replacing the codon from position 601-603 in the provided nucleic acid sequence with GGT. In one preferred embodiment, the DNA molecule comprises SEQ ID NO:130, with the proviso that nucleotide A at position 555 is replaced by C (to encode the 185E>D variant), and that nucleotide T at position 602 is replaced by G and that nucleotide G at position 603 is replaced by T (to encode the 201V>G variant), and with the further proviso that the start codon (ATG at positions 1-3) is replaced by either GTG or TTG. It will be clear to the skilled person that further variations can be prepared by the skilled person without departing from the teaching hereof, and such further variations are encompassed within the disclosure as long as the start codon is not ATG and the encoded protein provides resistance against neomycin (or G418). The 185D and 201G variants further improve the selection stringency hereof.

The term "monocistronic gene" is defined as a gene capable of providing a RNA molecule that encodes one polypeptide. A "multicistronic transcription unit," also referred to as multicistronic gene, is defined as a gene capable of providing an RNA molecule that encodes at least two polypeptides. The term "bicistronic gene" is defined as a gene capable of providing a RNA molecule that encodes two polypeptides. A bicistronic gene is therefore encompassed within the definition of a multicistronic gene. A "polypeptide" as used herein comprises at least five amino acids linked by peptide bonds, and can for instance be a protein or a part, such as a subunit, thereof. Mostly, the terms polypeptide and protein are used interchangeably herein. A "gene" or a "transcription unit" as used herein can comprise chromosomal DNA, cDNA, artificial DNA, combinations thereof, and the like. Transcription units comprising several cistrons are transcribed as a single mRNA.

A multicistronic transcription unit hereof can for instance be a bicistronic transcription unit coding from 5' to 3' for a selectable marker polypeptide and for a polypeptide of interest, or for instance a bicistronic transcription unit coding from 5' to 3' for a polypeptide of interest and for a selectable marker polypeptide. In the former case, the coding sequence for the selectable marker polypeptide is preferably devoid of ATG sequences in the coding strand. In the latter case, the polypeptide of interest is encoded upstream from the coding sequence for the selectable marker polypeptide and an internal ribosome entry site (IRES) is operably linked to the sequence encoding the selectable marker polypeptide, and hence the selectable marker polypeptide is dependent from (also referred to as "operably linked to") the IRES for its translation.

One may use separate transcription units for the expression of different polypeptides of interest, also when these form part of a multimeric protein (see, e.g., Example 6: the heavy and light chain of an antibody each are encoded by a separate transcription unit, each of these expression units being a bicistronic expression unit).

The DNA molecules described herein can be present in the form of double stranded DNA, having with respect to the selectable marker polypeptide and the polypeptide of interest a coding strand and a non-coding strand, the coding strand being the strand with the same sequence as the translated RNA, except for the presence of T instead of U. Hence, an AUG start codon is coded for in the coding strand by an ATG sequence, and the strand containing this ATG sequence corresponding to the AUG start codon in the RNA is referred to as the coding strand of the DNA. It will be clear to the skilled person that start codons or translation initiation sequences are in fact present in an RNA molecule, but that these can be considered equally embodied in a DNA molecule coding for such an RNA molecule; hence, wherever the disclosure refers to a start codon or translation initiation sequence, the corresponding DNA molecule having the same sequence as the RNA sequence but for the presence of a T instead of a U in the coding strand of the DNA molecule is meant to be included, and vice versa, except where explicitly specified otherwise. In other words, a start codon is for instance an AUG sequence in RNA, but the corresponding ATG sequence in the coding strand of the DNA is referred to as start codon as well in the disclosure. The same is used for the reference of "in frame" coding sequences, meaning triplets (3 bases) in the RNA molecule that are translated into an amino acid, but also to be interpreted as the corresponding trinucleotide sequences in the coding strand of the DNA molecule.

The selectable marker polypeptide and the polypeptide of interest encoded by the multicistronic gene each have their own translation initiation sequence, and therefore each have their own start codon (as well as stop codon), i.e., they are encoded by separate ORFs.

The term "selection marker" or "selectable marker" is typically used to refer to a gene and/or protein whose presence can be detected directly or indirectly in a cell, for example a polypeptide that inactivates a selection agent and protects the host cell from the agent's lethal or growth-inhibitory effects (e.g., an antibiotic resistance gene and/or protein). Another possibility is that the selection marker induces fluorescence or a color deposit (e.g., green fluorescent protein (GFP) and derivatives (e.g d2EGFP), luciferase, lacZ, alkaline phosphatase, etc.), which can be used for selecting cells expressing the polypeptide inducing the color deposit, e.g., using a fluorescence activated cell sorter (FACS) for selecting cells that express GFP. Preferably, the selectable marker polypeptide according to provided is resistance against lethal and/or growth-inhibitory effects of a selection agent. The selectable marker polypeptide is encoded by the DNA described herein. The selectable marker polypeptide described herein is functional in a eukaryotic host cell, and thus able to be selected for in eukaryotic host cells. Any selectable marker polypeptide fulfilling this criterion can in principle be used. Such selectable marker polypeptides are well known in the art and routinely used when eukaryotic host cell clones are to be obtained, and several examples are provided herein. In certain embodiments, a selection marker used is ZEOCIN® antibiotic. In other embodiments, blasticidin is used. The person skilled in the art will know that other selection markers are available and can be used, e.g., neomycin, puromycin, bleomycin, hygromycin, etc. In other embodiments, kanamycin is used. In yet other embodiments, the DHFR gene is used as a selectable marker, which can be selected for by methotrexate, especially by increasing the concentration of methotrexate cells can be selected for increased copy numbers of the DHFR gene. Similarly, the glutamine synthetase (GS) gene can be used, for which selection is possible in cells having insufficient GS (e.g., NS-0 cells) by culturing in media without glutamine, or alternatively in cells having sufficient GS (e.g., CHO cells) by adding an inhibitor of GS, methionine sulphoximine (MSX). Other selectable marker genes that could be used, and their selection agents, are for instance described in table 1 of U.S. Pat. No. 5,561,053, incorporated by reference herein; see also Kaufman, Methods in Enzymology, 185:537-566 (1990), for a review of these.

Other selectable marker polypeptides that can be used are enzymes involved in metabolic pathways. For instance, mammalian cells lack enzymes that are part of the metabolic pathway to create the amino acids tryptophan or histidine. Hence, these amino acids need to present in the culture medium when mammalian cell lines are to be cultured. However, providing the genetic information (which can be derived from the sequences present in bacteria) encoding the enzymes to the mammalian cells and that are essential for the synthesis of the respective amino acid can be used for selection purposes, by growing the cells in a culture medium lacking the respective amino acid, and containing certain precursors for the amino acid which precursor can then be converted into the amino acid by the encoded metabolic enzyme, if this is expressed in the mammalian cell. For example, tryptophan synthesizing enzyme (trp) can be used as a selection marker, by omitting tryptophan from the culture medium and including indol into the culture medium (Hartman and Mulligan, 1988). The trp (trpB) gene can be derived from *E. coli*, and can be used hereof, preferably by providing it with a GTG or TTG start codon (see, SEQ ID NO:134 for the sequence of the trp gene, and SEQ ID NO:136 for the sequence of the trp gene wherein all internal ATG sequences have been removed). As another example histindine synthesizing enzyme (his) can be used as a selection marker, by omitting histidine from the culture medium and including histidinol into the culture medium (Hartman and Mulligan, 1988). The his gene can be derived from *S. typhimurium*, and can be used hereof, preferably by providing it with a GTG or TTG start codon (see, SEQ ID NO:138 for the sequence of the his gene, and SEQ ID NO:140 for the sequence of the his gene wherein all internal ATG sequences have been removed). As another example, the mammalian 5,6,7,8 tetrahydrofolate synthesizing enzyme dihydrofolate reductase (dhfr) can be used as a selection marker in cells that have a dhfr⁻ phenotype (e.g., CHO-DG44 cells), by omitting glycine, hypoxanthine and thymidine from the culture medium and including folate (or (dihydro)folic acid) into the culture medium (Simonsen et al., 1988). The dhfr gene can for instance be derived from the mouse genome or mouse cDNA and can be used, preferably by providing it with a GTG or TTG start codon (see, SEQ ID NO:98 for the sequence of the dhfr gene, and SEQ ID NO:122 for the sequence of the dhfr gene wherein all internal ATG sequences have been removed). In all these embodiments, by "omitting from the culture medium" is meant that the culture medium has to be essentially devoid of the indicated component(s), meaning that there is insufficient of the indicated component present to sustain growth of the cells in the culture medium, so that a good selection is possible when the genetic information for the indicated enzyme is expressed in the cells and the indicated precursor component is present in the culture medium. For instance, the indicated component is present at a concentration of less than 0.1% of the concentration of that component that is normally used in the culture medium for a certain cell type. Preferably, the indicated component is absent from the culture medium. A culture medium lacking the indicated component can be prepared according to standard methods by the skilled person or can be obtained from commercial media suppliers. A potential advantage of the use of these types of metabolic enzymes as selectable marker polypeptides is that they can be used to keep the multicistronic transcription units under continuous selection, which may result in higher expression of the polypeptide of interest.

In another aspect, used are the trp, his, or dhfr metabolic selection markers as an additional selection marker in a multicistronic transcription unit hereof. In such embodiments, selection of host cell clones with high expression is first established by use of, for instance, an antibiotic selection marker, e.g., ZEOCIN® antibiotic, neomycin, etc, the coding sequences of which will have a GTG or TTG start codon hereof. After the selection of suitable clones, the antibiotic selection is discontinued, and now continuous or intermittent selection using the metabolic enzyme selection marker can be performed by culturing the cells in the medium lacking the appropriate identified components described supra and containing the appropriate precursor components described supra. In this aspect, the metabolic selection markers are operably linked to an IRES, and can have their normal ATG content, and the start codon can be suitably chosen from ATG, GTG or TTG. The multicistronic transcription units in this aspect are at least tricistronic.

When two multicistronic transcription units are to be selected for in a single host cell, each one preferably contains the coding sequence for a different selectable marker, to allow selection for both multicistronic transcription units. Of course, both multicistronic transcription units may be present on a single nucleic acid molecule or alternatively each one may be present on a separate nucleic acid molecule.

The term "selection" is typically defined as the process of using a selection marker/selectable marker and a selection agent to identify host cells with specific genetic properties (e.g., that the host cell contains a transgene integrated into its genome). It is clear to a person skilled in the art that numerous combinations of selection markers are possible. One antibiotic that is particularly advantageous is ZEOCIN®, because the ZEOCIN® antibiotic-resistance protein (ZEOCIN®-R) acts by binding the drug and rendering it harmless. Therefore, it is easy to titrate the amount of drug that kills cells with low levels of ZEOCIN®-R expression, while allowing the high-expressors to survive. All other antibiotic-resistance proteins in common use are enzymes, and thus act catalytically (not 1:1 with the drug). Hence, the antibiotic ZEOCIN® is a preferred selection marker. However, the disclosure also works with other selection markers.

A selectable marker polypeptide described herein is the protein that is encoded by the nucleic acid hereof, which polypeptide can be detected, for instance because it provides resistance to a selection agent such as an antibiotic. Hence, when an antibiotic is used as a selection agent, the DNA encodes a polypeptide that confers resistance to the selection agent, which polypeptide is the selectable marker polypeptide. DNA sequences coding for such selectable marker polypeptides are known, and several examples of wild-type sequences of DNA encoding selectable marker proteins are provided herein (FIGS. 15-21). It will be clear that mutants or derivatives of selectable markers can also be suitably used hereof, and are therefore included within the scope of the term "selectable marker polypeptide," as long as the selectable marker protein is still functional.

For convenience and as generally accepted in the art, in many publications as well as herein, often the gene and protein encoding the resistance to a selection agent is referred to as the "selectable agent (resistance) gene" or "selection agent (resistance) protein," respectively, although the official names may be different, e.g., the gene coding for the protein conferring resistance to neomycin (as well as to G418 and kanamycin) is often referred to as neomycin (resistance) (or neo$^r$) gene, while the official name is aminoglycoside 3'-phosphotransferase gene.

It is beneficial to have low levels of expression of the selectable marker polypeptide, so that stringent selection is possible. Herein, this is brought about by using a selectable marker coding sequence with a non-optimal translation efficiency. Upon selection, only cells that have nevertheless sufficient levels of selectable marker polypeptide will be selected, meaning that such cells must have sufficient transcription of the multicistronic transcription unit and sufficient translation of the selectable marker polypeptide, which provides a selection for cells where the multicistronic transcription unit has been integrated or otherwise present in the host cells at a place where expression levels from this transcription unit are high.

In certain embodiments, the DNA molecule hereof has the coding sequence for the selectable marker polypeptide upstream of the coding sequence for the polypeptide of interest, to provide for a multicistronic transcript (described in the incorporated '525 application). Thus, such a multicistronic transcription unit comprises in the 5' to 3' direction (both in the transcribed strand of the DNA and in the resulting transcribed RNA) the coding sequence for the selectable marker polypeptide and the sequence encoding the polypeptide of interest. In such embodiments, the ORF sequence encoding the selectable marker polypeptide has no ATG sequences in the coding strand.

In alternative embodiments (disclosed in detail in the incorporated '953 application), the DNA molecules hereof have the coding sequence for the selectable marker polypeptide downstream of the coding sequence for the polypeptide of interest. Hence, the multicistronic transcription unit comprises in the 5' to 3' direction (both in the transcribed strand of the DNA and in the resulting transcribed RNA) the sequence encoding the polypeptide of interest and the coding sequence for the selectable marker polypeptide. In such embodiments, an IRES is upstream of and operably linked to the coding sequence for the selectable marker polypeptide.

To decrease translation of the selectable marker cistron, hereof the nucleic acid sequence coding for the selectable marker polypeptide comprises a mutation in the start codon (or in the context thereof) that decreases the translation initiation efficiency of the selectable marker polypeptide in a eukaryotic host cell. Preferably, a GTG start codon or more preferably a TTG start codon is engineered into the selectable marker polypeptide. The translation efficiency is lower than that of the corresponding wild-type sequence in the same cell, i.e., the mutation results in less polypeptide per cell per time unit, and hence less selectable marker polypeptide. This can be detected using routine methods known to the person skilled in the art. For instance, in the case of antibiotic selection, the mutation will result in less resistance than obtained with the sequence having no such mutation and hence normal translation efficiency, which difference can easily be detected by determining the number of surviving colonies after a normal selection period, which will be lower when a translation efficiency decreasing mutation is present. As is well known to the person skilled in the art there are a number of parameters that indicate the expression level marker polypeptide such as, the maximum concentration of selection agent to which cells are still resistant, number of surviving colonies at a given concentration, growth speed (doubling time) of the cells in the presence of selection agent, combinations of the above, and the like.

The mutation that decreases the translation initiation efficiency hereof is established by providing the selectable marker polypeptide coding sequence with a non-optimal translation start sequence. For example, the translation initiation efficiency of the selectable marker gene in eukaryotic cells can be suitably decreased hereof by mutating the start codon and/or the nucleotides in positions −3 to −1 and +4 (where the A of the ATG start codon is nt+1), for instance in the coding strand of the corresponding DNA sequence, to provide a non-optimal translation start sequence. A translation start sequence is often referred to in the field as "Kozak sequence," and an optimal Kozak sequence is RCC<u>ATG</u>G, the start codon underlined, R being a purine, i.e., A or G (see, Kozak M, 1986, 1987, 1989, 1990, 1997, 2002). Hence, besides the start codon itself, the context thereof, in particular nucleotides −3 to −1 and +4, are relevant, and an optimal translation startsequence comprises an optimal start codon (i.e., ATG) in an optimal context (i.e., the ATG directly preceded by RCC and directly followed by G). A non-optimal translation start sequence is defined herein as any sequence that gives at least some detectable translation in a eukaryotic cell (detectable because the selection marker polypeptide is detectable), and not having the consensus sequence RCC ATGG (start codon underlined). Translation by the ribosomes is most efficient when an optimal Kozak sequence is present (see, Kozak M, 1986, 1987, 1989, 1990, 1997, 2002). However, in a small percentage of events, non-optimal translation initiation sequences are recognized and used by the ribosome to start translation. The disclosure makes use of this principle, and allows for decreasing and even fine-tuning of the amount of translation and hence expression of the selectable marker polypeptide, which can therefore be used to increase the stringency of the selection system.

In one embodiment, the ATG start codon of the selectable marker polypeptide (in the coding strand of the DNA, coding for the corresponding AUG start codon in the RNA transcription product) is left intact, but the positions at −3 to −1 and +4 are mutated such that they do not fulfill the optimal Kozak sequence any more, e.g., by providing the sequence TTT ATGT as the translation start site (ATG start codon underlined). It will be clear that other mutations around the start codon at positions −3 to −1 and/or +4 could be used with similar results using the teaching hereof, as can be routinely and easily tested by the person skilled in the art. The idea of this first embodiment is that the ATG start codon is placed in a "non-optimal" context for translation initiation.

In another embodiment, the ATG start codon itself of the selectable marker polypeptide is mutated. This will in general lead to even lower levels of translation initiation than the first embodiment. The ATG start codon in the second embodiment is mutated into another codon, which has been reported to provide some translation initiation, for instance to GTG, TTG, CTG, ATT, or ACG (collectively referred to herein as "non-optimal start codons"). In certain embodiments, the ATG start codon is mutated into a GTG start codon. This provides still lower expression levels (lower translation) than with the ATG start codon intact but in a non-optimal context. More preferably, the ATG start codon is mutated to a TTG start codon, which provides even lower expression levels of the selectable marker polypeptide than with the GTG start codon (Kozak M, 1986, 1987, 1989, 1990, 1997, 2002; see also Examples 2-6 herein). The use of non-ATG start codons in the coding sequence for a selectable marker polypeptide in a multicistronic transcription unit hereof was not disclosed nor suggested in the prior art and, preferably in combination with chromatin control elements, leads to very high levels of expression of the polypeptide of interest, as also shown in the incorporated '525 application.

For the embodiment where a non-ATG start codon is used, it is strongly preferred to provide an optimal context for such a start codon, i.e., the non-optimal start codons are preferably directly preceded by nucleotides RCC in positions −3 to −1 and directly followed by a G nucleotide (position +4). However, it has been reported that using the sequence TTTGTGG (start codon GTG underlined), some initiation is observed at least in vitro, so although strongly preferred it may not be absolutely required to provide an optimal context for the non-optimal start codons.

ATG sequences within the coding sequence for a polypeptide, but excluding the ATG start codon, are referred to as "internal ATGs," and if these are in frame with the ORF and therefore code for methionine, the resulting methionine in the polypeptide is referred to as an "internal methionine." It is strongly preferred according to certain embodiments (those of the incorporated '525 application, i.e., those where the sequence encoding the selectable marker polypeptide is upstream of the sequence encoding the polypeptide of interest) that the coding region (following the start codon, not necessarily including the start codon) coding for the selectable marker polypeptide is devoid of any ATG sequence in the coding strand of the DNA, up to (but not including) the start codon of the polypeptide of interest (obviously, the start codon of the polypeptide of interest may be, and in fact preferably is, an ATG start codon). This can be established by mutating any such ATG sequence within the coding sequence of the selectable marker polypeptide, following the start codon thereof (as is clear from the teaching above, the start codon of the selectable marker polypeptide itself may be an ATG sequence, but not necessarily so). To this purpose preferably, the degeneracy of the genetic code is used to avoid mutating amino acids in the selectable marker polypeptide wherever possible. Hence, wherever an ATG is present in the coding strand of the DNA sequence encoding the selectable marker polypeptide, which ATG is not in frame with the selectable marker polypeptide ORF, and therefore does not code for an internal methionine in the selectable marker polypeptide, the ATG can be mutated such that the resulting polypeptide has no mutations in its internal amino acid sequence. Where the ATG is an in-frame codon coding for an internal methionine, the codon can be mutated, and the resulting mutated polypeptide can be routinely checked for activity of the selectable marker polypeptide. In this way a mutation can be chosen which leads to a mutated selectable marker polypeptide that is still active as such (quantitative differences may exist, but those are less relevant, and in fact it could even be beneficial to have less active variants for the purpose hereof; the minimum requirement is that the selectable marker polypeptide can still be selected for in eukaryotic cells). The amino acids valine, threonine, isoleucine and leucine are structurally similar to methionine, and therefore codons that code for one of these amino acids are good starting candidates to be tested in place of methione within the coding sequence after the start codon. Of course, using the teachings hereof, the skilled person may test other amino acids as well in place of internal methionines, using routine molecular biology techniques for mutating the coding DNA, and routine testing for functionality of the selectable marker polypeptide. Besides routine molecular biology techniques for mutating DNA, it is at present also possible to synthesise at will (if required using subcloning steps) DNA sequences that have sufficient length for an ORF of a selectable marker polypeptide, and such synthetic DNA sequences can nowadays be ordered commercially from various companies. Hence, using the teachings hereof, the person skilled in the art may design appropriate sequences hereof encoding a selectable marker polypeptide (with a mutation decreasing translation initiation, and preferably having no internal ATGs), have this sequence synthesized, and test the DNA molecule for functionality of the encoded selectable marker by introducing the DNA molecule in eukaryotic host cells and test for expression of functional selectable marker polypeptide. The commercial availability of such sequences also makes feasible to provide without undue burden for selection marker coding sequences lacking internal ATG sequences, where the wild-type coding sequence of the selection marker polypeptide comprises several such internal ATGs.

By providing a coding sequence for a selectable marker polypeptide lacking any internal ATG sequence, the chances of inadvertent translation initiation by ribosomes that passed the (first, non-optimal) translation start sequence of the selectable marker polypeptide at a subsequent internal ATG trinucleotide is diminished, so that the ribosomes will continue to scan for the first optimal translation start sequence, i.e., that of the polypeptide of interest.

For alternative embodiments, i.e., those where the sequence encoding the polypeptide of interest is upstream of the sequence encoding the selectable marker polypeptide and the latter is operably linked to an IRES (disclosed in the incorporated '953 application), internal ATGs in the sequence encoding the selectable marker polypeptide can remain intact.

The translation start sequence of the polypeptide of interest may comprise an optimal translation start sequence, i.e., having the consensus sequence RCC<u>ATG</u>G (start codon ATG underlined). This will result in a very efficient translation of the polypeptide of interest.

By providing the coding sequence of the marker with different mutations leading to several levels of decreased translation efficiency, the stringency of selection can be increased. Fine-tuning of the selection system is thus possible using the multicistronic transcription units hereof: for instance using a GTG start codon for the selection marker polypeptide, only few ribosomes will translate from this start codon, resulting in low levels of selectable marker protein, and hence a high stringency of selection; using a TTG start codon even further increases the stringency of selection because even less ribosomes will translate the selectable marker polypeptide from this start codon.

It is demonstrated in the incorporated '525 application that the multicistronic expression units disclosed therein can be used in a very robust selection system, leading to a very large percentage of clones that express the polypeptide of interest at high levels, as desired. In addition, the expression levels obtained for the polypeptide of interest appear to be significantly higher than those obtained when an even larger number of colonies are screened using selection systems hitherto known.

In addition to a decreased translation initiation efficiency, it could be beneficial to also provide for decreased translation elongation efficiency of the selectable marker polypeptide, e.g., by mutating the coding sequence thereof so that it comprises several non-preferred codons of the host cell, in order to further decrease the translation levels of the marker polypeptide and allow still more stringent selection conditions, if desired. In certain embodiments, besides the mutation(s) that decrease the translation efficiency hereof, the selectable marker polypeptide further comprises a mutation that reduces the activity of the selectable marker polypeptide compared to its wild-type counterpart. This may be used to increase the stringency of selection even further. As non-limiting examples, proline at position 9 in the ZEOCIN® antibiotic-resistance polypeptide may be mutated, e.g., to Thr or Phe, and for the neomycin-resistance polypeptide, amino acid residue 182 or 261 or both may further be mutated (see, e.g., WO 01/32901).

In certain embodiments, for the neomycin-resistance polypeptide encoded by the sequences provided herein, amino acid residue 185 (glutamic acid) is mutated to aspartic acid and/or amino acid residue 201 (valine) is mutated into glycine (Sautter et al., 2005).

In some embodiments, a so-called spacer sequence is placed downstream of the sequence encoding the start codon of the selectable marker polypeptide, which spacer sequence preferably is a sequence in frame with the start codon and encoding a few amino acids, and that does not contain a secondary structure (Kozak, 1990), and does not contain the sequence ATG. Such a spacer sequence can be used to further decrease the translation initiation frequency if a secondary structure is present in the RNA (Kozak, 1990) of the selectable marker polypeptide (e.g., for ZEOCIN®, possibly for blasticidin), and hence increase the stringency of the selection system hereof.

Also provided is a DNA molecule comprising the sequence encoding a selectable marker protein hereof, which DNA molecule has been provided with a mutation that decreases the translation efficiency of the functional selectable marker polypeptide in a eukaryotic host cell. In certain embodiments hereof, the DNA molecule in the coding strand has been mutated compared to the wild-type sequence encoding the selectable marker polypeptide, such that the sequence ATG of the start codon is mutated into GTG (encoding Valine) or into TTG (encoding Leucine), and wherein the selectable marker polypeptide is still functional in a eukaryotic host cell. Such DNA molecules encompass a useful intermediate product hereof. These molecules can be prepared first, introduced into eukaryotic host cells and tested for functionality (for some markers this is even possible in prokaryotic host cells), if desired in a (semi-) quantitative manner, of the selectable marker polypeptide. They may then be further used to prepare a DNA molecule hereof, comprising the multicistronic transcription unit.

In one embodiment, provided is a DNA molecule comprising a sequence encoding a protein that confers resistance to ZEOCIN®, the sequence comprising SEQ ID NO:92, with the proviso that the first ATG (the start codon encoding methionine) is replaced by either a GTG (encoding valine) or a TTG (encoding leucine) start codon.

In another embodiment, provided is a DNA molecule comprising a sequence encoding a protein that confers resistance to blasticidin, the sequence comprising SEQ ID NO:94, with the proviso that the first ATG (the start codon encoding methionine) is replaced by either a GTG (encoding valine) or a TTG (encoding leucine) start codon.

In another embodiment, provided is a DNA molecule comprising a sequence encoding a protein that confers resistance to neomycin, the sequence comprising SEQ ID NO:102, with the proviso that the first ATG (the start codon encoding methionine) is replaced by either a GTG (encoding valine) or a TTG (encoding leucine) start codon.

In another embodiment, provided is a DNA molecule comprising a sequence encoding a protein that confers resistance to puromycin, the sequence comprising SEQ ID NO:96, with the proviso that the first ATG (the start codon encoding methionine) is replaced by either a GTG (encoding valine) or a TTG (encoding leucine) start codon.

In another embodiment, provided is a DNA molecule comprising a sequence encoding a protein that confers resistance to hygromycin, the sequence comprising SEQ ID NO:100, with the proviso that the first ATG (the start codon encoding methionine) is replaced by either a GTG (encoding valine) or a TTG (encoding leucine) start codon.

In another embodiment, provided is a DNA molecule comprising a sequence encoding a protein with dihydrofolate reductase (dhfr) activity (conferring resistance to methotrexate), the sequence comprising SEQ ID NO:98, with the proviso that the first ATG (the start codon encoding methionine) is replaced by either a GTG (encoding valine) or a TTG (encoding leucine) start codon.

In another embodiment, provided is a DNA molecule comprising a DNA sequence encoding a protein with glutamine synthetase (GS) activity, the sequence comprising SEQ ID NO:104, with the proviso that the first ATG (the start codon encoding methionine) is replaced by either a GTG (encoding valine) or a TTG (encoding leucine) start codon.

It will be clear that for these embodiments, any DNA molecules as described, but having mutations in the sequence downstream of the first ATG (start codon) coding for the selectable marker protein are also encompassed herein, as long as the respective encoded selectable marker protein still has activity. For instance, any silent mutations that do not alter the encoded protein because of the redundancy of the genetic code are also encompassed. Further mutations that lead to conservative amino acid mutations or to other mutations are also encompassed, as long as the encoded protein still has activity, which may or may not be lower than that of the wild-type protein as encoded by the indicated sequences. In particular, it is preferred that the encoded protein is at least 70%, preferably at least 80%, more preferably at least 90%, still more preferably at least 95% identical to the proteins encoded by the respective indicated sequences. Testing for activity of the selectable marker proteins can be done by routine methods.

Also provided is a selectable marker proteins encoded by these embodiments.

In one aspect, provided is an expression cassette comprising the DNA molecule hereof, having the multicistronic transcription unit. Such an expression cassette is useful to express sequences of interest, for instance, in host cells. An "expression cassette" as used herein is a nucleic acid sequence comprising at least a promoter functionally linked to a sequence of which expression is desired. Preferably, an expression cassette further contains transcription termination and polyadenylation sequences. Other regulatory sequences such as enhancers may also be included. Hence, provided is an expression cassette comprising in the following order: 5'—promoter—multicistronic transcription unit hereof, coding for either (i) {a polypeptide of interest and downstream thereof a selectable marker polypeptide} or (ii) {a selectable marker polypeptide and downstream thereof a polypeptide of interest}—transcription termination sequence—3'. The promoter is capable of functioning in a eukaryotic host cell, i.e., it is capable of driving transcription of the multicistronic transcription unit. The promoter is thus operably linked to the multicistronic transcription unit. The expression cassette may optionally further contain other elements known in the art, e.g., splice sites to comprise introns, and the like. In some embodiments, an intron is present behind the promoter and before the sequence encoding the polypeptide of interest. In the embodiments where the selectable marker polypeptide is encoded downstream of the polypeptide of interest, an IRES is operably linked to the cistron that contains the selectable marker polypeptide coding sequence. In the embodiments where the selectable marker polypeptide is encoded upstream of the polypeptide of interest, the sequence encoding the selectable marker polypeptide is devoid of ATG sequences in the coding strand.

To obtain expression of polynucleotides encoding protein, it is well known to those skilled in the art that sequences capable of driving such expression, can be functionally linked to the polynucleotides encoding the protein, resulting in recombinant polynucleotides encoding a protein in expressible format. Herein, the expression cassette comprises a multicistronic transcription unit. In general, the promoter sequence is placed upstream of the sequences that should be expressed. Much used expression vectors are available in the art, e.g., the pcDNA and pEF vector series of Invitrogen, pMSCV and pTK-Hyg from BD Sciences, pCMV-Script from Stratagene, etc, which can be used to obtain suitable promoters and/or transcription terminator sequences, polyA sequences, and the like.

Where the polynucleotide encoding the polypeptide of interest is properly inserted with reference to sequences governing the transcription and translation of the encoded polypeptide, the resulting expression cassette is useful to produce the polypeptide of interest, referred to as expression. Sequences driving expression may include promoters, enhancers and the like, and combinations thereof. These should be capable of functioning in the host cell, thereby driving expression of the nucleic acid sequences that are functionally linked to them. The person skilled in the art is aware that various promoters can be used to obtain expression of a gene in host cells. Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter (Kaufman, 2000). Some well-known and much used promoters for expression in eukaryotic cells comprise promoters derived from viruses, such as adenovirus, e.g., the E1A promoter, promoters derived from cytomegalovirus (CMV), such as the CMV immediate early (IE) promoter (referred to herein as the CMV promoter) (obtainable for instance from pcDNA, Invitrogen), promoters derived from Simian Virus 40 (SV40) (Das et al., 1985), and the like. Suitable promoters can also be derived from eukaryotic cells, such as methallothionein (MT) promoters, elongation factor 1α (EF-1α) promoter (Gill et al., 2001), ubiquitin C or UB6 promoter (Gill et al., 2001; Schorpp et al., 1996), actin promoter, an immunoglobulin promoter, heat shock promoters, and the like. Some preferred promoters for obtaining expression in eukaryotic cells, which are suitable promoters herein, are the CMV-promoter, a mammalian EF1-alpha promoter, a mammalian ubiquitin promoter such as a ubiquitin C promoter, or a SV40 promoter (e.g., obtainable from pIRES, cat. no. 631605, BD Sciences). Testing for promoter function and strength of a promoter is a matter of routine for a person skilled in the art, and in general may for instance encompass cloning a test gene such as lacZ, luciferase, GFP, etc., behind the promoter sequence, and test for expression of the test gene. Of course, promoters may be altered by deletion, addition, mutation of sequences therein, and tested for functionality, to find new, attenuated, or improved promoter sequences. Herein, strong promoters that give high transcription levels in the eukaryotic cells of choice are preferred.

In certain embodiments, a DNA molecule hereof is part of a vector, e.g., a plasmid. Such vectors can easily be manipulated by methods well known to the person skilled in the art, and can for instance be designed for being capable of replication in prokaryotic and/or eukaryotic cells. In addition, many vectors can directly or in the form of isolated desired fragment therefrom be used for transformation of eukaryotic cells and will integrate in whole or in part into the genome of such cells, resulting in stable host cells comprising the desired nucleic acid in their genome.

Conventional expression systems are DNA molecules in the form of a recombinant plasmid or a recombinant viral genome. The plasmid or the viral genome is introduced into (eukaryotic host) cells and preferably integrated into their genomes by methods known in the art. In certain embodiments, the disclosure also uses these types of DNA molecules to deliver its improved transgene expression system. A preferred embodiment hereof is the use of plasmid DNA for delivery of the expression system. A plasmid contains a number of components: conventional components, known in the art, are an origin of replication and a selectable marker for propagation of the plasmid in bacterial cells; a selectable marker that functions in eukaryotic cells to identify and isolate host cells that carry an integrated transgene expression system; the protein of interest, whose high-level transcription is brought about by a promoter that is functional in eukaryotic cells (e.g., the human cytomegalovirus major immediate early promoter/enhancer, pCMV (Boshart et al., 1985); and viral transcriptional terminators (e.g., the SV40 polyadenylation site (Kaufman & Sharp, 1982) for the transgene of interest and the selectable marker.

The vector used can be any vector that is suitable for cloning DNA and that can be used for transcription of a nucleic acid of interest. When host cells are used it is preferred that the vector is an integrating vector. Alternatively, the vector may be an episomally replicating vector.

Chromatin structure and other epigenetic control mechanisms may influence the expression of transgenes in eukaryotic cells (e.g., Whitelaw et al., 2001). The multicistronic expression units hereof form part of a selection system with a rather rigorous selection regime. This generally requires high transcription levels in the host cells of choice. To increase the chance of finding clones of host cells that survive the rigorous selection regime, and possibly increase the stability of expression in obtained clones, it will generally be preferable to increase the predictability of transcription. Therefore, in certain embodiments, the expression cassette further comprises at least one chromatin control element. A "chromatin control element" as used herein is a collective term for DNA sequences that may somehow have an effect on the chromatin structure and therewith on the expression level and/or stability of expression of transgenes in their vicinity (they function "in cis," and hence are placed preferably within 5 kb, more preferably within 2 kb, still more preferably within 1 kb from the transgene) within eukaryotic cells. Such elements have sometimes been used to increase the number of clones having desired levels of transgene expression. The mechanisms by which these elements work may differ for and even within different classes of such elements, and are not completely known for all types of such elements. However, such elements have been described, and for the purpose hereof chromatin control elements are chosen from the group consisting of matrix or scaffold attachment regions (MARs/SARs) (e.g., Phi-Van et al., 1990; WO 02/074969, WO 2005/040377), insulators (West et al., 2002) such as the beta-globin insulator element (5' HS4 of the chicken beta-globin locus), scs, scs', and the like (e.g., Chung et al., 1993, 1997; Kellum and Schedl, 1991; WO 94/23046, WO 96/04390, WO 01/02553, WO 2004/027072), a ubiquitous chromatin opening element (UCOE) (WO 00/05393, WO 02/24930, WO 02/099089, WO 02/099070), and anti-repressor sequences (also referred to as "STAR" sequences) (Kwaks et al., 2003; WO 03/004704). Non-limiting examples of MAR/SAR sequences that could be used in the current disclosure are the chicken lysosyme 5' MAR (Phi-Van et al., 1990) or fragments thereof, e.g., the B, K and F regions as described in WO 02/074969); DNA sequences comprising at least one bent DNA element and at least one binding site for a DNA binding protein, preferably containing at least 10% of dinucleotide TA, and/or at least 12% of dinucleotide AT on a stretch of 100 contiguous base pairs, such as a sequence selected from the group of comprising the sequences SEQ ID Nos 1 to 27 in WO 2005/040377, fragments of any one of SEQ ID Nos 1 to 27 in WO 2005/040377 being at least 100 nucleotides in length and having MAR activity, sequences that are at least 70% identical in nucleotide sequence to any one of SEQ ID Nos 1 to 27 in WO 2005/040377 or fragments thereof and having MAR activity, wherein MAR activity is defined as being capable of binding to nuclear matrices/scaffolds in vitro and/or of altering the expression of coding sequences operably linked to a promoter; sequences chosen from any one of SEQ ID NOS:1 to 5 in WO 02/074969, fragments of any one of any one of SEQ ID NOS:1 to 5 in WO 02/074969 and having MAR activity, sequences that are at least 70% identical in nucleotide sequence to any one of SEQ ID NOS:1 to 5 in WO 02/074969 or fragments thereof and having MAR activity; sequences chosen from SEQ ID NO:1 and SEQ ID NO:2 in WO 2004/027072, functional fragments thereof and sequences being at least 70% identical thereto. A non-limiting example of insulator sequences that could be used herein is a sequence that comprises SEQ ID NO:1 of WO 01/02553. Non-limiting examples of UCOEs that could be used herein are sequences depicted in FIGS. 2 and 7 of WO 02/24930, functional fragments thereof, and sequences at least 70% identical thereto while still retaining activity; sequences comprising SEQ ID NO:28 of US 2005/181428, functional fragments thereof and sequences at least 70% identical thereto while still retaining activity.

The chromatin control element may be an anti-repressor sequence, preferably selected from the group consisting of: a) any one SEQ ID NO:1 through SEQ ID NO:66; b) fragments of any one of SEQ ID NO:1 through SEQ ID NO:66, wherein the fragments have anti-repressor activity ("functional fragments"); c) sequences that are at least 70% identical in nucleotide sequence to a) or b) wherein the sequences have anti-repressor activity ("functional derivatives"); and d) the complement to any one of a) to c). The chromatin control element may be selected from the group consisting of STAR67 (SEQ ID NO:66), START (SEQ ID NO:7), STARS (SEQ ID NO:9), STAR17 (SEQ ID NO:17), STAR27 (SEQ ID NO:27), STAR29 (SEQ ID NO:29), STAR43 (SEQ ID NO:43), STAR44 (SEQ ID NO:44), STAR45 (SEQ ID NO:45), STAR47 (SEQ ID NO:47), STAR61 (SEQ ID NO:61), or a functional fragment or derivative of such sequences. In one embodiment, the STAR sequence is STAR 67 (SEQ ID NO:66) or a functional fragment or derivative thereof. In certain embodiments, STAR 67 or a functional fragment or derivative thereof is positioned upstream of a promoter driving expression of the multicistronic transcription unit. In other certain embodiments, the expression cassettes hereof are flanked on both sides by at least one anti-repressor sequence.

Sequences having anti-repressor activity as used herein are sequences that are able to at least in part counteract the repressive effect of HP1 or HPC2 proteins when these proteins are tethered to DNA. Sequences having anti-repressor activity (sometimes also referred to as anti-repressor sequences or anti-repressor elements herein) suitable for use herein, have been disclosed in WO 03/004704, incorporated herein by reference, and were coined "STAR" sequences therein (wherever a sequence is referred to as a STAR sequence herein, this sequence has anti-repressor activity). As a non-limiting example, the sequences of 66 anti-repressor elements, named STAR1-65 (see, WO 03/004704) and STAR67 (see, WO 2006/005718), are presented herein as SEQ ID NOS:1-65 and 66, respectively.

A functional fragment or derivative of a given anti-repressor element is considered equivalent to the anti-repressor element, when it still has anti-repressor activity. The presence of such anti-repressor activity can easily be checked by the person skilled in the art, for instance by the assay described below. Functional fragments or derivatives can easily be obtained by a person skilled in the art of molecular biology, by starting with a given anti-repressor sequence, and making deletions, additions, substitutions, inversions and the like (see, e.g., WO 03/004704). A functional fragment or derivative also comprises orthologs from other species, which can be found using the known anti-repressor sequences by methods known by the person skilled in the art (see, e.g., WO 03/004704). Hence, encompassed are fragments of the anti-repressor sequences, wherein the fragments still have anti-repressor activity. Also encompassed are sequences that are at least 70% identical in nucleotide sequence to the sequences having anti-repressor activity or to functional fragments thereof having anti-repressor activity, as long as these sequences that are at least 70% identical still have the anti-repressor activity hereof. Preferably, the sequences are at least 80% identical, more preferably at least 90% identical and still more preferably at least 95% identical to the reference native sequence or functional fragment thereof. For fragments of a given sequence, percent identity refers to that portion of the reference native sequence that is found in the fragment.

Sequences having anti-repressor activity can be obtained by various methods, including but not limited to the cloning from the human genome or from the genome of another organism, or by for instance amplifying known anti-repressor sequences directly from such a genome by using the knowledge of the sequences, e.g., by PCR, or can in part or wholly be chemically synthesized.

Sequences having anti-repressor activity, and functional fragments or derivatives thereof, are structurally defined herein by their sequence and in addition are functionally defined as sequences having anti-repressor activity, which can be determined with the assay described below.

Any sequence having anti-repressor activity hereof should at least be capable of surviving the following functional assay (see, WO 03/004704, example 1, incorporated herein by reference).

Human U-2 OS cells (ATCC HTB-96) are stably transfected with the pTet-Off plasmid (Clontech K1620-A) and with nucleic acid encoding a LexA-repressor fusion protein containing the LexA DNA binding domain and the coding region of either HP1 or HPC2 (Drosophila Polycomb group proteins that repress gene expression when tethered to DNA; the assay works with either fusion protein) under control of the Tet-Off transcriptional regulatory system (Gossen and Bujard, 1992). These cells are referred to below as the reporter cells for the anti-repressor activity assay. A reporter plasmid, which provides hygromycin resistance, contains a polylinker sequence positioned between four LexA operator sites and the SV40 promoter that controls the ZEOCIN®-resistance gene. The sequence to be tested for anti-repressor activity can be cloned in the polylinker. Construction of a suitable reporter plasmid, such as pSelect, is described in Example 1 and FIG. 1 of WO 00/004704. The reporter plasmid is transfected into the reporter cells, and the cells are cultured under hygromycin selection (25 μg/ml; selection for presence of the reporter plasmid) and tetracycline repression (doxycycline, 10 ng/ml; prevents expression of the LexA-repressor fusion protein). After 1 week of growth under these conditions, the doxycycline concentration is reduced to 0.1 ng/ml to induce the LexA-repressor gene, and after 2 days ZEOCIN® is added to 250 μg/ml. The cells are cultured for 5 weeks, until the control cultures (transfected with empty reporter plasmid, i.e., lacking a cloned anti-repressor sequence in the polylinker) are killed by the ZEOCIN® (in this control plasmid, the SV40 promoter is repressed by the LexA-repressor fusion protein that is tethered to the LexA operating sites, resulting in insufficient ZEOCIN® expression in such cells to survive ZEOCIN® selection). A sequence has anti-repressor activity if, when the sequence is cloned in the polylinker of the reporter plasmid, the reporter cells survive the 5 weeks selection under zeocin. Cells from such colonies can still be propagated onto new medium containing ZEOCIN® after the 5 weeks ZEOCIN® selection, whereas cells transfected with reporter plasmids lacking anti-repressor sequences cannot be propagated onto new medium containing zeocin. Any sequence not capable of conferring such growth after 5 weeks on ZEOCIN® in this assay, does not qualify as a sequence having anti-repressor activity, or functional fragment or functional derivative thereof. As an example, other known chromatin control elements such as those tested by Van der Vlag et al. (2000), including Drosophila scs (Kellum and Schedl, 1991), 5'-HS4 of the chicken β-globin locus (Chung et al., 1993, 1997) or Matrix Attachment Regions (MARs) (Phi-Van et al., 1990), do not survive this assay.

In addition, it is preferred that the anti-repressor sequence or functional fragment or derivative thereof confers a higher proportion of reporter over-expressing clones when flanking a reporter gene (e.g., luciferase, GFP) which is integrated into the genome of U-2 OS or CHO cells, compared to when the reporter gene is not flanked by anti-repressor sequences, or flanked by weaker repression blocking sequences such as Drosophila scs. This can be verified using for instance the pSDH vector, or similar vectors, as described in Example 1 and FIG. 2 of WO 03/004704.

Anti-repressor elements can have at least one of three consequences for production of protein: (1) they increase the predictability of identifying host cell lines that express a protein at industrially acceptable levels (they impair the ability of adjacent heterochromatin to silence the transgene, so that the position of integration has a less pronounced effect on expression); (2) they result in host cell lines with increased protein yields; and/or (3) they result in host cell lines that exhibit more stable protein production during prolonged cultivation.

Any STAR sequence can be used in the expression cassettes hereof, but the following STAR sequences are particularly useful: STAR67 (SEQ ID NO:66), START (SEQ ID NO:7), STAR9 (SEQ ID NO:9), STAR17 (SEQ ID NO:17), STAR27 (SEQ ID NO:27), STAR29 (SEQ ID NO:29), STAR43 (SEQ ID NO:43), STAR44 (SEQ ID NO:44), STAR45 (SEQ ID NO:45), STAR47 (SEQ ID NO:47), STAR61 (SEQ ID NO:61), or functional fragments or derivatives of these STAR sequences.

In certain embodiments, the anti-repressor sequence, preferably STAR67, is placed upstream of the promoter, preferably such that less than 2 kb are present between the 3' end of the anti-repressor sequence and the start of the promoter sequence. In certain embodiments, less than 1 kb, more preferably less than 500 nucleotides (nt), still more preferably less than about 200, less than about 100, less than about 50, or less than about 30 nt are present between the 3' end of the anti-repressor sequence and the start of the promoter sequence. In certain certain embodiments, the anti-repressor sequence is cloned directly upstream of the promoter, resulting in only about 0-20 nt between the 3' end of the anti-repressor sequence and the start of the promoter sequence.

For the production of multimeric proteins, two or more expression cassettes can be used. Preferably, both expression cassettes are multicistronic expression cassettes hereof, each coding for a different selectable marker protein, so that selection for both expression cassettes is possible. This embodiment has proven to give good results, e.g., for the expression of the heavy and light chain of antibodies. It will be clear that both expression cassettes may be placed on one nucleic acid molecule or both may be present on a separate nucleic acid molecule, before they are introduced into host cells. An advantage of placing them on one nucleic acid molecule is that the two expression cassettes are present in a single predetermined ratio (e.g., 1:1) when introduced into host cells. On the other hand, when present on two different nucleic acid molecules, this allows the possibility to vary the molar ratio of the two expression cassettes when introducing them into host cells, which may be an advantage if the preferred molar ratio is different from 1:1 or when it is unknown beforehand what is the preferred molar ratio, so that variation thereof and empirically finding the optimum can easily be performed by the skilled person. Preferably at least one of the expression cassettes, but more preferably each of them, comprises a chromatin control element, more preferably an anti-repressor sequence.

In another embodiment, the different subunits or parts of a multimeric protein are present on a single expression cassette.

Instead of or in addition to the presence of a STAR sequence placed upstream of a promoter in an expression cassette, it has proven highly beneficial to provide a STAR sequence on both sides of an expression cassette, such that expression cassette comprising the transgene is flanked by two STAR sequences, which in certain embodiments are essentially identical to each other.

It is shown herein that the combination of a first anti-repressor element upstream of a promoter and flanking the expression cassette by two other anti-repressor sequences provides superior results.

As at least some anti-repressor sequences can be directional (WO 00/004704), the anti-repressor sequences flanking the expression cassette (anti-repressor A and B) may beneficially placed in opposite direction with respect to each other, such that the 3' end of each of these anti-repressor sequences is facing inwards to the expression cassette (and to each other). Hence, in certain embodiments, the 5' side of an anti-repressor element faces the DNA/chromatin of which the influence on the transgene is to be diminished by the anti-repressor element. For an anti-repressor sequence upstream of a promoter in an expression cassette, the 3' end faces the promoter. The sequences of the anti-repressor elements in the sequence listing (SEQ ID NOS:1-66) are given in 5' to 3' direction, unless otherwise indicated.

In certain embodiments, transcription units or expression cassettes are provided, further comprising: a) a transcription pause (TRAP) sequence upstream of the promoter that drives transcription of the multicistronic transcription unit, the TRAP being in a 5' to 3' direction; or b) a TRAP sequence downstream of the ORF of the polypeptide of interest and preferably downstream of the transcription termination sequence of the multicistronic transcription unit, the TRAP being in a 3' to 5' orientation; or c) both a) and b); wherein a TRAP sequence is functionally defined as a sequence which when placed into a transcription unit, results in a reduced level of transcription in the nucleic acid present on the 3' side of the TRAP when compared to the level of transcription observed in the nucleic acid on the 5' side of the TRAP. Non-limiting examples of TRAP sequences are transcription termination and/or polyadenylation signals. One non-limiting example of a TRAP sequence is given in SEQ ID NO:126. Examples of other TRAP sequences, methods to find these, and uses thereof have been described in WO 2004/055215.

DNA molecules comprising multicistronic transcription units and/or expression cassettes hereof can be used for improving expression of nucleic acid, preferably in host cells. The terms "cell"/"host cell" and "cell line"/"host cell line" are respectively typically defined as a cell and homogeneous populations thereof that can be maintained in cell culture by methods known in the art, and that have the ability to express heterologous or homologous proteins.

Prokaryotic host cells can be used to propagate and/or perform genetic engineering with the DNA molecules hereof, especially when present on plasmids capable of replicating in prokaryotic host cells such as bacteria.

A host cell hereof preferably is a eukaryotic cell, more preferably a mammalian cell, such as a rodent cell or a human cell or fusion between different cells. In certain non-limiting embodiments, the host cell is a U-2 OS osteosarcoma, CHO (Chinese hamster ovary), HEK 293, HuNS-1 myeloma, WERI-Rb-1 retinoblastoma, BHK, Vero, non-secreting mouse myeloma Sp2/0-Ag 14, non-secreting mouse myeloma NS0, NCI-H295R adrenal gland carcinoma, or a PER.C6® cell.

In certain embodiments, a host cell is a cell expressing at least E1A, and preferably also E1B, of an adenovirus. As non-limiting examples, such a cell can be derived from for instance human cells, for instance from a kidney (example: HEK 293 cells, see Graham et al., 1977), lung (e.g., A549, see, e.g., WO 98/39411) or retina (example: HER cells marketed under the trade mark PER.C6®, see U.S. Pat. No. 5,994,128), or from amniocytes (e.g., N52.E6, described in U.S. Pat. No. 6,558,948), and similarly from other cells. Methods for obtaining such cells are described for instance in U.S. Pat. Nos. 5,994,128 and 6,558,948. PER.C6® cells for the purpose hereof means cells from an upstream or downstream passage or a descendent of an upstream or downstream passage of cells as deposited under ECACC no. 96022940, i.e., having the characteristics of those cells. It has been previously shown that such cells are capable of expression of proteins at high levels (e.g., WO 00/63403, and Jones et al., 2003). In other certain embodiments, the host cells are CHO cells, for instance CHO-K1, CHO-S, CHO-DG44, CHO-DUKXB11, and the like. In certain embodiments, the CHO cells have a dhfr⁻ phenotype.

Such eukaryotic host cells can express desired polypeptides, and are often used for that purpose. They can be obtained by introduction of a DNA molecule hereof, preferably in the form of an expression cassette, into the cells. Preferably, the expression cassette is integrated in the genome of the host cells, which can be in different positions in various host cells, and selection will provide for a clone where the transgene is integrated in a suitable position, leading to a host cell clone with desired properties in terms of expression levels, stability, growth characteristics, and the like. Alternatively the multicistronic transcription unit may be targeted or randomly selected for integration into a chromosomal region that is transcriptionally active, e.g., behind a promoter present in the genome. Selection for cells containing the DNA described herein can be performed by selecting for the selectable marker polypeptide, using routine methods known by the person skilled in the art. When such a multicistronic transcription unit is integrated behind a promoter in the genome, an expression cassette hereof can be generated in situ, i.e., within the genome of the host cells.

The host cells may be from a stable clone that can be selected and propagated according to standard procedures known to the person skilled in the art. A culture of such a clone is capable of producing polypeptide of interest, if the cells comprise the multicistronic transcription unit hereof. Cells hereof preferably are able to grow in suspension culture in serum-free medium.

In certain embodiments, the DNA molecule comprising the multicistronic transcription unit hereof, preferably in the form of an expression cassette, is integrated into the genome of the eukaryotic host cell. This will provide for stable inheritance of the multicistronic transcription unit.

Selection for the presence of the selectable marker polypeptide, and hence for expression, can be performed during the initial obtaining of the cells, and could be lowered or stopped altogether after stable clones have been obtained. It is however also possible to apply the selection agent during later stages continuously, or only occasionally, possibly at lower levels than during initial selection of the host cells.

A polypeptide of interest hereof can be any protein, and may be a monomeric protein or a (part of a) multimeric protein. A multimeric protein comprises at least two polypeptide chains. Non-limiting examples of a protein of interest are enzymes, hormones, immunoglobulin chains, therapeutic proteins like anti-cancer proteins, blood coagulation proteins such as Factor VIII, multi-functional proteins, such as erythropoietin, diagnostic proteins, or proteins or fragments thereof useful for vaccination purposes, all known to the person skilled in the art.

In certain embodiments, an expression cassette hereof encodes an immunoglobulin heavy or light chain or an antigen binding part, derivative and/or analogue thereof. In one embodiment, a protein expression unit is provided, wherein the protein of interest is an immunoglobulin heavy chain. In yet another preferred embodiment, a protein expression unit is provided, wherein the protein of interest is an immunoglobulin light chain. When these two protein expression units are present within the same (host) cell a multimeric protein and more specifically an immunoglobulin, is assembled. Hence, in certain embodiments, the protein of interest is an immunoglobulin, such as an antibody, which is a multimeric protein. Preferably, such an antibody is a human or humanized antibody. In certain embodiments thereof, it is an IgG, IgA, or IgM antibody. An immunoglobulin may be encoded by the heavy and light chains on different expression cassettes, or on a single expression cassette. Preferably, the heavy and light chain are each present on a separate expression cassette, each having its own promoter (which may be the same or different for the two expression cassettes), each comprising a multicistronic transcription unit hereof, the heavy and light chain being the polypeptide of interest, and preferably each coding for a different selectable marker protein, so that selection for both heavy and light chain expression cassette can be performed when the expression cassettes are introduced and/or present in a eukaryotic host cell.

The polypeptide of interest may be from any source, and in certain embodiments is a mammalian protein, an artificial protein (e.g., a fusion protein or mutated protein), and preferably is a human protein.

The configurations of the expression cassettes hereof may also be used when the ultimate goal is not the production of a polypeptide of interest, but the RNA itself, for instance for producing increased quantities of RNA from an expression cassette, which may be used for purposes of regulating other genes (e.g., RNAi, antisense RNA), gene therapy, in vitro protein production, etc.

In one aspect, provided is a method for generating a host cell expressing a polypeptide of interest, the method comprising the steps of: a) introducing into a plurality of precursor cells an expression cassette hereof, and b) culturing the generated cells under conditions selecting for expression of the selectable marker polypeptide, and c) selecting at least one host cell producing the polypeptide of interest. This novel method provides a very good result in terms of the ratio of obtained clones versus clones with high expression of the desired polypeptide. Using the most stringent conditions, i.e., the weakest translation efficiency for the selectable marker polypeptide (using the weakest translation start sequence), far fewer colonies are obtained using the same concentration of selection agent than with known selection systems, and a relatively high percentage of the obtained clones produces the polypeptide of interest at high levels. In addition, the obtained levels of expression appear higher than those obtained when an even larger number of clones using the known selection systems are used.

The selection system is swift because it does not require copy number amplification of the transgene. Hence, cells with low copy numbers of the multicistronic transcription units already provide high expression levels. High transgene copy numbers of the transgene may be prone to genetic instability and repeat-induced silencing (e.g., Kim et al., 1998; McBurney et al., 2002). Therefore, an additional advantage of the embodiments with relatively low transgene copy numbers is that lower copy numbers are anticipated to be less prone to recombination and to repeat-induced silencing, and therefore less problems in this respect are anticipated when using host cells with a limited number of copies of the transgene compared to host cells obtained using an amplification system where hundreds or even thousands of copies of the selectable marker and protein of interest coding sequences may be present in the genome of the cell. Also provided are examples of high expression levels, using the multicistronic transcription unit selection system, while the copy number of the transgene is relatively low, i.e., less than 30 copies per cell, or even less than 20 copies per cell. Thus, the disclosure allows for the generation of host cells comprising less than 30 copies of the multicistronic transcription unit in the genome of the host cells, preferably less than 25, more preferably less than 20 copies, while at the same time providing sufficient expression levels of the polypeptide of interest for commercial purposes, e.g., more than 15, preferably more than 20 pg/cell/day of an antibody.

While clones having relatively low copy numbers of the multicistronic transcription units and high expression levels can be obtained, the selection system hereof nevertheless can be combined with amplification methods to even further improve expression levels. This can, for instance, be accomplished by amplification of a co-integrated dhfr gene using methotrexate, for instance by placing dhfr on the same nucleic acid molecule as the multicistronic transcription unit hereof, or by cotransfection when dhfr is on a separate DNA molecule.

In one aspect, provided is a method for producing a polypeptide of interest, the method comprising culturing a host cell comprising a DNA molecule comprising a multicistronic expression unit or an expression cassette hereof, and expressing the polypeptide of interest from the coding sequence for the polypeptide of interest.

The host cell for this aspect is a eukaryotic host cell, preferably a mammalian cell, such as a CHO cell, further as described above.

Introduction of nucleic acid that is to be expressed in a cell, can be done by one of several methods, which as such are known to the person skilled in the art, also dependent on the format of the nucleic acid to be introduced. The methods include but are not limited to transfection, infection, injection, transformation, and the like. Suitable host cells that express the polypeptide of interest can be obtained by selection as described above.

In certain embodiments, selection agent is present in the culture medium at least part of the time during the culturing, either in sufficient concentrations to select for cells expressing the selectable marker polypeptide or in lower concentrations. In certain embodiments, selection agent is no longer present in the culture medium during the production phase when the polypeptide is expressed. In certain embodiments metabolic selection marker proteins such as trp, his, or dhfr, are used, and selection can be easily continued during the production phase by culturing in the suitable culture medium described supra.

Culturing a cell is done to enable it to metabolize, and/or grow and/or divide and/or produce recombinant proteins of interest. This can be accomplished by methods well known to persons skilled in the art, and includes but is not limited to providing nutrients for the cell. The methods comprise growth adhering to surfaces, growth in suspension, or combinations thereof. Culturing can be done for instance in dishes, roller bottles or in bioreactors, using batch, fed-batch, continuous systems such as perfusion systems, and the like. In order to achieve large scale (continuous) production of recombinant proteins through cell culture it is preferred in the art to have cells capable of growing in suspension, and it is preferred to have cells capable of being cultured in the absence of animal- or human-derived serum or animal- or human-derived serum components.

The conditions for growing or multiplying cells (see, e.g., Tissue Culture, Academic Press, Kruse and Paterson, editors (1973)) and the conditions for expression of the recombinant product are known to the person skilled in the art. In general, principles, protocols, and practical techniques for maximizing the productivity of mammalian cell cultures can be found in Mammalian Cell Biotechnology: a Practical Approach (M. Butler, ed., IRL Press, 1991).

In a preferred embodiment, the expressed protein is collected (isolated), either from the cells or from the culture medium or from both. It may then be further purified using known methods, e.g., filtration, column chromatography, etc, by methods generally known to the person skilled in the art.

The selection method hereof works in the absence of chromatin control elements, but improved results are obtained when the multicistronic expression units are provided with such elements. The selection method hereof works particularly well when an expression cassette hereof, comprising at least one anti-repressor sequence is used. Depending on the selection agent and conditions, the selection can in certain cases be made so stringent, that only very few or even no host cells survive the selection, unless anti-repressor sequences are present. Hence, the combination of the novel selection method and anti-repressor sequences provides a very attractive method to obtain only limited numbers of colonies with a greatly improved chance of high expression of the polypeptide of interest therein, while at the same time the obtained clones comprising the expression cassettes with anti-repressor sequences provide for stable expression of the polypeptide of interest, i.e., they are less prone to silencing or other mechanisms of lowering expression than conventional expression cassettes.

In certain embodiments, almost no clones are obtained when no anti-repressor sequence is present in the expression cassette hereof, providing for very stringent selection. The novel selection system disclosed herein therefore also provides the possibility to test parts of anti-repressor elements for functionality, by analyzing the effects of such sequences when present in expression cassettes hereof under selection conditions. This easy screen, which provides an almost or even complete black and white difference in many cases, therefore can contribute to identifying functional parts or derivatives from anti-repressor sequences. When known anti-repressor sequences are tested, this assay can be used to characterize them further. When fragments of known anti-repressor sequences are tested, the assay will provide functional fragments of such known anti-repressor sequences.

The incorporated '953 application provides a multicistronic transcription unit having an alternative configuration compared to the configuration disclosed in the incorporated '525 application: in the alternative configuration of the incorporated '953 application, the sequence coding for the polypeptide of interest is upstream of the sequence coding for the selectable marker polypeptide, and the selectable marker polypeptide is operably linked to a cap-independent translation initiation sequence, preferably an internal ribosome entry site (IRES). Such multicistronic transcription units as such were known (e.g., Rees et al., 1996, WO 03/106684), but had not been combined with a non-optimal start codon. According to the alternative of the incorporated '953 application, the start codon (or the context thereof) of the selectable marker polypeptide is changed into a non-optimal start codon, to further decrease the translation initiation rate for the selectable marker. This therefore leads to a desired decreased level of expression of the selectable marker polypeptide, and can result in highly effective selection host cells expressing high levels of the polypeptide of interest, as with the embodiments disclosed in the incorporated '525 application. One potential advantage of this alternative aspect of the incorporated '953 application, compared to the embodiments outlined in the incorporated '525 application, is that the coding sequence of the selectable marker polypeptide needs no further modification of internal ATG sequences, because any internal ATG sequences therein can remain intact since they are no longer relevant for translation of further downstream polypeptides. This may be especially advantageous if the coding sequence for the selectable marker polypeptide contains several internal ATG sequences, because the task of changing these and testing the resulting construct for functionality does not have to be performed for the disclosure: only mutation of the ATG start codon (or its context) suffices in this case. As will be understood by the person skilled in the art after reading the description, this aspect can further be advantageously combined with the embodiments outlined above for the multicistronic transcription units. For instance expression cassettes comprising the multicistronic transcription unit can further in certain embodiments comprise at least one chromatin control element. It is shown hereinbelow (Example 19) that this alternative provided by the incorporated '953 application also leads to very good results.

In this alternative embodiment (disclosed first in the incorporated '953 application), the coding sequence for the polypeptide of interest comprises a stop codon, so that translation of the first cistron (encoding the polypeptide of interest) ends upstream of the IRES, which IRES is operably linked to the second cistron (encoding the selectable marker polypeptide). In these embodiments, the IRES is required for the translation of the selectable marker polypeptide.

As used herein, an "internal ribosome entry site" or "IRES" refers to an element that promotes direct internal ribosome entry to the initiation codon, such as normally an ATG, but herein preferably GTG or TTG, of a cistron (a protein encoding region), thereby leading to the cap-independent translation of the gene. See, e.g., Jackson R J, Howell M T, Kaminski A (1990) Trends Biochem Sci 15 (12): 477-83) and Jackson R J and Kaminski, A. (1995) RNA 1 (10): 985-1000. Encompassed is the use of any IRES element, which is able to promote direct internal ribosome entry to the initiation codon of a cistron. "Under translational control of an IRES" (also referred to as "operably linked to an IRES") as used herein means that translation is associated with the IRES and proceeds in a cap-independent manner. As used herein, the term "IRES" encompasses functional variations of IRES sequences as long as the variation is able to promote direct internal ribosome entry to the initiation codon of a cistron. As used herein, "cistron" refers to a polynucleotide sequence, or gene, of a protein, polypeptide, or peptide of interest. "Operably linked" refers to a situation where the components described are in a relationship permitting them to function in their intended manner. Thus, for example, a promoter "operably linked" to a cistron is ligated in such a manner that expression of the cistron is achieved under conditions compatible with the promoter. Similarly, a nucleotide sequence of an IRES operably linked to a cistron is ligated in such a manner that translation of the cistron is achieved under conditions compatible with the IRES.

Internal ribosome binding site (IRES) elements are known from viral and mammalian genes (Martinez-Salas, 1999), and have also been identified in screens of small synthetic oligonucleotides (Venkatesan & Dasgupta, 2001). The IRES from the encephalomyocarditis virus has been analyzed in detail (Mizuguchi et al., 2000). An IRES is an element encoded in DNA that results in a structure in the transcribed RNA at which eukaryotic ribosomes can bind and initiate translation. An IRES permits two or more proteins to be produced from a single RNA molecule (the first protein is translated by ribosomes that bind the RNA at the cap structure of its 5' terminus, (Martinez-Salas, 1999)). Translation of proteins from IRES elements is less efficient than cap-dependent translation: the amount of protein from IRES-dependent ORFs ranges from less than 20% to 50% of the amount from the first ORF (Mizuguchi et al., 2000). The reduced efficiency of IRES-dependent translation provides an advantage that is exploited by this embodiment hereof. Furthermore, mutation of IRES elements can attenuate their activity, and lower the expression from the IRES-dependent ORFs to below 10% of the first ORF (Lopez de Quinto & Martinez-Salas, 1998, Rees et al., 1996). The advantage exploited hereby is as follows: when the IRES-dependent ORF encodes a selectable marker protein, its low relative level of translation means that high absolute levels of transcription must occur in order for the recombinant host cell to be selected. Therefore, selected recombinant host cell isolates will by necessity express high amounts of the transgene mRNA. Since the recombinant protein is translated from the cap-dependent ORF, it can be produced in abundance resulting in high product yields. On top of this, the non-optimal (i.e., non-ATG) start codon for the selectable marker polypeptide, further improves the chances of obtaining a preferred host cell, i.e., a host cell expressing high levels of recombinant protein of interest.

It is clear to a person skilled in the art that changes to the IRES can be made without altering the essence of the function of the IRES (hence, providing a protein translation initiation site with a reduced translation efficiency), resulting in a modified IRES. Use of a modified IRES which is still capable of providing a small percentage of translation (compared to a 5' cap translation) is therefore also included herein.

The practice of this disclosure will employ, unless otherwise indicated, conventional techniques of immunology, molecular biology, microbiology, cell biology, and recombinant DNA, which are within the skill of the art. See, e.g., Sambrook, Fritsch and Maniatis, Molecular Cloning: A Laboratory Manual, 2$^{nd}$ edition, 1989; Current Protocols in Molecular Biology, Ausubel F M, et al., eds, 1987; the series Methods in Enzymology (Academic Press, Inc.); PCR2: A Practical Approach, MacPherson M J, Hams B D, Taylor G R, eds, 1995; Antibodies: A Laboratory Manual, Harlow and Lane, eds, 1988.

The disclosure is further described with the aid of the following illustrative Examples.

EXAMPLES

Examples 1-18 describe details of several embodiments of the incorporated '525 application. Example 19 describes the selection system with the multicistronic transcription unit hereof, and it will be clear that the variations described in Examples 1-18 can also be applied and tested for the multicistronic transcription units hereof.

Example 1

Figure 2:
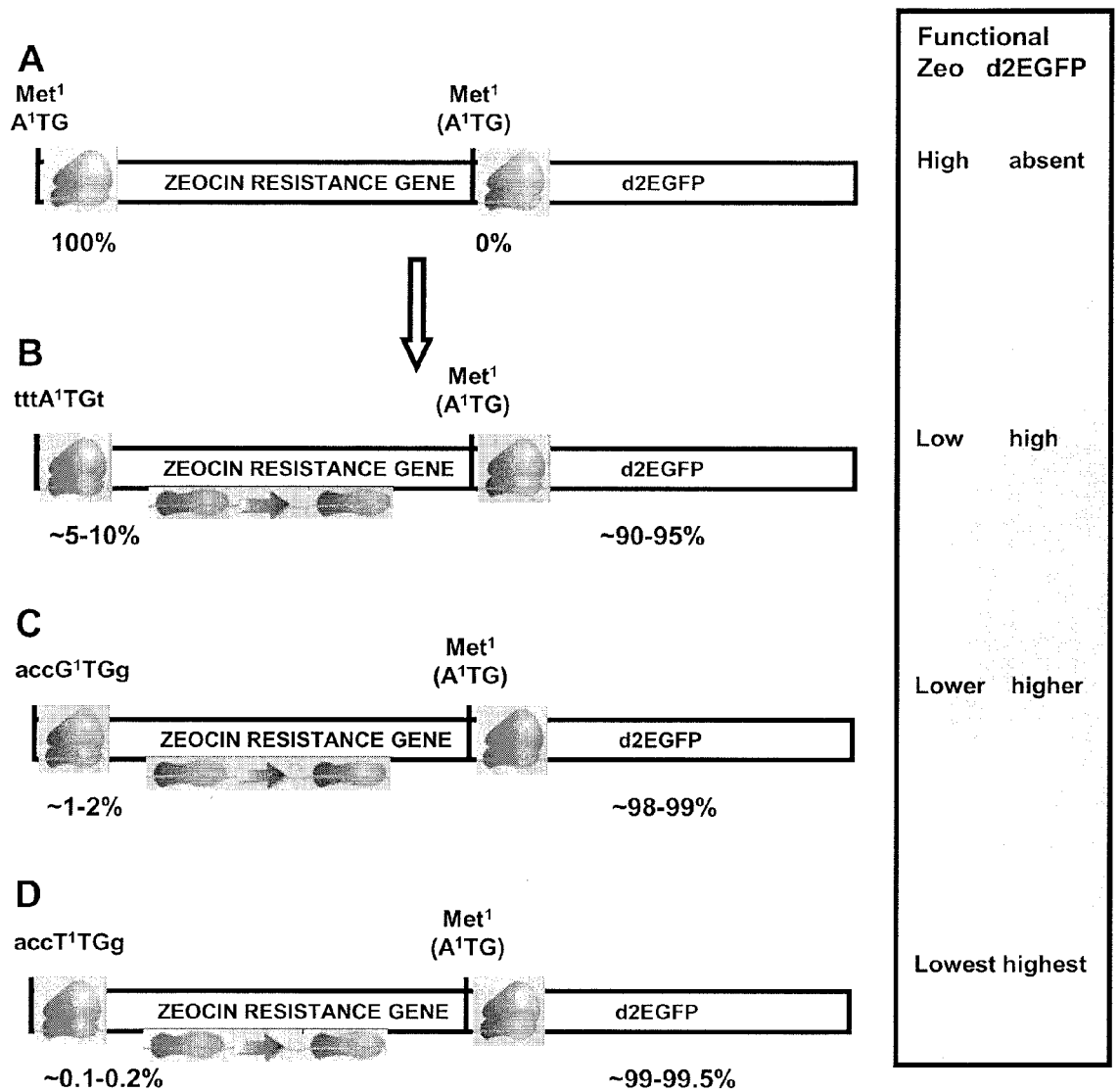
FIG. 2. Schematic representation of a multicistronic transcription unit of the incorporated '525 application, with more or less reciprocal interdependent translation efficiency. Explanation as for FIG. 1, but now a dEGFP gene (here exemplifying a gene of interest) has been placed downstream of the selectable marker polypeptide coding sequence. The ZEOCIN®-resistance gene comprises the internal Met→Leu mutation (see, FIG. 1B). See, Example 2 for details.

Construction and Testing of a ZEOCIN®-Resistance Gene Product with No Internal Methionine The basic idea behind the development of the novel selection system of the incorporated '525 application is to place the gene encoding the resistance gene upstream of a gene of interest, and one promoter drives the expression of this bicistronic mRNA. The translation of the bicistronic mRNA is such that only in a small percentage of translation events the resistance gene will be translated into protein and that most of the time the downstream gene of interest will be translated into protein. Hence the translation efficiency of the upstream resistance gene is severely hampered in comparison to the translation efficiency of the downstream gene of interest. To achieve this, three steps can be taken according to the incorporated '525 application:

1) within the resistance gene on the mRNA, the searching ribosome preferably should not meet another AUG, since any downstream AUG may serve as translation start codon, resulting in a lower translation efficiency of the second, downstream gene of interest. Hence, preferably any AUG in the resistance gene mRNA will have to be replaced. In case this AUG is a functional codon that encodes a methionine, this amino acid will have to be replaced by a different amino acid, for instance by a leucine (FIGS. 1A and B);

2) the start codon of the resistance gene has a bad context (be part of a non-optimal translation start sequence); i.e., the ribosomes must start translation at this start codon only in a limited number of events, and thus, in most events, continue to search for a better, more optimal start codon (FIG. 1C-E). Three different stringencies can be distinguished: a) the normal ATG start codon, but placed in a bad context (TTTATGT) (called ATGmut) (FIG. 1C), b) preferably when placed in an optimal context, GTG can serve as start codon (ACCGTGG) (FIG. 1D) and c) preferably when placed in an optimal context, TTG can serve as start codon (ACCTTGG) (FIG. 1E). The most stringent translation condition is the TTG codon, followed by GTG (FIG. 1). The Zeo mRNA with a TTG as start codon is expected to produce the least ZEOCIN®-resistance protein and will hence convey the lowest functional ZEOCIN® resistance to cells (FIGS. 1, 2).

3) preferably, the normal start codon (ATG) of the downstream gene of interest should have an optimal translation context (e.g., ACCATGG)(FIG. 2A-D). This warrants that, after steps 1 and 2, in most instances the start codon of the gene of interest will function as start codon of the bicistronic mRNA.

In this Example, step 1 is performed, that is, in the ZEOCIN®-resistance gene one existing internal methionine is replaced by another amino acid (FIG. 1B-E). It is important that after such a change the Zeo protein still confers ZEOCIN® resistance to the transfected cells. Since it is not known beforehand which amino acid will fulfill this criterium, three different amino acids have been tried: leucine, threonine and valine. The different constructs with distinct amino acids have than been tested for their ability to still confer ZEOCIN® resistance to the transfected cells.

Materials and Methods—Construction of the Plasmids

The original Zeo ORF has the following sequence around the start codon: AA<u>ACC</u> *ATG* GCC (start codon in bold; SEQ ID NO:67). This is a start codon with an optimal translational context (FIG. 1A). First the optimal context of the start codon of the Zeo ORF was changed through amplification from plasmid pCMV-zeo [Invitrogen V50120], with primer pair ZEOforwardMUT (SEQ ID NO:68): GATCTCGCGATACAGGATTT*ATG* TTGGCCAAGTTGACCAGTGCCGTTCCG and ZEO-WTreverse (WT=Wild type; SEQ ID NO:69): AGGCGAAT-TCAGTCCTGCTCCTCGGC, using pCMV-ZEO (Invitrogen; V50120) as a template. The amplified product was cut with NruI-EcoRI, and ligated into pcDNA3, resulting in pZEOATGmut.

The original Zeo ORF contains an in frame ATG, encoding methionine at amino acid position 94 (out of 124). This internal ATG, encoding the methionine at position 94 was changed in such a way that the methionine was changed into leucine, threonine or valine respectively:

1) To replace the internal codon for methionine in the Zeo ORF with the codon for leucine (FIG. 1B), part of the Zeo ORF was amplified using primer pair ZEOforwardMUT (SEQ ID NO:68) and ZEO-LEUreverse (SEQ ID NO:70): AGGCCCCGCCCCCACGGCTGCTCGCCGATCTCGGT<u>CAAGG</u> CCGGC. The PCR product was cut with BamHI-BglI and ligated into pZEOATGmut. This resulted in pZEO (leu). To replace the internal codon for methionine in the Zeo ORF with the codon for threonine (not shown, but as in FIG. 1B), part of the Zeo ORF was amplified using primer pair ZEOforwardMUT (SEQ ID NO:68) and ZEO-THRreverse (SEQ ID NO:71): AGGCCCCGCCCCCACGGCT-GCTCGCCGATCTCGGT<u>GGT</u>GGCCGGC. The PCR product was cut with BamHI-BglI and ligated into pZEOATGmut. This resulted in pZEO(thr). To replace the internal codon for methionine in the Zeo ORF with the codon for valine (not shown, but as in FIG. 1B)(GTG), part of the Zeo ORF was amplified using primer pair ZEOforwardMUT (SEQ ID NO:68) and ZEO-VALreverse (SEQ ID NO:72): AGGC-CCCGCCCCCACGGCTGCTCGCCGATCTCGGTC<u>CAC</u>GCCGG. The PCR product was cut with BamHI-BglI and ligated into pZEOATGmut. This resulted in pZEO(val).

Transfection and culturing of cells: The Chinese Hamster Ovary cell line CHO-K1 (ATCC CCL-61) was cultured in HAMS-F12 medium +10% Fetal Calf Serum containing 2 mM glutamine, 100 U/ml penicillin, and 100 micrograms/ml streptomycin at 37° C./5% $CO_2$. Cells were transfected with the plasmids using LIPOFECTAMINE® 2000 (Invitrogen) as described by the manufacturer. Briefly, cells were seeded to culture vessels and grown overnight to 70-90% confluence. LIPOFECTAMINE® reagent was combined with plasmid DNA at a ratio of 6 microliters per microgram (e.g., for a 10 cm Petri dish, 20 micrograms DNA and 120 microliters LIPOFECTAMINE®) and added to the cells. After overnight incubation the transfection mixture was replaced with fresh medium, and the transfected cells were incubated further. After overnight cultivation, cells were trypsinized and seeded into fresh culture vessels with fresh medium containing ZEOCIN® (100 µg/ml). When individual colonies became visible (approximately ten days after transfection) colonies were counted.

Results: Four plasmids were transfected to CHO-K1 cells, 1) pZEO(WT), 2) pZEO(leu), 3) pZEO(thr), and 4) pZEO (val). The cells were selected on 100 µg/ml zeocine. Transfection of pZEO(leu) resulted in an equal number of ZEOCIN®-resistant colonies in comparison with the control pZEO (WT). pZEO(thr) and pZEO(val) gave less colonies, but the differences were not in the order of a magnitude. Hence it was concluded that changes of the internal methionine into leucine, threonine or valine all resulted in a ZEOCIN®-resistance protein that is still able to confer ZEOCIN® resistance to the transfected cells. Rather arbitrarily, pZEO (leu) was chosen as starting point for creating different start codons on the Zeo ORF. Hence in the examples below the start as well as internal methionines are always replaced by leucine, for ZEOCIN®, but also for other selectable marker genes, as will be clear from further Examples.

Example 2

Creation and Testing of ZEOCIN®-d2EGFP Bicistronic Constructs with Differential Translation Efficiencies To create a bicistronic mRNA encompassing a mutated ZEOCIN®-resistance mRNA with less translational efficiency, and the d2EGFP gene as downstream gene of interest, the start codon of the d2EGFP gene was first optimized (step 3 in Example 1). After that, the different versions of the ZEOCIN®-resistance gene were created. The differences between these versions are that they have different start codons, with distinct translational efficiency (step 2 in Example 1, FIGS. 1C-E). These different ZEOCIN®-resistance gene versions were cloned upstream of the modified d2EGFP gene (FIG. 2).

Materials and Methods
Creation of Plasmids

The d2EGFP reporter ORF was introduced into pcDNA3. The sequence around the start codon of this d2EGFP cDNA is GAA<u>TTC</u> *ATG* GG (start codon in bold; SEQ ID NO:73), which is not optimal. As a first step, d2EGFP was amplified from pd2EGFP (Clontech 6010-1) with primers d2EGFPforwardBamHI (SEQ ID NO:74): GATCGGATC-CTATGAGGAATTCGCC<u>ACC</u> *ATG* GTGAGCAAGGGCGAGGAG and d2EGFPreverseNotI (SEQ ID NO:75): AAGGAAAAAAGCGGCCGCCTACA-CATTGATCCTAGCAGAAG. This product contains now a start codon with an optimal translational context (<u>ACC</u> *ATG* G). This created pd2EGFP and subsequently, the Zeo ORF was ligated into pd2EGFP, resulting in pZEO-d2EGFP. It is pointed out here that the optimization of the translational start sequence of the gene of interest (here: EGFP as a model gene) is not essential but preferred in order to skew the translation initiation frequency towards the gene of interest still further.

Now three classes of constructs were made:
1) ATG as a start codon in the Zeo resistance gene, but in a bad context (<u>TTT</u> *ATG* <u>T</u>) (not shown, but as in FIG. 2B) and followed by spacer sequence, instead of the optimal ATG (FIG. 2A). The spacer sequence is placed downstream of the ATG sequence. In the ZEOCIN® (and possibly in the blasticidin) RNA, a secondary structure is present, causing the ribosome to be temporarily delayed. Because of this, a poor start codon can in some cases be used by the ribosome, despite being a bad start codon or being in a non-optimal context for translation initiation. This causes the chance of translation to increase, and in case of the current disclosure therefore renders the stringency for selection lower. To decrease this effect, and hence to further decrease the translation initiation efficiency, a spacer sequence is introduced that does not contain a secondary structure (Kozak, 1990). Hence, the term "space" is introduced, and used in the plasmid and primer names to indicate the presence of such a spacer sequence. The spacer removes the "ribosome delaying sequence" from the neighborhood of the initiation codon, therewith causing the ribosome to start translating less frequently, and hence increasing the stringency of the selection hereof. The spacer introduces some extra amino acids in the coding sequence. This has been done in some cases for both ZEOCIN® and for blasticidin, as will be apparent from the examples. The nomenclature of the plasmids and primers in general in the following is along these lines: the name of the selectable marker polypeptide is referred to by abbreviation (e.g., Zeo, Blas, etc); the start codon is mentioned (e.g., ATG, GTG, TTG); when this start codon is placed in a non-optimal context for translation initiation, the addition "mut" is used (this is usually only done for ATG start codons, as combining a non-optimal context with a non-ATG start codon usually does not result in sufficient translation initiation to allow for selection); when a spacer sequence is used behind the start codon, the addition "space" is used (this is done usually for "ATGmut" start codons for Zeo or Blas selectable markers). The Zeo ORF was amplified with primer pair ZEOforward-BamHI-ATGmut/space (SEQ ID NO: 77): GATCG-GATCCTTGGTTT *ATG* TCGATCCAAAGAC TGC-CAAATCTAGATCCGAGATTTTCAGGAGCTAAG GAAGCTAAAGCCAAGTTGACCAGTGAAGTT C (wherein the sequence following the underlined sequence comprises the spacer sequence), and ZEOWTreverse (SEQ ID NO:69), the PCR product was cut with EcoRI-BamHI, and ligated into pd2EGF, cut with EcoRI-BamHI, creating pZEO-ATGmut/space-d2EGFP.

2) GTG as a start codon in the Zeo resistance gene, instead of ATG (FIG. 2C). The Zeo ORF was amplified with primer pair ZEOforwardBamHI-GTG (SEQ ID NO:78): GATCGGATCCACC*GTG* GCCAAGTTGACCAGTGCCGTTC and ZEOWTreverse (SEQ ID NO:69), the PCR product was cut with EcoRI-BamHI, and ligated into pd2EGFP, cut with EcoRI-BamHI, creating pZEO-GTG-d2EGFP.

3) TTG as a start codon in the Zeo resistance gene, instead of ATG (FIG. 2D). The Zeo ORF was amplified with primer pair ZEOforwardBamHI-TTG: GATCGGATCC ACC*TTG* GCCAAGTTGACCAGTGCCGTTC (SEQ ID NO:79) and ZEOWTreverse (SEQ ID NO:69), the PCR product was cut with EcoRI-BamHI, and ligated into pd2EGFP, cut with EcoRI-BamHI, creating pZEO-TTG-d2EGFP.

Transfection, Culturing and Analysis of CHO Cells

The Chinese Hamster Ovary cell line CHO-K1 (ATCC CCL-61) was cultured in HAMS-F12 medium +10% Fetal Calf Serum containing 2 mM glutamine, 100 U/ml penicillin, and 100 micrograms/ml streptomycin at 37° C./5% $CO_2$. Cells were transfected with the plasmids using LIPO-FECTAMINE® 2000 (Invitrogen) as described by the manufacturer. Briefly, cells were seeded to culture vessels and grown overnight to 70-90% confluence. LIPO-FECTAMINE® reagent was combined with plasmid DNA at a ratio of 15 microliters per 3 microgram (e.g., for a 10 cm Petri dish, 20 micrograms DNA and 120 microliters LIPO-FECTAMINE®) and added after 30 minutes incubation at 25° C. to the cells. After overnight incubation the transfection mixture was replaced with fresh medium, and the transfected cells were incubated further. After overnight cultivation, cells were trypsinized and seeded into fresh culture vessels with fresh medium. After another overnight incubation, ZEO-CIN® was added to a concentration of 50 µg/ml and the cells were cultured further. After another three days the medium was replaced by fresh medium containing ZEOCIN® (100 µg/ml) and cultured further. When individual colonies became visible (approximately ten days after transfection) medium was removed and replaced with fresh medium without zeocin. Individual clones were isolated and transferred to 24-well plates in medium without zeocin. One day after isolation of the colonies, ZEOCIN® was added to the medium. Expression of the d2EGFP reporter gene was assessed approximately 3 weeks after transfection. d2EGFP expression levels in the colonies were measured after periods of two weeks.

Figure 3:
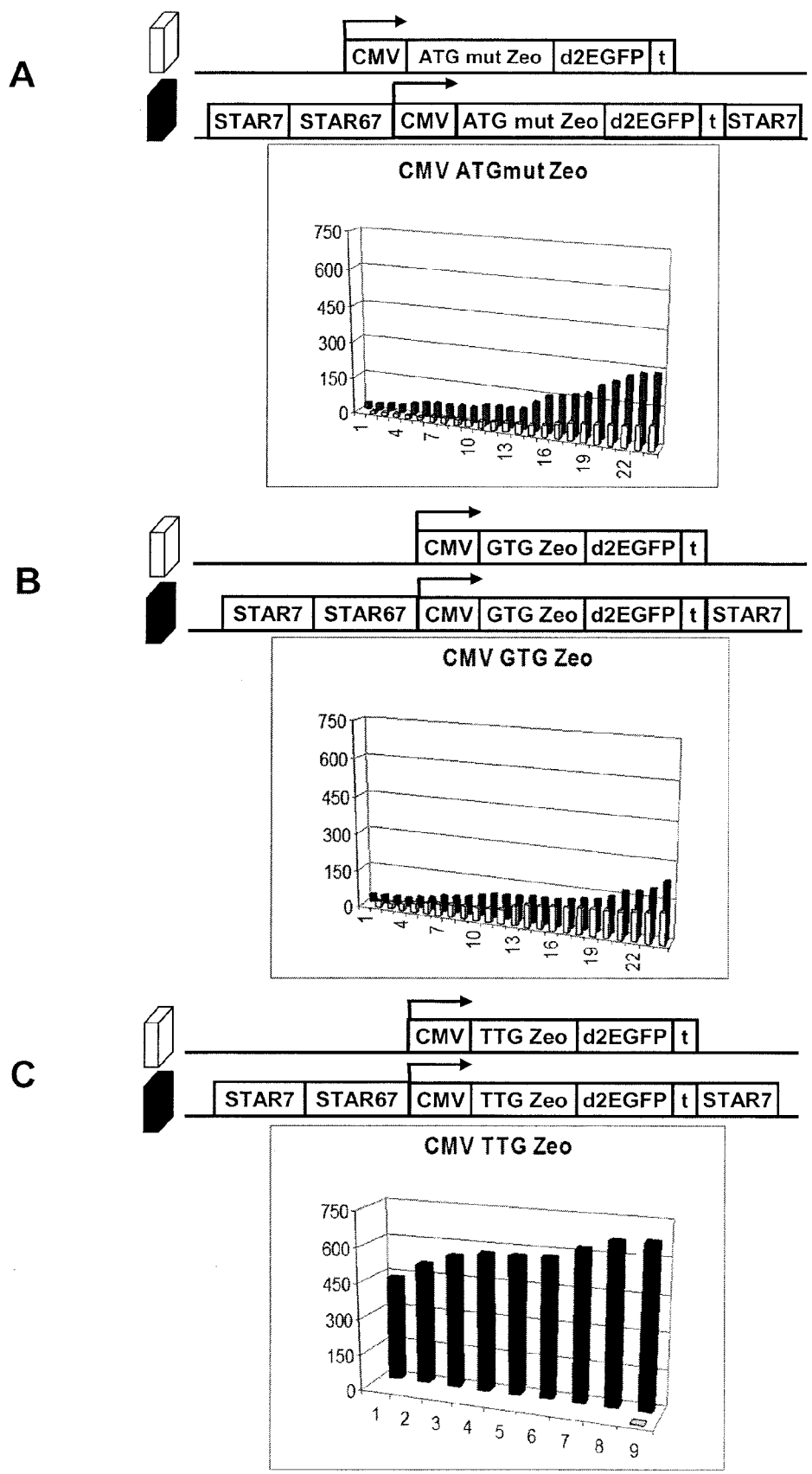
FIG. 3. Results of selection systems of the incorporated '525 application, with and without STAR elements. A. ZEOCIN®-resistance gene with ATG start codon in bad context (referred to as "ATGmut" in the picture, but including a spacer sequence behind the ATG in the bad context, so in the text generally referred to as "ATGmut/space"). B. ZEOCIN®-resistance gene with GTG start codon. C. ZEOCIN®-resistance gene with TTG start codon. d2EGFP signal for independent colonies is shown on the vertical axis. See, Example 2 for details.

Results: CHO-K1 cells were transfected with constructs that contain the ATGmut/space Zeo (FIG. 2B), GTG Zeo (FIG. 2C) and TTG Zeo (FIG. 2D) genes as selection gene, all being cloned upstream of the d2EGFP reporter gene. These three constructs were without STAR elements (Control) or with STAR elements 7 and 67 upstream of the CMV promoter and STAR 7 downstream from the d2EGFP gene (FIG. 3). FIG. 3 shows that both the control (without STAR elements) constructs with ATGmut/space Zeo (A) and GTG Zeo (B) gave colonies that expressed d2EGFP protein. The average d2EGFP expression level of 24 ATGmut/space Zeo colonies was 46 and of GTG Zeo colonies was 75. This higher average expression level in GTG Zeo colonies may reflect the higher stringency of GTG, in comparison with ATGmut/space (Example 1). Addition of STAR elements 7 and 67 to the constructs resulted in colonies that had higher average d2EGFP expression levels. Transfection of the ATGmut/space Zeo STAR 7/67/7 construct resulted in colonies with an average d2EGFP expression level of 118, which is a factor 2.6 higher than the average in the control cells (46). Addition of STAR elements to the GTG Zeo construct resulted in an average d2EGFP expression level of 99, which is a factor 1.3 higher than the average in the control cells (75).

Importantly, no colonies were established when the TTG Zeo construct was transfected. However, the construct with TTG Zeo, flanked with STARs 7 and 67 resulted in the establishment of 6 colonies, with an average d2EGFP expression level of 576 (FIG. 3C). Thus the highest translation stringency, brought about by the TTG start codon (FIG. 1) yields to the highest d2EGFP expression levels, as predicted in FIG. 2. The results also indicate that the stringency of the TTG Zeo alone (without STAR elements) is at least in some experiments too high for colonies to survive. However, in later independent experiments (see, below), some colonies were found with this construct without STAR elements, indicating that the stringency of the selection system with the TTG start codon in the ZEOCIN® selection marker not necessarily precludes the finding of colonies when no STAR elements are present, and that the number of colonies obtained may vary between experiments.

It is concluded that the use of STAR elements in combination with the stringent selection system hereof allows to readily identify high producers of the gene of interest.

Example 3

Establishment of a Higher Number of TTG Zeo STAR Colonies and Comparison with an IRES-Zeo Construct The results in example 2 indicate that the TTG Zeo has extremely stringent translation efficiency, which might be to high to convey ZEOCIN® resistance to the cells. The transfection was scaled up to test whether there would be some colonies that have such high expression levels that they survive. Scaling up the experiment could also address the question whether the high average of TTG Zeo STAR 7/67/7 would become higher when more colonies were analyzed.

Figure 4:
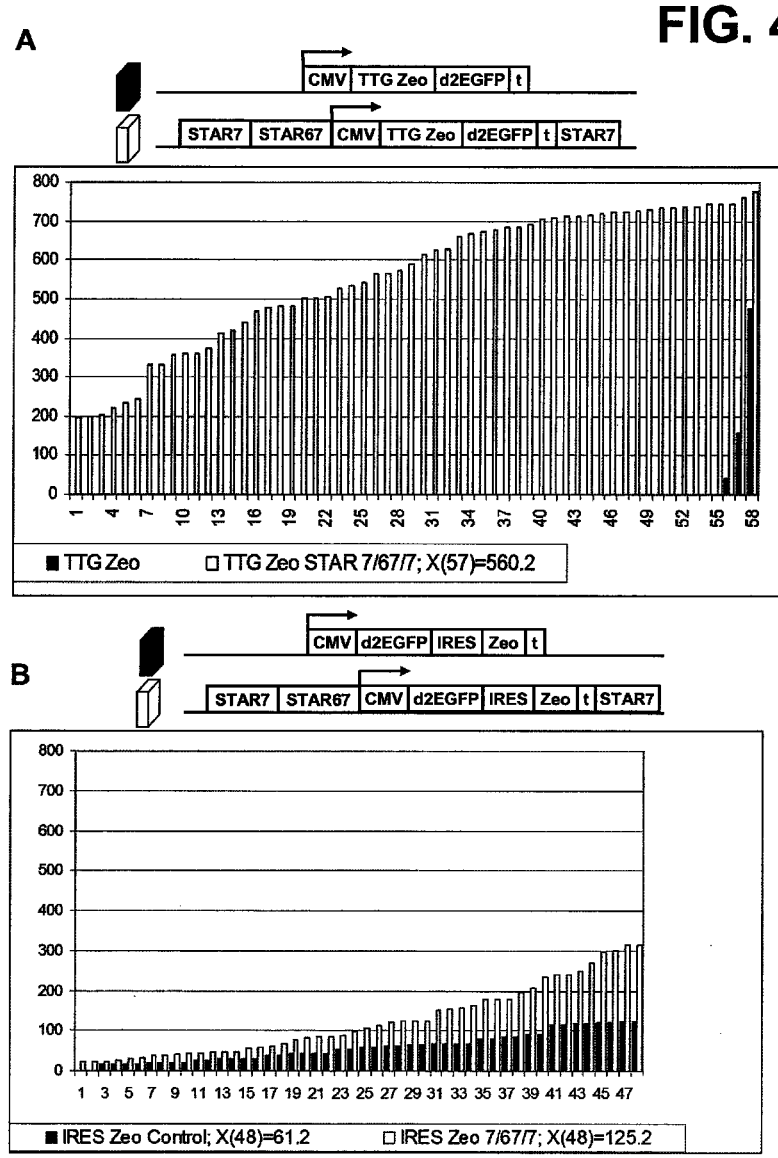
FIG. 4. Results of selection system of the incorporated '525 application in upscaled experiment (A), and comparison with selection system according to prior art using an IRES (B). d2EGFP signal for independent colonies is shown on the vertical axis. See, Example 3 for details.

Materials and methods: CHO-K1 cells were transfected with the constructs that have the TTG Zeo gene as selection marker, with and without STAR elements 7 and 67 (FIG. 4). Transfections, selection, culturing etc were as in Example 2, except that 6 times more cells, DNA and LIPO-FECTAMINE® 2000 were used. Transfections and selection were done in Petri dishes.

Results: FIG. 4A shows that transfection with the TTG Zeo STAR 7/67/7 construct resulted in the generation of many colonies with an average d2EGFP signal of 560. This is as high as in example 2, except that now 58 colonies were analyzed. When compared to a construct with the ZEOCIN®-resistance gene placed behind an IRES sequence (FIG. 4B), the average d2EGFP expression level was 61, and when STAR elements 7 and 67 were added to such a construct, the average d2EGFP expression level was 125, a factor 2 above the control (FIG. 4B). The average of the TTG Zeo STAR 7/67/7 colonies was therefore a factor 9.2 higher than the STAR-less IRES-Zeo colonies and a factor 4.5 higher than the STAR7/67/7 IRES Zeo colonies.

An observation is that the form of the curve of all expressing colonies differs between the TTG Zeo STAR7/67/7 and IRES-Zeo STAR 7/67/7. In the first case (TTG Zeo) the curve levels off, whereas in the second case (IRES-Zeo) the curve has a more "exponential" shape. The plateau in the TTG Zeo curve could indicate that the cells have reached a maximum d2EGFP expression level, above which the d2EGFP expression levels become toxic and the cells die. However, it later appeared that the high values were close to the maximum value that could be detected with the settings of the detector of the FACS analyser. In later experiments, the settings of the FACS analyser were changed to allow for detection of higher values, and indeed in some instances higher values than obtained here were measured in later independent experiments (see, below).

Due to up-scaling of the transfections three colonies with the STAR-less TTG Zeo construct could be picked. The d2EGFP expression levels of these colonies were 475, 158 and 43. The last colony died soon after the first measurement. This result indicates that the TTG Zeo construct can convey ZEOCIN® resistance, resulting in colonies that also can give high expression levels in some instances. Hence, the novel selection method hereof can be applied with expression cassettes that do not contain chromatin control elements, although it is clearly preferred to use expression cassettes comprising at least one such element, preferably a STAR element.

The results indicate that STAR elements allow a more stringent selection system hereof, such as exemplified in this example, resulting in the picking of colonies that have a very high average protein expression level.

Example 4

Figure 14:
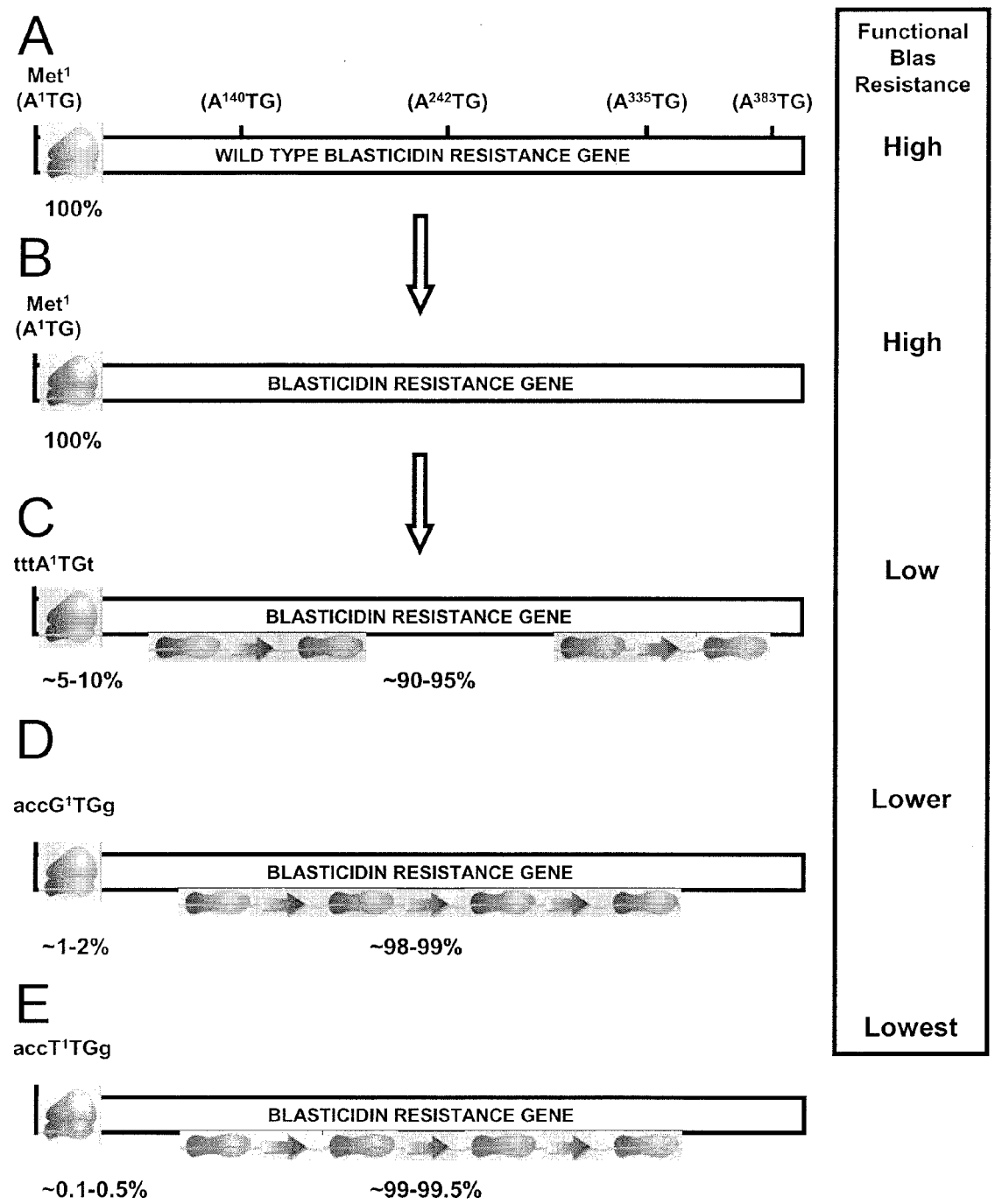
FIG. 14. As FIG. 1, but for the blasticidin resistance gene. None of the 4 internal ATGs in this gene are in frame coding for a methionine, and therefore the redundancy of the genetic code was used to mutate these ATGs without mutating the internal amino acid sequence of the encoded protein.

Creation and Testing of Blasticidin-d2EGFP Bicistronic Constructs with Differential Translation Efficiencies There are four internal ATGs in the blasticidine resistance gene, none of which codes for a methionine (FIG. 14A). These ATGs have to be eliminated though (FIG. 14B), since they will serve as start codon when the ATG start codon (or the context thereof) has been modified, and this will result in peptides that do not resemble blasticidine resistance protein. More importantly, these ATGs will prevent efficient translation of the gene of interest, as represented by d2EGFP in this example for purposes of illustration. To eliminate the internal ATGs, the blasticidine resistance protein ORF was first amplified with 4 primer pairs, generating 4 blasticidine resistance protein fragments. The primer pairs were:

A) BSDBamHIforward (SEQ ID NO:80)
BSD150reverse (SEQ ID NO:81)
B) BSD150forward (SEQ ID NO:82)
BSD250reverse (SEQ ID NO:83)
C) BSD250forward (SEQ ID NO:84)
BSD350reverse (SEQ ID NO:85)
D) BSD350forward (SEQ ID NO:86)
BSD399reverse (SEQ ID NO:87)

Fragments A to D were isolated from an agarose gel and mixed together. Next, only primers BSDBamHIforward and BSD399reverse were used to create the full length blasticidine resistance protein cDNA, but with all internal ATGs replaced. The reconstituted blasticidine was then cut with EcoRI-BamHI, and cloned into pZEO-GTG-d2EGFP, cut with EcoRI-BamHI (which releases Zeo), resulting in pBS-Dmut-d2EGFP. The entire blasticidine resistance protein ORF was sequenced to verify that all ATGs were replaced.

With this mutated gene encoding blasticidine resistance protein (Blas), three classes of constructs are made (FIGS. 14C-E):

1) ATG as a start codon, but in a bad context and followed by spacer sequence. The mutated blasticidine resistance protein ORF in pBSD-d2EGFP was amplified using primers BSDforwardBamHIAvrII-ATGmut/space (SEQ ID NO:88): GATCGGATCCTAGGTTGG*TTT ATG* TC GATCCAAAGACTGCCAAATCTAGATC-CGAGATTTTCAGGAGCTAAG-GAAGCTAAAGCCAAGCCT TTGTCTCAAGAAG, and BSD399reverseEcoRJAvrII (SEQ ID NO:89): GATC-GAATTCCCTAGGTTAGCCCTCCCAC ACGTAAC-CAGAGGGC, the PCR product is cut with BamHI-EcoRI, and ligated into pZEO-GTG-d2EGFP, cut with EcoRI-BamHI. This results in pBSD-ATGmut/space-d2EGFP.

2) GTG as a start codon instead of ATG. The mutated blasticidine resistance protein ORF in pBSD-d2EGFP was amplified using primers BSDforwardBamHIAvrII-GTG (SEQ ID NO:90): GATCGGATCCTAGG*ACC TTG* GCCAAGCCTTTGTCTCAAGAAG and BSD399reverseEcoRIAvrII (SEQ ID NO:89), the PCR product was cut with BamHI-EcoRI, and ligated into pZEO-GTG-d2EGFP, cut with EcoRI-BamHI. This results in pBSD-GTG-d2EGFP.

3) TTG as a start codon instead of ATG. The mutated blasticidine ORF in pBSD-d2EGFP was amplified using primers BSDforwardBamHIAvrII-TTG (SEQ ID NO:91): GATCGGATCCTAGG*ACC TTG* GCCAAGCCTTTGTCTCAAGAAG and BSD399reverseEcoRIAvrII (SEQ ID NO:89), the PCR product was cut with BamHI-EcoRI, and ligated into pZEO-GTG-d2EGFP, cut with EcoRI-BamHI. This results in pBSD-TTG-d2EGFP.

Figure 5:
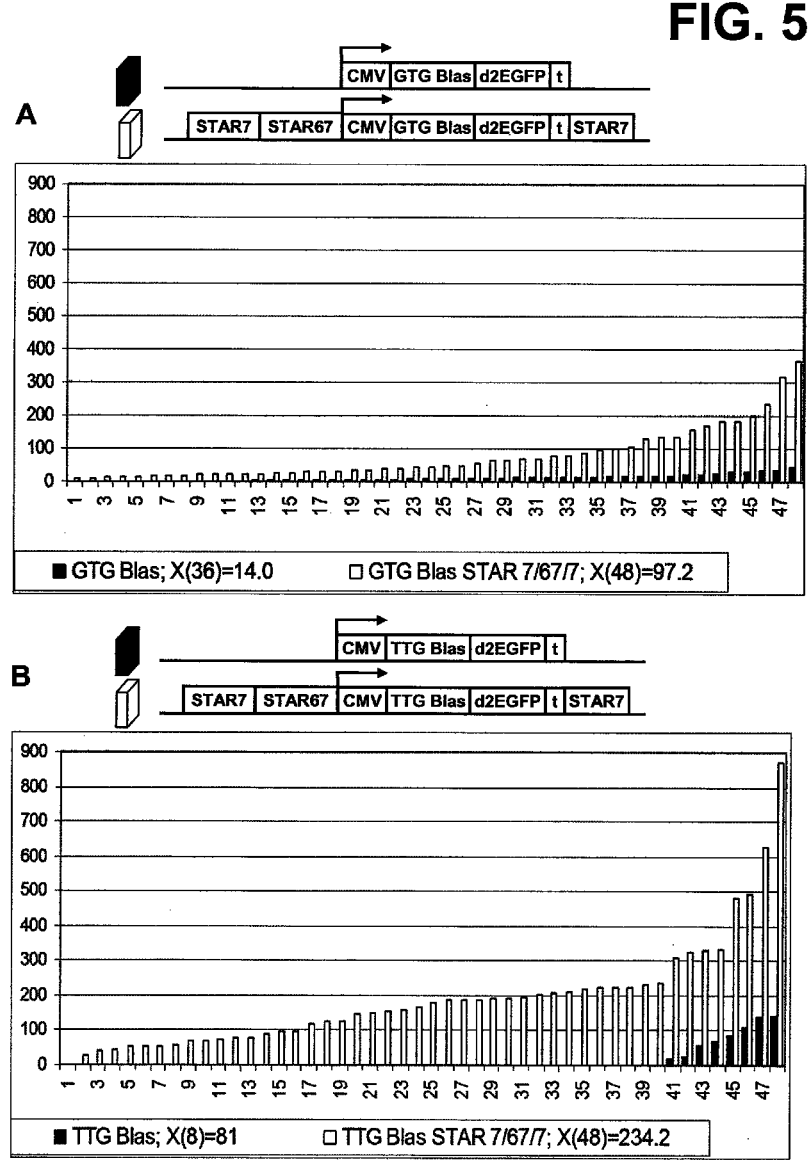
FIG. 5. Results of selection system with multicistronic transcription unit of the incorporated '525 application, using blasticidin as a selectable marker. A. blasticidin resistance gene mutated to comprise a GTG start codon. B. blasticidin resistance gene mutated to comprise a TTG start codon. The blasticidin resistance gene has further been mutated to remove all internal ATG sequences. d2EGFP signal for independent colonies is shown on the vertical axis. See, Example 4 for details.

Results: CHO-K1 cells were transfected with constructs that contain the GTG Blas (FIG. 5A) and TTG Blas (FIG. 5B) genes as selection gene, all being cloned upstream of the d2EGFP reporter gene. Selection took place in the presence of 20 µg/ml Blasticidine. The two constructs were without STAR elements (Control) or with STAR elements 7 and 67 upstream of the CMV promoter and START downstream from the d2EGFP gene (FIG. 5). FIG. 5 shows that both the control (without STAR elements) constructs with GTG Blas (A) and TTG Blas (B) gave colonies that expressed d2EGFP protein. The average d2EGFP signal of 24 GTG Blas colonies was 14.0 (FIG. 5A) and of TTG Blas colonies was 81 (FIG. 5B). This higher average expression level in TTG Blas colonies may reflect the higher stringency of TTG, in comparison with GTG (see, also Example 2). However, only 8 colonies survived under the more stringent TTG conditions.

Addition of STAR elements 7 and 67 to the constructs resulted in colonies that had higher average d2EGFP expression levels. Transfection of the GTG Blas STAR 7/67/7 construct resulted in colonies with an average d2EGFP expression level of 97.2 (FIG. 5A), which is a factor 6.9 higher than the average in the control cells (14.0). Addition of STAR elements to the TTG Blas construct resulted in an average d2EGFP signal of 234.2 (FIG. 5B), which is a factor 2.9 higher than the average in the control cells (81). However, note again that only 8 colonies survived the harsh selection conditions of TTG Blas, whereas 48 colonies survived with TTG Blas STAR 7/67/7. When only the five highest values are compared, the average of the five highest TTG Blas was 109.1 and the average of the five highest TTG Blas STAR 7/67/7 was 561.2, which is a factor 5.1 higher.

The results indicate that STAR elements allow a more stringent selection system, resulting in the picking of colonies that have a very high average protein expression level. They also show that this selection is not restricted to the ZEOCIN®-resistance protein alone, but that also other selection marker polypeptides, in this case the blasticidine resistance protein, can be used.

Example 5

Stability of d2EGFP Expression in the Novel Selection System

Colonies described in Example 3 were further cultured under several conditions to assess the stability of d2EGFP expression over an extended time period.

Results: The TTG Zeo STAR 7/67/7 containing colonies in FIG. 4A were cultured for an additional 70 days in the presence of 100 µg/ml Zeocin. As shown in FIG. 6, the average d2EGFP signal rose from 560.2 after 35 days to 677.2 after 105 days. Except for some rare colonies all colonies had a higher d2EGFP expression level.

When the level of ZEOCIN® was lowered to 20 µg/ml ZEOCIN®, there was still an increase in the average d2EGFP expression level, from 560.2 after 35 days to 604.5 after 105 days (FIG. 7).

When no selection pressure was present at all due to removal of the ZEOCIN® from the culture medium, approximately 50% of the colonies became mosaic, that is, within one colony non-d2EGFP expressing cells became apparent. This resulted in lowering of d2EGFP expression levels to less than 50% of the original levels. If the signal became less than 67% (decrease of at least one-third) from the original signal, the colony was considered to be unstable in respect to d2EGFP expression. Of the 57 original colonies 27 colonies remained stable according to this criterion; the average d2EGFP signal of these colonies after 35 days (while still under selection pressure) was 425.6, whereas the average d2EGFP signal without selection pressure after 65 days was 290.0. When measured after 105 days, the average signal in the 27 colonies was 300.9. Hence, after an initial decrease, the expression levels in the 27 colonies remained stable according to this criterion (FIG. 8).

Figure 12:
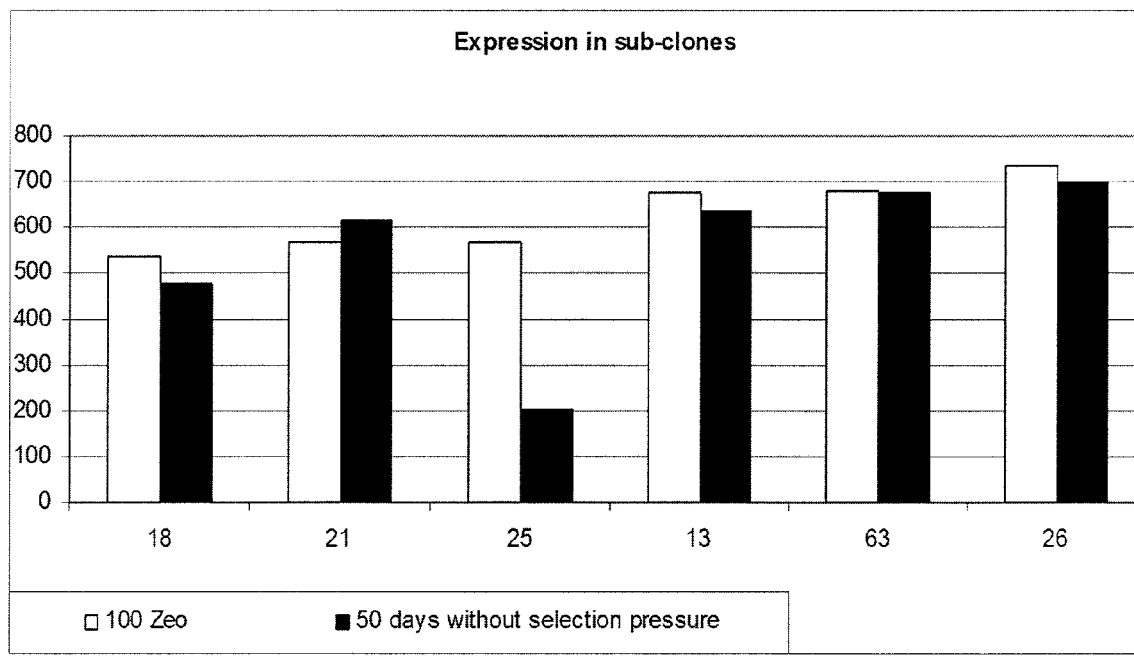
FIG. 12. Stability of expression in sub-clones in the absence of selection pressure (after establishing colonies under selection pressure, some colonies where sub-cloned in medium containing no zeocin). See, Example 5 for details.

Six of the colonies were subjected to one round of sub-cloning Cells were sown in 96-wells plates as such that each well contained approximately 0.3 cells. No ZEOCIN® was present in the medium so that from the start the sub clones grew without selection pressure. Of each original colony six sub clones were randomly isolated and grown in 6-wells plates till analysis. In FIG. 12 we compared the original values of the original clones, as already shown in FIG. 4A, with one of the sub clones. In one of the six clones (clone 25), no sub clone was present with d2EGFP signal in the range of the original clone. However, in five out of six cases at least one the sub clones had equal d2EGFP expression levels as the parent clone. These expression levels were determined after 50 days without selection pressure. We conclude that one round of sub cloning is sufficient to obtain a high number of colonies that remain stable for high expression in the absence of selection pressure. This has been confirmed in a similar experiment (not shown).

Figure 13:
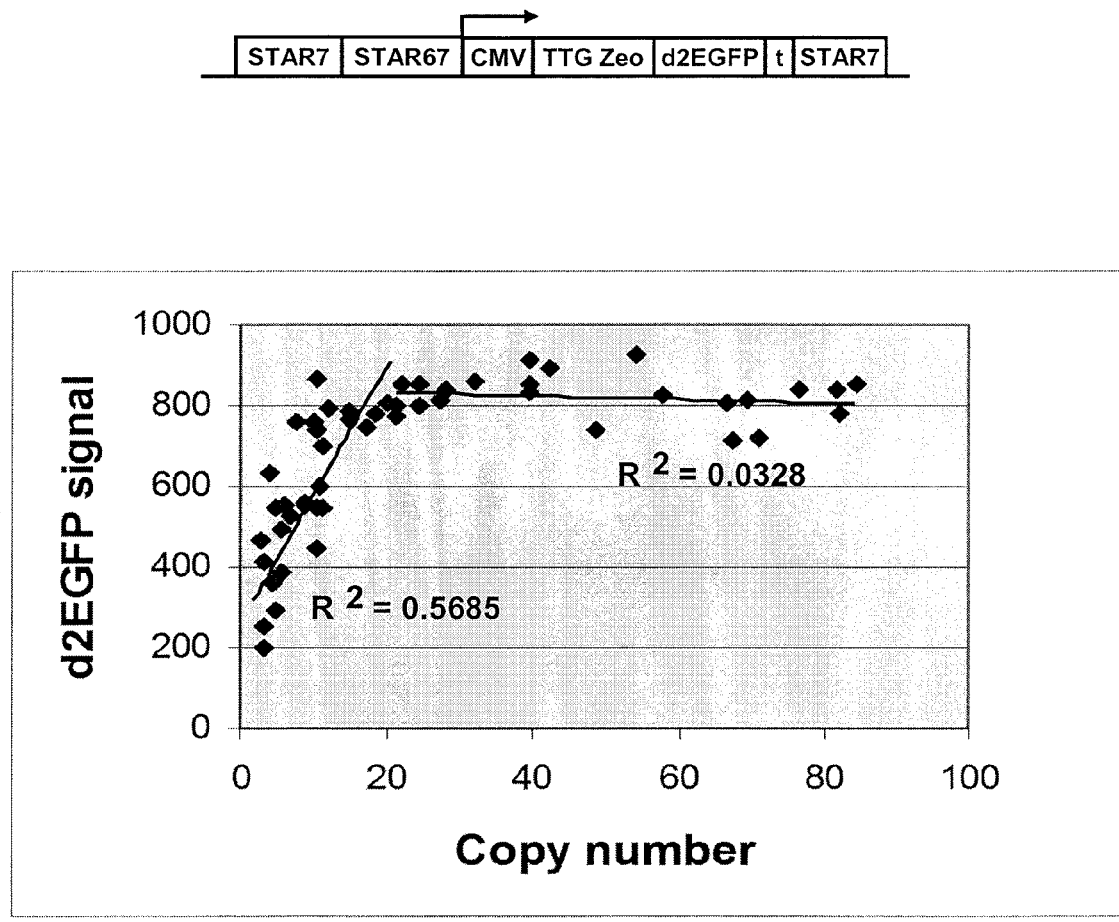
FIG. 13. Copy-number dependency of expression levels of an embodiment of the incorporated '525 application. See, Example 5 for details.

We compared the number of copies that integrated in the TTG Zeo STAR 7/67/7 colonies. DNA was isolated when colonies were 105 days under ZEOCIN® selection pressure (see, FIG. 6). As shown in FIG. 13 two populations could be distinguished. In FIG. 13 the cut off was made at 20 copies and the $R^2$ value is calculated and shown. Also the $R^2$ value from data with higher than 20 copies is shown. In the range from 100 to 800 d2EGFP signal there was a high degree of copy number dependency, as signified by a relatively high $R^2$ of 0.5685 (FIG. 13). However, in the population of colonies that fluctuate around a d2EGFP signal of 800 a high variation in copy number was observed (FIG. 13), as signified with a low $R^2$ of 0.0328. Together the data show that in the novel selection system, in colonies that contain TTG Zeo STAR 7/67/7 constructs there is copy number dependent d2EGFP expression up to ~20 copies. Also, although copy number dependency is lost when >20 copies are present, still a substantial proportion of the colonies with high (>800) d2EGFP signal have no more than 30 copies (FIG. 13). This combination between high d2EGFP expression and a relatively low copy number (between 10 and 30) may be important for identifying colonies that remain relatively stable without selection pressure. It is an advantage to have clones with relatively low copy numbers (less than about 30, more preferably less than about 20) that give high expression levels, because such clones are believed to be less amenable to genetic instability. The present selection system allows to generate such clones, including from CHO cells.

Example 6

Creation and Testing of ZEOCIN®-Blasticidin-EpCAM Bicistronic Constructs with Differential Translation Efficiencies To test the selection system on the production of an antibody, the anti-EpCAM antibody (see, also Example 5 of the incorporated '525 application and of WO2006/005718) was taken as example.

Figure 9:
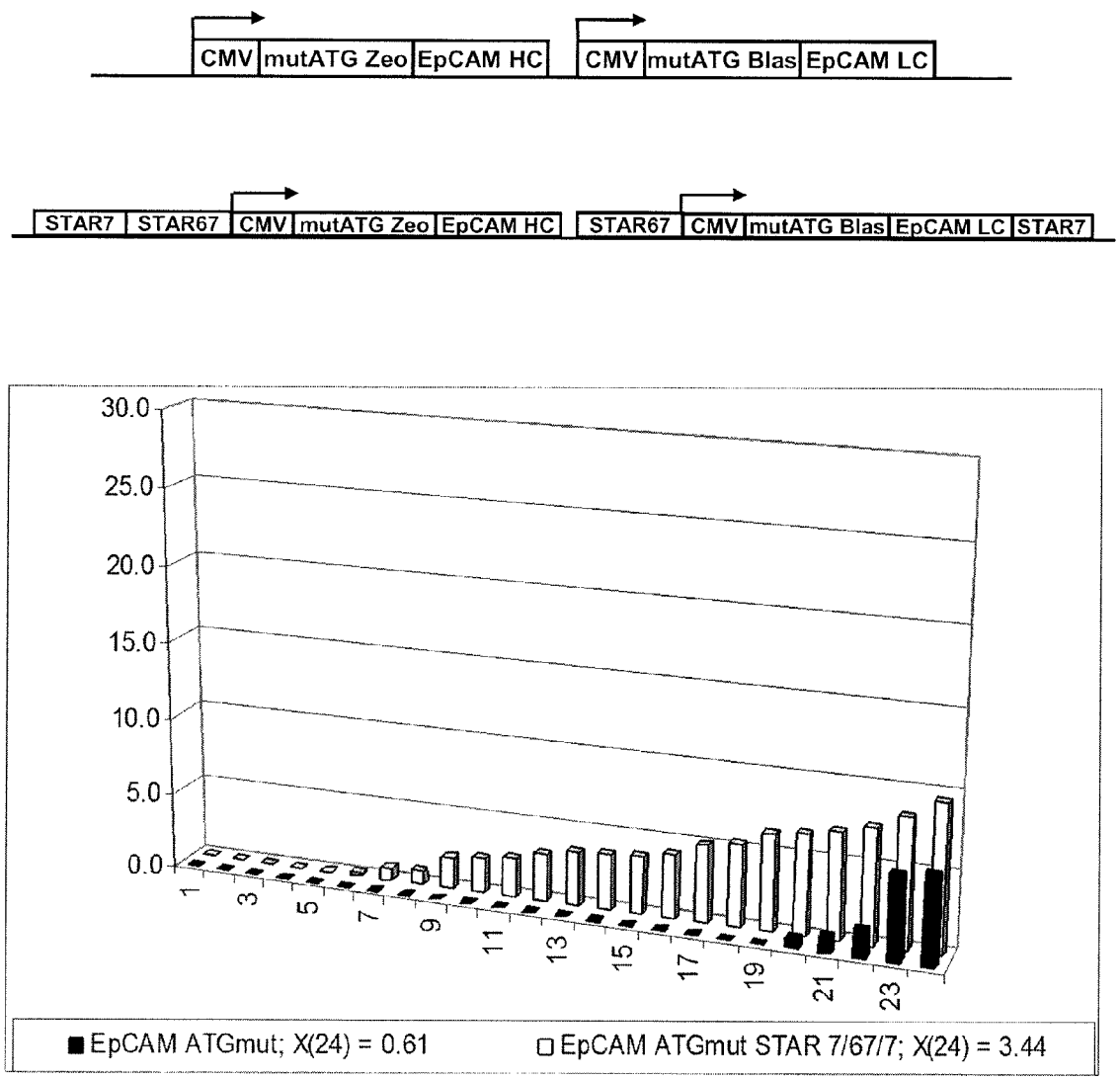
FIG. 9. Expression of an antibody (anti-EpCAM) using the selection system with the multicistronic transcription unit of the incorporated '525 application. The heavy chain (HC) and light chain (LC) are the polypeptide of interest in this example. Each of these is present in a separate transcription unit, which are both on a single nucleic acid molecule in this example. The HC is preceded by the ZEOCIN®-resistance gene coding for a selectable marker polypeptide, while the LC is preceded by the blasticidin resistance gene coding for a selectable marker polypeptide. Both resistance genes have been mutated to comprise an ATG start codon in a non-optimal context ("mutATG" in Figure, but including a spacer sequence, and hence in the text generally referred to as "ATGmut/space"). Each of the multicistronic transcription units is under control of a CMV promoter. Constructs with STAR sequences as indicated were compared to constructs without STAR sequences. The antibody levels obtained when these constructs were introduced into host cells are given on the vertical axis in pg/cell/day for various independent clones. See, Example 6 for details.
Figure 10:
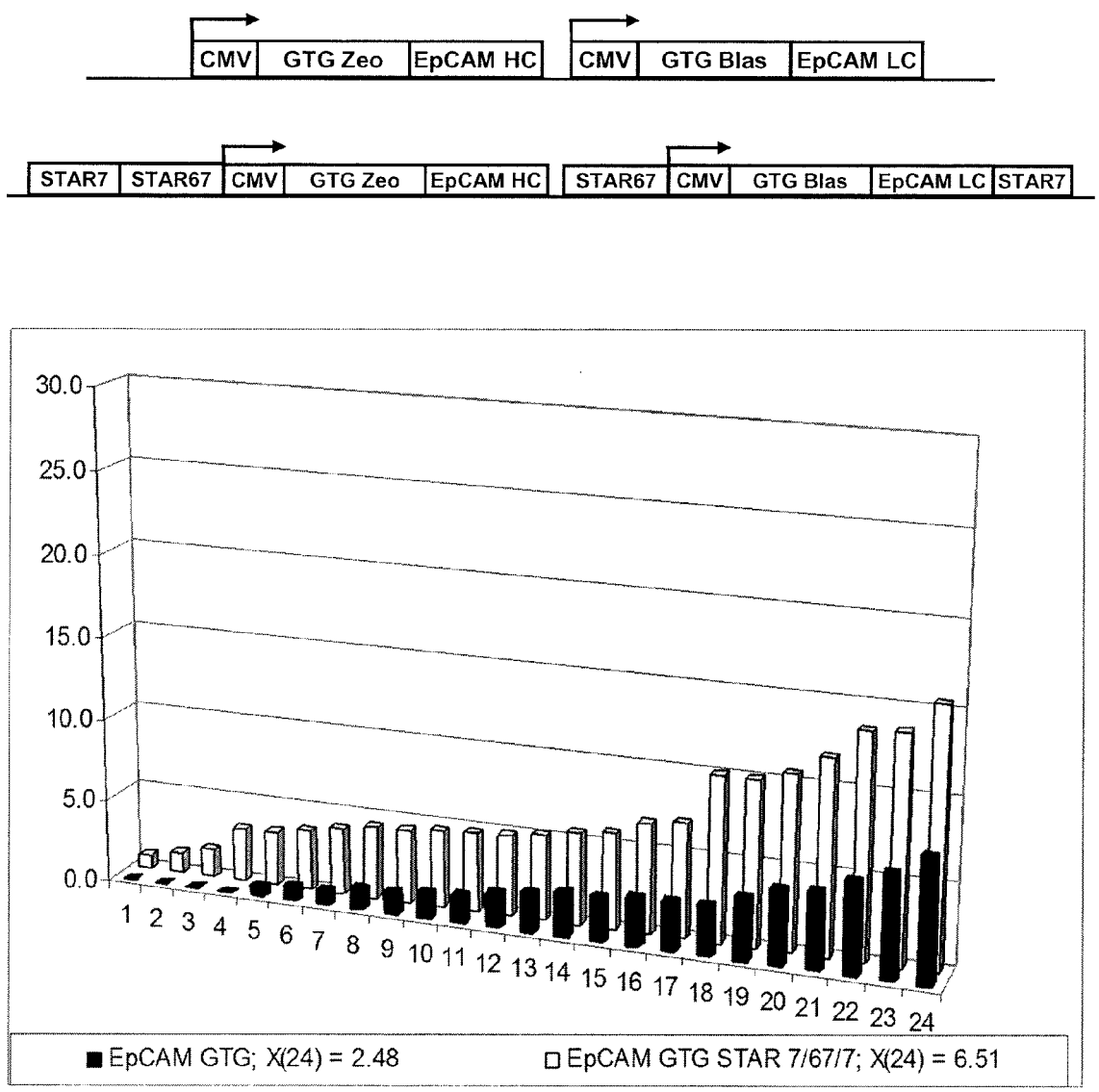
FIG. 10. As FIG. 9, but both the selection marker genes have been provided with a GTG start codon. See, Example 6 for details.
Figure 11:
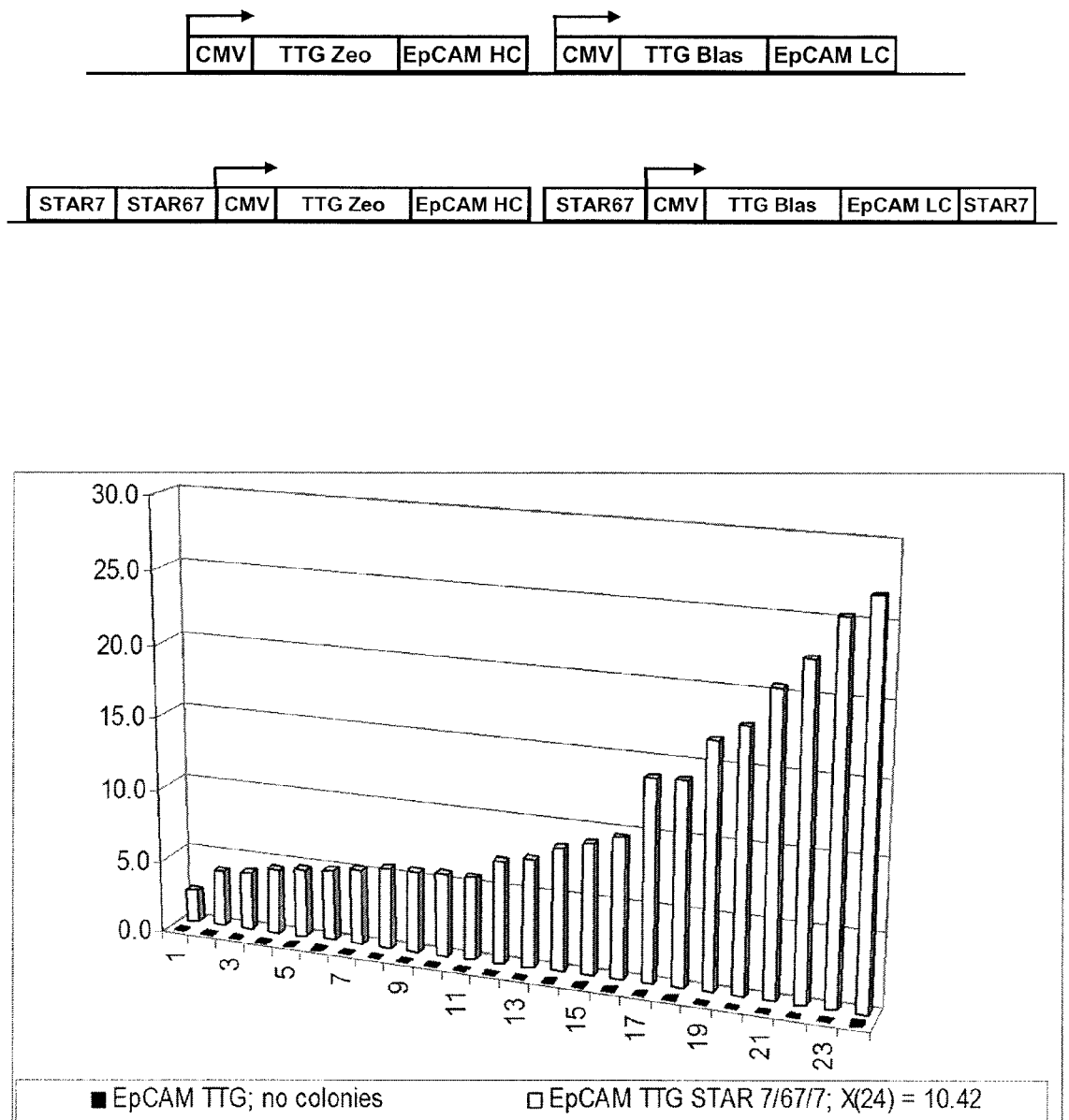
FIG. 11. As FIG. 9, but both the selection marker genes have been provided with a TTG start codon. See, Example 6 for details.

Results: A plasmid was created on which both the heavy chain (HC) and light chain (LC) were placed, each in a separate transcription unit (FIG. 9-11). Expression of both chains was driven by the CMV promoter. Upstream of the EpCAM heavy chain the ZEOCIN®-resistance gene was placed, either with the ATGmut/space (FIG. 9), GTG (FIG. 10) or TTG (FIG. 11) as start codon (See, Example 2). Upstream of the EpCAM light chain the Blasticidine resistance gene was placed, either with the ATGmut/space (FIG. 9), GTG (FIG. 10) or TTG (FIG. 11) as start codon (See, Example 4). Two types of constructs were made, one construct without STAR elements (Control) and one construct with a combination of STAR 7 and 67 elements. The STAR elements were placed as follows: upstream of each CMV promoter (i.e., one for the transcription unit comprising HC and one for the transcription unit comprising LC) STAR 67 was placed and the resulting construct was flanked with a 5' and 3' STAR 7 element (FIGS. 9-11). All constructs were transfected to CHO-K1 cells and selected on 100 µg/ml ZEOCIN® and 20 µg/ml Blasticidin (at the same time). After selection independent colonies were isolated and propagated under continuous selection pressure (using 100 µg/ml ZEOCIN® and 20 µg/ml blasticidin). FIG. 9 shows that the STAR 7/67/7 combination had a beneficial effect on EpCAM production. The ATGmut/space Zeo and ATGmut/space Blas had no effect on the number of colonies that were formed with plasmids containing STAR elements or not. However, the average EpCAM expression levels of either 24 control versus STAR 7/67/7 colonies ranged from 0.61 pg/cell/day in the control to 3.44 pg/cell/day in the STAR7/67/7 construct (FIG. 9). This is a factor 5.6 increase. Since there were many colonies in the ATGmut/space control with 0 pg/cell/day, also the average EpCAM production in the highest five colonies was compared. In the control ATGmut/space this was 3.0 pg/cell/day, versus 7.8 pg/cell/day with the ATGmut/space STAR 7/67/7 construct, an increase of a factor 2.6.

FIG. 10 also shows that the STAR 7/67/7 combination had a beneficial effect on EpCAM production, using the GTG start codon for the markers. With the GTG Zeo and GTG Blas STAR 7/67/7 construct approximately 2 times more colonies were formed. Also, the average EpCAM expression levels of either 24 control versus STAR 7/67/7 colonies ranged from 2.44 pg/cell/day in the control to 6.51 pg/cell/day in the STAR7/67/7 construct (FIG. 10). This is a factor 2.7 increase. Also the average EpCAM production in the highest five colonies was compared. In the control GTG this was 5.7 pg/cell/day, versus 13.0 pg/cell/day with the GTG STAR 7/67/7 construct, an increase of a factor 2.3. Also note that the average EpCAM production mediated by the GTG start codon for the selection markers was significantly higher than with the ATGmut/space start codon.

FIG. 11 shows that with the TTG Zeo and TTG Blas control construct no colonies were formed, similar as in example 2. With the STAR 7/67/7 TTG construct colonies were formed. The average EpCAM expression levels of the STAR 7/67/7 TTG colonies was 10.4 pg/cell/day (FIG. 11). This is again higher than with the ATGmut/space and GTG as start codon (see, FIGS. 9, 10 for comparison). The average EpCAM production in the highest five TTG STAR 7/67/7 colonies was 22.5 pg/cell/day.

The results show that the selection system can also be applied to two simultaneously produced polypeptides, in this case two polypeptides of a multimeric protein, casu quo an antibody. The EpCAM production closely follows the results obtained with d2EGFP. The TTG as start codon is more stringent than the GTG start codon, which in turn is more stringent than the ATGmut/space (FIGS. 1 and 2). Higher stringency results in a decreasing number of colonies, with no colonies in the case of the TTG control that has no STAR elements, and higher stringency of the selection marker is coupled to higher expression of the protein of interest.

Example 7

Creation and Testing of Additional GTG ZEOCIN®-d2EGFP Bicistronic Constructs with Differential Translation efficiencies Different versions of the ZEOCIN®-resistance gene with mutated start codons were described in Example 1. Besides the described GTG codons (Example 1, FIG. 22A), additional modified start codons with distinct translational efficiency are possible. These different ZEOCIN®-resistance gene versions were created (FIG. 22) and cloned upstream of the modified d2EGFP gene, as in Example 2.

Creation of plasmids: Four additional GTG constructs were made:
1) GTG as a start codon in the Zeo resistance gene (FIG. 22A), but followed by a spacer sequence (FIG. 22B). The mutspace-Zeo ORF was amplified with primer pair GTGspaceBamHIF (SEQ ID NO:106): GAATTCG-GATCCACC<u>GT</u>GGCGATCCAAAGACTGCCAAA TCTAG and (wherein the sequence following the underlined sequence comprises the spacer sequence), and ZEOWTreverse (SEQ ID NO:69), the PCR product was cut with EcoRI-BamHI, and ligated into pd2EGFP, cut with EcoRI-BamHI, creating pZEO-<u>GTG</u>space-d2EGFP.
2) GTG as a start codon in the Zeo resistance gene, but in a bad context (*TTTGTG*) (FIG. 22C). The Zeo ORF was amplified with primer pair ZEOTTTGTGBamHIF (SEQ ID NO:107): GAATTCGGATCC TTTGTGGCCAAGTTGACCAGTGCCGTTCCG and ZEOWTreverse (SEQ ID NO:69), the PCR product was cut with EcoRI-BamHI, and ligated into pd2EGFP, cut with EcoRI-BamHI, creating pZEO(leu)-TTTGTG-d2EGFP.
3) GTG as a start codon in the Zeo resistance gene, instead of ATG (FIG. 22A), but with an additional mutation in the Zeo ORF at Pro9, which was replaced with threonine (Thr) (FIG. 22D). The Thr9 mutation was introduced by amplifying the Zeo open reading with primer pair ZEO-ForwardGTG-Thr9 (SEQ ID NO:108): AATTGGATC-CACC<u>GT</u>GGCCAAGTTGACCAGTGCC GTT *ACC* GTGCTC and ZEOWTreverse (SEQ ID NO:69), the PCR product was cut with EcoRI-BamHI, and ligated into pd2EGFP, cut with EcoRI-BamHI, creating pZEO-<u>GTG</u>-Thr9-d2EGFP.
4) GTG as a start codon in the Zeo resistance gene, instead of ATG (FIG. 22A), but with an additional mutation in the Zeo ORF at Pro9, with was replaced with Phenylalanine (Phe) (FIG. 22E). The Phe9 mutation was introduced by amplifying the Zeo open reading with primer pair ZEOForward GTG-Phe9 (SEQ ID NO:109): AAT-TGGATCCACC<u>GT</u>GGCCAAGTTGACCAGTG CCGTT*TTC* GTGCTC and ZEOWTreverse (SEQ ID NO:69), the PCR product was cut with EcoRI-BamHI, and ligated into pd2EGFP, cut with EcoRI-BamHI, creating pZEO-<u>GTG</u>-Phe9-d2EGFP.

Transfection, culturing and analysis of CHO-K1 cells was performed as in Example 1.

Figure 22:
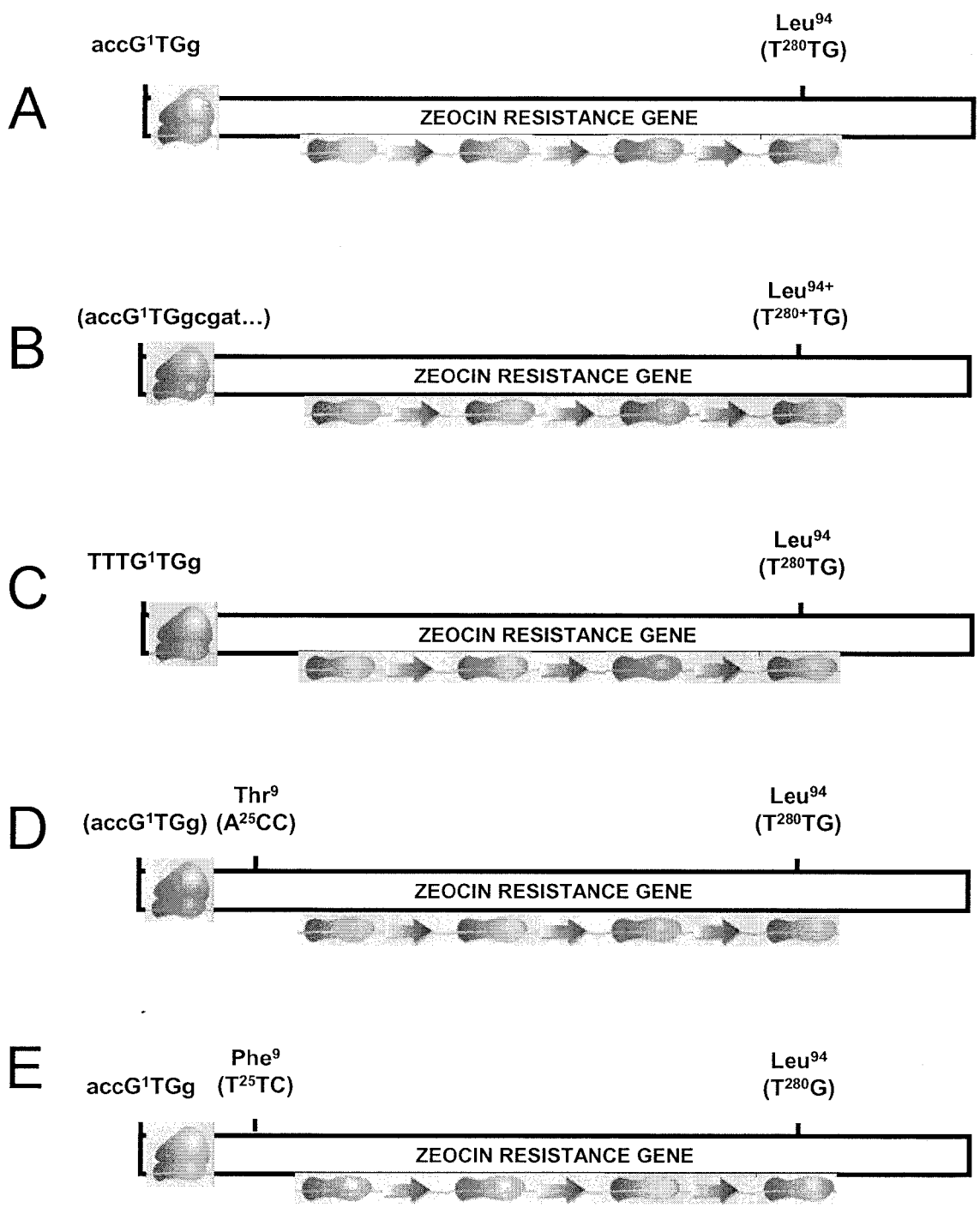
FIGS. 22A-22E. Schematic representation of some further modified ZEOCIN®-resistance selection marker genes with a GTG start codon hereof, allowing for further fine-tuning of the selection stringency. See, Example 7 for details.
Figure 23:
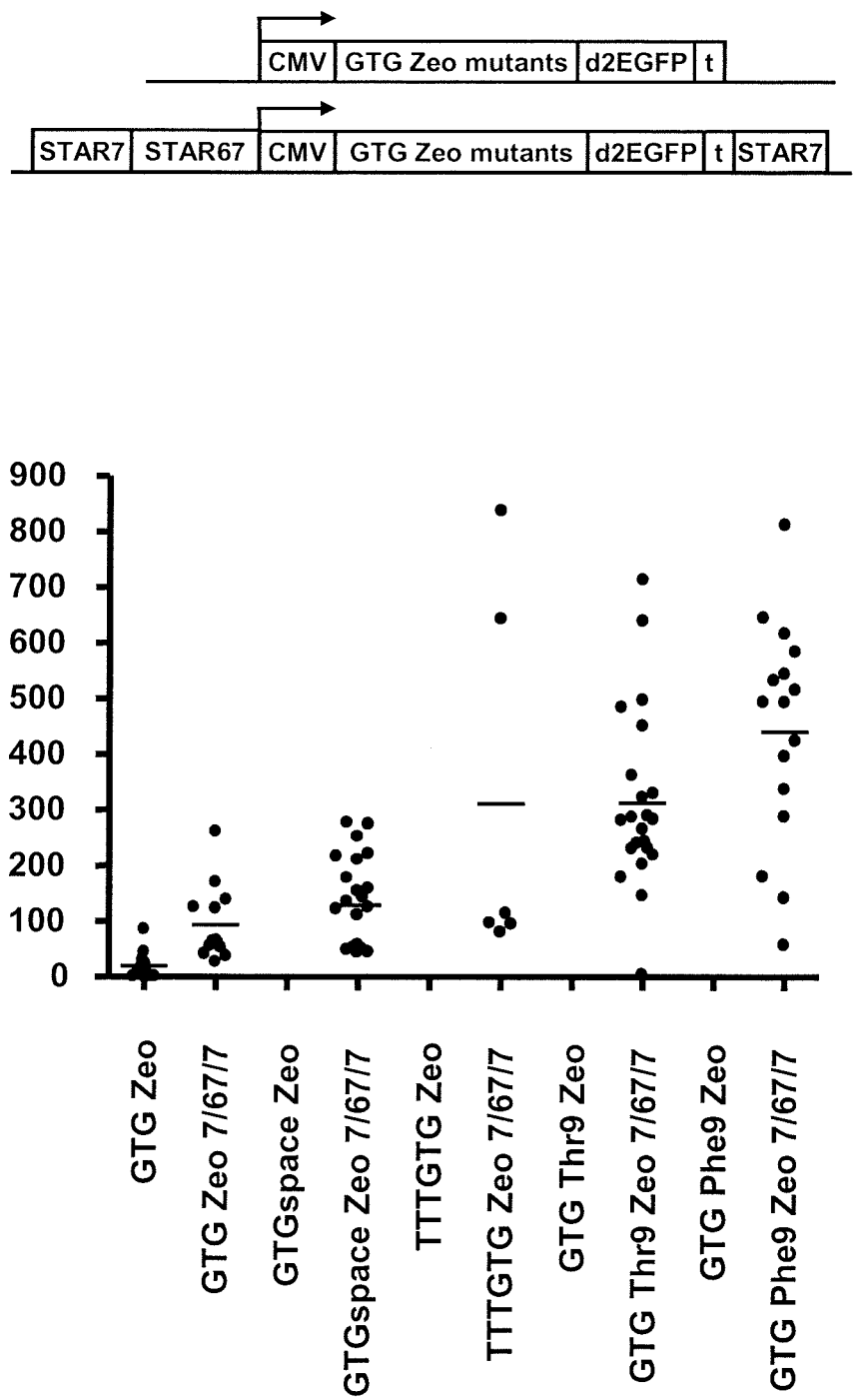
FIG. 23. Results with expression systems containing the further modified ZEOCIN®-resistance selection marker genes. See, Example 7 for details. Dots indicate individual data points; lines indicate the average expression levels; used constructs (see, also FIG. 22) are indicated on the horizontal axis (the addition of 7/67/7 at the end of the construct name indicates the presence of STAR sequences 7 and 67 upstream of the promoter and START downstream of the transcription termination site), and schematically depicted above the graph; vertical axis indicates d2EGFP signal.

Results: CHO-K1 cells were transfected with constructs that contain the GTG Zeo (FIG. 22A), GTGspace Zeo (FIG. 22B), TTT GTG Zeo (also called: GTGmut Zeo) (FIG. 22C), GTG Thr9 Zeo(leu) (FIG. 22D) and GTG Phe9 Zeo(leu) (FIG. 22D) genes as selection gene, all being cloned upstream of the d2EGFP reporter gene. These five constructs were without STAR elements (Control) or with STAR elements 7 and 67 upstream of the CMV promoter and STAR 7 downstream from the d2EGFP gene (FIG. 22). FIG. 23 shows that of the control constructs without STAR elements only the GTG Zeo construct without STAR elements gave colonies that expressed d2EGFP protein. In contrast, all constructs containing STAR elements gave colonies that expressed d2EGFP protein. The mean d2EGFP fluorescence signal of 11 GTG Zeo Control colonies was 20.3, of 13 GTG Zeo colonies with STARs 7/67/7 104.9, of 24 GTG space Zeo 7/67/7 colonies 201.5, of 6 TTT GTG Zeo 7/67/7 colonies 310.5, of 22 GTG Thr9 Zeo 7/67/7 colonies 423, and of 16 GTG Phe9 Zeo colonies 550.2 (FIG. 23).

The higher stringencies of the novel GTG mutations correlate with higher mean fluorescence signals (FIG. 23). The TTT GTG Zeo 7/67/7, however, gave only two high expressing colonies and a few low expressing colonies. This may indicate that this mutation is at the brink of the stringency that these cells can bear with a fixed concentration of ZEOCIN® added to the culture medium.

The Thr9 and Phe9 mutations do not influence the translation efficiency of the Zeo mutants. Instead they reduce the functionality of the ZEOCIN®-resistance protein, by preventing an optimal interaction between the two halves of the ZEOCIN®-resistance protein (Dumas et al., 1994). This implies that more of the protein has to be produced to achieve resistance against the ZEOCIN® in the culture medium. As a consequence, the entire cassette has to be transcribed at a higher level, eventually resulting in a higher d2EGFP expression level.

It is concluded that the use of the described translation efficiencies of the ZEOCIN®-resistance mRNA result in higher expression levels of the d2EGFP protein, this in combination with STAR elements.

This example further demonstrates the possibility to provide for fine-tuning of the stringency of the selection system hereof, to achieve optimal expression levels of a protein of interest. Clearly, the person skilled in the art will be capable of combining these and other possibilities within the concepts disclosed herein (e.g., mutate the ZEOCIN® at position 9 to other amino acids, or mutate it in other positions; use a GTG or other start codon in a non-optimal translation initiation context for ZEOCIN® or other selection markers; or mutate other selection markers to reduce their functionality, for instance use a sequence coding for a neomycin-resistance gene having a mutation at amino acid residue 182 or 261 or both, see, e.g., WO 01/32901), and the like, to provide for such fine-tuning, and by simply testing determine a suitable combination of features for the selection marker, leading to enhanced expression of the polypeptide of interest.

Example 8

Figure 24:
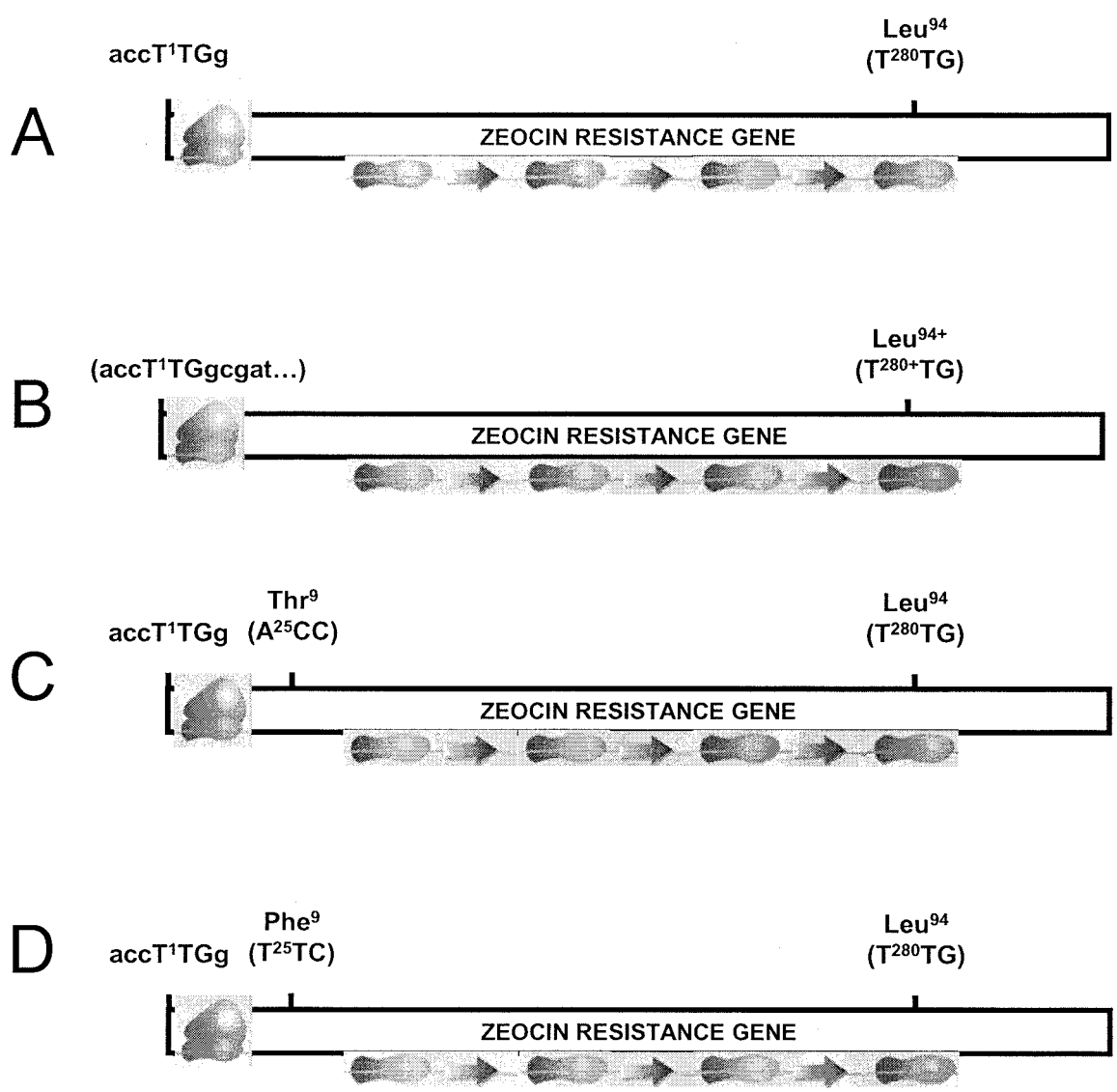
FIGS. 24A-24D. Schematic representation of some further modified ZEOCIN®-resistance selection marker genes with a TTG start codon hereof, allowing for further fine-tuning of the selection stringency. See, Example 8 for details.

Creation and Testing of Additional TTG ZEOCIN®-d2EGFP Bicistronic Constructs with Differential Translation Efficiencies Different versions of the ZEOCIN®-resistance gene with mutated start codons were described in Example 1. Besides the described TTG codons (FIG. 24A) additional modified start codons with distinct translational efficiency are possible. These different ZEOCIN®-resistance gene versions were created and cloned upstream of the modified d2EGFP gene (FIG. 24).

Creations of plasmids: Three additional TTG constructs were made:
1) TTG as a start codon in the Zeo resistance gene (FIG. 24A), but followed by a spacer sequence (FIG. 24B). The Zeo ORF (with the spacer sequence) was amplified with primer pair TTGspaceBamHIF (SEQ ID NO:110): GAATTCGGATCCACC TTGGCGATCCAAAGACTGCCAAATC TAG and ZEOWTreverse (SEQ ID NO:69), the PCR product was cut with EcoRI-BamHI, and ligated into pd2EGFP, cut with EcoRI-BamHI, creating pZEO-TTGspace-d2EGFP.
2) TTG as a start codon in the Zeo resistance gene, instead of ATG (FIG. 24A), but with an additional mutation in the Zeo ORF at Pro9, with was replaced with threonine (Thr) (FIG. 24C). The Thr9 mutation was introduced by amplifying the Zeo open reading with primer pair ZEO-ForwardTTG-Thr9 (SEQ ID NO:111): AATTGGATC-CACCTTGGCCAAGTTGACCAGTGCCGT T ACC GTGCTC and ZEOWTreverse (SEQ ID NO:69), the PCR product was cut with EcoRI-BamHI, and ligated into pd2EGFP, cut with EcoRI-BamHI, creating pZEO-TTG-Thr9-d2EGFP.
3) TTG as a start codon in the Zeo resistance gene, instead of ATG (FIG. 24A), but with an additional mutation in the Zeo ORF at Pro9, with was replaced with Phenylalanine (Phe) (FIG. 24D). The Phe9 mutation was introduced by amplifying the Zeo open reading with primer pair ZEOForwardTTG-Phe9 (SEQ ID NO:112): AAT-TGGATCCACCTTGGCCAAGTTGACCAGTGCC GTT *TTC* GTGCTC and ZEOWTreverse (SEQ ID NO:69), the PCR product was cut with EcoRI-BamHI, and ligated into pd2EGFP, cut with EcoRI-BamHI, creating pZEO-TTG-Phe9-d2EGFP.

Results: CHO-K1 cells were transfected with constructs that contain the TTG Zeo (FIG. 24A), TTGspace Zeo (FIG. 24B), TTG Thr9 Zeo (FIG. 24C) and TTG Phe9 Zeo (FIG. 24D) genes as selection gene, all being cloned upstream of the d2EGFP reporter gene. These four constructs were without STAR elements (Control) or with STAR elements 7 and 67 upstream of the CMV promoter and STAR 7 downstream from the d2EGFP gene (FIG. 24). FIG. 25 shows that of the control constructs without STAR elements only the TTG Zeo construct without STAR elements gave colonies that expressed d2EGFP protein. In contrast, all constructs containing STAR elements gave colonies that expressed d2EGFP protein. The mean d2EGFP fluorescence signal of 3 TTG Zeo Control colonies was 26.8, of 24 TTG Zeo colonies with STARs 7/67/7 426.8, of 24 TTGspace Zeo 7/67/7 colonies 595.7, of 2 TTG Thr9 Zeo 7/67/7 colonies 712.1, and of 3 TTG Phe9 Zeo colonies 677.1 (FIG. 25).

The higher stringencies of the novel TTG mutations correlate with higher mean fluorescence signals (FIG. 25). The TTG Thr9 Zeo 7/67/7 and TTG Phe9 Zeo 7/67/7 constructs, however, gave only two high expressing colonies each and a few low expressing colonies. This may indicate that these mutations are at the brink of the stringency that the cells can bear with a fixed concentration of ZEOCIN® added to the culture medium.

It is concluded that the use of the described translation efficiencies of the ZEOCIN®-resistance mRNA result in higher expression levels of the d2EGFP protein, this in combination with STAR elements.

Example 9

Figure 26:
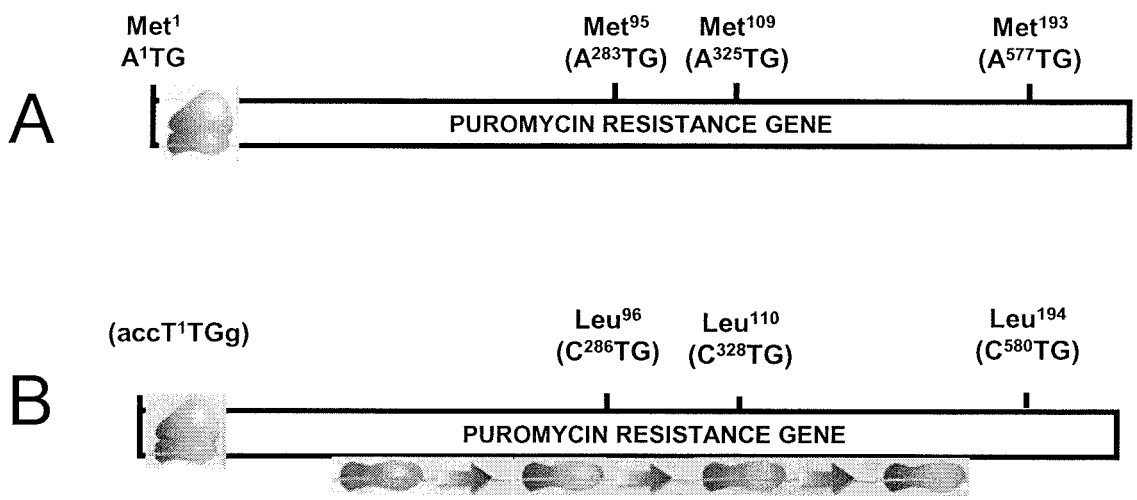
FIG. 26. As FIG. 1, but for the puromycin resistance gene. All three internal ATGs code for methione (panel A), and are replaced by CTG sequences coding for leucine (panel B). See, Example 9 for details.

Creation and Testing of Puromycin-d2EGFP Bicistronic Constructs with Differential Translation Efficiencies There are three internal ATGs in the puromycin resistance gene, each of which codes for a methionine (FIG. 17, FIG. 26A). These ATGs have to be eliminated (FIGS. 26B,C), since they will serve as start codon when the ATG start codon (or the context thereof) has been modified, and this will result in peptides that do not resemble puromycin resistance protein. More importantly, these ATGs will prevent efficient translation of the gene of interest, as represented by d2EGFP in this example for purposes of illustration. The methionines were changed into leucine, like in the ZEOCIN®-resistance protein (Example 1). However, instead of using the TTG codon for leucine (for instance in ZEOCIN® in Example 1), now the CTG codon for leucine was chosen (in humans, for leucine the CTG codon is used more often than the TTG codon). To eliminate the internal ATGs, the puromycin resistance protein ORF was first amplified with 4 primer pairs, generating 4 puromycin resistance protein fragments. The primer pairs were: PURO BamHI F (SEQ ID NO:113), PURO300 R LEU (SEQ ID NO:114); and PURO300FLEU (SEQ ID NO:115), PURO600RLEU (SEQ ID NO:116).

This generates two PCR products, corresponding to the 5' and 3' part of the puromycin resistance gene. The two products were added together and amplified with PURO BamHI F (SEQ ID NO:113)—PURO600RLEU (SEQ ID NO:116). The resulting PCR product was cut with BamHI-EcoRI and ligated, creating pCMV-ATGPURO (leu). Sequencing of this clone verified that all three internal ATGs had been converted. The entire puromycin ORF was then amplified with PUROBamHI TTG1F (SEQ ID NO:117): GAATTCG-GATCCACC<u>TTG</u>GTTACCGAGTACAAGCCCACGGTG and PURO600RLEU (SEQ ID NO:116). This primer introduces an extra codon (GTT) directly after the TTG start codon, because the "G" at nucleotide +4 is introduced for an optimal context, and hence two more nucleotides are introduced to preserve the reading frame.

Figure 27:
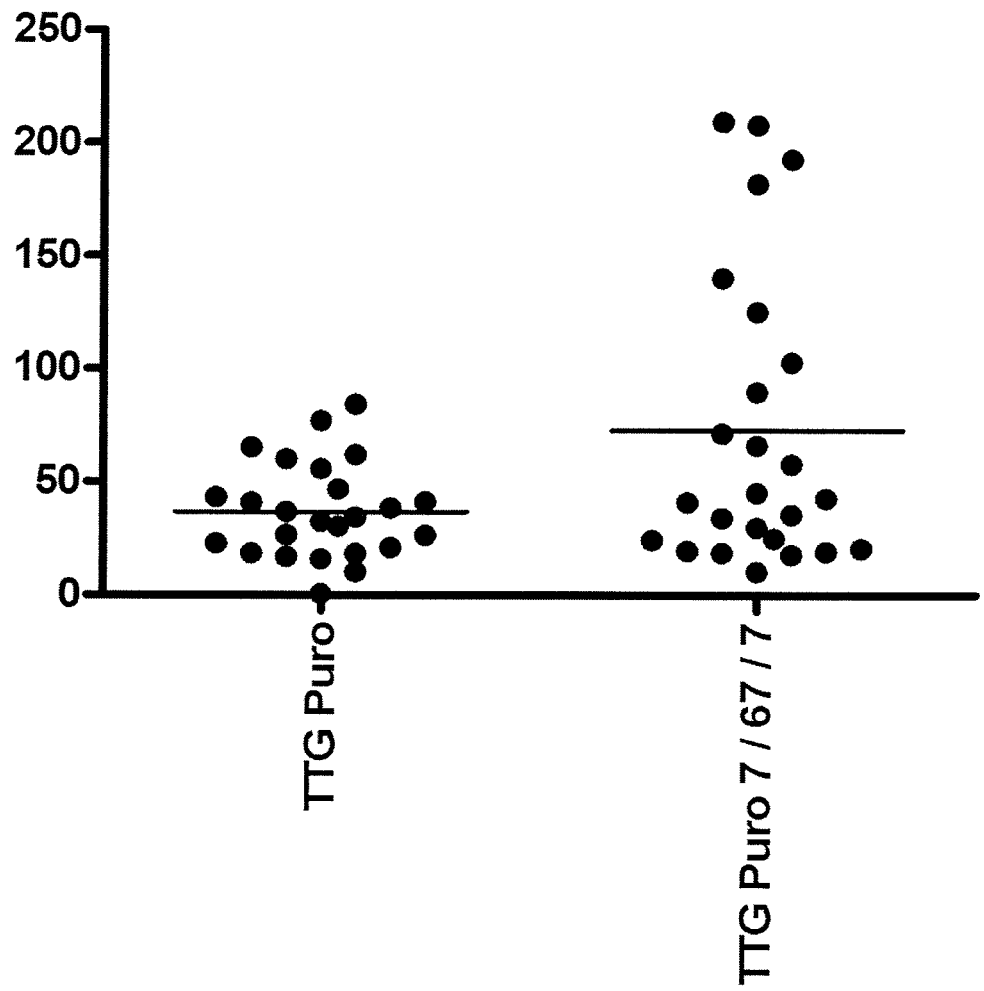
FIG. 27. Results with expression constructs containing the puromycin resistance gene with a TTG start codon and no internal ATG codons. See, Example 9 for details. Dots indicate individual data points; lines indicate the average expression levels; used constructs are indicated on the horizontal axis, and schematically depicted above the graph; vertical axis indicates d2EGFP signal.

Results: CHO-K1 cells were transfected with the construct that contains the TTG Puro (FIG. 27) gene as selection gene, cloned upstream of the d2EGFP reporter gene. Selection was under 10 µg/ml puromycin. The construct was without STAR elements (Control) or with STAR elements 7 and 67 upstream of the CMV promoter and STAR 7 downstream from the d2EGFP gene (FIG. 27). FIG. 27 shows that the average d2EGFP fluorescence signal of 24 TTG Puro Control colonies was 37.9, of 24 TTG Puro colonies with STARs 7/67/7 75.5. Moreover, when the average of the five highest values is taken, the d2EGFP fluorescence signal of TTG Puro Control colonies was 69.5, and of TTG Puro colonies with STARs 7/67/7 186.1, an almost three-fold increase in d2EGFP fluorescence signal. This shows that the described, modified translation efficiency of the Puromycin resistance mRNA result in higher expression levels of the d2EGFP protein, this in combination with STAR elements.

This experiment demonstrates that the puromycin resistance gene can be mutated to remove the ATG sequences therefrom, while remaining functional. Moreover it is concluded that the selection method hereof also works with yet another selection marker, puromycin.

Example 10

Figure 28:
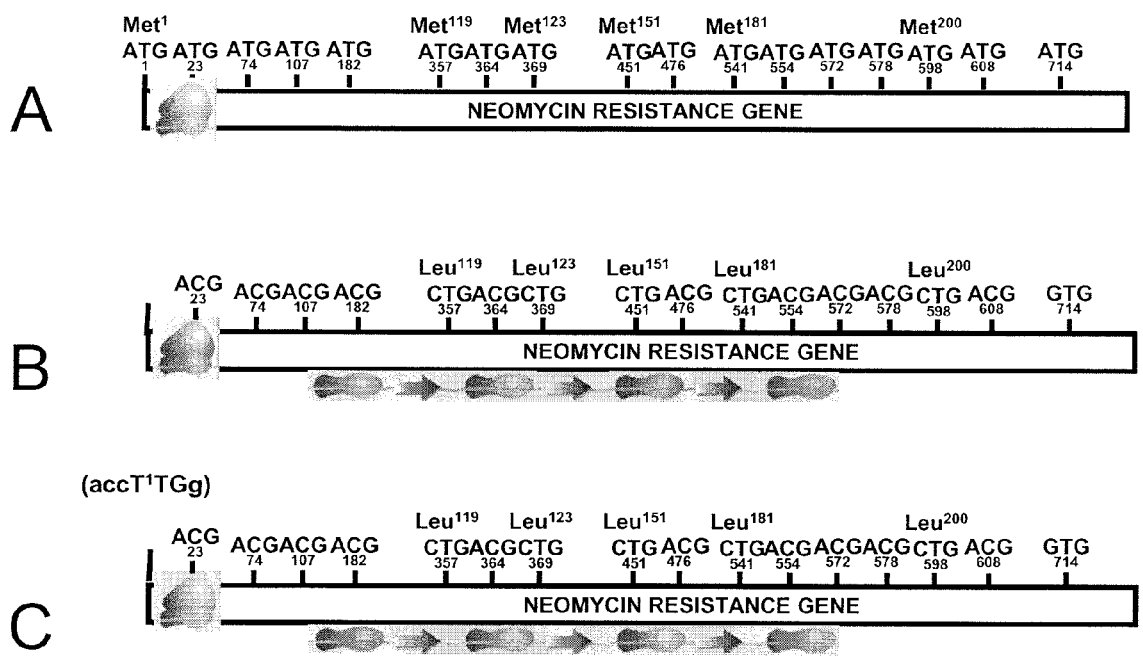
FIG. 28. As FIG. 1, but for the neomycin-resistance gene. See, Example 10 for details. A. wild-type neomycin-resistance gene; ATG sequences are indicated, ATGs coding for methionine are indicated by Met above the ATG. B. Neomycin-resistance gene without ATG sequences, and with a GTG start codon. C. Neomycin-resistance gene without ATG sequences, and with a TTG start codon.

Creation and Testing of Neomycin Constructs with Differential Translation Efficiencies There are sixteen internal ATGs in the neomycin-resistance gene, five of which code for a methionine in the neomycin ORF (FIG. 20, FIG. 28A). All these sixteen ATGs have to be eliminated (FIGS. 28B,C), since they will serve as start codon when the ATG start codon (or the context thereof) has been modified, and this will result in peptides that do not resemble neomycin-resistance protein, and this will decrease the translation from the downstream ORF coding for the polypeptide of interest in the transcription units hereof. To eliminate the internal ATGs, the neomycin-resistance protein ORF was entirely synthesized by a commercial provider (GeneArt, Germany), wherein all internal coding ATGs (for Met) where replaced by CTGs (coding for Leu), and non-coding ATGs were replaced such that a degenerated codon was used and hence no mutations in the protein sequence resulted; the synthesised sequence of the neomycin is given in SEQ ID NO:118. In order to replace the ATG start codon with GTG (FIG. 28B) or TTG FIG. 28C), the synthesized neomycin gene was amplified with primer pairs NEO-F-HindIII (SEQ ID NO:120) and NEO EcoRI 800R (SEQ ID NO:121).

Results: *E. coli* bacteria were used to test the functionality of the neomycin-resistance protein from which all ATGs were removed. *E. coli* bacteria were transformed with the constructs that contain the GTG Neo (FIG. 28B) or TTG Neo (FIG. 28C) gene as selection gene. Selection took place by growing the bacteria on kanamycin. Only a functional neomycin-resistance gene can give resistance against kanamycin. Transformation with either modified Neo gene resulted in the formation of *E. coli* colonies, from which the plasmid containing the gene could be isolated. This shows that the described, modified translation efficiencies of the neomycin-resistance mRNAs, as well as the removal of all ATGs from the Neo ORF result in the production of functional neomycin-resistance protein.

The mutated neomycin-resistance genes are incorporated in a multicistronic transcription unit hereof, and used for selection with G418 or neomycin in eukaryotic host cells.

Example 11

Figure 29:
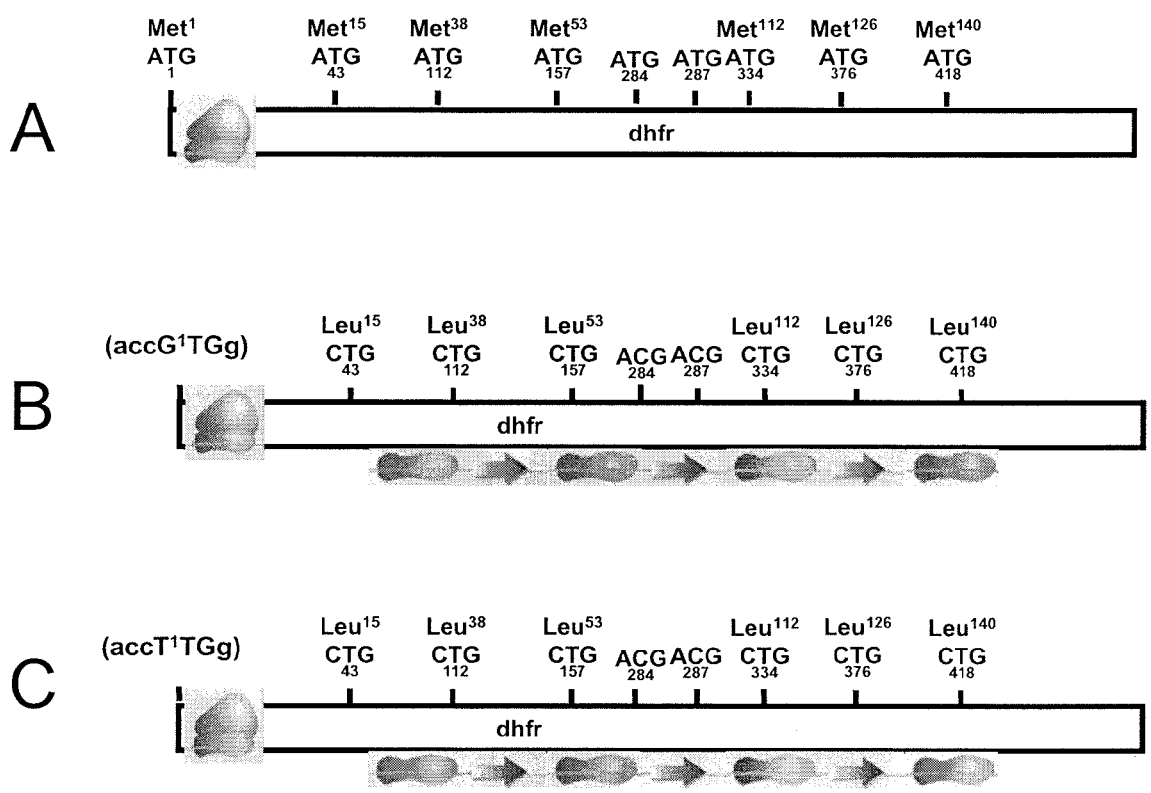
FIG. 29. As FIG. 1, but for the dhfr gene. See, Example 11 for details. A. wild-type dhfr gene; ATG sequences are indicated, ATGs coding for methionine are indicated by Met above the ATG. B. dhfr gene without ATG sequences, and with a GTG start codon. C. dhfr gene without ATG sequences, and with a TTG start codon.

Creation and Testing of dhfr Constructs with Differential Translation Efficiencies There are eight internal ATGs in the dhfr gene, six of which code for a methionine in the dhfr ORF (FIG. 18, FIG. 29A). All these ATGs have to be eliminated (FIGS. 29B,C), since they will serve as start codon when the ATG start codon (or the context thereof) has been modified, and this will result in peptides that do not resemble dhfr protein, and will decrease the translation from the downstream ORF coding for the polypeptide of interest in the transcription units hereof. To eliminate the internal ATGs, the dhfr protein ORF was entirely synthesized (SEQ ID NO:122), as described above for neomycin. In order to replace the ATG start codon with GTG (FIG. 29B) or TTG (FIG. 29C), the synthesized DHFR gene was amplified with primers DHFR-F-HindIII (SEQ ID NO:124) and DHFR-EcoRI-600-R (SEQ ID NO:125).

Results: *E. coli* bacteria were used to test the functionality of the dhfr protein from which all ATGs were removed. *E. coli* was transformed with the constructs that contain the GTG dhfr (FIG. 29B) or TTG dhfr (FIG. 29C) gene. Selection took place by growing the bacteria on trimethoprim (Sigma T7883-56). Only a functional dhfr gene can give resistance against trimethoprim. Transformation with either modified dhfr gene resulted in the formation of *E. coli* colonies, from which the plasmid containing the gene could be isolated. This shows that the described, modified translation efficiencies of the dhfr mRNAs, as well as the removal of all ATGs from the dhfr ORF result in the production of functional dhfr protein.

The mutated dhfr genes are incorporated in a multicistronic transcription unit hereof, and used for selection with methotrexate in eukaryotic host cells.

Example 12

Testing of ZEOCIN® and Blasticidin Constructs with Differential Translation Efficiencies in PER.C6® Cells Various ZEOCIN® and blasticidin genes with mutated start codons—all cloned upstream of the d2EGFP gene—were tested in the PER.C6® cell line.

Results: The GTG ZEOCIN® and GTGspace ZEOCIN®-resistance gene modifications (see, Example 7; FIG. 30) and the GTG blasticidin and TTG blasticidin resistance gene modifications (see, Example 4; FIG. 31), all cloned upstream of the d2EGFP gene were transfected to PER.C6® cells. As shown in FIG. 30, transfection with both the GTG ZEOCIN® and GTGspace ZEOCIN® genes resulted in colonies that expressed d2EGFP. The average d2EGFP fluorescence signal of 20 GTG Zeo colonies was 63.8, while the average d2EGFP signal of 20 GTGspace Zeo colonies was 185, demonstrating that in PER.C6® cells the GTGspace Zeo has a higher translation stringency than the GTG Zeo mRNA.

As shown in FIG. 31, transfection with both the GTG Blasticidin and TTG Blasticidin gene resulted in colonies that expressed d2EGFP. The average d2EGFP fluorescence signal of 20 GTG Blasticidin colonies was 71.4, while the average d2EGFP fluorescence signal of 20 TTG Blasticidin colonies was 135, demonstrating that also in PER.C6® cells the TTG Blasticidin has a higher translation stringency than the GTG Blasticidin mRNA.

This example demonstrates that the selection system can also be used in other cells than CHO cells.

Example 13

Testing of the Addition of a Transcriptional Pause Signal to a TTG ZEOCIN®-d2EGFP Construct A TRAnscription Pause (TRAP) sequence is thought to, at least in part, prevent formation of antisense RNA or, to at least in part, prevent transcription to enter the protein expression unit (see, WO 2004/055215). A TRAP sequence is functionally defined as a sequence that when placed into a transcription unit, results in a reduced level of transcription in the nucleic acid present on the 3' side of the TRAP when compared to the level of transcription observed in the nucleic acid on the 5' side of the TRAP, and non-limiting examples of TRAP sequences are transcription termination signals. In order to function to prevent or decrease transcription to enter the transcription unit, the TRAP is placed upstream of a promoter driving expression of the transcription unit and the TRAP should be in a 5' to 3' direction. In order to prevent (at least in part) formation of antisense RNA, the TRAP should be located downstream of the ORF in a transcription unit and present in a 3' to 5' direction (that is, in the opposite orientation of the normal orientation of a transcriptional termination sequence that is usually present behind the ORF in a transcription unit). A combination of a TRAP upstream of the promoter in a 5' to 3' orientation and a TRAP downstream of the ORF in a 3' to 5' orientation is preferred. Adding a TRAP sequence to a STAR element improves the effects of STAR elements on transgene expression (see, WO 2004/055215). Here we test the effects of the TRAP sequence in the context of the TTG Zeo resistance gene.

Figure 32:
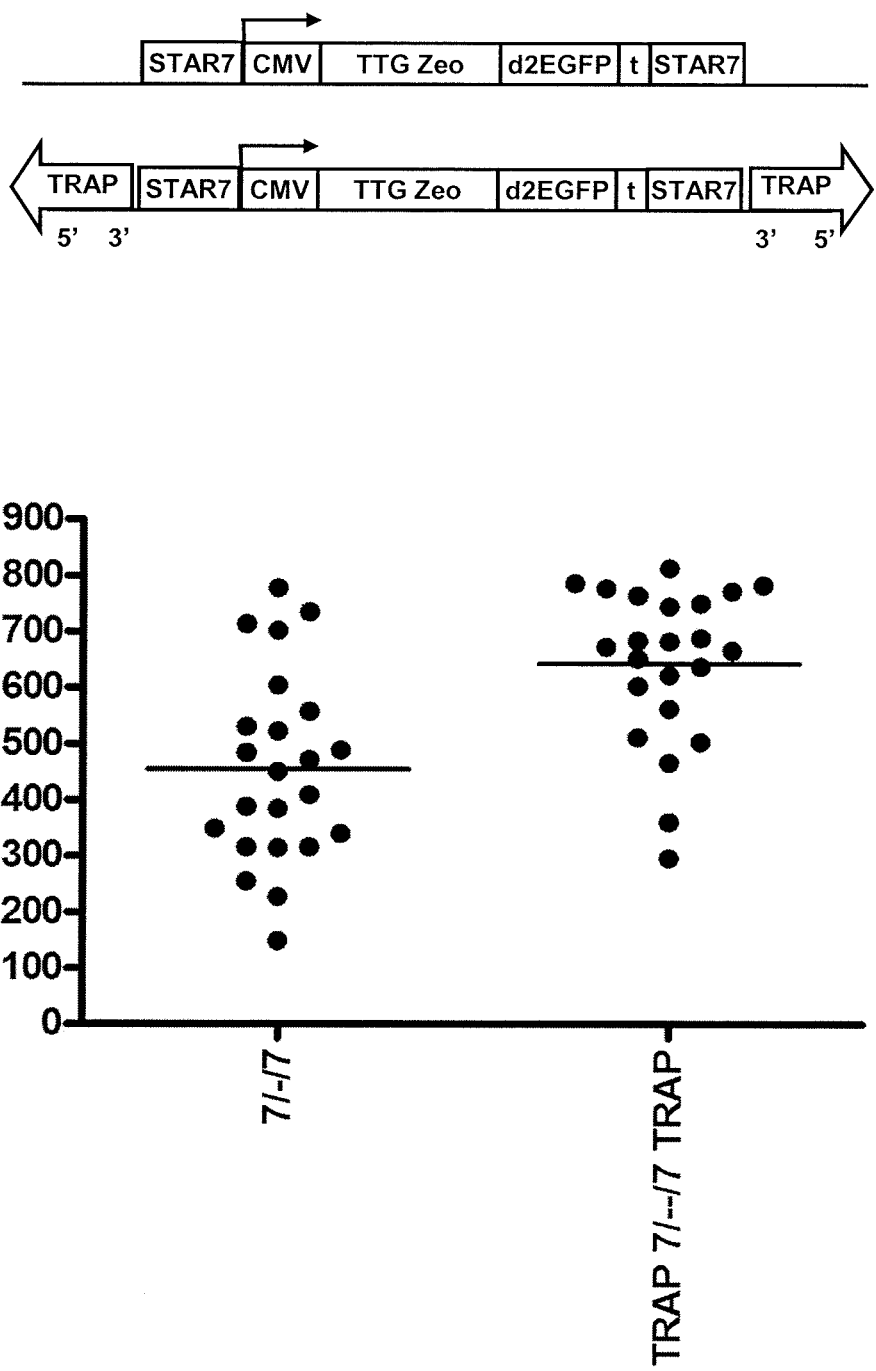
FIG. 32. Results with expression constructs of the incorporated '525 application, further comprising a transcription pause (TRAP) sequence. See, Example 13 for details. Dots indicate individual data points; lines indicate the average expression levels; used constructs are indicated on the horizontal axis, and schematically depicted above the graph; vertical axis indicates d2EGFP signal.
Figure 43:
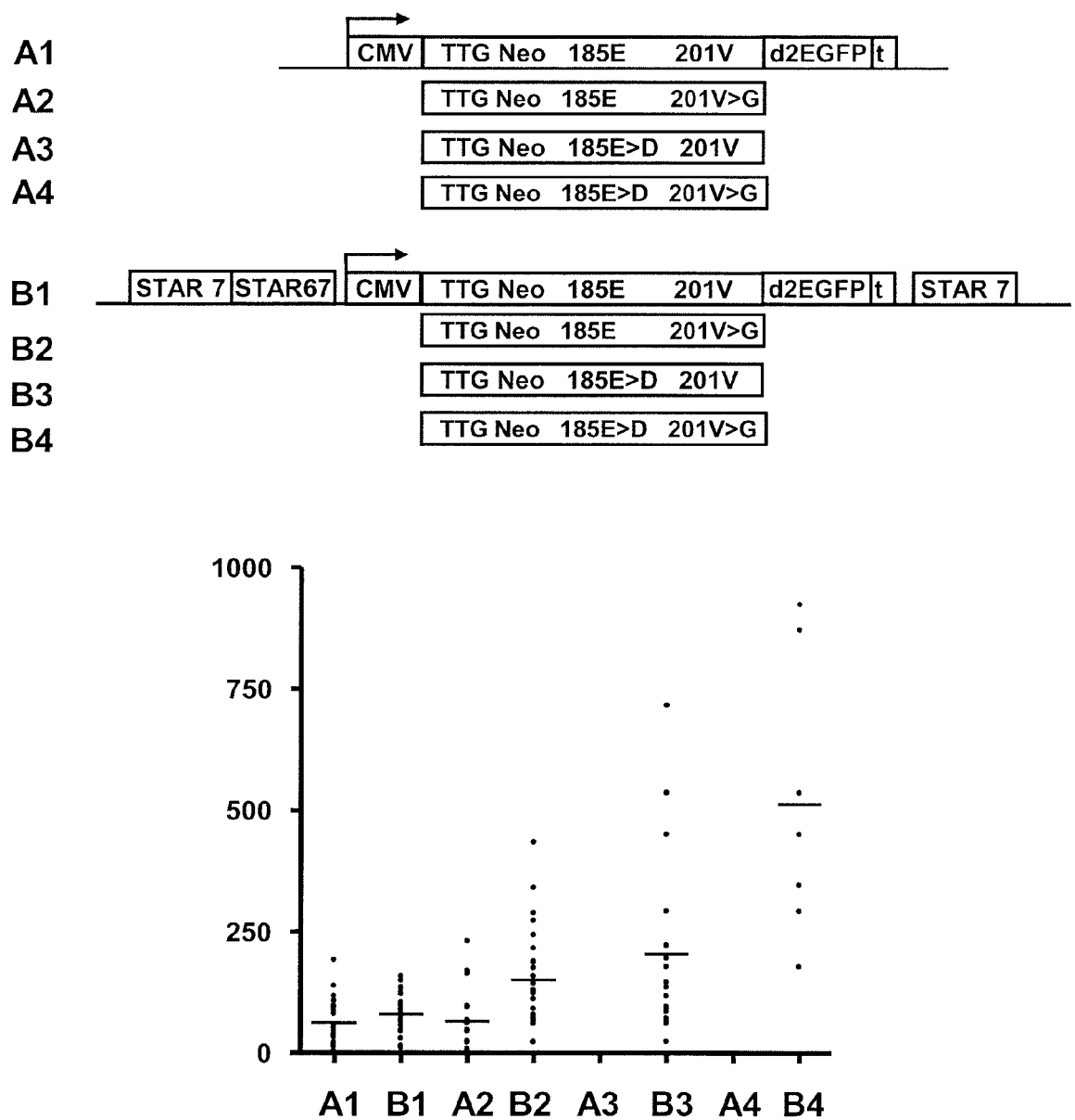
FIG. 43. Results with "CpG poor" neomycin-resistance marker having different mutations. Dots indicate individual data points; lines indicate the average expression levels; vertical axis indicates d2EGFP signal. See, Example 23 for details.

Results: The TTG ZEOCIN®-d2EGFP cassette that was flanked with STAR7 elements (FIG. 32) was modified by the addition of the SPA/pause TRAP sequence (see, WO 2004/055215); SEQ ID NO:126), both upstream of the 5' STAR7 (in 5' to 3' direction) and downstream of the 3' STAR7 (in 3' to 5' direction) (FIG. 32). Both STAR 7/7 and TRAP-STAR 7/7-TRAP containing vectors were transfected to CHO-K1. Stable colonies were isolated and the d2EGFP fluorescence intensities were measured. As shown in FIG. 43 the average d2EGFP fluorescence signal of 23 TTG Zeo STAR 7/7 colonies was 455.1, while the average d2EGFP fluorescence signal of 23 TTG Zeo TRAP-STAR 7/7-TRAP colonies was 642.3. The average d2EGFP fluorescence signal in highest 5 TTG Zeo STAR 7/7 colonies was 705.1, while the average d2EGFP fluorescence signal of 5 TTG Zeo TRAP-STAR 7/7-TRAP colonies was 784.7.

This result indicates that the addition of TRAPs does not enhance the d2EGFP fluorescence signal in the highest colonies, but that there is a significant raise in the number of high expressing colonies. Whereas only 5 TTG Zeo STAR 7/7 colonies had d2EGFP signal above 600, 17 TTG Zeo TRAP-STAR 7/7-TRAP colonies had a d2EGFP fluorescence signal above 600.

In the experiment 3 μg DNA of each plasmid was transfected. However, whereas the transfection efficiency was similar, the total number of colonies with the TTG Zeo STAR 7/7 plasmid was 62, while the total number of colonies with the TTG Zeo TRAP-STAR 7/7-TRAP plasmid was 116, almost a doubling.

We conclude that addition of TRAP elements to the STAR containing plasmids with modified ZEOCIN®-resistance gene translation codons results in a significantly higher overall number of colonies and that more colonies are present with the highest expression levels.

Example 14

Copy-Number Dependency of Expression

We analyzed the EpCAM antibody expression levels in relation to the number of integrated EpCAM DNA copies.

Results: The construct that was tested was TTG-Zeo-Light Chain (LC)-TTG-Blas-Heavy Chain (HC), both expression units being under the control of the CMV promoter (see, FIG. 33). This construct contained STAR 7 and 67 (see, FIG. 33). Selection conditions were such that with 200 μg/ml ZEOCIN® and 20 μg/ml blasticidin in the culture medium no control colonies (no STARs) survived and only STAR 7/67/7 colonies survived.

DNA was isolated when colonies were 60 days under ZEOCIN® and blasticidin selection pressure (see, FIG. 33). The $R^2$ value is calculated and shown. In the entire range from 5 to 40 pg/cell/day EpCAM there was a high degree of copy number dependency, as signified by a relatively high $R^2$ of 0.5978 (FIG. 33). The data show that in the novel selection system, in colonies that contain TTG Zeo-TTG Blas EpCAM STAR 7/67/7 constructs there is copy number dependent EpCAM expression.

Example 15

Methotrexate Induction of Higher EpCAM Expression

We analyzed EpCAM antibody expression levels after incubation of clones with methotrexate (MTX). The purpose of this experiment was to determine whether amplification of a STAR-containing construct would result in higher EpCAM expression. MTX acts through inhibition of the dhfr gene product. While some CHO strains that are dhfr-deficient have been described, CHO-K1 is dhfr⁺. Therefore relatively high concentrations of MTX in the culture medium have to be present to select for amplification by increased MTX concentrations in CHO-K1 cells.

Figure 34:
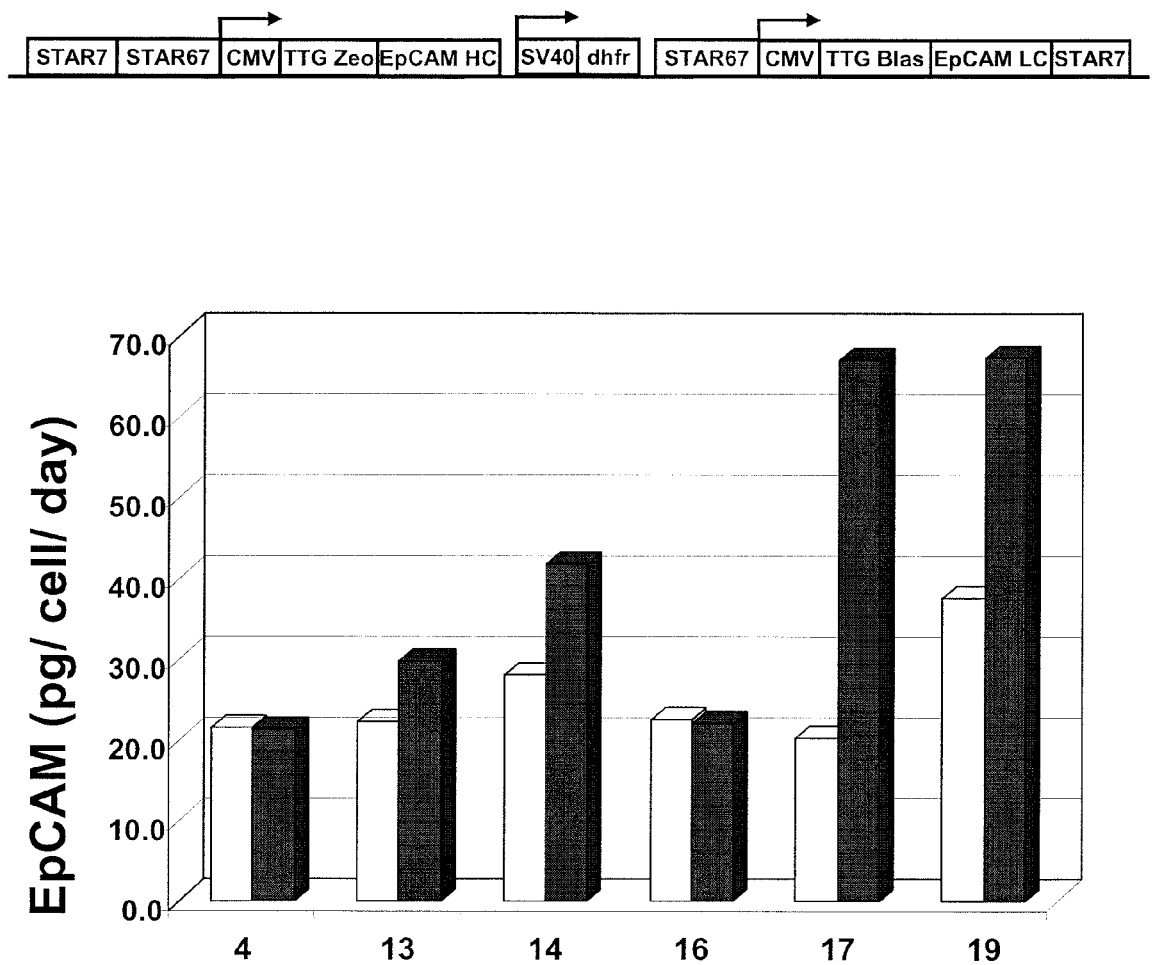
FIG. 34. Antibody expression from colonies containing expression constructs of the incorporated '525 application, wherein the copy number of the expression constructs is amplified by methotrexate. See, Example 15 for details. White bars: selection with ZEOCIN® and blasticidin; black bars: selection with ZEOCIN®, blasticidin and methotrexate (MTX). Numbers of tested colonies are depicted on the horizontal axis.

Results: The construct that was tested was TTG-Zeo-Heavy Chain (HC)-TTG-Blas-Light Chain (LC), both expression units being under the control of the CMV promoter. Upstream of each CMV promoter STAR67 was positioned and START was used to flank the entire cassette (see, also Example 6, FIG. 11 for such a construct). This construct was further modified by placing an SV40-dhfr cassette (a mouse dhfr gene under control of an SV40 promoter) between the HC and LC cassettes, upstream of the second STAR67 (FIG. 34). CHO-K1 cells were transfected. Selection was done with 100 µg/ml ZEOCIN® and 10 µg/ml Blasticidin in the culture medium. No control colonies (without STAR elements) survived and only colonies with constructs containing the STAR elements survived. Colonies were isolated and propagated before measuring EpCAM expression levels. Six colonies that produced between 20 and 35 pg/cell/day were transferred to medium containing 100 nM MTX. This concentration was raised to 500 nM, 1000 nM and finally to 2000 nM with two weeks periods in between each step. After two weeks on 2000 nM MTX, EpCAM concentrations were measured. As shown in FIG. 34, four colonies showed enhanced EpCAM production. Colony 13: from 22 to 30; colony 14: from 28 to 42; colony 17: from 20 to 67 and colony 19: from 37 to 67 pg/cell/day. Colonies 4 and 16 showed no enhanced EpCAM expression. We conclude that addition of methotrexate to the culture medium of CHO-K1 colonies created with the selection system hereof can result in enhanced protein expression. Hence, STAR elements and the selection method hereof can be combined with and are compatible with MTX-induced enhancement of protein expression levels.

Example 16

TTG-Zeo Selection Operates in the Context of Different Promoters

We analyzed d2EGFP expression levels in the context of the TTG Zeo selection marker and different promoters. We compared the action of STAR elements in the context of the CMV enhancer/promoter, the SV40 enhancer/promoter and the CMV enhancer/β-actin promoter.

Results: In FIG. 35 we indicate the promoters we tested in the context of the TTG Zeo selection marker. The tested plasmids consisted of the indicated control constructs with three different promoters and STAR constructs which were flanked with STAR 7 and STAR 67 at the 5' end and STAR 7 at the 3' end. The constructs were transfected to CHO-K1 cells and selection was performed with 200 µg/ml ZEOCIN® in the culture medium. Up to 23 independent colonies were isolated and propagated before analysis of d2EGFP expression levels. As shown in FIG. 35, incorporation of STAR elements in constructs with the CMV enhancer/promoter, the SV40 enhancer/promoter or the CMV enhancer/β-actin promoter all resulted in the formation of colonies with higher d2EGFP expression levels than with the corresponding control constructs. This shows that the selection system hereof, in combination with STAR elements, operates well in the context of different promoters. Further analysis showed that the mean of CMV-driven d2EGFP values was significantly higher than the mean of SV40-driven d2EGFP values ($p<0.05$). In contrast, the mean of CMV-driven d2EGFP values did not significantly differ from CMV/β actin-driven d2EGFP values ($p=0.2$).

Example 17

Comparison of Different STAR Elements in the TTG-Zeo Selection System

We analyzed d2EGFP expression levels in the context of the CMV promoter-TTG Zeo selection marker and 53 different STAR elements, to obtain more insight into which STAR elements give the best results.

Figure 36:
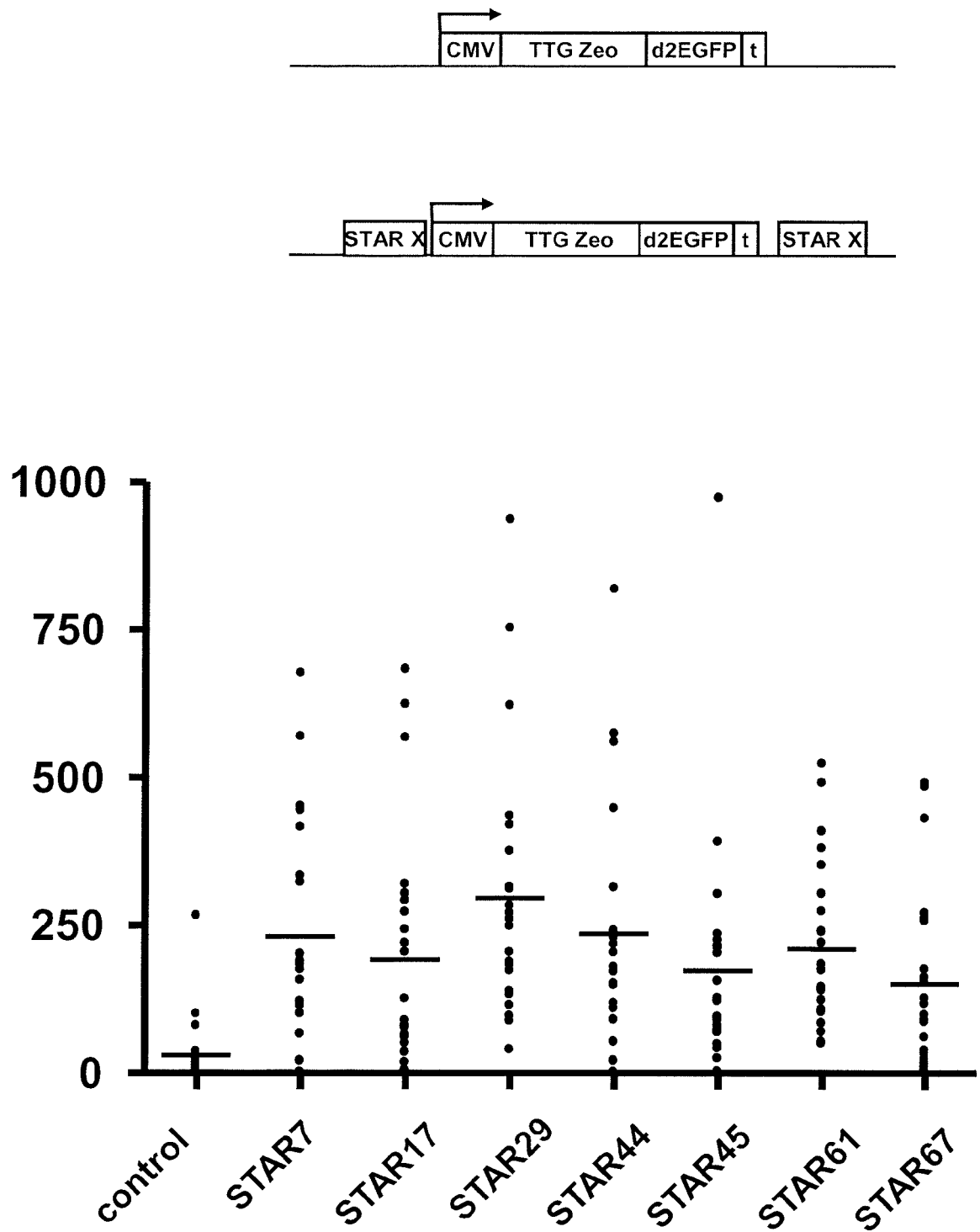
FIG. 36. Results with different STAR elements. See, Example 17 for details. Dots indicate individual data points; lines indicate the average expression levels; used constructs are indicated on the horizontal axis, and schematically depicted above the graph; vertical axis indicates d2EGFP signal.

Results: We cloned 53 STAR elements up- and downstream of the CMV promoter-TTG Zeo-d2EGFP cassette. The following STAR elements were tested in such constructs: STAR2-12, 14, 15, 17-20, 26-34, 36, 37, 39, 40, 42-49, 51, 52, 54, 55, 57-62, 64, 65, 67. The constructs were transfected to CHO-K1 cells and selection was performed with 200 µg/ml ZEOCIN® in the culture medium. Up to 24 independent colonies were isolated and propagated before analysis of d2EGFP expression levels. Incorporation of STAR elements in the constructs resulted in different degrees of enhanced d2EGFP expression, as compared to the control. Incorporation of STAR elements 14, 18 and 55 in this experiment did not result in an increase of average d2EGFP expression over the control (no STAR element). Although some constructs (with STAR elements 2, 3, 10, 42, 48 and 49) in this experiment gave rise to only a few colonies, all tested STAR elements except 14, 18 and 55 resulted in average d2EGFP expression levels higher than for the control. It should be noted that some STAR elements may act in a more cell type specific manner and that it is well possible that STAR 14, 18 and 55 work better in other cell types, with other promoters, other selection markers, or in different context or configuration than in the particular set of conditions tested here. Addition of 10 STAR elements, namely STAR elements 7, 9, 17, 27, 29, 43, 44, 45, 47 and 61, induced average d2EGFP expression levels higher than 5 times the average d2EGFP expression level of the control. We retransformed the control and 7 constructs with STAR elements and repeated the experiment. The results are shown in FIG. 36. Incorporation of STAR elements in the constructs resulted in different degrees of enhanced d2EGFP expression, as compared to the control (FIG. 47). The average d2EGFP expression level in colonies transfected with the control construct was 29. The averages from d2EGFP expression levels in colonies with the 7 different STAR constructs ranged between 151 (STAR 67) and 297 (STAR 29). This is a factor of 5 to 10-fold higher than the average in the control colonies.

We conclude that a) the vast majority of STAR elements have a positive effect on gene expression levels, b) there is variation in the degree of positive effects induced by the different STAR elements, and c) 10 out of 53 tested STAR elements induce more than 5-fold average d2EGFP expression levels, as compared to the control, and that STAR elements can induce a 10-fold higher average d2EGFP expression level, as compared to the control.

Example 18

Other Chromatin Control Elements in the Context of a Selection System Hereof

DNA elements such as the HS4 hypersensitive site in the locus control region of the chicken β-globin locus (Chung et al., 1997), matrix attachment regions (MAR) (Stief et al., 1989) and a ubiquitous chromatin opening element (UCOE) (Williams et al., 2005) have been reported to have beneficial effects on gene expression when these DNA elements are incorporated in a vector. We combined these DNA elements with the selection system hereof.

Results: The 1.25 kb HS4 element was cloned into the cassette encompassing the CMV promoter, TTG Zeo and d2EGFP by a three way ligation step to obtain a construct with a tandem of 2 HS4 elements (Chung et al., 1997). This step was done both for the 5' and 3' of the cassette encompassing the CMV promoter, TTG Zeo and d2EGFP. The 2959 bp long chicken lysozyme MAR (Stief et al., 1989) was cloned 5' and 3' of the cassette encompassing the CMV promoter, TTG Zeo and d2EGFP. The 2614 bp long UCOE (Williams et al., 2005) was a NotI-KpnI fragment, excised from a human BAC clone (RP11-93D5), corresponding to nucleotide 29449 to 32063. This fragment was cloned 5' of the CMV promoter. The STAR construct contained STAR7 and STAR67 5' of the CMV promoter and STAR73' of the cassette. These four constructs, as well as the control construct without flanking chromatin control DNA elements, were transfected to CHO-K1 cells. Selection was performed by 200 µg/ml ZEOCIN® in the culture medium. Colonies were isolated, propagated and d2EGFP expression levels were measured. As shown in FIG. 37, constructs with all DNA elements resulted in the formation of d2EGFP expressing colonies. However, incorporation of 2×HS4 elements and the UCOE did not result in the formation of colonies that displayed higher d2EGFP expression levels, in comparison with the control colonies. In contrast, incorporation of the lysozyme MAR resulted in the formation of colonies that expressed d2EGFP significantly higher. The mean expression level induced by MAR containing constructs was four-fold higher than in the control colonies. Best results were obtained, however, by incorporating STAR 7 and 67 in the construct. An almost ten-fold increase in the mean d2EGFP expression level was observed, as compared to the control colonies. We conclude that other chromatin control DNA elements such as MARs can be used in the context of the selection system hereof. However, the best results were obtained when STAR elements were used as chromatin control elements.

Example 19

Stringent Selection by Placing a Modified ZEOCIN® Resistance Gene Behind an IRES Sequence The previous examples (all from the incorporated '525 application) have shown a selection system where a sequence encoding a selectable marker protein is upstream of a sequence encoding a protein of interest in a multicistonic transcription unit, and wherein the translation initiation sequence of the selectable marker is non-optimal, and wherein further internal ATGs have been removed from the selectable marker coding sequence. This system results in a high stringency selection system. For instance, the Zeo selection marker wherein the translation initiation codon is changed into TTG was shown to give very high selection stringency, and very high levels of expression of the protein of interest encoded downstream.

In another possible selection system the selection marker, e.g., Zeo, is placed downstream from an IRES sequence. This creates a multicistronic mRNA from which the Zeo gene product is translated by IRES-dependent initiation. In the usual d2EGFP-IRES-Zeo construct, the Zeo start codon is the optimal ATG. It is therefore possible that changing the Zeo ATG start codon into, for instance, TTG (referred to as IRES-TTG Zeo) may result in increased selection stringencies compared to the usual IRES-ATG Zeo.

Results: The used constructs are schematically shown in FIG. 38. The control construct consisted of a CMV promoter, the d2EGFP gene, an IRES sequence (the sequence of the used IRES (Rees et al., 1996) in this example was SEQ ID NO:127), and a TTG Zeo selection marker, i.e., the ZEOCIN®-resistance gene with a TTG start codon ("d2EGFP-IRES-TTG Zeo"). The other construct was the same, but with a combination of STAR 7 and STAR 67 placed upstream of the expression cassette and STAR 7 downstream of the cassette ("STAR7/67 d2EGFP-IRES-TTG Zeo STAR7"). Both constructs were transfected to CHO-K1 cells and selection was performed with 100 µg/ml ZEOCIN® in the culture medium. Four colonies emerged after transfection with the control construct and six with the STAR containing construct. These independent colonies were isolated propagated before analysis of d2EGFP expression levels. As shown in FIG. 38, incorporation of STAR elements in the construct resulted in the formation of colonies with high d2EGFP expression levels. Of the control colonies without STAR elements ("d2EGFP-IRES-TTG Zeo") only one colony displayed some d2EGFP expression. The expression levels are also much higher than those obtained with other control constructs, containing the IRES with a normal Zeo with standard ATG start codon, either with or without STAR elements ("d2EGFP-IRES-ATG Zeo" and "STAR 7/67 d2EGFP-IRES-ATG Zeo STAR7"; also in these ATG Zeo constructs there was an enhancing effect of the STAR elements, but these are modest as compared to the novel TTG Zeo variant).

These results show that placing a Zeo selection marker with a TTG start codon downstream of an IRES sequence, in combination with STAR elements, operates well and establishes a stringent selection system.

From these data and the previous examples it will be clear that the marker can be varied along the same lines of the previous examples. For instance, instead of a TTG start codon, a GTG start codon can be used, and the marker can be changed from Zeo into a different marker, e.g., Neo, Blas, dhfr, puro, etc, all with either GTG or TTG as start codon. The STAR elements can be varied by using different STAR sequences or different placement thereof, or by substituting them for other chromatin control elements, e.g., MAR sequences. This leads to improvements over the prior art selection systems having an IRES with a marker with a normal ATG start codon.

As a non-limiting example, instead of the modified Zeo resistance gene (TTG Zeo) a modified neomycin-resistance gene is placed downstream of an IRES sequence. The modification consists of a replacement of the ATG translation initiation codon of the Neo coding sequence by a TTG translation initiation codon, creating TTG Neo. The CMV-d2EGF-IRES-TTG Neo construct, either surrounded by STAR elements or not, is transfected to CHO-K1 cells. Colonies are picked, cells are propagated and d2EGFP values are measured. This ("IRES-TTG Neo") leads to improvement over the known selection system having Neo with an ATG start codon downstream of an IRES ("IRES-ATG Neo"). The improvement is especially apparent when the TTG Neo construct comprises STAR elements.

Example 20

Increased Expression of Erythropoietin Using the Selection System

The previous examples (of the incorporated '525 and '953 applications) have shown selection systems based on altered translation initiation codons for the selectable marker gene, and have employed d2EGFP as test protein of interest, and antibodies as protein of interest. This example shows the applicability of a selection system hereof for improving protein expression levels of a secreted single chain protein that has therapeutic significance, viz. erythropoietin (EPO). EPO expression levels were analysed in the context of the TTG Zeo selection marker, using the CMV promoter and STAR elements in CHO cells.

STAR 7 and 67 were cloned to shield a TTG Zeo EPO cassette. Human EPO cDNA was derived from the plasmid pORF-hEPO (Invivogen). As control construct the TTG Zeo EPO cassette was not flanked with STAR elements (FIG. 39). In another control construct we used the IRES Zeo (with normal ATG start codon) configuration as selection system, considered the method giving the best results prior to the disclosure, which control construct was either flanked with STARs 7 and 67 or not (FIG. 39). The constructs were transfected to CHO-K1 cells with LIPOFECTAMINE® 2000 (Invitrogen) and selection was performed with 150 µg/ml ZEOCIN® in the culture medium. The culture medium consisted of HAMF12: DMEM=1:1, +10% foetal bovine serum. Up to 24 independent colonies were isolated and propagated before analysis of EPO expression levels. Per independent colony, $10^5$ cells were seeded and cultured in 6-well dishes for two days before cells were counted and the medium was collected. The amount of secreted human recombinant erythropoietin was determined using an ELISA-kit (R&D systems).

We found that the TTG Zeo-EPO control construct (A in FIG. 39) generated much less clones (5), as compared to the STAR containing TTG Zeo EPO construct (B in FIG. 39) (41 clones). Mean EPO expression levels increased from 3.3 pg/cell/day with the TTG Zeo-EPO control construct, to 17.7 pg/cell/day with the STAR containing TTG Zeo-EPO construct. The peak EPO expression level increased from respectively 5.5 to 28.3 pg/cell/day (FIG. 39). Also in comparison with the STAR containing EPO-IRES-Zeo construct (D in FIG. 39; 300 clones) and with the IRES construct without STARs (C in FIG. 39; 164 clones) we again found that much less clones were formed with the STAR containing TTG Zeo-EPO construct hereof (B in FIG. 39; 41 clones). Also, mean EPO expression levels increased from 9.0 pg/cell/day with the STAR containing EPO-IRES-Zeo control construct (D), to 17.7 pg/cell/day in the STAR containing TTG Zeo-EPO construct hereof (B; see FIG. 39).

The obtained EPO expression levels with the construct hereof are high in comparison to reported values of 12 pg/cell/day, which was achieved after gene amplification (Yoon et al., 2003, 2005). This result shows that the selection system hereof can readily be applied for the production of important therapeutic proteins, such as EPO. As shown in FIG. 39 incorporation of STAR elements gave significantly higher EPO expression levels. The results further demonstrate that STAR elements are able to increase EPO expression levels.

In an alternative embodiment, the EPO sequence is cloned upstream of an IRES, which IRES is operably linked to a sequence encoding ZEOCIN® resistance having a TTG start codon, analogously to example 19, and STAR sequences are included in the expression construct as described above. It is expected that also this embodiment will improve expression of EPO compared to the situation where the sequence encoding ZEOCIN® resistance has a normal ATG start codon (such as in situation D in FIG. 39).

Example 21

STAR Sequences Operate Well in the Context of the Selection System Hereof in CHO-DG44 Cells Several previous examples show the selection system hereof, with an impaired start codon for the selectable marker sequence, and preferably with the use of STAR sequences. In most cases in the examples above, CHO-K1 cells were used. CHO-DG44 is a different CHO cell line, which is dhfr⁻, and is a good suspension grower in contrast to CHO-K1, and hence has advantages for recombinant protein production on an industrial scale. Here it is shown that the selection system hereof works well with several tested STAR sequences also in the CHO-DG44 cell line.

Figure 40:
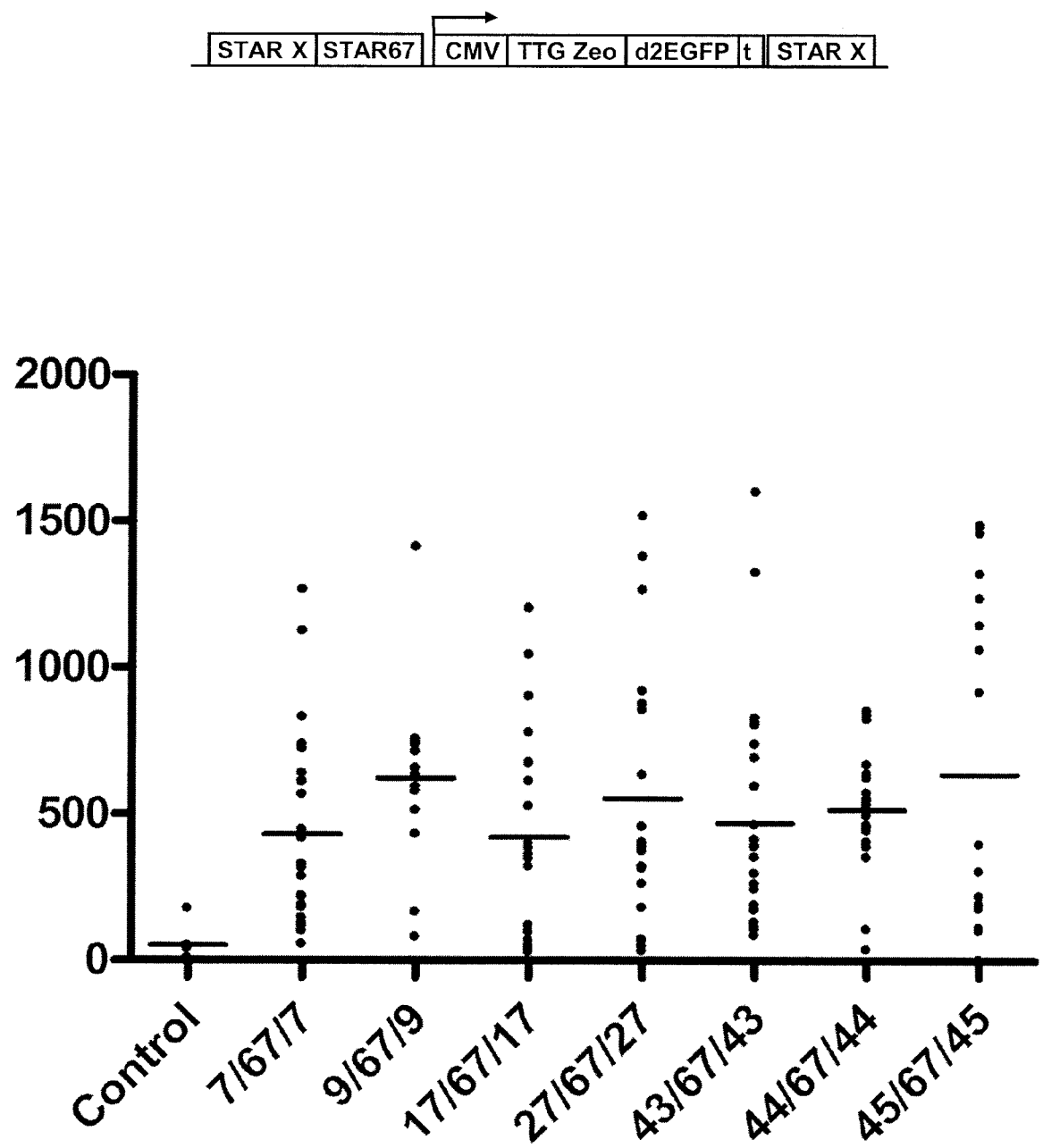
FIG. 40. Results with different STAR elements in the CHO-DG44 cell line. Dots indicate individual data points; lines indicate the average expression levels; vertical axis indicates d2EGFP signal. The construct is schematically shown above the graph, while the STAR elements tested in the construct are indicated below the horizontal axis. See, Example 21 for details.

Seven different STAR elements were tested in a construct that encompasses the CMV promoter, upstream of the TTG Zeo selection marker and the d2EGFP gene. In all constructs STAR 67 was included, cloned immediately upstream of the CMV promoter (FIG. 40). As a control, a construct without STAR elements was included. The following STAR elements were tested in such constructs: STAR 7/67-7, 9/67-9, 17/67-17, 27/67-27, 43/67-43, 44/67-44 and 45/67-45. The constructs were transfected to CHO-DG44 cells with LIPOFECTAMINE® 2000 (Invitrogen) and selection was performed with 150 µg/ml ZEOCIN® in the culture medium. The culture medium consisted of HAMF12:DMEM=1:1, +10% foetal bovine serum. Up to 24 independent colonies were isolated and propagated before analysis of d2EGFP expression levels. As expected and as shown in FIG. 40, incorporation of the seven different STAR elements gave significantly higher d2EGFP expression levels, compared to the control without STAR elements. From the results it is clear that STAR elements are able to increase d2EGFP expression levels also in the CHO-DG44 cell line.

Example 22

Removing CpG Dinucleotides from the Selectable Marker Coding Sequence Improves Expression Using the Selection Method The selection methods hereof, using different translation initiation codons for the selectable marker, such as GTG or TTG, can result in very stringent selection, and in very high levels of production for the polypeptide of interest, as shown in several examples above. In this example, the coding region of the selectable marker polypeptide gene itself was modified by removing CpG dinucleotides. The rationale is that the C nucleotide in the CpG nucleotide may be prone to methylation, which might result in gene silencing of the selectable marker, and thus removing CpG dinucleotides might improve the results. The ZEOCIN®-resistance gene with a TTG start codon was taken as the marker, and as many CpG dinucleotides were removed as was possible, without changing the amino acid sequence of the ZEOCIN®-resistance protein, and further without introducing ATG sequences in the coding strand, to prevent undesired translation initiation within the coding region of the ZEOCIN®-resistance protein (as explained, e.g., in Examples 1 and 2). Hence, some CpGs were not removed. The CpG content of the native sequence (here: containing a TTG start codon, and a mutation to remove the internal ATG sequence, see, e.g., Examples 1 and 2) is 13.3%, whereas after mutating the CpGs, the CpG content was reduced to 1.8% [referred to as "TTG Zeo (CpG poor)"]. The ZEOCIN®-resistance gene with decreased CpG content was cloned upstream of the d2EGFP coding sequence to result in a multicistronic expression construct hereof (see, e.g., Example 2). Expression levels of d2EGFP were measured.

Constructs were prepared containing STARs 7 and 67 upstream of the CMV promoter, followed by the TTG Zeo (CpG poor) selection marker (synthesized by GeneArt GmbH, Regensburg, Germany; see SEQ ID NO:132; see SEQ ID NO:92 for the ZEOCIN® antibiotic-resistance coding sequence with its natural CpG content), the d2EGFP gene and STAR 7 (FIG. 41). The constructs were transfected to CHO-K1 cells. DNA was transfected using LIPOFECTAMINE® 2000 (Invitrogen) and cells were grown in the presence of 150 μg/ml ZEOCIN® antibiotic in HAM-F12 medium (Invitrogen)+10% FBS (Invitrogen).

Eight colonies emerged after transfection with the control "CpG-rich" TTG Zeo construct (A in FIG. 41) and none with the "CpG-poor" TTG Zeo containing construct (C in FIG. 41). In contrast, with both "CpG-rich" TTG Zeo (B in FIG. 41) and "CpG-poor" TTG Zeo (D in FIG. 41) selection markers, more than 24 colonies emerged when STARs 7/67-7 was included in the construct. With the "CpG-rich" TTG ZEO-CIN® antibiotic selection marker (A in FIG. 41), the average d2EGFP expression with the STAR-less control construct was 140, and with the STAR containing construct 1332 (B in FIG. 41). This increase is due to the presence of the STAR elements. The average d2EGFP expression with the STAR containing construct and the "CpG-poor" Zeo was 2453 (D in FIG. 41), an almost two-fold increase in comparison with the "CpG-rich" TTG Zeo (B in FIG. 41). Also, the highest d2EGFP value achieved with the "CpG-rich" TTG Zeo construct (B) was 2481 and with the "CpG-poor" TTG Zeo (D) 4308.

We conclude that lowering the CpG content of the ZEO-CIN® antibiotic marker gene raises the stringency of the selection system. This results in higher d2EGFP expression values when STAR elements are included in the construct and no colonies with the control construct.

The same constructs were also transfected to CHO-DG44 cells, under the same conditions as in Example 21. With the "CpG-rich" TTG ZEOCIN® selection marker, the average d2EGFP expression with the STAR-less control construct was 43 (A in FIG. 42), and the average d2EGFP expression with the STAR containing constructs was 586 (B in FIG. 42). This is an increase due to the presence of the STAR elements. The average d2EGFP expression with the STAR constructs and the "CpG-poor" Zeo was 1152 (D in FIG. 42), an almost two-fold increase in comparison with the "CpG-rich" TTG Zeo (B in FIG. 42). Furthermore, the highest d2EGFP value achieved with the "CpG-rich" TTG Zeo construct was 1296 (B in FIG. 42) and with the "CpG-poor" TTG Zeo 2416 (D in FIG. 42). In contrast with CHO-K1, where no control colonies emerged with the "CpG-poor" TTG Zeo construct (C in FIG. 41), control colonies emerged with CHO-DG44, but the average d2EGFP value was 52 and the highest value in a colony was 115 (C in FIG. 42).

We conclude that also in CHO-DG44 addition of the "CpG-poor" TTG Zeo selection marker to the construct results in higher protein expression when STAR elements are employed.

It will be clear that the configuration where a ZEOCIN®-resistance gene with decreased CpG content and with a GTG or TTG start codon could also be placed downstream from the coding sequence for the polypeptide of interest (here d2EGFP as a model) when the ZEOCIN®-resistance protein coding sequences are placed under control of an IRES (see, e.g., Example 19). In that case, no care needs to be taken that mutation of CpG dinucleotides would introduce ATG sequences (as explained in the incorporated '953 application). It is expected that also in such embodiments, similar results can be obtained, i.e., that reduction of the CpG content of the selectable marker protein coding sequence will improve expression levels.

Example 23

Modifications in the Neomycin-Resistance Coding Sequence in the Selection System Hereof The selection system hereof, in which a modified start codon is employed for the sequence encoding the selectable marker polypeptide, is used here for the neomycin-resistance gene. As described in examples above (from the incorporated '525 and '953 applications), different stringencies for selection can be designed by using different translation initiation codons for the selectable marker coding sequence, such as GTG or TTG. In this example, also the coding region of the neomycin-resistance gene itself was modified, by removing as many CpG dinucleotides of the (ATG-less, so already devoid of ATG sequences in the coding strand) neomycin-resistance gene as possible, while not changing the amino acid sequence of the neomycin-resistance protein (except for the Met>Leu mutations where the internal ATG sequences were in-frame and replaced by CTG as compared to the wild-type sequence: obviously this was done for reasons of removing ATG sequences from the coding strand and independent from the effort of reducing the CpG content), and without introducing new ATG sequences in the coding strand, analogously to what was done in example 22 for the ZEO-CIN®-resistance gene. The CpG content of the "wild type" neomycin selection marker gene is 10.4% (SEQ ID NO:128), while after the changes the CpG content was reduced to 2.3% (SEQ ID NO:130). Constructs containing the sequences for the neomycin-resistance gene in this example were ordered from GeneArt GmbH, Regensburg, Germany. As a start codon, TTG was used in this example. The sequences used therefore consisted of SEQ ID NO:130, with the proviso that the start codon (first three nucleotides, ATG) was replaced by a TTG start codon, and further in certain cases contained one of the mutations indicated below.

In the "CpG poor" neomycin-resistance gene, some mutations were made to change amino acids in the neomycin-resistance protein, to test whether these have influence on the expression levels of the polypeptide of interest when used in the multicistronic transcription units hereof. The mutations (Sautter et al., 2005; it is noted that the neo sequence used in the present application encodes three additional amino acids immediately after the start codon as compared to the sequence used by (Sautter et al., 2005), and hence the amino acid numbering in the present application is three higher as compared to the numbering in (Sautter et al., 2005)) consisted of a change from amino acid valine 201 (198 in Sautter et al., 2005) to glycine 201 (TTG Neo 201V>G), glutamic acid 185 (182 in Sautter et al., 2005) to aspartic acid 185 (TTG Neo 185E>D) and a double mutation in which both amino acid valine 201 and glutamic acid 185 were changed to glycine 201 and aspartic acid 185, respectively (TTG Neo 185E>D/201V>G) (FIG. 43). These modifications were compared with the control Neomycin (CpG poor TTG Neo 185E/201V). In all cases constructs were prepared with and without STAR elements (FIG. 43).

The modified TTG Neo selection marker was incorporated in a construct containing STARs 7 and 67 upstream of the CMV promoter, followed by the TTG Neo selection marker, the d2EGFP gene and STAR 7 (FIG. 43). The constructs were transfected to CHO-K1 cells. DNA was transfected using LIPOFECTAMINE® 2000 (Invitrogen) and cells were grown in the presence of 500 μg/ml G418 GENETICIN® in HAM-F12 medium (Invitrogen)+10% FBS (Invitrogen).

With the control Neo construct (185E/201V) only a very limited effect of STAR elements was observed. This may at least in part be due to the numerous colonies that were generated under 500 μg/ml G418 GENETICIN®, indicating that the stringency of the TTG neomycin modification is low. However, the neomycin with modifications hereof is operational: in the TTG Neo 185E 201V construct all ATGs were removed from the coding strand of the neomycin-resistance gene, and although d2EGFP values were low, it is clear that the removal of ATGs still allowed proper selection under GENETICIN® selection pressure. When the neomycin-resistance gene was further modified, a distinctive effect of the addition of STAR elements was observed. The mean of 21 TTG Neo 201V>G control colonies was 65 (A2 in FIG. 43), whereas the mean d2EGFP signal of the 24 TTG Neo 201V>G colonies with STAR elements was 150 (B2 in FIG. 43). The selection stringency with the TTG Neo 185E>D mutation was further increased, since no control colonies survived without STAR elements (A3 in FIG. 43), whereas the mean d2EGFP signal of 17 surviving TTG Neo 185E>D STAR colonies was 204 (B3 in FIG. 43). This mean GFP fluorescence is higher than with the TTG Neo 201V>G colonies (B2 in FIG. 43). Also the highest d2EGFP value in TTG Neo 185E>D colonies was 715, as compared to 433 in the TTG Neo 201V>G colonies (compare B3 and B2 in FIG. 43). The highest stringency was observed in the double Neo mutant, TTG Neo 185E>D 201V>G. No control colonies survived (A4 in FIG. 43) and the mean d2EGFP value of 7 surviving STAR TTG Neo 185E>D 201V>G colonies was 513, with as highest d2EGFP value 923 (B4 in FIG. 43).

The introduction of specific mutations raises the stringency of selection of the neomycin-resistance gene when used according to the disclosure. Some of these modifications convey such selection stringency to the neomycin-resistance gene that only after incorporation with STAR elements colonies are able to survive, due to higher expression values. This concomitantly results in higher d2EGFP expression values. Clearly, the advantageous embodiments described for the neomycin-resistance gene further improve the suitability of this gene for use herein.

It will be clear that the configuration where a neomycin-resistance gene with decreased CpG content and with a GTG or TTG start codon, and with the indicated mutations (185E>D and/or 201V>G) could also be placed downstream from the coding sequence for the polypeptide of interest (here d2EGFP as a model) when the neomycin-resistance protein coding sequences are placed under control of an IRES (see, e.g., Example 19). In that case, no care needs to be taken that mutation of CpG dinucleotides would introduce ATG sequences (as explained in the incorporated '953 application). It is expected that also in such embodiments, good results can be obtained, i.e., that reduction of the CpG content and specific mutation at the indicated positions of the selectable marker protein coding sequence will improve expression levels.

Example 24

Use of Tryptophan Synthesizing Enzyme as Selection Marker in the Selection System Hereof Enzymes that are part of metabolic pathways can be effectively used as a selection marker. For instance, mammalian cells lack enzymes that are part of the metabolic pathway to create the amino acids tryptophan or histidine. Hence these amino acids need to be present in our food or, in case of cell lines, in the culture medium. These amino acids are therefore called essential. When the amino acids are omitted from the culture medium, the cells will die, unless a plasmid is transfected to the cells that encompass the (bacterial derived) enzymes that are lacking from the mammalian cell and that are essential for the synthesis of the respective amino acid. In this and the following two examples we describe the use of three enzymes that can be used as selection marker. Specifically, these markers with a GTG or TTG start codon are used in the context of constructs containing STAR elements, and are incorporated in the selection systems hereof.

Figure 44:
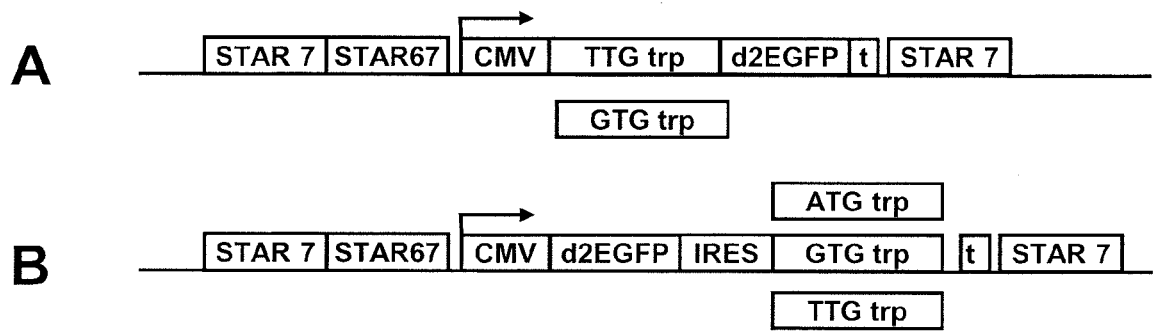
FIGS. 44A-44B. Schematic drawing of constructs with tryptophan synthesizing enzyme (trp) as selectable marker polypeptide hereof. See, Example 24 for details.

In this Example, the tryptophan synthesizing enzyme (trp) is used as a selectable marker polypeptide. The trp protein specifically converts indole and L-serine into L-tryptophan. For use of trp as a selectable marker, a culture medium that is essentially devoid of tryptophan and which contains the nontoxic substance indol is used (Hartman and Mulligan, 1988). Indol is used as substrate for the synthesis of tryptophan. Constructs are designed to contain the CMV promoter, the d2EGFP gene and the tryptophan synthesizing enzyme coding sequence (trp) in several configurations (FIG. 44).

The synthesized constructs are flanked by STAR elements 7 and 67. trp (the trpB gene) can be derived from *E. coli* by PCR. More conveniently, the desired trp gene is synthesized using standard DNA synthesis methods (e.g., by GeneArt GmbH, Regensburg, Germany).

In a first embodiment, the trp gene is modified such that all ATGs are removed. These include 14 ATGs that encode methionine (SEQ ID NO:136). The translation initiation codon is either GTG or TTG. These modified trp genes are placed upstream of d2EGFP (FIG. 44A).

Alternatively the wild type trp gene (containing all internal ATGs; SEQ ID NO:134) is placed downstream of the d2EGFP gene, but separated by an IRES sequence (See, Example 19) (FIG. 44B). Translation initiation of the trp mRNA will start at the translation initiation codon of trp. The first ATG (start codon) is replaced by GTG or TTG as a start codon. As a control in this configuration, a construct is also prepared with the normal ATG start codon for trp.

The constructs are transfected to CHO-K1 cells that are cultured in HAMF12 medium that is devoid of the amino acid tryptophan (Invitrogen). The medium contains 0.3 mM of the tryptophan precursor indole.

Example 25

Figure 45:
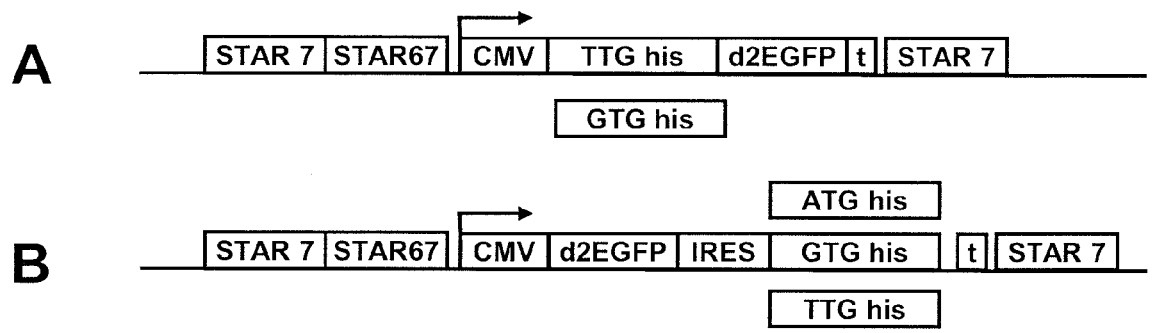
FIGS. 45A-45B. Schematic drawing of constructs with histidine synthesizing enzyme (his) as selectable marker polypeptide hereof. See, Example 25 for details.

Use of Histidine Synthesizing Enzyme as Selection Marker in the Selection System In this example, the enzyme that is involved in the synthesis of the essential amino acid histidine, named histidinol dehydrogenase (hisD, herein referred to as his), is used as a selectable marker. The hisD protein specifically converts 1-histidinol into 1-histidine. For use of his as a selectable marker, a culture medium that is essentially devoid of histidine and which contains the substance histidinol is used (Hartman and Mulligan, 1988). Histidinol is used as substrate for the synthesis of histidine. Constructs are designed to contain the CMV promoter, the d2EGFP gene and the hsitidine syntesizing enzyme coding sequence (his) in several configurations (FIG. 45).

The synthesized constructs are flanked by STAR elements 7 and 67. his can be derived from *Salmonella typhimurium* by PCR. More conveniently, the desired his gene is synthesized using standard DNA synthesis methods (e.g., by GeneArt GmbH, Regensburg, Germany).

In a first embodiment the his gene is modified such that all ATGs are removed. These include 4 ATGs that encode methionine (SEQ ID NO:140). The translation initiation codon is either GTG or TTG. These modified his genes are placed upstream of d2EGFP (FIG. 45A).

Alternatively the wild type his gene (containing all internal ATGs; SEQ ID NO:138) is placed downstream of the d2EGFP gene, but separated by an IRES sequence (See, Example 19) (FIG. 45B). Translation initiation of the his mRNA will start at the translation initiation codon of his. The first ATG (start codon) is replaced by GTG or TTG as a start codon. As a control in this configuration, a construct is also prepared with the normal ATG start codon for his.

The constructs are transfected to CHO-K1 cells, that are cultured in HAMF12 medium that is devoid of the amino acid histidine (Invitrogen). The medium contains 0.125 mM of the histidine precursor histidinol.

Example 26

Use of dhfr Enzyme as Selection Marker in the Selection System Hereof

Figure 46:
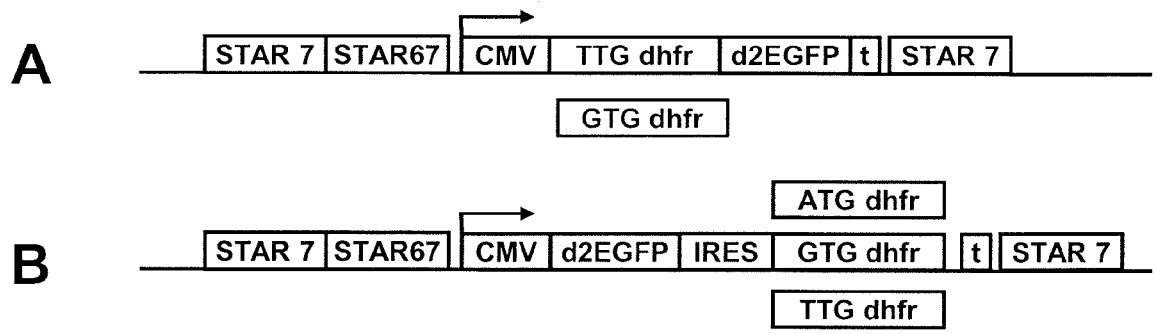
FIGS. 46A-46B. Schematic drawing of constructs with dhfr as selectable marker polypeptide hereof. See, Example 24 for details. See, Example 26 for details.

In this Example, the 5,6,7,8 tetrahydrofolate synthesizing enzyme dihydrofolate reductase (dhfr) is used as a selectable marker. The dhfr protein specifically converts folate into 5,6,7,8 tetrahydrofolate. For use of dhfr as a selectable marker, the non-toxic substance folate is present in the culture medium (Simonsen et al., 1988). Furthermore, the medium is essentially devoid of glycine, hypoxanthine, and thymidine, since when these are available for the cell, the need for the dhfr enzyme is by-passed. Constructs are designed to contain the CMV promoter, the d2EGFP gene and the dhfr coding sequence in several configurations (FIG. 46).

The synthesized constructs are flanked by STAR elements 7 and 67. dhfr can be derived from mouse by PCR. More conveniently, the desired dhfr gene is synthesized using standard DNA synthesis methods (e.g., by GeneArt GmbH, Regensburg, Germany).

In a first embodiment the dhfr gene is modified such that all ATGs are removed. These include 6 ATGs that encode methionine, which are changed for codons that encode leucine (SEQ ID NO:122). The translation initiation codon is either GTG or TTG. These modified dhfr genes are placed upstream of d2EGFP (FIG. 46A).

Alternatively the wild type dhfr gene (containing all internal ATGs; SEQ ID NO:98) is placed downstream of the d2EGFP gene, but separated by an IRES sequence (See, Example 19) (FIG. 46B). Translation initiation of the dhfr mRNA will start at the translation initiation codon of dhfr. The first ATG (start codon) is replaced by GTG or TTG as a start codon. As a control in this configuration, a construct is also prepared with the normal ATG start codon for dhfr.

The constructs are transfected to CHO-DG44 cells, that are cultured in DMEM:HAMF12 (1:1) medium (Gibco, cat no. 11320-074), supplemented with 2 mM L-glutamine (Gibco, 25030-024), which medium is essentially devoid of glycine, hypoxanthine and thymidine, and which medium contains 6 µM folic acid.

Example 27

Use of the Trp and dhfr Enzymes as Additional Selection Markers Combined with the Selection System Hereof In certain embodiments, it may be beneficial to maintain (some) selection pressure during culturing of host cells for expression of polypeptides of interest from expression cassettes in the host cell. Although it is possible to do this using selectable marker polypeptides that confer resistance to antibiotics, it is more advantageous in view of costs and/or regulatory/safety issues to use for instance metabolic enzymes such as trp and/or dhfr, as described in Examples 24 and 26, respectively. This Example describes the use of trp and dhfr as an additional selectable marker in combination with the selection system hereof, to be able to continuously select for the expression and of the expression unit that also expresses the polypeptide of interest. This selection pressure during the stage of expression of the polypeptide of interest may increase the expression levels in this stage as compared to a situation wherein only initially (for the establishment of selected clones) selection pressure is applied.

Constructs are designed to encompass the light (LC) and heavy chain (HC) of a monoclonal antibody, each under the control of the CMV promoter (FIG. 47A). The constructs are flanked by STAR elements 7 and 67. Also, between the expression cassettes for the LC and HC, STAR67 is placed. The cassette with the LC is placed upstream of the cassette with the HC, but of course the reverse order would also be possible, or alternatively the HC and LC expression cassettes could be on separate DNA molecules. The cassette with the LC is constructed as follows: the CMV promoter, the TTG Zeo selection marker (e.g., SEQ ID NO:132), the LC and an IRES sequence, followed by the trp gene (See, Example 24; SEQ ID NO:134). The trp gene is tested with an ATG, GTG or TTG translation initiation codon. The cassette with the HC is constructed as follows: the CMV promoter, the TTG Neo selection marker (See, Example 23; SEQ ID NO:130, but with a TTG start codon), the HC and an IRES sequence (see, e.g., Example 19), followed by the dhfr gene (See, Example 26; SEQ ID NO:98). The dhfr gene is tested with an ATG, GTG or TTG translation initiation codon (FIG. 47A).

Alternatively, a cassette can be constructed wherein the HC and/or LC are upstream of the two selectable marker sequences, wherein the selectable marker sequences each are preceded by an IRES (FIG. 47B).

It is clear that the same principle can be used for a single expression cassette, i.e., for expression of only one polypeptide of interest, for instance if that is not part of a multimeric protein. In that case only one of the two expression cassettes needs to be constructed (e.g., the one for HC, but with HC replaced by a sequence encoding another polypeptide of interest).

The constructs are transfected to CHO-DG44 cells cultured in DMEM:HAMF12 (1:1) medium. Selection takes place by 150 µg/ml ZEOCIN® and 500 µg/ml GENETICIN® G418. Colonies are isolated and cells are propagated. After first measurements of secreted monoclonal antibody in the culture medium, the cells are changed to DMEM:HAMF12 (1:1) medium (without ZEOCIN® and GENETICIN® G418) (Gibco, cat no. 11320-074), supplemented with 2 mM L-glutamine (Gibco, 25030-024), which medium is essentially devoid of glycine, hypoxanthine and thymidine, and which contains 6 µM folic acid, and/or to medium devoid of tryptophan, while containing 0.3 mM indole.

REFERENCES

Boshart M., F. Weber, G. Jahn, K. Dorsch-Hasler, B. Fleckenstein, and W. Schaffner (1985). A very strong enhancer is located upstream of an immediate early gene of human cytomegalovirus. *Cell* 41:521-530.

Chung J. H., M. Whiteley and G. Felsenfeld (1993). A 5' element of the chicken beta-globin domain serves as an insulator in human erythroid cells and protects against position effect in *Drosophila*. *Cell* 74:505-514.

Chung J. H., A. C. Bell, and G. Felsenfeld (1997). Characterization of the chicken beta-globin insulator. *Proc. Natl. Acad. Sci. U.S.A.* 94:575-580.

Das G. C., S. K. Niyogi, and N. P. Salzman (1985). SV40 promoters and their regulation. *Prog. Nucleic Acid Res. Mol. Biol.* 32:217-236.

Dumas P., M. Bergdoll, C. Cagnon, and J. M. Masson (1994). Crystal structure and site-directed mutagenesis of a bleomycin resistance protein and their significance for drug sequestering. *EMBO. J.* 13:2483-2492.

Gill D. R., S. E. Smyth, C. A. Goddard, I. A. Pringle, C. F. Higgins, W. H. Colledge, and S. C. Hyde (2001). Increased persistence of lung gene expression using plasmids containing the ubiquitin C or elongation factor 1α promoter. *Gene Therapy* 8:1539-1546.

Gossen M. and H. Bujard (1992). Tight control of gene expression in mammalian cells by tetracycline-responsive promoters. *Proc. Natl. Acad. Sci. U.S.A.* 89:5547-5551.

Graham F. O., J. Smiley, W. Russell and R. Nairn (1977). Characteristics of a human cell line transformed by DNA from human adenovirus type 5. *J. Gen. Virol.* 36:59-72.

Hartman S. C. and R. C. Mulligan (1988). Two dominant-acting selectable markers for gene transfer studies in mammalian cells. *Proc. Natl. Acad. Sci. U.S.A.* 85:8047-8051.

Huls G. A., I. A. F. M. Heijnen, M. E. Cuomo, J. C. Koningsberger, L. Wiegman, E. Boel, A.-R. van der Vuurst-de Vries, S. A. J. Loyson, W. Helfrich, G. P. van Berge Henegouwen, M. van Meijer, J. de Kruif, and T. Logtenberg (1999). A recombinant, fully human monoclonal antibody with antitumor activity constructed from phage-displayed antibody fragments. *Nat. Biotechnol.* 17:276-281.

Jones D., N. Kroos, R. Anema, B. Van Montfort, A. Vooys, S. Van Der Kraats, E. Van Der Helm, S. Smits, J. Schouten, K. Brouwer, F. Lagerwerf, P. Van Berkel, D.-J. Opstelten, T. Logtenberg, and A. Bout (2003). High-level expression of recombinant IgG in the human cell line PER.C6. *Biotechnol. Prog.* 19:163-168.

Kaufman R. J. (2000). Overview of vector design for mammalian gene expression. *Mol. Biotechnol.* 16:151-160.

Kaufman R. J. and P. A. Sharp (1982). Construction of a modular dihydrofolate reductase cDNA gene: analysis of signals utilized for efficient expression. *Mol. Cell. Biol.* 2:1304-1319.

Kellum R. and P. Schedl (1991). A position-effect assay for boundaries of higher order chromosomal domains. *Cell* 64:941-950.

Kim S. J., N. S. Kim, C. J. Ryu, H. J. Hong, and G. M. Lee (1998). Characterization of chimeric antibody producing CHO cells in the course of dihydrofolate reductase-mediated gene amplification and their stability in the absence of selective pressure. *Biotechnol. Bioeng.* 58:73-84.

Kozak M. (1986). Point mutations define a sequence flanking the AUG initiator codon that modulates translation by eukaryotic ribosomes. *Cell* 44:283-292.

Kozak M. (1987). An analysis of 5'-noncoding sequences from 699 vertebrate messenger RNAs. *Nucleic Acids Res.* 15:8125-8148.

Kozak M. (1989). Context effects and inefficient initiation at non-AUG codons in eucaryotic cell-free translation systems. *Mol. Cell. Biol.* 9:5073-5080.

Kozak M. (1990). Downstream secondary structure facilitates recognition of initiator codons by eukaryotic ribosomes. *Proc. Natl. Acad. Sci. U.S.A.* 87:8301-8305.

Kozak M. (1997). Recognition of AUG and alternative initiator codons is augmented by G in position +4 but is not generally affected by the nucleotides in positions +5 and +6. *EMBO. J.* 16:2482-2492.

Kozak M. (2002). Pushing the limits of the scanning mechanism for initiation of translation. *Gene* 299:1-34.

Kwaks T. H., P. Barnett, W. Hemrika, T. Siersma, R. G. Sewalt, D. P. Satijn, J. F. Brons, R. van Blokland, P. Kwakman, A. L. Kruckeberg, A. Kelder, and A. P. Otte (2003). Identification of anti-repressor elements that confer high and stable protein production in mammalian cells. *Nat. Biotechnol.* 21:553-558. Erratum in: Nat. Biotechnol. 21:822 (2003).

Lopez de Quinto S, and E. Martinez-Salas (1998). Parameters influencing translational efficiency inaphthovirus IRES-based bicistronic expression vectors. *Gene* 217:51-6.

Phi-Van L., J. P. Von Kreis, W. Ostertag, and W. H. Strätling (1990). The chicken lysozyme 5' matrix attachment region increases transcription from a heterologous promoter in heterologous cells and dampens position effects on the expression of transfected genes. *Mol. Cell. Biol.* 10:2302-2307.

Martinez-Salas E. (1999). Internal ribosome entry site biology and its use in expression vectors *Curr. Opin. Biotechnol.* 10:458-64.

McBurney M. W., T. Mai, X. Yang, and K. Jardine (2002). Evidence for repeat-induced gene silencing in cultured Mammalian cells: inactivation of tandem repeats of transfected genes. *Exp. Cell. Res.* 274:1-8.

Mizuguchi H., Z. Xu, A. Ishii-Watabe, E. Uchida, and T. Hayakawa (2000). IRES-dependent second gene expression is significantly lower than cap-dependent first gene expression in a bicistronic vector. *Mol. Ther.* 1:376-82.

Rees S., J. Coote, J. Stables, S. Goodson, S. Harris, and M. G. Lee (1996). Bicistronic vector for the creation of stable mammalian cell lines that predisposes all antibiotic-resistant cells to express recombinant protein *Biotechniques* 20:102-104, 106, 108-110.

Sautter K., B. Enenkel (2005). Selection of high-producing CHO cells using NPT selection marker with reduced enzyme activity. *Biotechnol. Bioeng.* 89:530-538.

Schorpp M., R. Jager, K. Schellander, J. Schenkel, E. F. Wagner, H. Weiher, and P. Angel (1996). The human ubiquitin C promoter directs high ubiquitous expression of transgenes in mice. *Nucleic Acids Res.* 24:1787-8.

Simonsen C. S., M. Waltter, and A. D. Levinson (1988). Expression of the plasmid-encoded type I dihydrofolate reductase gene in cultured mammalian cells: a novel selectable marker. *Nucleic Acids Res.* 16:22355-22246.

Stief A., D. M. Winter, W. H. Stratling, and A. E. Sippel (1989). A nuclear DNA attachment element mediates elevated and position-independent gene activity. *Nature* 341:343-345.

Van der Vlag J., J. L. den Blaauwen, R. G. Sewalt, R. van Driel, and A. P. Otte (2000). Transcriptional repression mediated by polycomb group proteins and other chromatin-associated repressors is selectively blocked by insulators. *J. Biol. Chem.* 275:697-704.

Venkatesan A. and A. Dasgupta (2001). Novel fluorescence-based screen to identify small synthetic internal ribosome entry site elements. *Mol. Cell. Biol.* 21:2826-37.

West A. G., M. Gaszner, and G. Felsenfeld (2002). Insulators: many functions, many mechanisms. *Genes Dev.* 16:271-288.

Whitelaw E., H. Sutherland, M. Kearns, H. Morgan, L. Weaving, and D. Garrick (2001). Epigenetic effects on transgene expression. *Methods Mol. Biol.* 158:351-68.

Williams S., T. Mustoe, T. Mulcahy, M. Griffiths, D. Simpson, M. Antoniou, A. Ivine, A. Mountain, and R. Crombie (2005). CpG-island fragments from the HNRPA2B1/CBX3 genomic locus reduce silencing and enhance transgene expression from the hCMV promoter/enhancer in mammalian cells. *BMC Biotechnol.* 5:17.

Yoon S. K., J. Y. Song, and G. M. Lee (2003). Effect of low culture temperature on specific productivity, transcription level, and heterogeneity of erythropoietin in Chinese hamster ovary cells. *Biotechnol Bioeng.* 82:289-298.

What is claimed is:

1. A DNA molecule comprising an open reading frame that encodes a selectable marker polypeptide that provides resistance against neomycin antibiotic, and wherein the DNA molecule comprises SEQ ID NO: 130, with the proviso that nucleotide A at position 555 is replaced by C, and that nucleotide T at position 602 is replaced by G and that nucleotide G at position 603 is replaced by T, at positions set forth in SEQ ID NO: 130 and with the further proviso that the start codon at positions 1-3 of SEQ ID NO: 130 is replaced by either GTG or TTG.

2. The DNA molecule of claim 1, further comprising a multicistronic transcription unit that comprises an open reading frame encoding a polypeptide of interest.

3. The DNA molecule of claim 2, wherein the open reading frame that encodes the selectable marker polypeptide is upstream of the open reading frame encoding the polypeptide of interest, and wherein the open reading frame that encodes the selectable marker polypeptide has no ATG sequence in the coding strand.

4. The DNA molecule of claim 2, wherein the open reading frame encoding the polypeptide of interest is upstream of the open reading frame that encodes the selectable marker polypeptide, and wherein the open reading frame that encodes the selectable marker polypeptide is operably linked to an internal ribosome entry site (IRES).

5. The DNA molecule of claim 2, further comprising a promoter upstream of the multicistronic expression unit and a transcription termination sequence downstream of the multicistronic expression unit.

6. The DNA molecule of claim 1, further comprising at least one element selected from the group consisting of matrix or scaffold attachment regions (MAR/SAR), and anti-repressor (STAR) sequences.

7. An isolated host cell comprising the DNA molecule of claim 2.

8. The host cell of claim 7, wherein the DNA molecule further comprises a promoter upstream of the multicistronic expression unit and a transcription termination sequence downstream of the multicistronic expression unit.

9. An in vitro method of generating a host cell able to express a polypeptide of interest, the method comprising:
introducing into a plurality of precursor host cells the DNA molecule of claim 2;
culturing the plurality of precursor cells;
expressing the selectable marker polypeptide; and
selecting at least one host cell expressing the polypeptide of interest.

10. The method according to claim 9, wherein the DNA molecule further comprises:
a promoter upstream of the multicistronic expression unit; and
a transcription termination sequence downstream of the multicistronic expression unit.

11. A method of expressing a polypeptide of interest, the method comprising:
culturing the host cell of claim 7; and
expressing the polypeptide of interest.

12. The method according to claim 11, further comprising:
harvesting the polypeptide of interest.

* * * * *

UNITED STATES PATENT AND TRADEMARK OFFICE
CERTIFICATE OF CORRECTION

PATENT NO. : 9,228,004 B2
APPLICATION NO. : 14/081938
DATED : January 5, 2016
INVENTOR(S) : Arie Pieter Otte et al.

It is certified that error appears in the above-identified patent and that said Letters Patent is hereby corrected as shown below:

In the specification:

| | | |
|---|---|---|
| COLUMN 1, | LINE 7, | change "of U.S." to --of co-pending U.S.-- |
| COLUMN 1, | LINE 8, | change "2011, which" to --2011, now abandoned, which-- |
| COLUMN 1, | LINE 10, | change "2006, which" to --2006, abandoned, which-- |
| COLUMN 1, | LINES 11-12, | change "2005, which" to --2005, pending, which-- |
| COLUMN 1, | LINES 19-20, | change "aforementioned U.S." to --aforementioned co-pending U.S.-- |
| COLUMN 1, | LINE 29, | change "11/416,490, filed" to --11/416,490, abandoned, filed-- |
| COLUMN 6, | LINE 1, | change "NO:66), START" to --NO:66), STAR7-- |
| COLUMN 9, | LINE 56, | change "FIGS. 22A-22E." to --FIG. 22-- |
| COLUMN 9, | LINE 67, | change "and START" to --and STAR7-- |
| COLUMN 10, | LINE 3, | change "FIGS. 24A-24D." to --FIG. 24-- |
| COLUMN 11, | LINE 55, | change "FIGS. 44A-44B." to --FIG. 44-- |
| COLUMN 11, | LINE 58, | change "FIGS. 45A-45B." to --FIG. 45-- |
| COLUMN 11, | LINE 61, | change "FIGS. 46A-46B." to --FIG. 46-- |
| COLUMN 11, | LINES 62-63, | change "Example 24 for details. See, Example 26" to --Example 26-- |
| COLUMN 11, | LINE 64, | change "FIGS. 27A-47B." to --FIG. 47-- |
| COLUMN 26, | LINE 26, | change "NO:66), START" to --NO:66), STAR7-- |
| COLUMN 26, | LINE 26, | change "NO:7), STARS" to --NO:7), STAR9-- |
| COLUMN 28, | LINE 34, | change "NO:66), START" to --NO:66), STAR7-- |
| COLUMN 42, | LINE 64, | change "and START" to --and STAR7-- |
| COLUMN 43, | LINES 65-66, | change "of sub-cloning Cells" to --of sub-cloning. Cells-- |
| COLUMN 52, | LINE 66, | change "and START was" to --and STAR7 was-- |
| COLUMN 55, | LINE 6, | change "and STAR73′ of" to --and STAR7 3′ of-- |
| COLUMN 66, | LINE 5, | change "inaphthovirus" to --in aphthovirus-- |

Signed and Sealed this
Ninth Day of August, 2016

Michelle K. Lee
*Director of the United States Patent and Trademark Office*

SEQUENCE LISTING

<160> NUMBER OF SEQ ID NOS: 141

<210> SEQ ID NO 1
<211> LENGTH: 749
<212> TYPE: DNA
<213> ORGANISM: Homo sapiens
<220> FEATURE:
<221> NAME/KEY: misc_feature
<223> OTHER INFORMATION: sequence of STAR1

<400> SEQUENCE: 1

| | | | | | | |
|---|---|---|---|---|---|---|
| atgcggtggg | ggcgcgccag | agactcgtgg | gatccttggc | ttggatgttt | ggatctttct | 60 |
| gagttgcctg | tgccgcgaaa | gacaggtaca | tttctgatta | ggcctgtgaa | gcctcctgga | 120 |
| ggaccatctc | attaagacga | tggtattgga | gggagagtca | cagaaagaac | tgtggcccct | 180 |
| ccctcactgc | aaaacggaag | tgattttatt | ttaatggag | ttggaatatg | tgagggctgc | 240 |
| aggaaccagt | ctccctcctt | cttggttgga | aaagctgggg | ctggcctcag | agacaggttt | 300 |
| tttggccccg | ctgggctggg | cagtctagtc | gacccttgt | agactgtgca | caccctaga | 360 |
| agagcaacta | cccctataca | ccaggctggc | tcaagtgaaa | ggggctctgg | gctccagtct | 420 |
| ggaaaatctg | gtgtcctggg | gacctctggt | cttgcttctc | tcctcccctg | cactggctct | 480 |
| gggtgcttat | ctctgcagaa | gcttctcgct | agcaaaccca | cattcagcgc | cctgtagctg | 540 |
| aacacagcac | aaaaagccct | agagatcaaa | agcattagta | tgggcagttg | agcgggaggt | 600 |
| gaatatttaa | cgcttttgtt | catcaataac | tcgttggctt | tgacctgtct | gaacaagtcg | 660 |
| agcaataagg | tgaaatgcag | gtcacagcgt | ctaacaaata | tgaaaatgtg | tatattcacc | 720 |
| ccggtctcca | gccggcgcgc | caggctccc | | | | 749 |

<210> SEQ ID NO 2
<211> LENGTH: 883
<212> TYPE: DNA
<213> ORGANISM: Homo sapiens
<220> FEATURE:
<221> NAME/KEY: misc_feature
<223> OTHER INFORMATION: sequence of STAR2

<400> SEQUENCE: 2

| | | | | | | |
|---|---|---|---|---|---|---|
| gggtgcttcc | tgaattcttc | cctgagaagg | atggtggccg | gtaaggtccg | tgtaggtggg | 60 |
| gtgcggctcc | ccaggccccg | gcccgtggtg | gtggccgctg | cccagcggcc | cggcaccccc | 120 |
| atagtccatg | gcgcccgagg | cagcgtgggg | gaggtgagtt | agaccaaaga | gggctggccc | 180 |
| ggagttgctc | atgggctcca | catagctgcc | ccccacgaag | acggggcttc | cctgtatgtg | 240 |
| tggggtccca | tagctgccgt | tgccctgcag | gccatgagcg | tgcgggtcat | agtcgggggt | 300 |
| gccccctgcg | cccgccctg | ccgccgtgta | gcgcttctgt | gggggtggcg | ggggtgcgca | 360 |
| gctgggcagg | gacgcagggt | aggaggcggg | gggcagcccg | taggtaccct | gggggggctt | 420 |
| ggagaagggc | gggggcgact | gggctcata | cgggacgctg | ttgaccagcg | aatgcataga | 480 |
| gttcagatag | ccaccggctc | cgggggcac | ggggctgcga | cttggagact | ggccccccga | 540 |
| tgacgttagc | atgcccttgc | ccttctgatc | cttttgtac | ttcatgcggc | gattctggaa | 600 |
| ccagatcttg | atctggcgct | cagtgaggtt | cagcagattg | gccatctcca | cccggcgcgg | 660 |
| ccggcacagg | tagcggttga | agtggaactc | tttctccagc | tccaccagct | gcgcgctcgt | 720 |
| gtaggccgtg | cgcgcgcgct | tggacgaagc | ctgccccggc | gggctcttgt | cgccagcgca | 780 |

| gctttcgcct gcgaggacag agagaggaag agcggcgtca ggggctgccg cggccccgcc | 840 |
| cagcccctga cccagcccgg cccctccttc caccaggccc caa | 883 |

<210> SEQ ID NO 3
<211> LENGTH: 2126
<212> TYPE: DNA
<213> ORGANISM: Homo sapiens
<220> FEATURE:
<221> NAME/KEY: misc_feature
<223> OTHER INFORMATION: sequence of STAR3

<400> SEQUENCE: 3

| atctcgagta ctgaaatagg agtaaatctg aagagcaaat aagatgagcc agaaaaccat | 60 |
| gaaaagaaca gggactacca gttgattcca caaggacatt cccaaggtga aaggccata | 120 |
| tacctccact acctgaacca attctctgta tgcagattta gcaaggttat aaggtagcaa | 180 |
| aagattagac ccaagaaaat agagaacttc caatccagta aaaatcatag caaatttatt | 240 |
| gatgataaca attgtctcca aaggaacaag gcagagtcgt gctagcagag aagcacgtg | 300 |
| agctgaaaac agccaaatct gctttgtttt catgacacag gagcataaag tacacaccac | 360 |
| caactgacct attaaggctg tggtaaaccg attcatagag agaggttcta aatacattgg | 420 |
| tccctcacag gcaaactgca gttcgctccg aacgtagtcc ctggaaattt gatgtccagt | 480 |
| atagaaaagc agagcagtca aaaatatag ataaagctga accagatgtt gcctgggcaa | 540 |
| tgttagcagc accacactta agatataacc tcaggctgtg gactccctcc ctggggagcg | 600 |
| gtgctgccgg cggcgggcgg gctccgcaac tccccggctc tctcgcccgc cctcccgttc | 660 |
| tcctcgggcg gcggcggggg ccgggactgc gccgctcaca gcggcggctc ttctgcgccc | 720 |
| ggcctcggag gcagtggcgg tggcggccat ggcctcctgc gttcgccgat gtcagcattt | 780 |
| cgaactgagg gtcatctcct tgggactggt tagacagtgg gtgcagccca cggagggcga | 840 |
| gttgaagcag ggtgggggtgt cacctccccc aggaagtcca gtgggtcagg gaactccctc | 900 |
| ccctagccaa gggaggccgt gagggactgt gcccggtgag agactgtgcc ctgaggaaag | 960 |
| gtgcactctg gcccagatac tacacttttc ccacggtctt caaaacccgc agaccaggag | 1020 |
| attccctcgg gttcctacac caccaggacc ctgggtttca accacaaaac cgggccattt | 1080 |
| gggcagacac ccagctagct gcaagagttg ttttttttttt tatactcctg tggcacctgg | 1140 |
| aacgccagcg agagagcacc tttcactccc ctggaaaggg ggctgaaggc agggacccttt | 1200 |
| agctgcgggc taggggggttt ggggttgagt gggggagggg agagggaaaa ggcctcgtca | 1260 |
| ttggcgtcgt ctgcagccaa taaggctacg ctcctctgct gcgagtagac ccaatccttt | 1320 |
| cctagaggtg gagggggcgg gtaggtggaa gtagaggtgg cgcggtatct aggagagaga | 1380 |
| aaaagggctg gaccaatagg tgcccggaag aggcggaccc agcggtctgt tgattggtat | 1440 |
| tggcagtgga ccctcccccg gggtggtgcc ggagggggggg atgatgggtc gagggggtgtg | 1500 |
| tttatgtgga agcgagatga ccggcaggaa cctgccccaa tggctgcag agtggttagt | 1560 |
| gagtgggtga cagacagacc cgtaggccaa cgggtggcct taagtgtctt tggtctcctc | 1620 |
| caatggagca gcggcgggc gggaccgcga ctcgggttta atgagactcc attgggctgt | 1680 |
| aatcagtgtc atgtcggatt catgtcaacg acaacaacag ggggacacaa aatgcgggcg | 1740 |
| gcttagtcct accccctggcg gcggcgcag cggtggcgga ggcgacggca ctcctccagg | 1800 |
| cggcagccga gtttctcag gcagcggcag cgccccgc aggcgcggtg cggtggcgc | 1860 |
| gcagccaggt ctgtcaccca ccccgcgcgt tcccagggg aggagactgg gcgggagggg | 1920 |

-continued

| | |
|---|---|
| ggaacagacg ggggggatt cagggcttg cgacgcccct cccacaggcc tctgcgcgag | 1980 |
| ggtcaccgcg gggccgctcg gggtcaggct gccctgagc gtgacggtag ggggcggggg | 2040 |
| aaaggggagg agggacaggc cccgcccctc ggcagggcct ctagggcaag ggggcggggc | 2100 |
| tcgaggagcg gaggggggcg gggcgg | 2126 |

```
<210> SEQ ID NO 4
<211> LENGTH: 1625
<212> TYPE: DNA
<213> ORGANISM: Homo sapiens
<220> FEATURE:
<221> NAME/KEY: misc_feature
<223> OTHER INFORMATION: sequence of STAR4

<400> SEQUENCE: 4
```

| | |
|---|---|
| gatctgagtc atgttttaag gggaggattc ttttggctgc tgagttgaga ttaggttgag | 60 |
| ggtagtgaag gtaaaggcag tgagaccacg taggggtcat tgcagtaatc caggctggag | 120 |
| atgatggtgg ttcagttgga atagcagtgc atgtgctgta acaacctcag ctgggaagca | 180 |
| gtatatgtgg cgttatgacc tcagctggaa cagcaatgca tgtggtggtg taatgacccc | 240 |
| agctgggtag ggtgcatgtg gtgtaacgac ctcagctggg tagcagtgtg tgtgatgtaa | 300 |
| caacctcagc tgggtagcag tgtacttgat aaaatgttgg catactctag atttgttatg | 360 |
| agggtagtgc cattaaattt ctccacaaat tggttgtcac gtatgagtga aaagaggaag | 420 |
| tgatggaaga cttcagtgct tttggcctga ataaatagaa gacgtcattt ccagttaatg | 480 |
| gagacaggga agactaaagg tagggtggga ttcagtagag caggtgttca gttttgaata | 540 |
| tgatgaactc tgagagagga aaaactttt ctacctctta gttttgtga ctggacttaa | 600 |
| gaattaaagt gacataagac agagtaacaa gacaaaaata tgcgaggtta tttaatattt | 660 |
| ttacttgcag aggggaatct tcaaaagaaa aatgaagacc caaagaagcc attagggtca | 720 |
| aaagctcata tgccttttta agtagaaaat gataaatttt aacaatgtga aagacaaag | 780 |
| gtgtttgagc tgagggcaat aaattgtggg acagtgatta agaaatatat gggggaaatg | 840 |
| aaatgataag ttattttagt agatttattc ttcatatcta ttttggcttc aacttccagt | 900 |
| ctctagtgat aagaatgttc ttctcttcct ggtacagaga gagcaccttt ctcatgggaa | 960 |
| attttatgac cttgctgtaa gtagaaaggg gaagatcgat ctcctgtttc ccagcatcag | 1020 |
| gatgcaaaca tttcccctcca ttccagttct caaccccatg gctgggcctc atggcattcc | 1080 |
| agcatcgcta tgagtgcacc tttcctgcag gctgcctcgg gtagctggtg cactgctagg | 1140 |
| tcagtctatg tgaccaggag ctgggcctct ggcaatgcc agttggcagc ccccatcccc | 1200 |
| ccactgctgg gggcctccta tccagaaggg cttggtgtgc agaacgatgg tgcaccatca | 1260 |
| tcattcccca cttgccatct ttcagggac agccagctgc tttgggcgcg gcaaaaaaca | 1320 |
| cccaactcac tcctcttcag gggcctctgg tctgatgcca ccacaggaca tccttgagtg | 1380 |
| ctgggcagtc tgaggacagg gaaggagtga tgaccacaaa acaggaatgg cagcagcagt | 1440 |
| gacaggagga agtcaaaggc ttgtgtgtcc tggccctgct gagggctggc gagggccctg | 1500 |
| ggatggcgct cagtgcctgg tcggctgcaa gaggccagcc ctctgcccat gaggggagct | 1560 |
| ggcagtgacc aagctgcact gccctggtgg tgcatttcct gccccactct ttccttctaa | 1620 |
| gatcc | 1625 |

```
<210> SEQ ID NO 5
<211> LENGTH: 1571
<212> TYPE: DNA
```

<213> ORGANISM: Homo sapiens
<220> FEATURE:
<221> NAME/KEY: misc_feature
<223> OTHER INFORMATION: sequence of STAR5

<400> SEQUENCE: 5

```
cacctgattt aaatgatctg tctggtgagc tcactgggtc tttactcgca tgctgggtcc      60
acagctccac tgtcctgcag ggtccgtgag tgtgggcccc ttatctattt catcatcata     120
accctgcgtg tcctcaactc ctggcacata ttgggtggcc ccatccacac acggttgttg     180
agtgaatcca tgagatgaca aaggctatga tgtagactat atcatgagcc agaaccaggc     240
tttcctacct ccagacaatc aagggccttg atttgggatt gagggagaaa ggagtagaag     300
ccaggaagga gaagagattg aggtttacca agggtgcaaa gtcctggccc ctgactgtag     360
gctgaaaact atagaaatga tagaacaatt ttgcaatgaa atgcagaaga ccctgcatca     420
actttaggtg ggacttcggg tattttatg gccacagaac atcctcccat ttacctgcat      480
ggcccagaca cagacttcaa aacagttgag gccagcaggc tccaggtaag tggtaggatt     540
ccagaatgcc ctcagagtgt tgtgggaggc agcaggcgat tttcctggac ttctgagttt     600
atgagaaccc caaccccaa ttggcattaa cattgaggtc tcaatgtatc atggcaggaa      660
gcttccgagt ggtgaaaagg aaagtgaaca tcaaagctcg aagacaaga gggtggagtg      720
atggcaacca agagcaagac ccttccctct cctgtgatgg ggtggctcta tgtgaagccc     780
ccaaactgga cacaggtctg gcagaatgag gaacccactg agatttagcg ccaacatcca     840
gcataaaagg gagactgaca tagaatttga gttagttaaa aataaggcac aatgcttttc     900
atgtattcct gagttttgtg gactggtgtt caatttgcag cattcttagt tgattaaatc     960
tgagatgaag aaagagtgtc caacactttc accttggaaa gctctggaaa agcaaaaggg    1020
agagacaatt agcttcatcc attaactcac ttagtcatta tgcattcatt catgtaacta    1080
ccaaacacgt actgagtgcc taacactcct gagacactga gaagtttctt gggaatacaa    1140
agatgaataa aaaccacgcc aggcaggagt tggaggaagg ttctggatgc caccacgctc    1200
tacctcctgg ctggacacca ggcaatgttg gtaaccttct gcctccaatt tctgcaaata    1260
cataattaat aaacacaagg ttatcttcta aacagttctt aaaatgagtc aactttgttt    1320
aaacttgttc tttttagaga aaatgtatt tttgaaagag ttggttagtg ctaggggaaa     1380
tgtctgggca cagctcagtc tggtgtgaga gcaggaagca gctctgtgtg tctggggtgg    1440
gtacgtatgt aggacctgtg ggagaccagg ttgggggaag gcccctcctc atcaagggct    1500
cctttgcttt ggtttgcttt ggcgtgggag gtgctgtgcc acaagggaat acgggaaata    1560
agatctctgc t                                                         1571
```

<210> SEQ ID NO 6
<211> LENGTH: 1173
<212> TYPE: DNA
<213> ORGANISM: Homo sapiens
<220> FEATURE:
<221> NAME/KEY: misc_feature
<223> OTHER INFORMATION: sequence of STAR6

<400> SEQUENCE: 6

```
tgacccacca cagacatccc ctctggcctc ctgagtggtt tcttcagcac agcttccaga      60
gccaaattaa acgttcactc tatgtctata gacaaaaagg ttttgactaa aactctgtgt     120
tttagagagg gagttaaatg ctgttaactt tttaggggtg ggcgagaggg atgacaaata     180
acaacttgtc tgaatgtttt acatttctcc ccactgcctc aagaaggttc acaacgaggt     240
```

```
catccatgat aaggagtaag acctcccagc cggactgtcc ctcggccccc agaggacact    300
ccacagagat atgctaactg gacttggaga ctggctcaca ctccagagaa aagcatggag    360
cacgagcgca cagagcaggg ccaaggtccc agggacagaa tgtctaggag ggagattggg    420
gtgagggtaa tctgatgcaa ttactgtggc agctcaacat tcaagggagg gggaagaaag    480
aaacagtccc tgtcaagtaa gttgtgcagc agagatggta agctccaaaa tttgaaactt    540
tggctgctgg aaagttttag ggggcagaga taagaagaca taagagactt tgagggttta    600
ctacacacta gacgctctat gcatttattt atttattatc tcttatttat tactttgtat    660
aactcttata ataatcttat gaaaacggaa accctcatat acccatttta cagatgagaa    720
aagtgacaat tttgagagca tagctaagaa tagctagtaa gtaaaggagc tgggacctaa    780
accaaaccct atctcaccag agtacacact cttttttttt ttccagtgta attttttta     840 attttttattt tactttaagt tctgggatac atgtgcagaa ggtatggttt gttacatagg    900
tatatgtgtg ccatagtgga ttgctgcacc tatcaacccg tcatctaggt ttaagcccca    960
catgcattag ctatttgtcc tgatgctctc cctccctcc ccacaccaga caggccttgg    1020
tgtgtgatgt tcccctccct gtgtccatgt gttctcactg ttcagctccc acttatgagt   1080
gagaacgtgt ggtatttggt tttctgttcc tgtgttagtt tgctgaggat gatggcttcc   1140
agcttcatcc atgtccctgc aaaggacacg atc                                1173
```

<210> SEQ ID NO 7
<211> LENGTH: 2101
<212> TYPE: DNA
<213> ORGANISM: Homo sapiens
<220> FEATURE:
<221> NAME/KEY: misc_feature
<223> OTHER INFORMATION: sequence of STAR7

<400> SEQUENCE: 7

```
aggtgggtgg atcacccgag gtcaggagtt caagaccagc ctggccaaca tggtaaaacc     60
tcgtctctac taaaaatac gaaaaattag ctggttgtgg tggtgcgtgc ttgtaatccc    120
agctactcgg gaggctgagg caggagaatc acttgaatct gggaggcaga ggttgcagtg    180
agctgagata gtgccattgc actccagcct gggcaacaga cggagactct gtctccaaaa    240
aaaaaaaaaa aaatcttaga ggacaagaat ggctctctca aacttttgaa gaaagaataa    300
ataaattatg cagttctaga agaagtaatg gggatatagg tgcagctcat gatgaggaag    360
acttagctta actttcataa tgcatctgtc tggcctaaga cgtggtgagc ttttatgtc     420 tgaaaacatt ccaatataga atgataataa taatcacttc tgaccccccct ttttttcct    480 ctccctagac tgtgaagcag aaaccccata ttttttcttag ggaagtgget acgcactttg    540 tatttatatt aacaactacc ttatcaggaa attcatattg ttgccctttt atggatgggg    600
aaactggaca agtgacagag caaaatccaa acacagctgg ggatttccct cttttagatg    660 atgatttttaa aagaatgctg ccagagagat tcttgcagtg ttggaggaca tatatgacct    720
ttaagatatt ttccagctca gagatgctat gaatgtatcc tgagtgcatg gatggacctc    780 agtttttgcag attctgtagc ttatacaatt tggtggtttt ctttagaaga aaataacaca    840
tttataaata ttaaaatagg cccaagacct tacagggca ttcatacaaa tgagaggctc     900
tgaagtttga gttttgttcac tttctagtta attatctcct gcctgtttgt cataaatgcg    960
tttagtaggg agctgctaat gacaggttcc tccaacagag tgtggaagaa ggagatgaca   1020
gctggcttcc cctctgggac agcctcagag ctagtgggga aactatgtta gcagagtgat   1080
```

```
gcagtgacca agaaaatagc actaggagaa agctggtcca tgagcagctg gtgagaaaag   1140
gggtggtaat catgtatgcc ctttcctgtt ttatttttta ttgggtttcc ttttgcctct   1200
caattccttc tgacaataca aaatgttggt tggaacatgg agcacctgga agtctggttc   1260
attttctctc agtctcttga tgttctctcg ggttcactgc ctattgttct cagttctaca   1320
cttgagcaat ctcctcaata gctaaagctt ccacaatgca gattttgtga tgacaaattc   1380
agcatcaccc agcagaactt aggttttttt ctgtcctccg tttcctgacc ttttttcttct  1440 gagtgcttta tgtcacctcg tgaaccatcc tttccttagt catctaccta gcagtcctga   1500
ttcttttgac ttgtctccct acaccacaat aaatcactaa ttactatgga ttcaatccct   1560
aaaatttgca caaacttgca aatagattac gggttgaaac ttagagattt caaacttgag   1620
aaaaaagttt aaatcaagaa aaatgacctt taccttgaga gtagaggcaa tgtcatttcc   1680
aggaataatt ataataatat tgtgtttaat atttgtatgt aacatttgaa taccttcaat   1740
gttcttattt tgtgttatttt aatctcttga tgttactaac tcatttggta gggaagaaaa   1800
catgctaaaa taggcatgag tgtcttatta aatgtgacaa gtgaatagat ggcagaaggt   1860
ggattcatat tcagttttcc atcaccctgg aaatcatgcg gagatgattt ctgcttgcaa   1920
ataaaactaa cccaatgagg ggaacagctg ttcttaggtg aaaacaaaac aaacacgcca   1980 aaaacccttta ttctctttat tatgaatcaa attttttcctc tcagataatt gtttatttta   2040 tttatttta ttattattgt tattatgtcc agtctcactc tgtcgcctaa gctggcatga   2100
t                                                                  2101

<210> SEQ ID NO 8
<211> LENGTH: 1821
<212> TYPE: DNA
<213> ORGANISM: Homo sapiens
<220> FEATURE:
<221> NAME/KEY: misc_feature
<223> OTHER INFORMATION: sequence of STAR8

<400> SEQUENCE: 8
gagatcacct cgaagagagt ctaacgtccg taggaacgct ctcgggttca caaggattga     60
ccgaacccca ggatacgtcg ctctccatct gaggcttgct ccaaatggcc ctccactatt    120
ccaggcacgt gggtgtctcc cctaactctc cctgctctcc tgagcccatg ctgcctatca    180
cccatcggtg caggtccttt ctgaagagct cgggtggatt ctctccatcc cacttccttt    240
cccaagaaag aagccaccgt tccaagacac ccaatgggac attccccttc cacctccttc    300
tccaaagttg cccaggtgtt catcacaggt tagggagaga agcccccagg tttcagttac    360
aaggcatagg acgctggcat gaacacacac acacacacac acacacacac acacacacac    420
acacgactcg aagaggtagc cacaagggtc attaaacact tgacgactgt tttccaaaaa    480
cgtggatgca gttcatccac gccaaagcca agggtgcaaa gcaaacacgg aatggtggag    540
agattccaga ggctcaccaa accctctcag gaatattttc ctgaccctgg ggcagaggt    600 tggaaacatt gaggacattt cttgggacac acggagaagc tgaccgacca ggcattttcc    660
tttccactgc aaatgaccta tggcggggc atttcacttt ccctgcaaa tcacctatgg    720 cgaggtacct ccccaagccc ccacccccac ttccgcgaat cggcatggct cggcctctat    780
ccgggtgtca ctccaggtag gcttctcaac gctctcggct caagaagga caatcacagg    840 tccaagccca aagcccacac ctcttccttt tgttataccc acagaagtta gagaaaacgc    900
cacactttga gacaaattaa gagtccttta tttaagccgg cggccaaaga gatggctaac    960
```

-continued

```
gctcaaaatt ctctgggccc cgaggaaggg gcttgactaa cttctatacc ttggtttagg    1020
aaggggaggg gaactcaaat gcggtaattc tacagaagta aaaacatgca ggaatcaaaa    1080
gaagcaaatg gttatagaga gataaacagt tttaaaaggc aaatggttac aaaaggcaac    1140
ggtaccaggt gcggggctct aaatccttca tgacacttag atataggtgc tatgctggac    1200
acgaactcaa ggctttatgt tgttatctct tcgagaaaaa tcctgggaac ttcatgcact    1260
gtttgtgcca gtatcttatc agttgattgg ctcccttga aatgctgagt atctgcttac    1320
acaggtcaac tccttgcgga aggggttgg gtaaggagcc cttcgtgtct cgtaaattaa    1380
ggggtcgatt ggagtttgtc cagcattccc agctacagag agccttattt acatgagaag    1440
caaggctagg tgattaaaga gaccaacagg gaagattcaa agtagcgact tagagtaaaa    1500
acaaggttag gcatttcact ttcccagaga acgcgcaaac attcaatggg agagaggtcc    1560
cgagtcgtca aagtcccaga tgtggcgagc ccccgggagg aaaaaccgtg tcttccttag    1620
gatgcccgga acaagagcta ggcttccgga gctaggcagc catctatgtc cgtgagccgg    1680
cgggagggag accgccggga ggcgaagtgg ggcggggcca tccttctttc tgctctgctg    1740
ctgccgggga gctcctggct ggcgtccaag cggcaggagg ccgccgtcct gcagggcgcc    1800
gtagagtttg cggtgcagag t                                               1821
```

<210> SEQ ID NO 9
<211> LENGTH: 1929
<212> TYPE: DNA
<213> ORGANISM: Homo sapiens
<220> FEATURE:
<221> NAME/KEY: misc_feature
<223> OTHER INFORMATION: sequence of STAR9

<400> SEQUENCE: 9

```
cacttcctgg gagtggagca gaggctctgc gtggagcatc catgtgcagt actcttaggt     60
acggaaggga ttgggctaaa ccatggatgg gagctgggaa gggaagggac caacttcagg    120
ccccactggg acactggagc tgccaccctt tagagccctc ctaaccctac accagaggct    180
gagggggacc tcagacatca cacacatgct ttcccatgtt ttcagaaatc tggaaacgta    240
gaacttcagg ggtgagagtg cctagatatt gaatacaagg ctagattggg cttctgtaat    300
atcccaaagg accctccagc ttttttcacca gcacctaatg cccatcagat accaaagaca    360
cagcttagga gaggttcacc ctgaagctga ggaggaggca gccggattag agttgactga    420
gcaaggatga ctgccttctc cacctgacga tttcagctgc tgccctttc ttttcctggg    480 aatgcctgtc gccatggcct tctgtgtcca caggagagtt tgacccagat actcatggac    540
caggcaaagg tgctgttcct cccagcccag ggcccaccat gaagcatgcc tgggagcctg    600
gtaaggaccc agccactcct gggctgttga cattggcttc tcttgcccag cattgtagcc    660
acgccactgc attgtactgt gagataagtc aaggtgggct caccaggacc tgcactaaat    720
tgtgaaattc agctccaaag aactttggaa attacccatg catttaagca aaatgaatga    780
tacctgagca aacccttca cattggcaca agttacaatc ctgtctcatc ctcttgatta    840
caaattccat ccaggcaaga gctgtatcac cctgaggtct ccccattcat gttttggtca    900
ataatattta gtttcctttt gaaaatagat ttttgtgtta ctccattatg atgggcagag    960
gccagatgct tatattctat ttaaatgact atgttttct atctgtaact gggtttgtgt    1020
tcaggtggta aatgcttttt ttttgcagtc agaagattcc tggaaggcga ccagaaatta    1080
gctggccgct gtcagacctg aagttacttc taaagggcct ttagaaatga attctttttt    1140
```

```
atgccttctc tgaattctga gaagtaggct tgacttcccc taagtgtgga gttgggagtc    1200
aactcttctg aaaagaaagt ttcagagcat tttccaaagc catggtcagc tgtgggaagg    1260
gaagacgatg gatagtacag ttgccggaaa acactgatgg aggcggatgc tccagctcag    1320
ccaaagacct ttgttctgcc caccccagaa atgccccttc ctcaatcgca gaaacgttgc    1380
cccatggctc ctgatactca gaatgcagcc tctgaccagg accatctgca tcctccagga    1440
gctcgtaaga aatgcagcat cgtgggacct gctggcacct ggtgaaccca aacctgcagg    1500
gctcctgggt gtgcttgggg cggctgcagg ggaagaggga gtcagcagcc tcctcctgac    1560
cttcccgggg gctgcttttc tgaggggcca gaatgcaccg gttgaccttg ttgcatcact    1620
ggcccatgac tggctgcttt ggtcaggtgt aaaaaggtgt ttccagaggg tctgctcctc    1680
tcactatcgg accaggtttc catggagagc tcagcctccc agcaaggata gagaacttca    1740
aatggctcaa agaactgaga ggccacacat gtgtgacctg aatagtctct gctgcaaaac    1800
aaagggtttc ttaatgtaaa acgttctctt cctcacagag gggttcccag ctgctagtgg    1860
gcatgttgca ggcatttcct gggctgcatc aggttgtcat aagccagagg atcatttttg    1920
ggggctcat                                                           1929

<210> SEQ ID NO 10
<211> LENGTH: 1167
<212> TYPE: DNA
<213> ORGANISM: Homo sapiens
<220> FEATURE:
<221> NAME/KEY: misc_feature
<223> OTHER INFORMATION: sequence of STAR10
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t

<400> SEQUENCE: 10
aggtcaggag ttcaagacca gcctggccaa catggtgaaa ccctgtccct acaaaaaata     60
caaaaattag ccgggcgtgg tggggggcgc ctataatccc agctactcag gatgctgaga    120
caggagaatt gtttgaaccc gggaggtgga ggttgcagtg aactgagatc gcgccactgc    180
actccagcct ggtgacagag agagactccg tctcaacaac agacaaacaa acaaacaaac    240
aacaacaaaa atgtttactg acagctttat tgagataaaa ttcacatgcc ataaaggtca    300
ccttctacag tatacaattc agtggattta gtatgttcac aaagttgtac gttgttcacc    360
atctactcca gaacatttac atcaccccta aaagaagctc tttagcagtc acttctcatt    420
ctccccagcc cctgccaacc acgaatctac tntctgtctc tattctgaat atttcatata    480
aaggagtcct atcatatggg ccttttacgt ctaccttctt tcacttagca tcatgttttt    540
aagattcatc cacagtgtag cacgtgtcag ttaattcatt tcatcttatg gctggataat    600
gctctattgt atgcatatcc ctcacttttgc ttatccattc atcaactgat tgacatttgg    660
gttatttcta cttttgact attatgagta atgctgctat gaacattcct gtaccaatcg    720
ttacgtggac atatgctttc aattctcctg agtatgtaac tagggttgga gttgctgggt    780
catatgttaa ctcagtgttt cattttttg aagaactacc aaatggtttt ccaaagtgga    840
tgcaacactt tacattccca ccagcaagat atgaaggttc caatgtctct acattttgc    900 caacacttgt gattttcttt tatttattta tttatttatt tattttgag atggagtctc    960
```

```
actctgtcac ccaggctgga gtgcagtggc acaatttcag ctcactgcaa tctccacctc    1020
tcgggctcaa gcgatactcc tgcctcaacc tcccgagtaa ctgggattac aggcgcccac    1080
caccacacca agctaatttt ttgtattttt agtagagacg gggtttcatc atgtcggcca    1140
ggntgtactc gaactctgac ctcaagt                                         1167
```

<210> SEQ ID NO 11
<211> LENGTH: 1377
<212> TYPE: DNA
<213> ORGANISM: Homo sapiens
<220> FEATURE:
<221> NAME/KEY: misc_feature
<223> OTHER INFORMATION: sequence of STAR11

<400> SEQUENCE: 11

```
aggatcactt gagcccagga gttcaagacc agcctgggca acatagcgag aacatgtctc      60
aaaaaggaaa aaaatggggg aaaaaaccct cccagggaca gatatccaca gccagtcttg     120
ataagctcca tcattttaaa gtgcaaggcg gtgcctccca tgtggatgat tatttaatcc     180
tcttgtactt tgtttagtcc tttgtggaaa tgcccatctt ataaattaat agaattctag     240
aatctaatta aaatggttca actctacatt ttacttttagg ataatatcag gaccatcaca    300
gaatgtctga gatgtggatt taccctatct gtagctcact tcttcaacca ttcttttagc    360
aaggctagtt atcttcagtg acaacccctt gctgccctct actatctcct ccctcagatg    420
gactactctg attaagcttg agctagaata agcatgttat cccgggattt catatggaat    480
attttataca tgagtgagcc attatgagtt gtttgaaaat ttattatgtt gagggagggt    540
aaccgctgta acaaccatca ccaaatctaa tcgactgaat acatttgacg tttatttctt    600
gttcacctga cagttcagtg ttacctaaat ttacatgaag acccagaggc ccacgctcct    660
tcattttggg ctccaccgac ctccaaggtt tcagggccct ctgccccgcc ttctgcaccc    720
acaggggaag agagtggagg atgcacacgc ccaggcctgg aagtgacgca tgtggcttcc    780
ccgtccacag acttcaccca cagtccattg gccttcttaa gtcatggact cctgctgagc    840
tgccagggtg catgggaaat ccatgtgact gtgtgccctg gaggaagggg agcgtttcgg    900
tgagcacaca ggagtctttg ccactagacg ctgatgagga ttccccacag gcgatgaagc    960
atggagactc atcttgtaac aaacagatga gttgttgaca tctcttaagt ttactttgtg   1020
tgcagttttt attcagatag gaaaggctgt taaaatctta acacctaact ggaagaaggg   1080
ttttagagaa gtgtggtttt cagtaagcca gttctttcca caatccaaga aacgaaataa   1140
atttccagca tggagcagtt ggcaggtaag gttttttgttg tggtctcgcc caggcttgag   1200
tgtaaccggt gtggtcatag ctcactacat tctcaaactc ctggccttaa gtcatcctcc   1260
tgcctcagcc tcccaaaggc aagtaaggtt aagaataggg gaaaggtgaa gtttcacagc   1320
ttttctagaa ttcttttttat tcaagggact ctcagatcat caaacccacc cagaatc     1377
```

<210> SEQ ID NO 12
<211> LENGTH: 1051
<212> TYPE: DNA
<213> ORGANISM: Homo sapiens
<220> FEATURE:
<221> NAME/KEY: misc_feature
<223> OTHER INFORMATION: sequence of STAR12

<400> SEQUENCE: 12

```
atcctgcttc tgggaagaga gtggcctccc ttgtgcaggt gactttggca ggaccagcag     60
```

```
aaacccaggt tccctgtcag gaggaagtgc tcagcttatc tctgtgaagg gtcgtgataa      120
ggcacgagga ggcaggggct tgccaggatg ttgcctttct gtgccatatg ggacatctca      180
gcttacgttg ttaagaaata tttggcaaga agatgcacac agaatttctg taacgaatag      240
gatggagttt taagggttac tacgaaaaaa agaaaactac tggagaagag ggaagccaaa      300
caccaccaag tttgaaatcg attttattgg acgaatgtct cactttaaat ttaaatggag      360
tccaacttcc ttttctcacc cagacgtcga aaggtggca ttcaaaatgt ttacacttgt       420
ttcatctgcc ttttttgctaa gtcctggtcc cctacctcct ttccctcact tcacatttgt    480
cgtttcatcg cacacatatg ctcatcttta tatttacata tatataattt ttatatatgg     540
cttgtgaaat atgccagacg agggatgaaa tagtcctgaa aacagctgga aaattatgca     600
acagtgggga gattgggcac atgtacattc tgtactgcaa agttgcacaa cagaccaagt    660
ttgttataag tgaggctggg tggttttat tttttctcta ggacaacagc ttgcctggtg      720
gagtaggcct cctgcagaag gcatttctt aggagcctca acttcccaa gaagaggaga       780 gggcgagact ggagttgtgc tggcagcaca gagacaaggg ggcacggcag gactgcagcc     840
tgcagagggg ctggagaagc ggaggctggc acccagtggc cagcgaggcc caggtccaag     900
tccagcgagg tcgaggtcta gagtacagca aggccaaggt ccaaggtcag tgagtctaag     960
gtccatggtc agtgaggctg agacccaggg tccaatgagg ccaaggtcca gagtccagta    1020
aggccgagat ccagggtcca gggaggtcaa g                                   1051

<210> SEQ ID NO 13
<211> LENGTH: 1291
<212> TYPE: DNA
<213> ORGANISM: Homo sapiens
<220> FEATURE:
<221> NAME/KEY: misc_feature
<223> OTHER INFORMATION: sequence of STAR13

<400> SEQUENCE: 13
agccactgag gtcctaactg cagccaaggg gccgttctgc acatgtcgct caccctctgt      60
gctctgttcc ccacagagca aacgcacatg gcaacgttgg tccgctcagc cactggttct      120
gtggtggaac ggtggatgtc tgcactgtga catcagctga gtaagtaaca acgactgagg      180
atgccgctga cccagggctg ggaaggggga ctcccagctc agacaggctt ggctgtggtt      240
tgctttggga ggagagtgaa catcacaggg aatggctcat gtcagcccca ggagggtggg      300
ctggcccctg gtccccgggc tccttctggc cctgcaggcg atagagagcc tcaacctgct      360
gccgcttctc cttggcccgg gtgatggccg tctggaagag cctgcagtag aggtgcacag      420
ccagcggaga gtcgtcattg ccgggtacag ggtaggtgat gaggcagggg ttgcagttgg      480
tgtccacgat gcccactgtg gggatgttca tcttggctgc gtctctcacg ccacgtgtg      540 gctcaaagat gttgttgagc gtgtgcagga agatgatgag gtccggcagg cggaccgtgg     600
ggccaaagag gaggcgcgcg ttggtcagca tgccgcccct gaagtagcga gtgtgggcgt     660
actcgccaca gtcacgggcc atgttctcaa tcaggtacga gaactgccgg ttgcggctta     720
taaacaagat gatgcccttg cggtaggcca tgtgggcggt gaagttcaag gccagctgga     780
ggtgcgtggc tgtctgttcc aggtcgatga tgtcgtggtc caggcggctc ccaaagatgt     840
acggctccat aaacctgcca gagaccccac caaggcaagg gggatgagag ttcacggggc     900
catctccact ggctccttgc aggaacacag acgcccacca gggactcccg ggctcctctg     960
tgggggcact atgggctggg aagcacaatt tgcaacgctc cccgtgtgca tggacagcag    1020
```

| | |
|---|---:|
| tgcagaccca tccaggccac ccctctgcat gcctcgtctc gtggcttaac ccctcctacc | 1080 |
| ctctacctct tcccgaagga atcctaatag aactgacccc atatgatgt gtggacatcc | 1140 |
| aacatgacgc caaaaggaca ttctgccccg tgcagctcac agggcagccg cctccgtcac | 1200 |
| tgtcctcttc ccgaggcttt gcggatgagg cccctctggg gttggactta gcggggtgct | 1260 |
| ctgggccaaa agcattaagg gatcagggca g | 1291 |

<210> SEQ ID NO 14
<211> LENGTH: 711
<212> TYPE: DNA
<213> ORGANISM: Homo sapiens
<220> FEATURE:
<221> NAME/KEY: misc_feature
<223> OTHER INFORMATION: sequence of STAR14

<400> SEQUENCE: 14

| | |
|---|---:|
| ccctggacca gggtccgtgg tcttggtggg cactggcttc ttcttgctgg gtgttttcct | 60 |
| gtgggtctct ggcaaggcac tttttgtggc gctgcttgtg ctgtgtgcgg gaggggcagg | 120 |
| tgctctttcc tcttggagct ggaccctctg ggcgggtcc ccgtcggcct ccttgtgtgt | 180 |
| tttctgcacc tggtacagct ggatggcctc ctcaatgccg tcgtcgctgc tggagtcgga | 240 |
| cgcctcgggc gcctgtacgg cgctcgtgac tcgctttccc ctccttgcgg tgctggcgtt | 300 |
| ccttttaatc ccacttttat tctgtactgc ttctgaaggg cggtgggggt tgctggcttt | 360 |
| gtgctgccct ccttctcctg cgtggtcgtg gtcgtgacct tggacctgag gcttctgggc | 420 |
| tgcacgtttg tctttgctaa ccgggggagg tctgcagaag gcgaactcct tctggacgcc | 480 |
| catcaggccc tgccggtgca ccacctttgt agccggctct tggtgggatt tcgagagtga | 540 |
| cttcgccgaa ttttcatgtg tgtctggttt cttctccact gacccatcac attttttgggt | 600 |
| ctcatgctgt cttttctcat tcagaaactg ttctatttct gccctgatgc tctgctcaaa | 660 |
| ggagtctgct ctgctcatgc tgactgggga ggcagagccc tggtccttgc t | 711 |

<210> SEQ ID NO 15
<211> LENGTH: 1876
<212> TYPE: DNA
<213> ORGANISM: Homo sapiens
<220> FEATURE:
<221> NAME/KEY: misc_feature
<223> OTHER INFORMATION: sequence of STAR15

<400> SEQUENCE: 15

| | |
|---|---:|
| gagtccaaga tcaaggtgcc agcatcttgt gagggccttc ttgttacgtc actccctagc | 60 |
| gaaagggcaa agagagggtg agcaagagaa aggggggctg aactcgtcct tgtagaagag | 120 |
| gcccattccc gagacaatgg cattcatcca ttcactccac cctcatggcc tcaccacctc | 180 |
| tcatgaggct ccacctccca gccctggttt gttggggatt aaatttccaa cacatgcctt | 240 |
| ttgggggaca tgttaaaatt atagcacccc aaatgttaca ctatcttttg atgagcggta | 300 |
| gttctgattt taagtctagc tggcctactt tttcttgcac gtgggatgct ttctgcctgt | 360 |
| tccagggcag gcagctcttc tctgtccctc tgctggcccc acctcatcct ctgttgtcct | 420 |
| cttccctcct tctgtgccct ggggtcctgg tgggggtgtg actgtcaact gcgttgggct | 480 |
| aactttttc cctgctggtg gcccgtaatg aaagaaagct tcttgctccc aagttcctta | 540 |
| aatccaagct catagacaac gcggtctcac agcaggcctg ggccagcct cacgtgagcc | 600 |
| ccttccctgg tgtagtcact ggcatggggg aatgggattt cctgttgccc tactgtgtgg | 660 |
| ctgaggtggg ggttgcttcc tggagccagg ccttgtggaa gggcagtgcc cactgcagtg | 720 |

```
gatgctgggc cctgaatctg accccagtgt tcattggctc tgtgagaccc agtgagggca        780
gggagggaag tggagctggg gtgagaagta gaggccctgc agggcccacg tgccagccac        840
caggcctcag actaggctca gatgacggag agctgcacac ctgcccaacc caggccctgc        900
agtgcccaca tgccagccgc tggggcccag acttgctcca gagggcggag agctttacac        960
cggcccaacc caggccatgg ctccaaatgc gtgacagttt tgctgttgct tcttttagtc       1020
attgtcaagt tgatgcttgt tttgcagagg accaaggctt tatgaaccta ttaccctgtg       1080
tgaagagttt caccaggtta tggaaatttc tttaaaacca taccacagtt ttttcattat       1140
tcatgtatat ttttaaaaat aattactgca ctcagtagaa taacatgaaa atgttgcctg       1200
ttagcccttt tccagtttgc cccgagaata ctggggcac ttgtggctgc aatgtttatc        1260
ctgcggcagc tttgccatga agtatctcac ttttattatt attttttgcat tgctcgagta       1320 tattgacttt ggaaacaaaa gacatcattc tatttatagc attatgtttt tagtagtggt       1380
atttccatat acaagataca gtaattttcc gtcaatgaaa atgtcaaatt ctagaaaatg       1440
taacattcct atgcgtggtg ttaacatcgt tctctaacag ttgttggccg aagattcgtt       1500
tgatgaatcc gattttccca aaatagccga ttctgatgat tcagacgatt ctgatgttct       1560
gtttagaaat aattccaaga acagttttta cattttattt tcacattgaa aatcagtcag       1620
atttgcttca gcctcaaaga gcacgtttat gtaaaattaa atgagtgctg gcagccagct       1680
gcgctttgtt tttctaaatg ggaaaagggt taaatttcac tcagcttta aatgacagcg        1740 cacagcctgt gtcatagagg gttggaggag atgactttaa ctgcctgtgg ttaggatccc       1800
tttcccccag gaatgtctgg gagcccactg ccgggtttgc tgtccgtctc gtttggactc       1860
agttctgcat gtactg                                                      1876

<210> SEQ ID NO 16
<211> LENGTH: 1282
<212> TYPE: DNA
<213> ORGANISM: Homo sapiens
<220> FEATURE:
<221> NAME/KEY: misc_feature
<223> OTHER INFORMATION: sequence of STAR16

<400> SEQUENCE: 16
cgcccacctc ggcttttccaa agtgctggga ttacaggcat gagtcactgc gcccatcctg         60
attccaagtc tttagataat aacttaactt tttcgaccaa ttgccaatca ggcaatcttt        120
gaatctgcct atgacctagg acatccctct ccctacaagt tgcccgcgt ttccagacca         180 aaccaatgta catcttacat gtattgattg aagttttaca tctccctaaa acatataaaa        240
ccaagctata gtctgaccac ctcaggcacg tgttctcagg acctccctgg ggctatggca        300
tgggtcctgg tcctcagatt tggctcagaa taaatctctt caaatatttt ccagaatttt        360
actcttttca tcaccattac ctatcaccca taagtcagag ttttcacaa ccccttcctc         420 agattcagta atttgctaga atggccacca aactcaggaa agtattttac ttacaattac        480
caatttatta tgaagaactc aaatcaggaa tagccaaatg gaagaggcat agggaaaggt        540
atggaggaag gggcacaaag cttccatgcc ctgtgtgcac accaccctct cagcatcttc        600
atgtgttcac caactcagaa gctcttcaaa ctttgtcatt taggggtttt tatggcagtt        660
ccactatgta ggcatggttg ataaatcact ggtcatcggt gatagaactc tgtctccagc        720
tcctctctct ctcctcccca gaagtcctga ggtgggctg aaagtttcac aaggttagtt         780
gctctgacaa ccagccccta tcctgaagct attgaggggt cccccaaaag ttaccttagt        840
```

| | |
|---|---|
| atggttggaa gaggcttatt atgaataaca aaagatgctc ctattttttac cactagggag | 900 |
| catatccaag tcttgcggga acaaagcatg ttactggtag caaattcata caggtagata | 960 |
| gcaatctcaa ttcttgcctt ctcagaagaa agaatttgac caaggggggca taaggcagag | 1020 |
| tgagggacca agataagttt tagagcagga gtgaaagttt attaaaaagt tttaggcagg | 1080 |
| aatgaaagaa agtaaagtac atttggaaga gggccaagtg ggcgacatga gagagtcaaa | 1140 |
| caccatgccc tgtttgatgt ttggcttggg gtcttatatg atgacatgct tctgagggtt | 1200 |
| gcatccttct cccctgattc ttcccttggg gtgggctgtc cgcatgcaca atggcctgcc | 1260 |
| agcagtaggg aggggccgca tg | 1282 |

<210> SEQ ID NO 17
<211> LENGTH: 793
<212> TYPE: DNA
<213> ORGANISM: Homo sapiens
<220> FEATURE:
<221> NAME/KEY: misc_feature
<223> OTHER INFORMATION: sequence of STAR17

<400> SEQUENCE: 17

| | |
|---|---|
| atccgagggg aggaggagaa gaggaaggcg agcagggcgc cggagcccga ggtgtctgcg | 60 |
| agaactgttt taaatggttg gcttgaaaat gtcactagtg ctaagtggct tttcggattg | 120 |
| tcttatttat tactttgtca ggtttcctta aggagagggt gtgttggggg tggggaggga | 180 |
| ggtggactgg ggaaacctct gcgtttctcc tcctcggctg cacagggtga gtaggaaacg | 240 |
| cctcgctgcc acttaacaat ccctctatta gtaaatctac gcggagactc tatgggaagc | 300 |
| cgagaaccag tgtcttcttc cagggcagaa gtcacctgtt gggaacggcc cccgggtccc | 360 |
| cctgctgggc tttccggctc ttctaggcgg cctgatttct cctcagccct ccacccagcg | 420 |
| tccctcaggg acttttcaca cctccccacc cccatttcca ctacagtctc ccagggcaca | 480 |
| gcacttcatt gacagccaca cgagccttct cgttctcttc cctctgttc cttctctttc | 540 |
| tcttctcctc tgttccttct cttttctctgt cataatttcc ttggtgcttt cgccacctta | 600 |
| aacaaaaaag agaaaaaaat aaaataaaaa aaacccattc tgagccaaag tattttaaga | 660 |
| tgaatccaag aaagcgaccc acatagccct ccccacccac ggagtgcgcc aagacgcacc | 720 |
| caggctccat cacagggccg agagcagcgc cactctggtc gtacttttgg gtcaagagat | 780 |
| cttgcaaaag agg | 793 |

<210> SEQ ID NO 18
<211> LENGTH: 492
<212> TYPE: DNA
<213> ORGANISM: Homo sapiens
<220> FEATURE:
<221> NAME/KEY: misc_feature
<223> OTHER INFORMATION: sequence of STAR18

<400> SEQUENCE: 18

| | |
|---|---|
| atcttttttgc tctctaaatg tattgatggg ttgtgttttt tttcccacct gctaataaat | 60 |
| attacattgc aacattcttc cctcaacttc aaaactgctg aactgaaaca atatgcataa | 120 |
| aagaaaatcc tttgcagaag aaaaaaagct attttctccc actgattttg aatggcactt | 180 |
| gcggatgcag ttcgcaaatc ctattgccta ttccctcatg aacattgtga atgaaacct | 240 |
| ttggacagtc tgccgcattg cgcatgagac tgcctgcgca aggcaagggt atggttccca | 300 |
| aagcacccag tggtaaatcc taacttatta ttcccttaaa attccaatgt aacaacgtgg | 360 |

```
gccataaaag agtttctgaa caaaacatgt catctttgtg gaaaggtgtt tttcgtaatt      420
aatgatggaa tcatgctcat ttcaaaatgg aggtccacga tttgtggcca gctgatgcct      480
gcaaattatc ct                                                          492
```

<210> SEQ ID NO 19
<211> LENGTH: 1840
<212> TYPE: DNA
<213> ORGANISM: Homo sapiens
<220> FEATURE:
<221> NAME/KEY: misc_feature
<223> OTHER INFORMATION: sequence of STAR19

<400> SEQUENCE: 19

```
tcacttcctg atattttaca ttcaaggcta gctttatgca tatgcaacct gtgcagttgc       60
acagggcttt gtgttcagaa agactagctc ttggtttaat actctgttgt tgccatcttg      120
agattcatta taatataatt tttgaatttg tgttttgaac gtgatgtcca atgggacaat      180
ggaacattca cataacagag gagacaggtc aggtggcagc ctcaattcct tgccacccett      240 ttcacataca gcattggcaa tgccccatga gcacaaaatt tgggggaacc atgatgctaa      300
gactcaaagc acatataaac atgttacctc tgtgactaaa agaagtggag gtgctgacag      360
cccccagagg ccacagtttta tgttcaaacc aaaacttgct tagggtgcag aaagaaggca      420
atggcagggt ctaagaaaca gcccatcata tccttgttta ttcatgttac gtccctgcat      480
gaactaatca cttacactga aaatattgac agaggaggaa atggaaagat agggcaaccc      540 atagttctt  ttcctttttag tctttcctta tcagtaaacc aaagatagta ttggtaaaat      600
gtgtgtgagt taattaatga gttagttta ggcagtgttt ccactgttgg ggtaagaaca       660
aaatatatag gcttgtattg agctattaaa tgtaaattgt ggaatgtcag tgattccaag      720
tatgaattaa atatccttgt atttgcattt aaaattggca ctgaacaaca aagattaaca      780
gtaaaattaa taatgtaaaa gtttaatttt tacttagaat gacattaaat agcaaataaa      840
agcaccatga taaatcaaga gagagactgt ggaaagaagg aaaacgtttt tattttagta      900
tatttaatgg gactttcttc ctgatgtttt gttttgtttt gagagagagg gatgtggggg      960
cagggaggtc tcattttgtt gcccaggctg gacttgaact cctgggctcc agctatcctg     1020
ccttagcttc ttgagtagct gggactacag gcacacacca cagtgtctga cattttctgg     1080 atttttttt ttttttttatt tttttttgtga acaggttct ggctctgtta ctcaggttgc      1140
agtgcagtgg catgatagcg gctcactgca gcctcaacct cctcagctta agctactctc     1200
ccacttcagc ctcctgagta gccaggacta cagtgtgtg ccaccacacc tgtggctaat     1260
ttttgtagag atggggtctc tccacgttgc cgaggctggt ctccaactcc tggtctcaag     1320
cgaacctcct gacttggcct cccgaagtgc tgggattaca ggcttgagcc actgcatcca     1380
gcctgtcctc tgtgttaaac ctactccaat ttgtctttca tctctacata aacggctctt     1440
ttcaaagttc ccatagacct cactgttgct aatctaataa taaattatct gccttttctt     1500
acatggttca tcagtagcag cattagattg ggctgctcaa ttcttcttgg tatattttct     1560
tcatttggct tctggggcat cacactctct ttgagttact cattcctcat tgatagcttc     1620
ttcctagtct tctttactgg ttcttcctct tctccctgac tccttaatat tgtttttctc     1680
cccaggcttt agttcttagt cctcttctgt tatctatttta cacccaattc tttcagagtc     1740
tcatccagag tcatgaactt aaacctgttt ctgtgcagat aattcacatt attatatctc     1800
cagcccagac tctcccgcaa actgcagact gatcctactg                           1840
```

<210> SEQ ID NO 20
<211> LENGTH: 780
<212> TYPE: DNA
<213> ORGANISM: Homo sapiens
<220> FEATURE:
<221> NAME/KEY: misc_feature
<223> OTHER INFORMATION: sequence of STAR20

<400> SEQUENCE: 20

| | | | | | |
|---|---|---|---|---|---|
| gatctcaagt | ttcaatatca | tgttttggca | aaacattcga | tgctcccaca | tccttaccta | 60 |
| aagctaccag | aaaggctttg | ggaactgtca | acagagctac | agaaagtca | gtaaagacca | 120 |
| atggacccct | caaacaaaaa | cagccaagct | tttctgccaa | aaagatgact | gagaagactg | 180 |
| ttaaagcaaa | aaactctgtt | cctgcctcag | atgatggcta | tccagaaata | gaaaaattat | 240 |
| ttcccttcaa | tcctctaggc | ttcgagagtt | ttgacctgcc | tgaagagcac | cagattgcac | 300 |
| atctcccctt | gagtgaagtg | cctctcatga | tacttgatga | ggagagagag | cttgaaaagc | 360 |
| tgtttcagct | gggccccccct | tcaccttgga | agatgccctc | tccaccatgg | aaatccaatc | 420 |
| tgttgcagtc | tcctttaagc | attctgttga | ccctggatgt | tgaattgcca | cctgtttgct | 480 |
| ctgacataga | tatttaaatt | tcttagtgct | ttagagtttg | tgtatatttc | tattaataaa | 540 |
| gcattatttg | tttaacagaa | aaaagatat | atacttaaat | cctaaataa | aataaccatt | 600 |
| aaaaggaaaa | acaggagtta | taactaataa | gggaacaaag | gacataaaat | gggataataa | 660 |
| tgcttaatcc | aaaataaagc | agaaaatgaa | gaaaaatgaa | atgaagaaca | gataaataga | 720 |
| aaacaaatag | caatatgaaa | gacaaacttg | accgggtgtg | gtggctgatg | cctgtaatcc | 780 |

<210> SEQ ID NO 21
<211> LENGTH: 607
<212> TYPE: DNA
<213> ORGANISM: Homo sapiens
<220> FEATURE:
<221> NAME/KEY: misc_feature
<223> OTHER INFORMATION: sequence of STAR21

<400> SEQUENCE: 21

| | | | | | |
|---|---|---|---|---|---|
| gatcaataat | ttgtaatagt | cagtgaatac | aaagggtat | atactaaatg | ctacagaaat | 60 |
| tccattcctg | ggtataaatc | ctagacatat | ttatgcatat | gtacaccaag | atatatctgc | 120 |
| aagaatgttc | acagcaaatc | tctttgtagt | agcaaaaggc | caaaaggtct | atcaacaaga | 180 |
| aaattaatac | attgtggcac | ataatggcat | ccttatgcca | ataaaaatgg | atgaaattat | 240 |
| agttaggttc | aaaaggcaag | cctccagata | atttatatca | tataattcca | tgtacaacat | 300 |
| tcaacaacaa | gcaaaactaa | acatatacaa | atgtcaggga | aaatgatgaa | caaggttaga | 360 |
| aaatgattaa | tataaaaata | ctgcacagtg | ataacattta | atgagaaaaa | aagaaggaag | 420 |
| ggcttaggga | gggacctaca | gggaactcca | aagttcatgg | taagtactaa | atacataatc | 480 |
| aaagcactca | aaatagaaaa | tattttagta | atgttttagc | tagttaatat | cttacttaaa | 540 |
| acaaggtcta | ggccaggcac | ggtggctcac | acctgtaatc | ccagcacttt | gggaggctga | 600 |
| ggcgggt | | | | | | 607 |

<210> SEQ ID NO 22
<211> LENGTH: 1380
<212> TYPE: DNA
<213> ORGANISM: Homo sapiens
<220> FEATURE:
<221> NAME/KEY: misc_feature
<223> OTHER INFORMATION: sequence of STAR22

<400> SEQUENCE: 22

```
ccccttgtgat ccacccgcct tggcctccca aagtgctggg attacaggcg tgagtcacta     60
cgcccggcca ccctccctgt atattatttc taagtatact attatgttaa aaaaagttta    120
aaaatattga tttaatgaat tcccagaaac taggatttta catgtcacgt tttcttatta    180
taaaataaa aatcaacaat aaatatatgg taaaagtaaa aagaaaaaca aaacaaaaa      240
gtgaaaaaaa taacaacac tcctgtcaaa aacaacagt tgtgataaaa cttaagtgcc      300
tgaaaattta gaaacatcct tctaaagaag ttctgaataa aataaggaat aaaataatca    360
catagttttg gtcattggtt ctgtttatgt gatggattat gtttattgat ttgtgtatgt    420
tgaacttatc tcaatagatg cagacaaggc cttgataaaa gttttttaaca ccttttcatg    480
ttgaaaactc tcaatagact aggtattgat gaaacatatc tcaaaataat agaagctatt    540
tatgataaac ccatagccaa tatcatactg agtgggcaaa agctggaagc attcccttttg    600
aaaactggca aagacaagg atgccctctc tcaccactcc tattaaatgt agtattggaa     660
gttctggcca gagcaatcag gcaggagaaa gaaaaggtat taaaatagga agagaggaag    720
tcaaattgtc tctgtttgca gtaaacatga ttgtatattt agaaaacccc attgtctcat    780
cctaaaaact ccttaagctg ataaacaact tcagcaaagt ctcaggatac aaaatcaatg    840
tgcaaaaatc acaagcattc ctatacaccg ataatagaca gcagagagcc aaatcatgag    900
tgaagtccca ttcacaattg cttcaaagaa aataaaatac ttaggaatac aacttttcacg    960
ggacatgaag gacattttca aggacaacta aaaccactg ctcaaggaaa tgagagagga    1020
cacaagaaa tggaaaaaca ttccatgctc atggaagaat caatatcatg aaaatggcca    1080
tactgcccaa agtaattat agattcaatg ctaaccccat caagccacca ttgactttct    1140
tcacagaact agaaaaaaac tattttaaaa ctcatatgta gtcaaaaaga gtcggtatag   1200
ccaagacaat cctaagcata aagaacaaag ctggatgcat cacgctgact tcaaaccata   1260
ctacaaggct acagtaacca aaacagcatg gtactggtac caaaacagat agatagaccg   1320
atagaacaga acagaggcct cggaaataac accacacatc tacaaccctt tgatcttcaa   1380
```

<210> SEQ ID NO 23
<211> LENGTH: 1246
<212> TYPE: DNA
<213> ORGANISM: Homo sapiens
<220> FEATURE:
<221> NAME/KEY: misc_feature
<223> OTHER INFORMATION: sequence of STAR23

<400> SEQUENCE: 23

```
atcccctcat ccttcagggc agctgagcag ggcctcgagc agctgggga gcctcactta      60
atgctcctgg gagggcagcc agggagcatg gggtctgcag gcatggtcca gggtcctgca    120
ggcggcacgc accatgtgca gccgccccca cctgttgctc tgcctccgcc acctggccat    180
gggcttcagc agccagccac aaagtctgca gctgctgtac atggacaaga agcccacaag    240
cagctagagg accttgtgtt ccacgtgccc agggagcatg gcccacagcc caaagaccag    300
tcaggagcag gcaggggctt ctggcaggcc cagctctacc tctgtcttca cacagatggg    360
agatttctgt tgtgattttg agtgatgtgc ccctttggtg acatccaaga tagttgctga    420
agcaccgctc taacaatgtg tgtgtattct gaaaacgaga acttctttat tctgaaataa    480
ttgatgcaaa ataaattagt ttggatttga aattctattc atgtaggcat gcacacaaaa    540
gtccaacatt gcatatgaca caagaaaag aaaaagcttg cattccttaa atacaaatat    600
```

```
ctgttaacta tatttgcaaa tatatttgaa tacacttcta ttatgttaca tataatatta    660
tatgtatatg tatatataat atacatatat atgttacata taatatactt ctattatgtt    720
acatataata tttatctata agtaaataca taaatataaa gatttgagta gctgtagaac    780
attgtcttat gtgttatcag ctactactac aaaaatatct cttccactta tgccagtttg    840
ccatataaat atgatcttct cattgatggc ccagggcaag agtgcagtgg gtacttattc    900
tctgtgagga gggaggagaa aagggaacaa ggagaaagtc acaaagggaa aactctggtg    960
ttgccaaaat gtcaagtttc acatattccg agacggaaaa tgacatgtcc cacagaagga   1020
ccctgcccag ctaatgtgtc acagatatct caggaagctt aaatgatttt tttaaaagaa   1080
aagagatggc attgtcactt gtttcttgta gctgaggctg tgggatgatg cagatttctg   1140
gaaggcaaag agctcctgct ttttccacac cgagggactt tcaggaatga ggccagggtg   1200
ctgagcacta caccaggaaa tccctggaga gtgttttttct tactta                 1246

<210> SEQ ID NO 24
<211> LENGTH: 939
<212> TYPE: DNA
<213> ORGANISM: Homo sapiens
<220> FEATURE:
<221> NAME/KEY: misc_feature
<223> OTHER INFORMATION: sequence of STAR24

<400> SEQUENCE: 24
acgaggtcac gagttcgaga ccagcctggc caagatggtg aagccctgtc tctactaaaa     60
atacaacaag tagccgggcg cggtgacggg cgcctgtaat cccagctact caggaggctg    120
aagcaggaga atctctagaa cccaggaggc ggaggtgcag tgagctgaga ctgccccgct    180
gcactctagc ctgggcaaca cagcaagact ctgtctcaaa taaataaata aataaataaa    240
taaataaata aataaataaa tagaaaggga gagttggaag tagatgaaag agaagaaaag    300
aaatcctaga tttcctatct gaaggcacca tgaagatgaa ggccacctct tctgggccag    360
gtcctcccgt tgcaggtgaa ccgagttctg gcctccattg gagaccaaag gagatgactt    420
tggcctggct cctagtgagg aagccatgcc tagtcctgtt ctgtttgggc ttgatcctgt    480
atcacttgat tgtctctcct ggactttcca tggattccag ggatgcaact gagaagttta    540
tttttaatgc acttacttga agtaagagtt attttaaaac attttagcaa aggaaatgaa    600
ttctgacagg ttttgcactg aagacattca catgtgagga aaacaggaaa accactatgc    660
tagaaaaagc aaatgctgtt gagattgtct cacaaacaca aattgcgtgc cagcaggtag    720
gtttgagcct caggttgggc acattttacc ttaagcgcac tgttggtgga acttaaggtg    780
actgtaggac ttatatatac atacatacat ataatatata tacatattta tgtgtatata    840
cacacacaca cacacacaca cacacagggt cttgctatct tgcccagggt ggtctccaac    900
tctgggtctc aagcgatcct ctgcctcccc ttcccaaag                           939

<210> SEQ ID NO 25
<211> LENGTH: 1067
<212> TYPE: DNA
<213> ORGANISM: Homo sapiens
<220> FEATURE:
<221> NAME/KEY: misc_feature
<223> OTHER INFORMATION: sequence of STAR25

<400> SEQUENCE: 25
cagcccctct tgtgtttttc tttatttctc gtacacacac gcagttttaa gggtgatgtg     60
tgtataatta aaaggaccct tggcccatac tttcctaatt ctttagggac tgggattggg    120
```

```
tttgactgaa atatgttttg gtggggatgg gacggtggac ttccattctc cctaaactgg      180
agttttggtc ggtaatcaaa actaaaagaa acctctggga gactggaaac ctgattggag      240
cactgaggaa caagggaatg aaaaggcaga ctctctgaac gtttgatgaa atggactctt      300
gtgaaaatta acagtgaata ttcactgttg cactgtacga agtctctgaa atgtaattaa      360 aagttttat tgagccccg agctttggct tgcgcgtatt tttccggtcg cggacatccc        420
accgcgcaga gcctcgcctc cccgctgccc tcagcctccg atgactccc cgccccgcc       480 ctgctcggtg acagacgttc tactgcttcc aatcggaggc acccttcgcg ggagcggcca      540
atcgggagct ccggcaggcg gggaggccgg gccagttaga tttggaggtt caacttcaac      600
atggccgaag caagtagcgc caatctaggc agcggctgtg aggaaaaag gcatgagggg       660 tcgtcttcgg aatctgtgcc acccggcact accatttcga gggtgaagct cctcgacacc      720
atggtggaca cttttcttca gaagctggtc gccgccggca ggtaaagtgg acgcagccgc      780
ggtgggagtg tttgttggca ccgaagctca aatcccgcga ggtcaggacg gccgcaggct      840
ggcgcgcggt gacgtgggtc cgcgttgggg gcggggcagt cggacgaggc gacccagtca     900
aatcctgagc cttaggagtc agggtattca cgcactgata acctgtagcg gaccgggata     960
gctagctact ccttcctaca ggaagccccg ttttcactaa aatttcaggt ggttgggagg     1020
aaagatagag cctttgcaaa ttagagcagg gttttttatt tttttat                   1067

<210> SEQ ID NO 26
<211> LENGTH: 540
<212> TYPE: DNA
<213> ORGANISM: Homo sapiens
<220> FEATURE:
<221> NAME/KEY: misc_feature
<223> OTHER INFORMATION: sequence of STAR26

<400> SEQUENCE: 26 cccctgaca agccccagtg tgtgatgttc cccactctgt gtccatgcat tctcattgtt         60
caactcccat ctgtgagtga aacatgcag tgtttggttt tctgtccttg agatagtttg       120
ctgagaatga tggtttccag cttcatccat gtccttgcaa aggaagtgaa cttatccttt      180
tttatggctt catagtattc catggcacat atgtgccaca ttttttaat ccagtctatc       240 attgatggac atttggggttg gttccaagtc tttgctattg tgaatagcac acaattaac      300 atatgtgtgc atgtatacat ctttatagta gcatgattta taatccttcg ggtatatacc     360
ctgtaatggg atcgctgggt caaatggtat ttctagttct agatccttga ggaatcacca     420
cactgctttc cacaatggtt gaactaattt acgctcccac cagcagtgta aaagcattcc     480
tatttctcca cgtcctctcc agtatctgtt gtttcctgac ttttttaatga tcatcattct    540

<210> SEQ ID NO 27
<211> LENGTH: 1520
<212> TYPE: DNA
<213> ORGANISM: Homo sapiens
<220> FEATURE:
<221> NAME/KEY: misc_feature
<223> OTHER INFORMATION: sequence of STAR27

<400> SEQUENCE: 27
cttggccctc acaaagcctg tggccaggga acaattagcg agctgcttat tttgctttgt       60
atccccaatg ctgggcataa tgcctgccat tatgagtaat gccggtagaa gtatgtgttc      120
aaggaccaaa gttgataaat accaaagaat ccagagaagg gagagaacat tgagtagagg      180
```

| | |
|---|---:|
| atagtgacag aagagatggg aacttctgac aagagttgtg aagatgtact aggcaggggg | 240 |
| aacagcttaa ggagagtcac acaggaccga gctcttgtca agccggctgc catggaggct | 300 |
| gggtggggcc atggtagctt tcccttcctt ctcaggttca gagtgtcagc cttgaacttc | 360 |
| taattcccag aggcatttat tcaatgtttt cttctagggg catacctgcc ctgctgtgga | 420 |
| agactttctt ccctgtgggt cgccccagtc cccagatgag acggtttggg tcagggccag | 480 |
| gtgcaccgtt gggtgtgtgc ttatgtctga tgacagttag ttactcagtc attagtcatt | 540 |
| gagggaggtg tggtaaagat ggagatgctg ggtcacatcc ctagagaggt gttccagtat | 600 |
| gggcacatgg gagggctgga aggataggtt actgctagac gtagagaagc cacatccttt | 660 |
| aacaccctgg cttttcccac tgccaagatc cagaaagtcc ttgtggtttc gctgctttct | 720 |
| cctttttttt tttttttttt tttctgagat ggagtctggc tctgtcgccc aggctggagt | 780 |
| gcagtggcac gatttcggct cactgcaagt tccgcctcct aggttcatac cattctccca | 840 |
| cctcagcctc ccgagtagct gggactacag gcgccaccac acccagctaa ttttttgtat | 900 |
| ttttagtaga gacggcgttt caccatgtta gccaggatgg tcttgatccg cctgcctcag | 960 |
| cctcccaaag tgctgggatt acaggcgtga gccaccgcgc ccggcctgct tcttctttc | 1020 |
| atgaagcatt cagctggtga aaaagctcag ccaggctggt ctggaactct tgacctcaag | 1080 |
| tgatctgcct gcctcagcct cccaaagtgc tgagattaca ggcatgagcc agtccgaatg | 1140 |
| tggcttttt tgttttgttt tgaaacaagg tctcactgtt gcccaggctg cagtgcagtg | 1200 |
| gcatacctca gctccactgc agcctcgacc tcctgggctc aagcaatcct cccaactgag | 1260 |
| cctccccagt agctggggct acaagcgcat gccaccacgc ctggctattt ttttttttt | 1320 |
| ttttttttt gagaaggagt ttcattcttg ttgcccaggc tggagtgcaa tggcacagtc | 1380 |
| tcagctcact gcagcctccg cctcctgggt tcaagcgatt ctcctgcctc agcctcccga | 1440 |
| gtagctggga ttataggcac ctgccaccat gcctggctaa tttttttgta tttttagtag | 1500 |
| ggatggggtt tcaccatgtt | 1520 |

<210> SEQ ID NO 28
<211> LENGTH: 961
<212> TYPE: DNA
<213> ORGANISM: Homo sapiens
<220> FEATURE:
<221> NAME/KEY: misc_feature
<223> OTHER INFORMATION: sequence of STAR28

<400> SEQUENCE: 28

| | |
|---|---:|
| aggaggttat tcctgagcaa atggccagcc tagtgaactg gataaatgcc catgtaagat | 60 |
| ctgtttaccc tgagaagggc atttcctaac tctccctata aaatgccaag tggagcaccc | 120 |
| cagatgaaat agctgatatg ctttctatac aagccatcta ggactggctt tatcatgacc | 180 |
| aggatattca cccactgaat atggctatta cccaagttat ggtaaatgct gtagttaagg | 240 |
| gggtcccttc cacatggaca ccccaggtta taaccagaaa gggttcccaa tctagactcc | 300 |
| aagagagggt tcttagacct catgcaagaa agaacttggg gcaagtacat aaagtgaaag | 360 |
| caagtttatt aagaaagtaa agaaacaaaa aaatggctac tccataagca agttatttc | 420 |
| tcacttatat gattaataag agatggatta ttcatgagtt ttctgggaaa ggggtgggca | 480 |
| attcctggaa ctgagggttc ctcccacttt tagaccatat agggtatctt cctgatattg | 540 |
| ccatggcatt tgtaaactgt catggcactg atggagtgt cttttagcat tctaatgcat | 600 |
| tataattagc atataatgag cagtgaggat gaccagaggt cacttctgtt gccatattgg | 660 |

```
tttcagtggg gtttggttgg cttttttttt tttttaacca caacctgttt tttatttatt    720
tatttattta tttatttatt tatattttttt attttttttt agatggagtc ttgctctgtc    780
acccaggtta gagtgcagtg gcaccatctc ggctcactgc aagctctgcc tccttggttc    840
acgccattct gctgcctcag cctcccgagt agctgggact acaggtgcct gccaccatac    900
ccggctaatt ttttctattt ttcagtagag acggggtttc accgtgttag ccaggatggt    960
c                                                                     961
```

<210> SEQ ID NO 29
<211> LENGTH: 2233
<212> TYPE: DNA
<213> ORGANISM: Homo sapiens
<220> FEATURE:
<221> NAME/KEY: misc_feature
<223> OTHER INFORMATION: sequence of STAR29

<400> SEQUENCE: 29

```
agcttggaca cttgctgatg ccactttgga tgttgaaggg ccgccctctc ccacaccgct     60
ggccactttt aaatatgtcc cctctgccca aagggcccc agaggagggg ctggtgaggg    120
tgacaggagt tgactgctct cacagcaggg ggttccggag ggacctttc tccccattgg    180
gcagcataga aggacctaga agggccccct ccaagcccag ctgggcgtgc agggccagcg    240
attcgatgcc ttcccctgac tcaggtgcg ctgtcctaaa ggtgtgtgtg ttttctgttc    300
gccaggggt ggcggataca gtggagcatc gtgcccgaag tgtctgagcc cgtggtaagt    360
ccctggaggg tgcacggtct cctccgactg tctccatcac gtcaggcctc acagcctgta    420
ggcaccgctc ggggaagcct ctggatgagg ccatgtggtc atcccctgg agtcctggcc    480
tggcctgaag aggaggggag gaggaggcca gcccctccct agcccaagg cctgcgaggc    540
tgcaagcccg gccccacatt ctagtccagg cttggctgtg caagaagcag attgcctggc    600
cctggccagg cttcccagct aggatgtggt atggcagggg tgggggacat tgaggggctg    660
ctgtagcccc cacaacctcc ccaggtaggg tggtgaacag taggctggac aagtggacct    720
gttcccatct gagattcaag agcccactc tcggaggttg cagtgagccg agatccctcc    780
actgcactcc agcctgggca acagagcaag actctgtctc aaaaaaacag aacaacgaca    840
acaaaaaacc cacctctggc ccactgccta actttgtaaa taagttttta ttggcacata    900
gacacaccca ttcatttaca tactgctgcg gctgcttttg cattacccctt gagtagcga    960
cagaccacgt ggccatggaa gccaaaaata tttactgtct ggcccttttac agaagtctgc   1020
tctagaggga gaccccggcc catggggcag gaccactggg cgtgggcaga agggaggcct   1080
cggtgcctcc acgggcctag ttgggtatct cagtgcctgt ttcttgcatg gagcaccagg   1140
ggtcagggca agtacctgga ggaggcaggc tgttgccgc ccagcactgg gacccaggag   1200
accttgagag gctcttaacg aatgggagac aagcaggacc agggctccca ttggctgggc   1260
ctcagttttcc ctgcctgtaa gtgagggagg gcagctgtga aggtgaactg tgaggcagag   1320
cctctgctca gccattgcag gggcggctct gccccactcc tgttgtgcac ccagagtgag   1380
gggcacgggg tgagatgtca ccatcagccc atagggtgt cctcctggtg ccaggtcccc   1440
aagggatgtc ccatccccc tggctgtgtg ggacagcag agtccctggg gctggaggg   1500
ctccacactg ttttgtcagt ggttttttctg aactgttaaa tttcagtgga aaattctctt   1560
tccccttta ctgaaggaac ctccaaagga agacctgact gtgtctgaga agttccagct   1620
ggtgctggac gtcgcccaga aagcccaggt actgccacgg gcgccggcca ggggtgtgtc   1680
```

```
tgcgccagcc atgggcacca gccaggggtg tgtctacgcc ggccaggggt aggtctccgc    1740
cggcctccgc tgctgcctgg ggagggccgt gcctgacact gcaggcccgg tttgtccgcg    1800
gtcagctgac ttgtagtcac cctgcccttg gatggtcgtt acagcaactc tggtggttgg    1860
ggaaggggcc tcctgattca gcctctgcgg acggtgcgcg agggtggagc tcccctccct    1920
ccccaccgcc cctggccagg gttgaacgcc cctgggaagg actcaggccc gggtctgctg    1980
ttgctgtgag cgtggccacc tctgcccctag accagagctg gccttcccc ggcctaggag     2040 cagccgggca ggaccacagg gctccgagtg acctcagggc tgcccgacct ggaggccctc    2100
ctggcgtcgc ggtgtgactg acagcccagg agcgggggct gttgtaattg ctgtttctcc    2160
ttcacacaga acctttcgg gaagatggct gacatcctgg agaagatcaa gaagtaagtc     2220
ccgcccccca ccc                                                       2233

<210> SEQ ID NO 30
<211> LENGTH: 1851
<212> TYPE: DNA
<213> ORGANISM: Homo sapiens
<220> FEATURE:
<221> NAME/KEY: misc_feature
<223> OTHER INFORMATION: sequence of STAR30

<400> SEQUENCE: 30
gggtgcattt ccacccaggg gacacttggc aatggtggga gacattgctt gttgtcacaa      60
ctgggcatgg gagtgctgct gcgtctagtg ggtagaggcc agagatgctc ctaatatcct    120
acaaggcaca gaacagcccc ccacaacaga gaattatcca gcctgaaaat gtccacagtg    180
ctgaggttgg gaaaccctat tctagagcca acaggctgtg aagcttgact catggttcca    240
tcaccaatag ctgcgtgacc ttggtgagtt ccttagctgc tctgtgcctc ggattcatgg    300
taggttttcc ttgttaggtt taaatgagtg aagttataca gagggcctga agtctcatgg    360
tattttacta gagcctcatt gtgttttagt tataattaga aattgggtaa ggtaaggaca    420
cagaagaagc catctgatct gggggcttca cacttagaag tgacctcgga gcaattgtat    480
tggggtggaa agggactaac agccaggagc agagggcaca ttggaattgg ggccagaggg    540
cacagactgc cttgtccatc aggcatagca atggacagag aagggggaat gactagttat    600
ggctgcaagg ccaagtacag gggacttatt tctcatatct atctatctat ctacctaccg    660
tctatttatc tatcatctat ctacttattt atctatctat ttatgcatgt gtaccaaccg    720
aaagttttag taaatgcaca aactgcgata taatgaaaat ggaatttttc aaaagaagag    780
aaatcacctg ccacctgact accttaacaa atgagtggtt ttcatctctc cttccaggcc    840
tgtcattttt acagtgcttt agtcataaaa caggtcctct attctattgt tttatgtcac    900
atgaaattgt accataagca ttttccatga tgtgactcca ctgtttcatt ttccatttt     960 ttccagaatg aagataaacct cattgttttt ttcctgattg taaaaatgct ctgtgctctt   1020
tttttttttt tttaacaatg caggcagtac caaaaagtat gaagaagaat gtaatagttc    1080
ccatttccca tctcactctt taaggccagc attttggtga acatccatcc gaacaaatct    1140
ccacgcgttt atcaatttgt tgacttactc cttcttttat gtaaatatga acatgattta    1200
actgccagtc catttggaac cttaaagtga aggtttttta ttgttggggt ttgctatggt    1260
ctgaatatgt gtgtcccccc aaaatttatg ttgaatccta acgcccaatg cgattaggag    1320
gtggggccat taggaggtga ttaagtcatg aagtcatcag ccctaatgaa tgggatttgt    1380
ggccttgaaa agggacccca gagagctgcc ttgccccttc tgccatgtaa ggacacagtg    1440
```

-continued

| | | | | |
|---|---|---|---|---|
| aggagctagg | aaggggggcct | cagcagagac | caaatgtgat | ggtgcctcga tattggactt | 1500 |
| cccagcctcc | agaatgtgag | aaatgaattt | ctgttgttta | taagtcaccc agtctatagt | 1560 |
| attttgttct | agcagcccaa | acagactaag | tcagggttgt | tgttttagga agtggggaat | 1620 |
| ggggccatgc | atgggtgtac | gccagaacaa | aggaagccag | caagtcctga aagatactgg | 1680 |
| aaaagggaat | agtgggcacg | tgcagtgtgt | tagtttcctg | aggctgctat aacaaagcac | 1740 |
| cacaggttgg | gtggcttaaa | taacagaaat | tcattctccc | atcattctgg ggaccagacg | 1800 |
| tctgaaatca | agactcctat | gccatgctcc | ttctgaaggc | tccaggggag g | 1851 |

<210> SEQ ID NO 31
<211> LENGTH: 1701
<212> TYPE: DNA
<213> ORGANISM: Homo sapiens
<220> FEATURE:
<221> NAME/KEY: misc_feature
<223> OTHER INFORMATION: sequence of STAR31
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (1667)..(1667)
<223> OTHER INFORMATION: n is a, c, g, or t
<220> FEATURE:
<221> NAME/KEY: misc_feature
<222> LOCATION: (1677)..(1677)
<223> OTHER INFORMATION: n is a, c, g, or t
<220> FEATURE:
<221> NAME/KEY: misc_feature
<222> LOCATION: (1683)..(1684)
<223> OTHER INFORMATION: n is a, c, g, or t
<220> FEATURE:
<221> NAME/KEY: misc_feature
<222> LOCATION: (1686)..(1687)
<223> OTHER INFORMATION: n is a, c, g, or t
<220> FEATURE:
<221> NAME/KEY: misc_feature
<222> LOCATION: (1690)..(1690)
<223> OTHER INFORMATION: n is a, c, g, or t
<220> FEATURE:
<221> NAME/KEY: misc_feature
<222> LOCATION: (1693)..(1696)
<223> OTHER INFORMATION: n is a, c, g, or t

<400> SEQUENCE: 31

| | | | | |
|---|---|---|---|---|
| cacccgcctt | ggccccccag | agtgctggga | ttacaagtgt | aaaccaccat tcctggctag | 60 |
| atttaatttt | ttaaaaaata | aagagaagta | ggaatagttc | attttaggga gagcccctta | 120 |
| actgggacag | gggcaggaca | gggtgaggc | ttcccttant | tcaagctcac ctcaaaccca | 180 |
| cccaggactg | tgtgtcacat | tctccaataa | aggaaaggtt | gctgccccg cctgtgagtg | 240 |
| ctgcagtgga | gggtagaggg | ccgtgggcag | agtgcttcat | ggactgctca tcaagaaagg | 300 |
| cttcatgaca | atcggcccag | ctgctgtcat | cccacattct | acttccagct aggagaaggc | 360 |
| ggcttgccca | cagtcaccca | gccggcaagt | gtcacccctg | ggttgaccc agagctatga | 420 |
| tcctgcccag | gggtccagct | gagaatcagg | cccacgttct | aggcagaggg gctcacctac | 480 |
| tgggactcca | gtagctgtag | tgcatggagg | catcatggct | gcagcagcct ggacctggtc | 540 |
| tcacactggc | tgtccctgtg | ggcaggccat | cctcaatgcc | aggtcaggcc caagcatgta | 600 |
| tcccagacaa | tgacaatggg | gtggaatcct | ctcttgtccc | agaagccact cctcactgtt | 660 |
| ctacctgagg | aaggcagggg | catggtggaa | tcctgaagcc | tgctgtgagg gtctccagcg | 720 |
| aacttgcaca | tggtcagccc | tgccttctcc | tccctgaact | agattgagcg agagcaagaa | 780 |

| | |
|---|---|
| ggacattgaa ccagcaccca agaattttg gggaacggcc tctcatccag gtcaggctca | 840 |
| cctcctttt aaaatttaat taattaatta attaattttt ttttagagac agagtcttac | 900 |
| tgtgtggccc aggctgtagt gcagtggcac aatcatagtt cactgcagcc tcaaactccc | 960 |
| cacctcagcc tctggattag ctgagactac aggtgcacca ccaccacacc cagctaatat | 1020 |
| ttttattttt gtagagagag ggtttcacca tcttgcccag gctggtctca aactcctggg | 1080 |
| ctcaagtgat cccgcccagg tctgaaagcc cccaggctgg cctcgactg tggggttttc | 1140 |
| catgcagcca cccgagggcg cccccaagcc agttcatctc ggagtccagg cctggccctg | 1200 |
| ggagacagag tgaaaccagt ggttttatg aacttaactt agagtttaaa agatttctac | 1260 |
| tcgatcactt gtcaagatgc gccctctctg gggagaaggg aacgtgactg gattccctca | 1320 |
| ctgttgtatc ttgaataaac gctgctgctt catcctgtgg gggccgtggc cctgtccctg | 1380 |
| tgtgggtggg gcctcttcca tttccctgac ttagaaacca cagtccacct agaacagggt | 1440 |
| ttgagaggct tagtcagcac tgggtagcgt tttgactcca ttctcggctt tcttctttt | 1500 |
| ctttccagga ttttttgtgca gaaatggttc ttttgttgcc gtgttagtcc tccttggaag | 1560 |
| gcagctcaga aggcccgtga aatgtcgggg gacaggaccc ccaggagggg aaccccaggc | 1620 |
| tacgcacttt agggttcgtt ctccaggag ggcgacctga ccccgnatc cgtcggngcg | 1680 |
| cgnngnnacn aannnnttcc c | 1701 |

<210> SEQ ID NO 32
<211> LENGTH: 771
<212> TYPE: DNA
<213> ORGANISM: Homo sapiens
<220> FEATURE:
<221> NAME/KEY: misc_feature
<223> OTHER INFORMATION: sequence of STAR32

<400> SEQUENCE: 32

| | |
|---|---|
| gatcacacag cttgtatgtg ggagctagga ttggaacccc agaagtctgg ccccaggttc | 60 |
| atgctctcac ccactgcata caatggcctc tcataaatca atccagtata aacattaga | 120 |
| atctgcttta aaaccataga attagtagcg taagtaataa atgcagagac catgcagtga | 180 |
| atggcattcc tggaaaaagc ccccagaagg aattttaaat cagctttcgt ctaatcttga | 240 |
| gcagctagtt agcaaatatg agaatacagt tgttcccaga taatgcttta tgtctgacca | 300 |
| tcttaaactg gcgctgtttt tcaaaaactt aaaaacaaaa tccatgactc ttttaattat | 360 |
| aaaagtgata catgtctact tgggaggctg aggtggtggg aggatggctt gagtttgagg | 420 |
| ctgcagtatg ctactatcat gcctataaat agccgctgca ttccagcttg ggcaacatac | 480 |
| ccaggcccta tctcaaaaaa ataaaagta atacatctac attgaagaaa attaatttta | 540 |
| ttgggttttt ttgcattttt attatacaca gcacacacag cacatatgaa aaaatgggta | 600 |
| tgaactcagg cattcaactg gaagaacagt actaaatcaa tgtccatgta gtcagcgtga | 660 |
| ctgaggttgg tttgtttttt cttttttctt ctcttctctt ctcttttctt ttttttgag | 720 |
| acggagcttt gctctttttg cccaggcttg attgcaatgg cgtgatctca g | 771 |

<210> SEQ ID NO 33
<211> LENGTH: 1368
<212> TYPE: DNA
<213> ORGANISM: Homo sapiens
<220> FEATURE:
<221> NAME/KEY: misc_feature
<223> OTHER INFORMATION: sequence of STAR33

<400> SEQUENCE: 33

```
gcttttatcc tccattcaca gctagcctgg cccccagagt acccaattct ccctaaaaaa      60
cggtcatgct gtatagatgt gtgtggcttg gtagtgctaa gtggccaca tacagagctc     120 tgacaccaaa cctcaggacc atgttcatgc cttctcactg agttctggct tgttcgtgac     180
acattatgac attatgatta tgatgacttg tgagagcctc agtcttctat agcactttta     240
gaatgcttta taaaaccat ggggatgtca ttatattcta acctgttagc acttctgttc     300
gtattaccca tcacatccca acatcaattc tcatatatgc aggtacctct tgtcacgcgc     360
gtccatgtaa ggagaccaca aaacaggctt tgtttgagca acaaggtttt tatttcacct     420
gggtgcaggt gggctgagtc tgaaaagaga gtcagtgaag ggagacaggg gtgggtccac     480
tttataagat ttgggtaggt agtggaaaat acaatcaaa ggggttgtt ctctggctgg      540 ccagggtggg ggtcacaagg tgctcagtgg gagagccttt gagccaggat gagccagaag     600
gaatttcaca aggtaatgtc atcagttaag cagggactg gccattttca cttcttttgt     660 ggtgaatgt catcagttaa ggcaggaacc ggccattttc acttcttttg tgattcttca     720
cttgcttcag gccatctgga cgtataggtg caggtcacag tcacagggga taagatggca     780
atggcatagc ttgggctcag aggcctgaca cctctgagaa actaaagatt ataaaaatga     840
tggtcgcttc tattgcaaat ctgtgtttat tgtcaagagg cacttatttg tcaattaaga     900
acccagtggg agaatcgaat gtccgaatgt aaaacaaaat acaaaacctc tgtgtgtgtg     960
tgtgtgtgag tgtgtgtgta tgtgtgtgtg tgtgtattag agaggaaaag cctgtatttg    1020
gaggtgtgat tcttagattc taggttcttt cctgcccacc ccatatgcac ccaccccaca    1080
aaagaacaaa caacaaatcc caggacatct tagcgcaaca tttcagtttg catattttac    1140
atatttactt ttcttacata ttaaaaaact gaaaatttta tgaacacgct aagttagatt    1200
ttaaattaag tttgttttta cactgaaaat aatttaatat ttgtgaagaa tactaataca    1260
ttggtatatt tcattttctt aaaattctga accctcttc ccttatttcc ttttgacccg    1320
attggtgtat tggtcatgtg actcatggat ttgccttaag gcaggagg                 1368
```

<210> SEQ ID NO 34
<211> LENGTH: 755
<212> TYPE: DNA
<213> ORGANISM: Homo sapiens
<220> FEATURE:
<221> NAME/KEY: misc_feature
<223> OTHER INFORMATION: sequence of STAR34

<400> SEQUENCE: 34

```
actgggcacc ctcctaggca ggggaatgtg agaactgccg ctgctctggg gctgggcgcc      60
atgtcacagc aggagggagg acggtgttac accacgtggg aaggactcag ggtggtcagc     120
cacaaagctg ctggtgatga ccagggggctt gtgtcttcac tctgcagccc taacacccag     180
gctgggttcg ctaggctcca tcctgggggt gcagaccctg agagtgatgc cagtgggagc     240
ctcccgcccc tcccccttcct cgaaggccca ggggtcaaac agtgtagact cagaggcctg     300
agggcacatg tttatttagc agacaaggtg gggctccatc agcggggtgg cctggggagc     360
agctgcatgg gtggcactgt ggggagggtc tcccagctcc ctcaatggtg ttcgggctgg     420
tgcggcagct ggcggcaccc tggacagagg tggatatgag ggtgatgggt ggggaaatgg     480
gaggcacccg agatggggac agcagaataa agacagcagc agtgctgggg ggcaggggga     540
tgagcaaagg caggcccaag accccagcc cactgcaccc tggcctccca caagcccct      600 cgcagccgcc cagccacact cactgtgcac tcagccgtcg atacactggt ctgttaggga     660
```
gaaagtccgt cagaacaggc agctgtgtgt gtgtgtgcgt gtatgagtgt gtgtgtgtga    720
tccctgactg ccaggtcctc tgcactgccc ctggg    755

<210> SEQ ID NO 35
<211> LENGTH: 1193
<212> TYPE: DNA
<213> ORGANISM: Homo sapiens
<220> FEATURE:
<221> NAME/KEY: misc_feature
<223> OTHER INFORMATION: sequence of STAR35
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (355)..(355)
<223> OTHER INFORMATION: n is a, c, g, or t
<220> FEATURE:
<221> NAME/KEY: misc_feature
<222> LOCATION: (361)..(361)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (422)..(423)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (578)..(578)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature

```
<222> LOCATION: (624)..(624)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (868)..(868)
<223> OTHER INFORMATION: n is a, c, g, or t
<220> FEATURE:
<221> NAME/KEY: misc_feature
<222> LOCATION: (880)..(881)
<223> OTHER INFORMATION: n is a, c, g, or t
<220> FEATURE:
<221> NAME/KEY: misc_feature
<222> LOCATION: (923)..(923)
<223> OTHER INFORMATION: n is a, c, g, or t
<220> FEATURE:
<221> NAME/KEY: misc_feature
<222> LOCATION: (925)..(925)
<223> OTHER INFORMATION: n is a, c, g, or t
<220> FEATURE:
<221> NAME/KEY: misc_feature
<222> LOCATION: (1019)..(1019)
<223> OTHER INFORMATION: n is a, c, g, or t
<220> FEATURE:
<221> NAME/KEY: misc_feature
<222> LOCATION: (1021)..(1021)
<223> OTHER INFORMATION: n is a, c, g, or t
<220> FEATURE:
<221> NAME/KEY: misc_feature
<222> LOCATION: (1055)..(1055)
<223> OTHER INFORMATION: n is a, c, g, or t
<220> FEATURE:
<221> NAME/KEY: misc_feature
<222> LOCATION: (1062)..(1063)
<223> OTHER INFORMATION: n is a, c, g, or t
<220> FEATURE:
<221> NAME/KEY: misc_feature
<222> LOCATION: (1074)..(1074)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1100)..(1101)
<223> OTHER INFORMATION: n is a, c, g, or t
<220> FEATURE:
<221> NAME/KEY: misc_feature
<222> LOCATION: (1106)..(1107)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t
<220> FEATURE:
```

<221> NAME/KEY: misc_feature
<222> LOCATION: (1138)..(1138)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1145)..(1146)
<223> OTHER INFORMATION: n is a, c, g, or t
<220> FEATURE:
<221> NAME/KEY: misc_feature
<222> LOCATION: (1158)..(1159)
<223> OTHER INFORMATION: n is a, c, g, or t
<220> FEATURE:
<221> NAME/KEY: misc_feature
<222> LOCATION: (1180)..(1180)
<223> OTHER INFORMATION: n is a, c, g, or t
<220> FEATURE:
<221> NAME/KEY: misc_feature
<222> LOCATION: (1187)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t

<400> SEQUENCE: 35

```
cgacttggtg atgcgggctc ttttttggtt ccatatgaac tttaaagtag tcttttccaa     60
ttctgtgaag aaagtcattg gtaggttgat ggggatggca ttgaatctgt aaattacctt    120
gggcagtatg gccattttca caatgttgat tcttcctatc catgatgatg gaatgttctt    180
ccattagttt gtatcctctt ttatttcctt gagcagtggt tgtagttct ccttgaagag     240
gtccttcaca tcccttgtaa gttggattcc taggtatttt attctctttg aagcaaattg    300
tgaatgggag tncactcacg atttggctct ctgtttgtct gctgggtgta taaanaatgt    360
ngtgatnttn gtacattgat ttngtatccn tgagacttng ctgaatttgc ttnatcngct    420
tnngggaacc ttttgggctg aaacnatggg attttctaaa tatacaatca tgtcgtctgc    480
aaacagggaa caatttgact tcctcttttc ctaattgaat acactttatc tccttctcct    540
gcctaattgc cctgggcaaa acttccaaca ctatgntngn aataggagnt ggtgagagag    600
ggcatccctg ttcttgttgc cagnttttca aagggaatgc ttccagtttt ggcccattca    660
gtatgatatg ggctgtgggt ngtgtcataa atagctctta tnattttgaa atgtgtccca    720
tcaataccta atttattgaa agttttttagc atgaangcat ngttgaattt ggtcaaaggc    780
tttttctgca tctatggaaa taatcatgtg gttttgtct ttggctcntg tttatatgct      840
ggatnacatt tattgatttg tgtatatnga accagcctn ncatcccagg gatgaagccc     900
acttgatcca agcttggcgc gcngnctagc tcgaggcagg caaaagtatg caaagcatgc    960
atctcaatta gtcagcaccc atagtccgcc cctacctccg cccatccgcc cctaactcng   1020
nccgttcgcc cattctcgcc catggctgac taatnttttt annatccaag cggngccgcc   1080
ctgcttganc attcagagtn nagagnnttg gaggccnagc cttgcaaaac tccgacngn    1140
ttctnnggat tgacccntt taaatatttg gttttttgtn ttttcanngg nga           1193
```

<210> SEQ ID NO 36
<211> LENGTH: 1712
<212> TYPE: DNA
<213> ORGANISM: Homo sapiens
<220> FEATURE:
<221> NAME/KEY: misc_feature
<223> OTHER INFORMATION: sequence of STAR36

<400> SEQUENCE: 36

```
gatcccatcc ttagcctcat cgatacctcc tgctcacctg tcagtgcctc tggagtgtgt      60
gtctagccca ggcccatccc ctggaactca ggggactcag gactagtggg catgtacact     120
tggcctcagg ggactcagga ttagtgagcc ccacatgtac acttggcctc agtggactca     180
ggactagtga gccccacatg tacacttggc ctcagtggac tcaggattag tgaccccca     240
catgtacact tggcctcagg ggactcagga ttagtgagcc ccacatgtac acttggcctc     300
aggggactca ggactagtga gccccacatg tacacttggc ctcaggggac tcagaactag     360
tgagccccac atgtacactt ggcttcaggg gactcaggat tagtgagccc cacatgtaca     420
cttggacacg tgaaccacat cgatgtgctg cagagctcag ccctctgcag atgaaatgtg     480
gtcatggcat tccttcacag tggcacccct cgttccctcc ccacctcatc tcccattctt     540
gtctgtcttc agcacctgcc atgtccagcc ggcagattcc accgcagcat cttctgcagc     600
accccgacc acacacctcc cagcgcctg cttggccctc cagcccagct cccgcctttc      660
ttccttgggg aagctccctg gacagacacc ccctcctccc agccatggct ttttcctgct     720
ctgccccacg cgggaccctg ccctggatgt gctacaatag acacatcaga tacagtcctt     780
cctcagcagc cggcagaccc agggtggact gtccggggcc tgcctgtgag gtcacacagg     840
tgtcgttaac ttgccatctc agcaactagt gaatatgggc agatgctacc ttccttccgg     900
ttccctggtg agaggtactg gtggatgtcc tgtgttgccg gccaccttt gtccctggat       960
gccatttatt ttttccaca aatatttccc aggtctcttc tgtgtgcaag gtattagggc    1020
tgcagcgggg gccaggccac agatctctgt cctgagaaga cttggattct agtgcaggag    1080
actgaagtgt atcacaccaa tcagtgtaaa ttgttaactg ccacaaggag aaaggccagg    1140
aaggagtggg gcatggtggt gttctagtgt tacaagaaga agccagggag ggcttcctgg    1200
atgaagtggc atctgacctg ggatctggag gaggagaaaa atgtcccaaa agagcagaga    1260
gcccacccta ggctctgcac caggaggcaa cttgctgggc ttatggaatt cagagggcaa    1320
gtgataagca gaaagtcctt gggggccaca attaggattt ctgtcttcta aagggcctct    1380
gccctctgct gtgtgacctt gggcaagtta cttcacctct agtgctttgg ttgcctcatc    1440
tgtaaagtgg tgaggataat gctatcacac tggttgagaa ttgaagtaat tattgctgca    1500
aagggcttat aagggtgtct aatactagta ctagtaggta cttcatgtgt cttgacaatt    1560
ttaatcatta ttattttgtc atcaccgtca ctcttccagg ggactaatgt ccctgctgtt    1620
ctgtccaaat taaacattgt ttatccctgt gggcatctgg cgaggtggct aggaaagcct    1680
ggagctgttt cctgttgacg tgccagacta gt                                  1712
```

<210> SEQ ID NO 37
<211> LENGTH: 1321
<212> TYPE: DNA
<213> ORGANISM: Homo sapiens
<220> FEATURE:
<221> NAME/KEY: misc_feature
<223> OTHER INFORMATION: sequence of STAR37

<400> SEQUENCE: 37

```
aggatcacat ttaaggaagt gtgtggggtc cctggatgac accagcaccc agtgcggctc      60
tgtctggcaa ccgctcccaa ggtggcagga gtgggtgtcc cctgtgtgtc agtgggcagc     120
tcctgctgag cctacagctc actggggagc ctgcagcgg ggccatgtgc ctgacactcc      180
tctctgcttg tggacctggc aaggcaggga gcagaaaaca gagccacttg aaggctttct     240
```

```
gtctgcgtct gtgtgcagtg tggatttagt tgtgcttttt tcttgctggg agagcacagc    300
caccatttac aagcagtgtc accctcatgg gtggcgagga cagaacagga gcctctgctc    360
tctgtaccta tctgggcccg gtgggctccc ttgtcctggc ttccatctct gtctcagcga    420
ccattcagcc ctgcgcagga acacatgttg cttagaaaag ccaaattcag cccttgtctc    480
tgcctcctct ggtctcatga tgtgcatctg ttaccttgaa actggaaacc agtctatcaa    540
tgtctgtgcc aattttttat tccctcccca acctccttcc ccatacgact ttttatttat    600
gtaggatgtg tgctgtctaa tgatgggatg accacatttt tccatgttct aaaagtgctc    660
ctctcccgca gggtcccagg gctggtggtt gctttgggtc tacagctacg tcttacccgc    720
ctcctgcctc aacagcctgt gtggtggcaa gccggtgtg gggctgggga acgcagcgtt     780
ctccaggagg gggacccggc tctccttctg cagtgcaggc gaaggcctag atgccagtgt    840
gacctcccac aaggcgtggc ttccagactc cccggctgga agtgatgctt ttttgcctcc    900
ggccctgggt ttgaagcagc ctggctttct cttggtaagt ggctggtgtc ttagcagctg    960
caatctgagc tcagccacct acacaccacc gtggccgaca ctttcattaa aaagtttcct   1020
gagacgactt gcgtgcatgt tgacttcatg atcagcgccg ctgggaagaa cccctgagcc   1080
ggtggggtgg ggctggaagc agcaggtgca gtgatgggc tgggtgccca ggaggcctca    1140
gtgctcaatc aggccaaggt ggccaagccc aggctgcagg gaaggccggc ctggggggttg  1200 tgggtgagca caggcaggca ccagctgggc agtgttagga tgctgagca gcatccgtaa    1260 ccccactgag tggggtagtc tggttggggc agggaccgct gttgctttgg cagagagaga   1320
t                                                                   1321

<210> SEQ ID NO 38
<211> LENGTH: 1445
<212> TYPE: DNA
<213> ORGANISM: Homo sapiens
<220> FEATURE:
<221> NAME/KEY: misc_feature
<223> OTHER INFORMATION: sequence of STAR38
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (949)..(949)
<223> OTHER INFORMATION: n is a, c, g, or t

<400> SEQUENCE: 38
gatctatggg agtagcttcc ttagtgagct ttcccttcaa atactttgca accaggtaga     60
gaattttgga gtgaaggttt tgttcttcgt ttcttcacaa tatggatatg catcttcttt    120
tgaaaatgtt aaagtaaatt acctctcttt tcagatactg tcttcatgcg aacttggtat    180 cctgttttcca tccagccttt ctataaccca gtaacatctt ttttgaaacc agtgggtgag   240
aaagacacct ggtcaggaac gcggaccaca ggacaactca ggctcaccca cggcatcaga    300
ctaaaggcaa acaaggactc tgtataaagt accggtggca tgtgtatnag tggagatgca    360
gcctgtgctc tgcagacagg gagtcacaca gacactttc tataatttct taagtgcttt     420
```

```
gaatgttcaa gtagaaagtc taacattaaa tttgattgaa caattgtata ttcatggaat    480
attttggaac ggaataccaa aaaatggcaa tagtggttct ttctggatgg aagacaaact    540
tttcttgttt aaaataaatt ttatttata tatttgaggt tgaccacatg accttaagga    600
tacatataga cagtaaactg gttactacag tgaagcaaat taacatatct accatcgtac    660
atagttacat tttttgtgt gacaggaaca gctaaaatct acgtatttaa caaaaatcct    720
aaagacaata cattttatt aactatagcc ctcatgatgt acattagatc gtgtggttgt    780
ttcttccgtc cccgccacgc cttcctcctg ggatgggat tcattccta gcaggtgtcg    840
gagaactggc gcccttgcag ggtaggtgcc ccggagcctg aggcgggnac tttaanatca    900
gacgcttggg ggccggctgg gaaaaactgg cggaaaatat tataactgna ctctcaatgc    960
cagctgttgt agaagctcct gggacaagcc gtggaagtcc cctcaggagg cttccgcgat   1020
gtcctaggtg gctgctccgc ccgccacggt catttccatt gactcacacg cgccgcctgg   1080
aggaggaggc tgcgctggac acgccggtgg cgccttgcc tggggagcg cagcctggag   1140
ctctggcggc agcgctggga gcggggcctc ggaggctggg cctggggacc caaggttggg   1200
cggggcgcag gaggtgggct cagggttctc cagagaatcc ccatgagctg acccgcaggg   1260
cggccgggcc agtaggcacc gggcccccgc ggtgacctgc ggacccgaag ctggagcagc   1320
cactgcaaat gctgcgctga ccccaaatgc tgtgtccttt aaatgtttta attaagaata   1380
attaataggt ccgggtgtgg aggctcaagc cttaatcccc agcacctggc gaggccgagg   1440
aggga                                                                1445
```

\<210\> SEQ ID NO 39
\<211\> LENGTH: 2331
\<212\> TYPE: DNA
\<213\> ORGANISM: Homo sapiens
\<220\> FEATURE:
\<221\> NAME/KEY: misc_feature
\<223\> OTHER INFORMATION: sequence of STAR39

\<400\> SEQUENCE: 39

```
gtgaaataga tcactaaagc tgattcctct tgtctaaatg aaactttcta ccctttgatg     60
gacagctatg ctttccccat cctctcccgt ccccagccc ttggtaacca tcatcctact    120
ctctacttgt aggagttcaa cttgtttaga ttttgtgagt gagaacatgt ggtatttgcc    180
tttagagtcc tctaggttta tccatattgt gttaaatgac aggattccct gccttttaa    240
ggctgaatag tatttcattg taatatat acatacacac acacatatac acacacatat    300
atatacatat atacatatat gtacatagat acatatatat gtacatatat acacacacat    360
atacacacat atatacacat atatacatat acatatatac acatatatgt acatatatat    420
aactttttt catttatcca ttcacttaat acatatgatg gagggcttta tatatgccag    480
gctctgtgat gaatgctgga aattcaatag tgagaaagac tcagtctctg cctccaaaga    540
gcatcatggg ctaggtgctg caacgaggaa ttgccaactg ttgtcatgag agcacagaga    600
agggactcaa ccagccttga agaatcaggg gaggcttcta agctaatggt gtgtgcctgg    660
ggatcacatt gtttcaagca gcagtaacag gatgtgctca ggtccagatg tgagagagag    720
agagagcata tgtcttcaag aaactaacag tagctcccta tagctgaagc aggagtacaa    780
aatagtgagt ttaagtgatg aggcaagaga tatgaagaag cttgaccatg cagctacacc    840
gggcagcatg ccctctgaga catctcatgg aagccggaaa tgggagtgcc ttgataccaa    900
gccagagaaa ttataatact aagtagatag actgagcagc actcctcctg ggaagaatga    960
```

```
gacaagccct gaatttggag gtaagttgtg gattggtgat tagaggagag gtaacaggca      1020
ccaaagcaag aaatagtatt gatgcaaagc tgaggttaat tggatgacaa aatgaagagc      1080
ataaggggct cagacacaga ctgagcagaa acgagtagc atctgaacct agattgagtt       1140
actaatggat gagaaagagt tcttaaagtt gatgaccacg ggatccatat ataagaatgt      1200
ccaatctccc caaattgatc cacgagttca gtgcaatgcc aatcaaaatc ccactaacaa      1260
gtttatttta aaatgtaaat gaaaatacaa aattttttaaa aagcaaagca atattgaaaa     1320
cccaggaaaa attaggagga cttacacaac ctgatctcaa aacttaccat tatcaagaca      1380
gagtgttatt gacacaagga gagacaaata gataaacgga atgtggtagt ctggagatgc      1440
acccacatgt atgtggtcaa ttgattttg gccaaggcac caagtcaatt caaaggagca      1500
aggaaagtag tacagaaaca accaaatatt gttttggaaa ataatgacaa agggcttata     1560
accagaatat aagcatataa atataattct ttcaaatcaa taataagaag gcaaatatct     1620
aataaaaatg agcaaagact tgaaaagtca cttaaaaagg cttattaatt agaaatatgc    1680
aaatgttatt agtcttcagt ggaatttaca ttaaaccaca agggatacta ttatatctta    1740
tgcccactag aataaccaaa ggaaaaaaga cagacaaaac aaaatgctgg tgaggatgtg    1800
aagcaactgg aactctcata cattattggt ggtaatgtaa aatttataca accattatga    1860
ataaaggttt ggcagtttct tacaaagttg aatgcacttc tccacgatga ctaggctttt   1920
cactcatagg cgtctggctc cctagaactg aaaacatatg ttcacaagaa gacttgcaaa   1980
tatatattct cccacgtcag gagatatttg ctatgcattt aactgacata agattagtgc   2040
tagagtttat aatgaggttc ttcaaatcta aagaaaatg caaagcatat aatagtaagg    2100
ggtgcaggcc aggcgcagtg gctcactctg taatcccagc actttgggag gccgaggtgg   2160
gcggatcaca aggtcaggag ttcgagacca acctggccaa catagtgaaa ccctgtctct    2220
actaaaaata caaaaactag ccaggtgcgg tgtcatgcac ctgtagtccc agctactcgg    2280
gaggccgagg caggagaatc acttgaacct gggaggtgga ggttgcagtg a              2331
```

<210> SEQ ID NO 40
<211> LENGTH: 1071
<212> TYPE: DNA
<213> ORGANISM: Homo sapiens
<220> FEATURE:
<221> NAME/KEY: misc_feature
<223> OTHER INFORMATION: sequence of STAR40

<400> SEQUENCE: 40

```
gctgtgattc aaactgtcag cgagataagg cagcagatca agaaagcact ccgggctcca      60
gaaggagcct tccaggccag ctttgagcat aagctgctga tgagcagtga gtgtcttgag     120
tagtgttcag ggcagcatgt taccattcat gcttgacttc tagccagtgt gacgagaggc    180
tggagtcagg tctctagaga gttgagcagc tccagcctta gatctcccag tcttatgcgg    240
tgtgcccatt cgctttgtgt ctgcagtccc ctggccacac ccagtaacag ttctgggatc   300
tatgggagta gcttccttag tgagctttcc cttcaaatac tttgcaacca ggtagagaat   360
tttggagtga aggttttgtt cttcgttcct tcacaatatg gatatgcatc ttcttttgaa   420
aatgttaaag taaattacct ctcttttcag atactgtctt catgcgaact tggtatcctg   480
tttccatccc agccttctat aacccagtaa catctttttt gaaaccagtg ggtgagaaag   540
acacctggtc aggaacgcgg accacaggac aactcaggct cacccacggc atcagactaa   600
aggcaaacaa ggactctgta taaagtaccg gtggcatgtg tattagtgga gatgcagcct   660
```

| | |
|---|---|
| gtgctctgca gacagggagt cacacagaca cttttctata atttcttaag tgctttgaat | 720 |
| gttcaagtag aaagtctaac attaaatttg attgaacaat tgtatattca tggaatattt | 780 |
| tggaacggaa taccaaaaaa tggcaatagt ggttctttct ggatggaaga caaacttttc | 840 |
| ttgtttaaaa taaattttat tttatatatt tgaggttgac cacatgacct taaggataca | 900 |
| tatagacagt aaactggtta ctacagtgaa gcaaattaac atatctacca tcgtacatag | 960 |
| ttacatttttt ttgtgtgaca ggaacagcta aaatctacgt atttaacaaa atcctaaag | 1020 |
| acaatacatt tttattaact atagccctca tgatgtacat tagatctcta a | 1071 |

<210> SEQ ID NO 41
<211> LENGTH: 1135
<212> TYPE: DNA
<213> ORGANISM: Homo sapiens
<220> FEATURE:
<221> NAME/KEY: misc_feature
<223> OTHER INFORMATION: sequence of STAR41

<400> SEQUENCE: 41

| | |
|---|---|
| cgtgtgcagt ccacggagag tgtgttctcc tcatcctcgt tccggtggtt gtggcgggaa | 60 |
| acgtggcgct gcaggacacc aacatcagtc acgtatttca ttctggaaaa aaaagtagca | 120 |
| caagcctcgg ctggttccct ccagctctta ccaggcagcc taagcctagg ctccattccc | 180 |
| gctcaaggcc ttcctcaggg gcctgctcac cacaggagct gttcccatgc agggactaag | 240 |
| gacatgcagc ctgcatagaa accaagcacc caggaaaaca tgattggatg gagcgggggg | 300 |
| gtgtggtctc tagccttgtc cacctccggt cctcatgggt ctcacacctc ctgagaatgg | 360 |
| gcaccgcaga ggccacagcc catacagcca agatgacaga ctccgtaagt gacagggatc | 420 |
| cacagcagag tgggtgaaat gttccctata aactttacaa aattaatgag ggcaggggga | 480 |
| ggggagaaat gaaatgaac ccagctcgca gcacatcagc atcagtcact aggtcggcgt | 540 |
| gctctctgac tgcttcctcg tagctgcttg gtgtctcatt gcctcagaag catgtagacc | 600 |
| ctgtcacaag attgtagttc ccctaactgc tccgtagatc acaacttgaa ccttaggaaa | 660 |
| tgctgttttc cctttgagat attcctttgg gtcctgtata ctgatggagc tactgactga | 720 |
| gctgctccga aggaccccac gaggagctga ctaaaccaag agtgcagttt gtacaccctg | 780 |
| atgattacat cccccttgcc ccaccaatca actctcccaa ttttccagcc cctcaccctc | 840 |
| cagtcccctt aaaagcccca gcccaggccg ggcacagtgg ctcatgcctg taatcccagc | 900 |
| actttgggag gccaaggtgg gcagatcacc tgagggcagg aatttgagac cagcctgacc | 960 |
| aacatgaaga aaccccgtct ctattacaaa tacaaaatta gccgggcgtg ttgctgcata | 1020 |
| ctggtaatcc cagctacttg ggagggtgag gcaggagaat cacttgaatc tgggaggcgg | 1080 |
| aggttgcgat gagccgagac agcgccattg cactgcagcc tgggcaacaa gagca | 1135 |

<210> SEQ ID NO 42
<211> LENGTH: 735
<212> TYPE: DNA
<213> ORGANISM: Homo sapiens
<220> FEATURE:
<221> NAME/KEY: misc_feature
<223> OTHER INFORMATION: sequence of STAR42

<400> SEQUENCE: 42

| | |
|---|---|
| aagggtgaga tcactaggga gggaggaagg agctataaaa gaaagaggtc actcatcaca | 60 |
| tcttacacac ttttaaaac cttggttttt taatgtccgt gttcctcatt agcagtaagc | 120 |
| cctgtggaag caggagtctt tctcattgac caccatgaca agaccctatt tatgaaacat | 180 |

```
aatagacaca caaatgttta tcggatattt attgaaatat aggaattttt cccctcacac      240
ctcatgacca cattctggta cattgtatga atgaatatac cataatttta cctatggctg      300
tatatttagg tcttttcgtg caggctataa aaatatgtat gggccggtca cagtgactta      360
cgcccgtagt cccagaactt tgggaggccg aggcgggtgg atcacctgag gtcgggagtt      420
caaaaccagc ctgaccaaca tggagaaacc ccgtctctgc taaaaataca aaaattaact      480
ggacacggtg gcgtatgcct gtaatcccag ctactcggga agctgaggca ggagaactgc      540
ttgaacccag gaggcggagg ttgtggtgag tcgagattgc gccattgcac tccagcctgg      600
gcaacaagag cgaaattcca tctcaaaaaa agaaaaaaag tatgactgta tttagagtag      660
tatgtggatt tgaaaaatta ataagtgttg ccaacttacc ttagggttta taccatttat      720
gagggtgtcg gtttc                                                      735
```

<210> SEQ ID NO 43
<211> LENGTH: 1227
<212> TYPE: DNA
<213> ORGANISM: Homo sapiens
<220> FEATURE:
<221> NAME/KEY: misc_feature
<223> OTHER INFORMATION: sequence of STAR43

<400> SEQUENCE: 43

```
caaatagatc tacacaaaac aagataatgt ctgcccattt ttccaaagat aatgtggtga       60
agtgggtaga gagaaatgca tccattctcc ccacccaacc tctgctaaat tgtccatgtc      120
acagtactga gaccagggggg cttattccca gcgggcagaa tgtgcaccaa gcacctcttg     180
tctcaatttg cagtctaggc cctgctattt gatggtgtga aggcttgcac ctggcatgga      240
aggtccgttt tgtacttctt gctttagcag ttcaaagagc agggagagct gcgagggcct      300
ctgcagcttc agatggatgt ggtcagcttg ttggaggcgc cttctgtggt ccattatctc      360 cagccccct gcggtgttgc tgtttgcttg gcttgtctgg ctctccatgc cttgttggct      420
ccaaaatgtc atcatgctgc accccaggaa gaatgtgcag gcccatctct tttatgtgct      480
ttgggctatt tgattcccc gttgggtata ttccctaggt aagacccaga agacacagga      540
ggtagttgct ttgggagagt ttggacctat gggtatgagg taatagacac agtatcttct      600
ctttcatttg gtgagactgt tagctctggc cgcggactga attccacaca gctcacttgg      660
gaaaacttta ttccaaaaca tagtcacatt gaacattgtg gagaatgagg acagagaag      720 aggccctaga tttgtacatc tgggtgttat gtctataaat agaatgcttt ggtggtcaac      780
tagacttgtt catgttgaca tttagtcttg ccttttcggt ggtgatttaa aaattatgta      840
tatcttgttt ggaatatagt ggagctatgg tgtggcatt tcatctggct ttttgtttag      900
ctcagcccgt cctgttatgg gcagccttga agctcagtag ctaatgaaga ggtatcctca      960
ctccctccag agagcggtcc cctcacggct cattgagagt ttgtcagcac cttgaaatga    1020
gtttaaactt gtttatttt aaaacattct tggttatgaa tgtgcctata ttgaattact    1080
gaacaacctt atggttgtga agaattgatt tggtgctaag gtgtataaat ttcaggacca    1140
gtgtctctga agagttcatt tagcatgaag tcagcctgtg gcaggttggg tggagccagg    1200
gaacaatgga gaagctttca tgggtgg                                        1227
```

<210> SEQ ID NO 44
<211> LENGTH: 1586
<212> TYPE: DNA
<213> ORGANISM: Homo sapiens

```
<220> FEATURE:
<221> NAME/KEY: misc_feature
<223> OTHER INFORMATION: sequence of STAR44

<400> SEQUENCE: 44
cacctgcctc agcctcccaa agtgctgaga ttcaaagaaa ttttcatgga gaggggacag      60
atggagtcaa ttcttgtggg gtgaacatga gtaccacagt tagactgagg ttgggaaaga    120
ttttccagac aattggaaga gcatgtgaaa gacacagatt ttgagaaatg ttaagtctag    180
ggaactgcaa ggcttttggc acaagaaagc cactgtagac tatagaggca ggatgcctag    240
attcaaatcc caactgctac acttctaagc tttgtaattt tggcaagttt ttaccctcta    300
ttttcttatc tataaaatat agattttata tatatagata tagatatata gatagataat    360
aattgtgcat gcctaataaa gttgtcaaag attaaatgtt atatgtgaag tattttgtac    420
ggtgatagga acccaggaag ggctctatga atattatgta ttattattat tctaaagtag    480
ctggaataca atgttcaaag gagatagtgg caggagataa gtttgaattg aaagattgag    540
gccagaacat aaagtgcctc ctatattata ttttacaata ttggaacatc attgaaaaat    600
ttaagtatta tttatgtgtg tatgtgtgtt ttatataatt aattctagtt catcatttta    660
aaatatcttt ctgatgtcac tgtgaacaac agatgagaag aagtgaatcc tgagttaagg    720
agaccagctc tctgattact gccataatcc agggagggta ccataaggat ttcaactgga    780
agtgaatcca tcatgatgga gaggaaggac agggctgaaa aatacttagg aagtagtatc    840
agtaggactg gttaagagag agcagaggca ggctacaggg gttggaggtg tcaatcacag    900
agatagggaa aatgggagga gaagcaggct ttgaaaaagt ggcttgtctt gtaaaattat    960
gtgctgttaa aacagtacaa gaaattaata tattcaatcc caaaatacag ggacaattct   1020
ttttgaaaga gttacccaga tagtcttcct tgaagttttc agttaaagaa atttcttgtt   1080
aacaaataat gtagtcatag aagaaaacac ttaaaacttt attgaataaa gctaataaat   1140
catttaatat aatttatagg aaattgttac ataacacaca cattcaatac tttttgctaa   1200
agtataaatt aatggaagga gagcacgcac acagaggttg aattatgttt atgactttat   1260
tagtcaagaa tacaaaattg agtagctaca tcaagcagaa gcacatgctt tacaatccag   1320
cacagaatcc cttgacatcc aaactcccga aacagacatg taaatacaga tgacattgtc   1380
agaacaaaat agggtctcac ccgacctata atgttctttt cttgatataa atatgcacat   1440
gaattgcata cggtcatatg gttccaatta ccattatttc ctctgggctt agctatccat   1500
ctaaggggaa tttacaccaa cactgtactt ctacttgcaa gaatatatga aagcatagtt   1560
aacttctggc ttaggacccc aactca                                        1586

<210> SEQ ID NO 45
<211> LENGTH: 1981
<212> TYPE: DNA
<213> ORGANISM: Homo sapiens
<220> FEATURE:
<221> NAME/KEY: misc_feature
<223> OTHER INFORMATION: sequence of STAR45

<400> SEQUENCE: 45
atggatcata gggtaaataa atttataatt tcttgagaaa gcttcgtact gttttccaag     60
atggctgtac taatttccat tcctaccaac agtgtacagg gtttcttttt ctccacatcc    120
tcaccaacac ttatcttcca tctttttttta taatagccct agtaaaatgt gtgaggtgat    180
atctcattgt ggcattgatt tgcacttctc tgataattag gaatgtttat gattttttca    240
```

```
tgtacctggt tggccttttg tatgatgtag gaaatgtcta ttctgattct ttgcttattt      300
tttaataagc atagtttttt tcttatttt gagtaggttg agttgcttat atattattat       360
atgagcccct tacctgatgt atggtttaaa aatattatcc catttgtggg ttctcttaat      420
tctatcattg cttcttttcc tgtggaaaag ttttaagttt tatgcagtct catttgtgtg     480
ttttgctttt gttgcctttt ggaataatct acagaaaatc atagctcagg ccaatgtcat      540
acagtctcct tctatatttc cttgtagtag ttttacattt aaactttaat tttgatttga     600
tgcttgtata aagagcaaaa taaaagtcaa atttttattct tctgtatgtg gatagtcagt    660
tttgtctaca ccatttattg aaaataattt tctttcttca ctgtgtattt ttagttattt     720
tatcaaaaaa tcaattgacc acagacacac ggatttattt acaggttcta tatcccttg      780 tactgtttta catgtctgtt tttatgccat tgctatgctg ttttaattcc tatagctttg     840
taatagagtt tggagtcagg tagtctgatg cctccagctt tgttcttttt gttcaagatt     900
gctttggttg gtccaggtct tttgtggttc catacaaatt ttagcagtaa ttttttctatt    960 tctgtgaaga atgacattgg aatttgatag tggttgcatt taatctgtag attgctttgg    1020
gtagcattga cacttttaca atactaattt ttgaatccat caatgaagga tgtttctcca    1080
tttatttatg ccatttttaat tttttttcatc aatgtgctat agtttcagt atgtaaatct   1140 tttatggttt tgattaaatt tactcctgtc ttttatatat ttatatatct gttttgattc    1200
tattataaat tgaattgcct ttattttca ggtaatagtt tgtcattagt taatagaaac     1260
aataatgata tttgtatgtt gattttgtaa ctattaactt tattgaattt cttcatcagc    1320
tataaccatt tattttggtg gaatctttaa gattttctct atcttaagat tatatttca    1380 aaaacagaa acaatcttac ctcttccttc cctatgtgga tttcttttac gtctttgtct     1440
tgtgtaactg ttctggctag gcaattacac ataatgttttt catcatttat aattttacat   1500
cacatccatc tattgtggca cattgattgc tacttttcaa gttgtaaacc tggacattta   1560
tcactactct tcctccaata cagagtcca tggcgtggtg tgggccctac tgtgccacag    1620
tccagggcac ggctgggctg aggttctctt gtgcaagagt ccgtggctct gcggagcaag   1680
agttctccag tgccttagtc cagggttagg caggggtggg gctccttcag tagcttagtc    1740
cagtgcgccg ccctgcgagg gtcctcctga gcaggagtac acgatgaggc agggtcctac   1800
tgtgccttag cccaggaagc ggggggctgg gtcctctggt gccatagtcc aggctgccgg   1860
gagctgggtc ctctggtgcc atagctcagg ccggcgggag ctgggtcctc tggtgccgta   1920
gtccagggtg cagcagaaca ggagtcctgc ggagcagtag tccagggcac gctggggcgt    1980
g                                                                    1981
```

<210> SEQ ID NO 46
<211> LENGTH: 1859
<212> TYPE: DNA
<213> ORGANISM: Homo sapiens
<220> FEATURE:
<221> NAME/KEY: misc_feature
<223> OTHER INFORMATION: sequence of STAR46

<400> SEQUENCE: 46

```
attgttttc tcgcccttct gcatttctg caaattctgt tgaatcattg cagttactta       60
ggtttgcttc gtctccccca ttacaaacta cttactgggt ttttcaaccc tagttccctc    120 attttttatga tttatgctca tttctttgta cacttcgtct tgctccatct cccaactcat   180
ggcccctggc tttggattat tgttttggtc ttttattttt tgtcttcttc tacctcaaca   240
```

-continued

| | |
|---|---|
| cttatcttcc tctcccagtc tccggtaccc tatcaccaag gttgtcatta acctttcata | 300 |
| ttattcctca ttatccatgt attcatttgc aaataagcgt atattaacaa aatcacaggt | 360 |
| ttatggagat ataattcaca taccttaaaa ttcaggcttt taaagtgtac ctttcatgtg | 420 |
| gttttggta tattcacaaa gttatgcatt gatcaccacc atctgattcc ataacatgtt | 480 |
| caatacctca aaaagaagtc tgtactcatt agtagtcatt tcacattcac cactccctct | 540 |
| ggctctgggc agtcactgat cttgtgtct ctatggattt gcctagtcta ggtatttta | 600 |
| tgtaaatggc atcatacaac atgtgacctt tgtttggct tttcattt agcaaaatgt | 660 |
| tatcaaggtc tgtccctgtt gtagcatgta ttagcacttc atttcttata tgctgaatga | 720 |
| tatactttat ttgtccatca gttgttcatg ctttatttgt ccatcagttg atgaacattt | 780 |
| gcgtttttgc cactttgggc tattaagaat aatgctactg tgaacaagtg tgtacaagtt | 840 |
| cctctacaaa tttttgtgtg acatatcct ttcagttctc tcaggtgtat atctgggaat | 900 |
| tgaattgctg ggtcgtgtag tagctatgtt aaacactttg agaaactgct ataatgttct | 960 |
| ccagagctgt accattttaa attctgtgta tgaggattcc acgttctcca cttcctcacc | 1020 |
| agtgtatgga tttgggggta acttttttaa aaagtgggat taggctgggc acagtggctc | 1080 |
| acacctgtaa tcccaacact tcaggaagct gaggtgggag gatcacttga gcctagtagt | 1140 |
| ttgagaccag cctgggcaac atagggagac cctgtctcta caaaaataa tttaaaataa | 1200 |
| attagctggg cgttgtggca cacctgta gtcccagcta catgggaggc tgaggtggaa | 1260 |
| ggattccctg agcccagaag tttgaggttg cagtgagcca tgatggcagc actatactgt | 1320 |
| agcctgggtg tcagagcaag actccgtttc agggaagaaa aaaaaagtg ggatgatatt | 1380 |
| tttgacactt tcttcttgt tttcttaatt tcatacttct ggaaattcca ttaaattagc | 1440 |
| tggtaccact ctaactcatt gtgtttcatg gctgcatagt aatattgcat aatataaata | 1500 |
| taccattcat tcatcaaagt tagcagatat tgactgttag gtgccaggca ctgctctaag | 1560 |
| cgttaaagaa aaacacacaa aaactttgc attcttagag tttatttcc aatggagggg | 1620 |
| gtggagggag gtaagaattt aggaaataaa ttaattacat atatagcata gggtttcacc | 1680 |
| agtgagtgca gcttgaatcg ttggcagctt tcttagtagt ataaatacag tactaaagat | 1740 |
| gaaattactc taaatggtgt tacttaaatt actggaatag gtattactat tagtcacttt | 1800 |
| gcaggtgaaa gtggaaacac catcgtaaaa tgtaaaatag gaaacagctg gttaatgtt | 1859 |

<210> SEQ ID NO 47
<211> LENGTH: 1082
<212> TYPE: DNA
<213> ORGANISM: Homo sapiens
<220> FEATURE:
<221> NAME/KEY: misc_feature
<223> OTHER INFORMATION: sequence of STAR47

<400> SEQUENCE: 47

| | |
|---|---|
| atcattagtc attagggaaa tgcaaatgaa aaacacaagc agccaccaat atacacctac | 60 |
| taggatgatt taaaggaaaa taagtgtgaa gaaggacgta aagaaattgt aaccctgata | 120 |
| cattgatggt agaaatggat aaagttgcag ccactgtgaa aaacagtctg cagtggctca | 180 |
| gaaggttaaa tatagaaccc ctgttggacc caggaactct actcttaggc accccaaaga | 240 |
| atagagaaca gaaatcaaac agatgtttgt atactaatgt ttgtagcatc acttttcaca | 300 |
| ggagccaaaa ggtggaaata atccaaccat cagtgaacaa atgaatgtaa taaaagcaag | 360 |
| gtggtctgca tgcaatgcta catcatccat ctgtaaaaaa cgaacatcat tttgatagat | 420 |

```
gatacaacat gggtggacat tgagaacatt atgcttagtg aaataagcca gacacaaaag      480
gaatatattg tataattgta attacatgaa gtgcctagaa tagtcaaatt catacaagag      540
aaagtgggat aggaatcacc atgggctgga aataggggga aggtgctata ctgcttattg      600
tggacaaggt ttcgtaagaa atcatcaaaa ttgtgggtgt agatagtggt gttggttatg      660
caaccctgtg aatatattga atgccatgga gtgcacactt tggttaaaag gttcaaatga      720
taaatattgt gttatatata tttccccacg atagaaaaca cgcacagcca agcccacatg      780
ccagtcttgt tagctgcctt cctttacctt caagagtggg ctgaagcttg tccaatcttt      840
caaggttgct gaagactgta tgatggaagt catctgcatt gggaagaaa ttaatggaga       900 gaggagaaaa cttgagaatc cacactactc accctgcagg gccaagaact ctgtctccca      960
tgctttgctg tcctgtctca gtatttcctg tgaccacctc cttttcaac tgaagacttt      1020 gtacctgaag gggttcccag ttttttcacc tcggcccttg tcaggactga tcctctcaac      1080
ta                                                                    1082

<210> SEQ ID NO 48
<211> LENGTH: 1242
<212> TYPE: DNA
<213> ORGANISM: Homo sapiens
<220> FEATURE:
<221> NAME/KEY: misc_feature
<223> OTHER INFORMATION: sequence of STAR48

<400> SEQUENCE: 48
atcatgtatt tgttttctga attaattctt agatacatta atgttttatg ttaccatgaa       60
tgtgatatta taatataata ttttaattg gttgctactg tttataagaa tttcattttc       120
tgtttacttt gccttcatat ctgaaaacct tgctgatttg attagtgcat ccacaaattt      180
tcttggattt tctatgggta attacaaatc tccacacaat gaggttgcag tgagccaaga      240
tcacaccact gtactccagc ctgggcgaca gagtgagaca ccatctcaca aaaacacata      300
aacaaacaaa cagaaactcc acacaatgac aacgtatgtg ctttcttttt tcttcctct      360 ttctataata tttctttgtc ctatcttaac tgaactggcc agaaacccca ggacaatgat      420
aaatacgagc agtgtcaaca gacatctcat tcccttttcct agcttttata aaaataacga      480
ttatgcttca acattacata tggtggtgtc gatggttttg ttatagataa gcttatcagg      540
ttaagaaatt tgtctgcgtt tcctagtttg gtataaagat tttaatataa atgaatgttg      600 tatttttatca tcttattttt ttcctacatc tgctaaggta atcctgtgtt ttcccctttt      660
caatctccta atgtggtgaa tgacattaaa ataccttcta ttgttaaaat attcttgcaa      720
cgctgtatag aaccaatgcc tttattctgt attgctgatg attttttgaa aaatatgtag      780
gtggacttag ttttctaagg ggaatagaat ttctaatata tttaaaatat tttgcatgta      840
tgttctgaag gacattggtg tgtcatttct ataccatctg gctactagag gagccgactg      900
aaagtcacac tgccggagga ggggagaggt gctcttccgt ttctggtgtc tgtagccatc      960
tccagtggta gctgcagtga taataatgct gcagtgccga cagttctgga aggagcaaca     1020
acagtgattt cagcagcagc agtattgcgg gatcccacg atggagcaag ggaaataatt      1080
ctggaagcaa tgacaatatc agctgtggct atagcagctg agatgtgagt tctcacggtg     1140
gcagcttcaa ggacagtagt gatggtccaa tggcgcccag acctagaaat gcacatttcc     1200
tcagcaccgg ctccagatgc tgagcttgga cagctgacgc ct                        1242

<210> SEQ ID NO 49
```

<211> LENGTH: 1015
<212> TYPE: DNA
<213> ORGANISM: Homo sapiens
<220> FEATURE:
<221> NAME/KEY: misc_feature
<223> OTHER INFORMATION: sequence of STAR49

<400> SEQUENCE: 49

```
aaaccagaaa cccaaaacaa tgggagtgac atgctaaaac cagaaaccca aaacaatggg      60
agggtcctgc taaccagaa acccaaaaca atgggagtga agtgctaaaa ccagaaaccc     120
aaaacaatgg gagtgtcctg ctacaccaga aacccaaaac gatgggagtg acgtgataaa    180
accagacacc caaaacaatg ggagtgacgt gctaaaccag aaacccaaaa caatgggagt    240
gacgtgctaa aacctggaaa cctaaaacaa tgcgagtgag gtgctaacac cagaatccat    300
aacaatgtga gtgacgtgct aaaccagaac ccaaaacaat gggagtgacg tgctaaaaca    360
ggaacccaaa acaatgagag tgacgtgcta aaccagaaac ccaaaacaat gggaatgacg    420
tgctaaaacc ggaacccaaa acaatgggag tgatgtgcta aaccagaaac ccaaaacaat    480
gggaatgaca tgctaaaact ggaacccaaa acaatggtaa ctaagagtga tgctaaggcc    540
ctacattttg gtcacactct caactaagtg agaacttgac tgaaaaggag gatttttttt    600
tctaagacag agttttggtc tgtcccccag agtggagtgc agtggcatga tctcggctca    660
ctgcaagctc tgcctccgg gttcaggcca ttctcctgcc tcagcctcct gagtagctgg    720
gaatacaggc acccgccacc acacttggct aatttttttgt attttttagta gagatggggt    780
ttcaccatat tagcaaggat ggtctcaatc tcctgacctc gtgatctgcc cacctcaggc    840
tcccaaagtg ctgggattac aggtgtgagc caccacaccc agcaaaaagg aggaattttt    900
aaagcaaaat tatgggaggc cattgttttg aactaagctc atgcaatagg tcccaacaga    960
ccaaaccaaa ccaaaccaaa atggagtcac tcatgctaaa tgtagcataa tcaaa       1015
```

<210> SEQ ID NO 50
<211> LENGTH: 2355
<212> TYPE: DNA
<213> ORGANISM: Homo sapiens
<220> FEATURE:
<221> NAME/KEY: misc_feature
<223> OTHER INFORMATION: sequence of STAR50

<400> SEQUENCE: 50

```
caaccatcgt tccgcaagag cggcttgttt attaaacatg aaatgaggga aaagcctagt      60
agctccattg gattgggaag aatggcaaag agagacaggc gtcatttttct agaaagcaat    120
cttcacacct gttggtcctc acccattgaa tgtcctcacc caatctccaa cacagaaatg    180
agtgactgtg tgtgcacatg cgtgtgcatg tgtgaaagta tgagtgtgaa tgtgtctata    240
tgggaacata tatgtgattg tatgtgtgta actatgtgtg actggcagcg tggggagtgc    300
tggttggagt gtggtgtgat gtgagtatgc atgagtggct gtgtgtatga ctgtggcggg    360
aggcggaagg ggagaagcag caggctcagg tgtcgccaga gaggctggga ggaaactata    420
aacctgggca atttcctcct catcagcgag cctttcttgg gcaataggg cagagctcaa    480
agttcacaga gatagtgcct gggaggcatg aggcaaggcg gaagtactgc gaggagggc    540
agagggtctg acacttgagg ggttctaatg gaaaggaaa gacccacact gaattccact    600
tagccccaga ccctgggccc agcggtgccg gcttccaacc ataccaacca tttccaagtg    660
ttgccggcag aagttaacct ctcttagcct cagtttcccc acctgtaaaa tggcagaagt    720
aaccaagctt accttcccgg cagtgtgtga ggatgaaaag agctatgtac gtgatgcact    780
```

```
tagaagaagg tctagggtgt gagtggtact cgtctggtgg gtgtggagaa gacattctag    840
gcaatgagga ctggggagag cctggcccat ggcttccact cagcaaggtc agtctcttgt    900
cctctgcact cccagccttc cagagaggac cttcccaacc agcactcccc acgctgccag    960
tcacacatag ttacacacat acaatcacat atatgttccc atatagacac attcacactc   1020
ataccttcac acatgcacac gcatgtgcac acacagtcac tcatttctgt gttggagatt   1080
gggtgaggac attcaatggg tgaggaccaa caggtgtgaa gattgctttc tagaaaatga   1140
ctcctgtctc tctttgccat tcttcccaat ccgatggagc tactaggctt ttccctcatt   1200
tcatgtttaa taaaccttcc caatggcgaa atgggctttc tcaagaagtg gtgagtgtcc   1260
catccctgcg gtggggacag gggtggcagc ggacaagcct gcctggaggg aactgtcagg   1320
ctgattccca gtccaactcc agcttccaac acctcatcct ccaggcagtc ttcattcttg   1380
gctctaattt cgctcttgtt ttcttttta tttttatcga gaactgggtg gagagctttt   1440
ggtgtcattg gggattgctt tgaaacccctt ctctgcctca cactgggagc tggcttgagt   1500
caactggtct ccatggaatt tcttttttta gtgtgtaaac agctaagttt taggcagctg   1560
ttgtgccgtc cagggtggaa agcagcctgt tgatgtggaa ctgcttggct cagatttctt   1620
gggcaaacag atgccgtgtc tctcaactca ccaattaaga agcccagaaa atgtggcttg   1680
gagaccacat gtctggttat gtctagtaat tcagatggct tcacctggga agcccttct   1740 gaatgtcaaa gccatgagat aaaggacata tatatagtag ctagggtggt ccacttctta   1800
ggggccatct ccggaggtgg tgagcactaa gtgccaggaa gagaggaaac tctgttttgg   1860
agccaaagca taaaaaaacc ttagccacaa accactgaac atttgttttg tgcaggttct   1920
gagtccaggg agggcttctg aggagagggg cagctggagc tggtaggagt tatgtgagat   1980
ggagcaaggg ccctttaaga ggtgggagca gcatgagcaa aggcagagag gtggtaatgt   2040
ataaggtatg tcatgggaaa gagtttggct ggaacagagt ttacagaata gaaaaattca   2100
acactattaa ttgagcctct actacgtgct cgacattgtt ctagtcactg agataggttt   2160
ggtatacaaa acaaaatcca tcctctatgg acattttagt gactaacaac aatataaata   2220
ataaaagtga acaaaagctc aaaacatgcc aggcactatt atttatttat ttatttattt   2280
atttatttat tttttgaaac agagtctcgc tctgttgccc aggctggagt gtagtggtgc   2340
gatctcggct cactg                                                   2355

<210> SEQ ID NO 51
<211> LENGTH: 2289
<212> TYPE: DNA
<213> ORGANISM: Homo sapiens
<220> FEATURE:
<221> NAME/KEY: misc_feature
<223> OTHER INFORMATION: sequence of STAR51

<400> SEQUENCE: 51
tcacaggtga caccaatccc ctgaccacgc tttgagaagc actgtactag attgactttc     60
taatgtcagt cttcattttc tagctctgtt acagccatgg tctccatatt atctagtaca    120
acacacatac aaatatgtgt gatacagtat gaatataata taaaaatatg tgttataata    180
taaatataat attaaaatat gtctttatac tagataataa tacttaataa cgttgagtgt    240
ttaactgctc taagcacttt acctgcagga aacagttttt tttttatttt ggtgaaatac    300
aactaacata aatttatttta caattttaag catttttaag tgtatagttt agtggagtta    360
atatattcaa aatgttgtgc agccgtcacc atcatcagtc ttcataactc ttttcatatt    420
```

```
gtaaaattaa aagtttatgc tcatttaaaa atgactccca atttcccccc tcctcaacct    480
ctggaaacta ccattctatt ttctgcctcc gtagttttgc ccactctaag tacctcacat    540
aagtggaatt tgtcttattt gcctgtttgt gaccggctga tttcatttag tataatgtcc    600
tcaagtttta ttcacgttat atagcatatg tcataatttt cttcactttt aagcttgagt    660
aatatttcat cgtatgtatc tcacattttg cttatccatt catctctcag tggacacttg    720
agttgcttct acatttttagc tgttgtgaat actgctgcta tgaacatggg tgtataaata    780
tctcaagacc tttttatcag ttttttaaaa tatatactca gtagtagttt agctggatta    840
tatggtaatt ttatttttaa ttttttgagga actgtcctac cctttttattc aatagtagct    900 ataccaattg acaattggca ttcctaccaa cagggcataa gggttctcaa ttctccacat    960
attccctgat acttgttatt ttcaggtgtt tttttttttt tttttttttt atgggagcca    1020
tgttaatggg tgtaaggtga tatttcatta tagttttgat ttgcatttcc ctaatgatta    1080
gtgatgttaa gcatctcttc atgtgcctat tggccatttg tatatcttct ttaaaaatat    1140
atatatactc attcctttgc ccattttga attatgttta ttttttgtta ttgagtttca    1200
atacttttct ataaaccta ggtattaatc ctttatcaga cttaagattt gcaaatattc    1260
tctttcattc cacaggttgc taattctctc tgttggtaat atcttttgat gctgttgtgt    1320
ccagaattga ttcattcctg tgggttcttg gtctcactga cttcaagaat aaagctgcgg    1380
accctagtgg tgagtgttac acttcttata gatggtgttt ccggagtttg ttccttcaga    1440
tgtgtccaga gtttcttcct tccaatgggt tcatggtctt gctgacttca ggaatgaagc    1500
cgcagacctt cgcagtgagg tttacagctc ttaaaggtgg cgtgtccaga gttgtttgtt    1560 cccctggtg ggttcgtggt cttgctgact tcaggaatga agccgcagac cctcgcagtg    1620
agtgttacag ctcataaagg tagtgcggac acagagtgag ctgcagcaag atttactgtg    1680
aagagcaaaa gaacaaagct tccacagcat agaaggacac cccagcgggt tcctgctgct    1740
ggctcaggtg gccagttatt attcccttat ttgccctgcc cacatcctgc tgattggtcc    1800
attttacaga gtactgattg gtccatttta cagagtgctg attggtgcat ttacaatcct    1860
ttagctagac acagagtgct gattgctgca ttcttacaga gtgctgattg gtgcatttac    1920
agtcctttag ctagatacag aacgctgatt gctgcgtttt ttacagagtg ctgattggtg    1980
catttacaat ccttttagcta gacacagtgc tgattggtgg gttttttacag agtgctgatt    2040 ggtgcgtctt tacagagtgc tgattggtgc atttacaatc ctttagctag acacagagtg    2100
ctgattggtg cgtttataat cctctagcta gacagaaaag ttttccaagt ccccacctga    2160
ccgagaagcc ccactggctt cacctctcac tgttatactt tggacatttg tccccccaaa    2220
atctcatgtt gaaatgtaac ccctaatgtt ggaactgagg ccagactgga tgtggctggg    2280
ccatgggga                                                             2289
```

<210> SEQ ID NO 52
<211> LENGTH: 1184
<212> TYPE: DNA
<213> ORGANISM: Homo sapiens
<220> FEATURE:
<221> NAME/KEY: misc_feature
<223> OTHER INFORMATION: sequence of STAR52

<400> SEQUENCE: 52

```
ctcttctttg ttttttttatt ttgggtgtg tgggtacgtg taagatgaga aatgtacaaa     60
cacaagtatt tcagaaactc caagtaatat tctgtctgtg agttcacggt aaataaataa    120
```

```
aaagggcaaa gtgacagaaa tacaggatta ttaaaagcaa aataatgttc tttgaaatcc      180 ccccettggt gtatttttta tcttaggatg cagcactttc agcatgccca agtattgaaa      240
gcagtgtttt tacgctacca cggtaatttt atttagaaac cccatgttca cttttagttt      300
taaaatggtc tttatgacat aaaattatca gcattcatat ttttgtgttt taatattcct      360
ttggctactt attgaaacag taaacattac gaaaattagt aaacaaatct tgatagttg       420 cttattttg tttaattgaa tgtttatttt attaggtaaa tatacaatca aatttattta      480 aaataatga ggaaaagaat acttttcttt cgctttgcga agcaaagtg attttcatt         540 cttctccgtc cgattccttc tcttccagct gccacagccg actgacaggc tcccggcggc      600
ctgaggagta gtatgcaaat tttggatgat tgacacctac agtagaagcc aatcacgtca      660
aagtaggatg ctgattggtt gacaacaata ggcgtaaacc ttgacgtttt aaaaacctga      720
cacccaatcc aggcgattca tgcaaataaa ggaagggagt cacattacca ggggccagag      780
agacttgagt acgacctcac gtgttcagtg gtggatattg cacagacgtc tgcaaggtct      840
atataaacgc tacataatgt tcaactcaat tgcttgcctt ggccttttccc aaacttgtca      900 ctggaatata aattatccct tttttaaaaa taaaaaaata agaattatgt agtgcacata      960
tatgatggtt catgtagaaa tctaaatgga cttccaacgc atggaattttc cctatttccc    1020 cctttctta aattaatcct cagtgaagga ggctgttttc ccctagattt caaaaggacg      1080
agatttacag agcctttcct tggagaaacc cgctctaggc acagatggtc agtaaattta     1140
gcttcttcag cgaagttcca catggcaccg ccagatggca taag                     1184
```

<210> SEQ ID NO 53
<211> LENGTH: 1431
<212> TYPE: DNA
<213> ORGANISM: Homo sapiens
<220> FEATURE:
<221> NAME/KEY: misc_feature
<223> OTHER INFORMATION: sequence of STAR53

<400> SEQUENCE: 53

```
ccctgaggaa gatgacgagt aactccgtaa gagaaccttc cactcatccc ccacatccct      60
gcagacgtgc tattctgtta tgatactggt atcccatctg tcacttgctc cccaaatcat     120
tcccttctta caattttcta ctgtacagca ttgaggctga acgatgagag atttcccatg     180
ctctttctac tccctgccct gtatatatcc ggggatcctc cctacccagg atgctgtggg    240
gtcccaaacc ccaagtaagc cctgatatgc gggccacacc tttctctagc ctaggaattg    300
ataacccagg cgaggaagtc actgtggcat gaacagatgg ttcacttcga ggaaccgtgg    360
aaggcgtgtg caggtcctga gatagggcag aatcggagtg tgcagggtct gcaggtcagg   420
aggagttgag attgcgttgc cacgtggtgg gaactcactg ccacttattt ccttctctct    480
tcttgcctca gcctcaggga tacgacacat gcccatgatg agaagcagaa cgtggtgacc   540
tttcacgaac atgggcatgg ctgcggaccc ctcgtcatca ggtgcatagc aagtgaaagc    600
aagtgttcac aacagtgaaa agttgagcgt cattttcttt agtgtgccaa gagttcgatg    660
ttagcgttta cgttgtattt tcttacactg tgtcattctg ttagatacta acattttcat    720
tgatgagcaa gacatactta atgcatattt tggtttgtgt atccatgcac ctaccttaga    780
aaacaagtat tgtcggttac ctctgcatgg aacagcatta ccctcctctc tccccagatg    840
tgactactga gggcagttct gagtgtttaa tttcagattt tttcctctgc atttacacac    900
acacgcacac aaaccacacc acacacacac acacacacac acacacacac acacacacac    960
```

```
acacaccaag taccagtata agcatctgcc atctgctttt cccattgcca tgcgtcctgg    1020
tcaagctccc ctcactctgt ttcctggtca gcatgtactc ccctcatccg attcccctgt    1080
agcagtcact gacagttaat aaacctttgc aaacgttccc cagttgtttg ctcgtgccat    1140
tattgtgcac acagctctgt gcacgtgtgt gcatatttct ttaggaaaga ttcttagaag    1200
tggaattgct gtgtcaaagg agtcatttat tcaacaaaac actaatgagt gcgtcctcgt    1260
gctgagcgct gttctaggtg ctggagcgac gtcaggaaac aaggcagaca ggagttcctg    1320
acccccgttc tagaggagga tgtttccagt tgttgggttt tgtttgtttg tttcttctag    1380
agatggtggt cttgctctgt ccaggctaga gtgcagtggc atgatcatag c             1431

<210> SEQ ID NO 54
<211> LENGTH: 975
<212> TYPE: DNA
<213> ORGANISM: Homo sapiens
<220> FEATURE:
<221> NAME/KEY: misc_feature
<223> OTHER INFORMATION: sequence of STAR54

<400> SEQUENCE: 54
ccataaaagt gtttctaaac tgcagaaaaa tcccccctaca gtcttacagt tcaagaattt     60
tcagcatgaa atgcctggta gattacctga cttttttgc caaaaataag gcacagcagc    120
tctctcctga ctctgacttt ctatagtcct tactgaatta tagtccttac tgaattcatt    180
cttcagtgtt gcagtctgaa ggacacccac attttctctt tgtctttgtc aattctttgt    240
gttgtaaggg caggatgttt aaaagttgaa gtcattgact tgcaaaatga gaaatttcag    300
agggcatttt gttctctaga ccatgtagct tagagcagtg ttcacactga ggttgctgct    360
aatgtttctg cagttcttac caatagtatc atttacccag caacaggata tgatagagga    420
cttcgaaaac cccagaaaat gttttgccat atatccaaag cccttggga atggaaagg     480 aattgcgggc tcccattttt atatatggat agatagagac caagaaagac caaggcaact    540
ccatgtgctt tacattaata aagtacaaaa tgttaacatg taggaagtct aggcgaagtt    600
tatgtgagaa ttctttacac taattttgca acatttaat gcaagtctga aattatgtca    660
aaataagtaa aaatttttac aagttaagca gagaataaca atgattagtc agagaaataa    720
gtagcaaaat cttcttctca gtattgactt ggttgctttt caatctctga ggacacagca    780
gtcttcgctt ccaaatccac aagtcacatc agtgaggaga ctcagctgag actttggcta    840
atgttggggg gtccctcctg tgtctcccca ggcgcagtga gcctgcaggc cgacctcact    900
cgtggcacac aactaaatct ggggagaagc aacccgatgc cagcatgatg cagatatctc    960
agggtatgat cggcc                                                      975

<210> SEQ ID NO 55
<211> LENGTH: 501
<212> TYPE: DNA
<213> ORGANISM: Homo sapiens
<220> FEATURE:
<221> NAME/KEY: misc_feature
<223> OTHER INFORMATION: sequence of STAR55

<400> SEQUENCE: 55
cctgaactca tgatccgccc acctcagcct cctgaagtgc tgggattaca ggtgtgagcc     60
accacaccca gccgcaacac actcttgagc aaccaatgtg tcataaaaga aataaaatgg    120
aaatcagaaa gtatcttgag acagacaaaa atggaaacac aacataccaa aatttatggg    180
```

```
acacagcaaa agcagtttta ggagggaagt ttatagtgat gaatacctac ctcaaaatca       240
ttagcctgat tggatgacac tacagtgtat aaatgaattg aaaaccacat tgtgccccat       300
acatatatac aattttttatt tgttaattaa aaataaaata aaactttaaa aagaagaaa        360 gagctcaaat aaacaaccta actttatacc tcaaggaaat agaagagcca gctaagccca       420
aagttgacag aaggaaaaaa atattggcag aaagaaatga acagagact agaaagacaa       480 ttgaagagat cagcaaaact a                                                  501

<210> SEQ ID NO 56
<211> LENGTH: 741
<212> TYPE: DNA
<213> ORGANISM: Homo sapiens
<220> FEATURE:
<221> NAME/KEY: misc_feature
<223> OTHER INFORMATION: sequence of STAR56

<400> SEQUENCE: 56
acacaggaaa agatcgcaat tgttcagcag agctttgaac cggggatgac ggtctccctc        60
gttgcccggc aacatggtgt agcagccagc cagttatttc tctggcgtaa gcaataccag       120
gaaggaagtc ttactgctgt cgccgccgga gaacaggttg ttcctgcctc tgaacttgct       180
gccgccatga agcagattaa agaactccag cgcctgctcg gcaagaaaac gatggaaaat       240
gaactcctca aagaagccgt tgaatatgga cgggcaaaaa agtggatagc gcacgcgccc       300
ttattgcccg gggatgggga gtaagcttag tcagccgttg tctccgggtg tcgcgtgcgc       360
agttgcacgt cattctcaga cgaaccgatg actggatgga tggccgccgc agtcgtcaca       420
ctgatgatac ggatgtgctt ctccgtatac accatgttat cggagagctg ccaacgtatg       480
gttatcgtcg ggtatgggcg ctgcttcgca gacaggcaga acttgatggt atgcctgcga       540
tcaatgccaa acgtgtttac cggatcatgc gccagaatgc gctgttgctt gagcgaaaac       600
ctgctgtacc gccatcgaaa cgggcacata caggcagagt ggccgtgaaa gaaagcaatc       660
agcgatggtg ctctgacggg ttcgagttct gctgtgataa cggagagaga ctgcgtgtca       720
cgttcgcgct ggactgctgt g                                                 741

<210> SEQ ID NO 57
<211> LENGTH: 1365
<212> TYPE: DNA
<213> ORGANISM: Homo sapiens
<220> FEATURE:
<221> NAME/KEY: misc_feature
<223> OTHER INFORMATION: sequence of STAR57

<400> SEQUENCE: 57
tccttctgta aataggcaaa atgtatttta gtttccacca cacatgttct tttctgtagg        60
gcttgtatgt tggaaatttt atccaattat tcaattaaca ctataccaac aatctgctaa       120
ttctggagat gtggcagtga ataaaaaagt tatagtttct gattttgtgg agcttggact       180
ttaatgatgg acaaaacaac acattcttaa atatatatttt catcaaaatt atagtgggtg     240
aattatttat atgtgcattt acatgtgtat gtatacataa atgggcggtt actggctgca       300
ctgagaatgt acacgtggcg cgaacgaggc tgggcggtca gagaaggcct cccaaggagg       360
tggctttgaa gctgagtggt gcttccacgt gaaaaggctg gaaagggcat tccaagaaaa       420
ggctgaggcc agcggaaag  aggttccagt gcgctctggg aacggaaagc gcacctgcct       480
gaaacgaaaa tgagtgtgct gaaataggac gctagaaagg gaggcagagg ctggcaaaag      540
cgaccgagga ggagctcaaa ggagcgagcg gggaaggccg ctgtggagcc tggaggaagc       600
```

```
acttcggaag cgcttctgag cgggtaaggc cgctgggagc atgaactgct gagcaggtgt    660
gtccagaatt cgtgggttct tggtctcact gacttcaaga atgaagaggg accgcggacc    720
ctcgcggtga gtgttacagc tcttaaggtg gcgcgtctgg agtttgttcc ttctgatgtt    780
cggatgtgtt cagagtttct tccttctggt gggttcgtgg tctcgctggc tcaggagtga    840
agctgcagac cttcgcggtg agtgttacag ctcataaaag cagggtggac tcaaagagtg    900
agcagcagca agatttattg caaagaatga agaacaaag cttccacact gtggaagggg    960
accccagcgg gttgccactg ctggctccgc agcctgcttt tattctctta tctggcccca   1020
cccacatcct gctgattggt agagccgaat ggtctgtttt gacggcgctg attggtgcgt   1080
ttacaatccc tgcgctagat acaaaggttc tccacgtccc caccagatta gctagataga   1140
gtctccacac aaaggttctc caaggcccca ccagagtagc tagatacaga gtgttgattg   1200
gtgcattcac aaaccctgag ctagacacag ggtgatgact ggtgtgttta caaaccttgc   1260
ggtagataca gagtatcaat tggcgtattt acaatcactg agctaggcat aaaggttctc   1320
caggtcccca ccagactcag gagcccagct ggcttcaccc agtgg              1365

<210> SEQ ID NO 58
<211> LENGTH: 1401
<212> TYPE: DNA
<213> ORGANISM: Homo sapiens
<220> FEATURE:
<221> NAME/KEY: misc_feature
<223> OTHER INFORMATION: sequence of STAR58

<400> SEQUENCE: 58
aagtttacct tagccctaaa ttatttcatt gtgattggca ttttaggaaa tatgtattaa     60
ggaatgtctc ttaggagata aggataacat atgtctaaga aaattatatt gaaatattat    120
tacatgaact aaaatgttag aactgaaaaa aaattattgt aactccttcc agcgtaggca    180
ggagtatcta gataccaact ttaacaactc aactttaaca acttcgaacc aaccagatgg    240
ctaggagatt cacctattta gcatgatatc ttttattgat aaaaaaatat aaaacttcca    300 ttaaatttttt aagctactac aatcctatta aattttaact taccagtgtt ctcaatgcta    360
cataatttaa aatcattgaa atcttctgat tttaactcct cagtcttgaa atctacttat    420
ttttagttac atatatatcc aatctactgc cgctagtaga agaagcttgg aatttgagaa    480
aaaaatcaga cgttttgtat attctcatat tcactaattt attttttaaa tgagtttctg    540
caatgcatca agcagtggca aaacaggaga aaaattaaaa ttggttgaaa agatatgtgt    600
gccaaacaat cccttgaaat ttgatgaagt gactaatcct gagttattgt ttcaaatgtg    660
tacctgttta tacaagggta tcacctttga aatctcaaca ttaaatgaaa ttttataagc    720
aatttgttgt aacatgatta ttataaaatt ctgatataac attttttatt acctgtttag    780
agtttaaaga gagaaaagga gttaagaata attacatttt cattagcatt gtccgggtgc    840
aaaaacttct aacactatct tcaaatcttt ttctccattg ccttctgaac atacccactt    900
gggtatctca ttagcactgc aaattcaaca ttttcgattg ctaattttc ccctaaata    960 tttatttgtt ttctcagctt tagccaatgt ttcactattg accatttgct caagtatagt   1020
gacgcttcaa tgaccttcag agagctgttt cagtccttcc tggactactt gcatgcttcc   1080
aacaaaatga agcactcttg atgtcagtca ctcaaataaa tggaaatggg cccatttact   1140
aggaatgtta acagaataaa aagatagacg tgacaccagt tgcttcagtc catctccatt   1200
tacttgctta aggcctggcc atatttctca cagttgatat ggcgcagggc acatgtttaa   1260
```

```
atggctgttc ttgtaggatg gtttgactgt tggattcctc atcttccctc tccttaggaa    1320
ggaaggttac agtagtactg ttggctcctg gaatatagat tcataaagaa ctaatggagt    1380
atcatctccc actgctcttg t                                              1401
```

<210> SEQ ID NO 59
<211> LENGTH: 866
<212> TYPE: DNA
<213> ORGANISM: Homo sapiens
<220> FEATURE:
<221> NAME/KEY: misc_feature
<223> OTHER INFORMATION: sequence of STAR59

<400> SEQUENCE: 59

```
gagatcacgc cactgcactc cagcctgggg gacagagcaa gactccatct cagaaacaaa     60
caaacacaca aagccagtca aggtgtttaa ttcgacggtg tcaggctcag gtctcttgac    120
aggatacatc cagcacccgg gggaaacgtc gatgggtggg gtggaatcta ttttgtggcc    180
tcaagggagg gtttgagagg tagtcccgca agcggtgatg gcctaaggaa gcccctccgc    240
ccaagaagcg atattcattt ctagcctgta gccacccaag agggagaatc gggctcgcca    300
cagacctcac aaccccaac ccaccccacc cccaccctc ccacctcgtg aaatgggctc       360
tcgctccgtc aggctctagt cacaccgtgt ggttttggaa cctccagcgt gtgtgcgtgg    420
gttgcgtggt ggggtggggc cggctgtgga cagaggaggg gataaagcgg cggtgtcccg    480
cgggtgcccg ggacgtgggg cgtggggcgt gggtggggtg gccagagcct tgggaactcg    540
tcgcctgtcg ggacgtctcc cctcctggtc ccctctctga cctacgctcc acatcttcgc    600
cgttcagtgg ggaccttgtg ggtggaagtc accatccctt tggactttag ccgacgaagg    660
ccgggctccc aagagtctcc ccggaggcgg ggccttgggc aggctcacaa ggatgctgac    720
ggtgacggtt ggtgacggtg atgtacttcg gaggcctcgg gccaatgcag aggtatccat    780
ttgacctcgg tgggacaggt cagctttgcg gagtcccgtg cgtccttcca gagactcatc    840
cagcgctagc aagcatggtc ccgagg                                          866
```

<210> SEQ ID NO 60
<211> LENGTH: 2067
<212> TYPE: DNA
<213> ORGANISM: Homo sapiens
<220> FEATURE:
<221> NAME/KEY: misc_feature
<223> OTHER INFORMATION: sequence of STAR60
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (344)..(345)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (465)..(465)

```
<223> OTHER INFORMATION: n is a, c, g, or t
<220> FEATURE:
<221> NAME/KEY: misc_feature
<222> LOCATION: (902)..(902)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (1522)..(1522)
<223> OTHER INFORMATION: n is a, c, g, or t
<220> FEATURE:
<221> NAME/KEY: misc_feature
<222> LOCATION: (1590)..(1590)
<223> OTHER INFORMATION: n is a, c, g, or t
<220> FEATURE:
<221> NAME/KEY: misc_feature
<222> LOCATION: (1601)..(1601)
<223> OTHER INFORMATION: n is a, c, g, or t
<220> FEATURE:
<221> NAME/KEY: misc_feature
<222> LOCATION: (1647)..(1647)
<223> OTHER INFORMATION: n is a, c, g, or t
<220> FEATURE:
<221> NAME/KEY: misc_feature
<222> LOCATION: (1677)..(1677)
<223> OTHER INFORMATION: n is a, c, g, or t
<220> FEATURE:
<221> NAME/KEY: misc_feature
<222> LOCATION: (1777)..(1777)
<223> OTHER INFORMATION: n is a, c, g, or t

<400> SEQUENCE: 60
```

| | | | | | |
|---|---|---|---|---|---|
| agcagtgcag | aactggggaa | gaagaagagt | ccctacacca | cttaatactc | aaaagtactc | 60 |
| gcaaaaaata | acacccctca | ccaggtggca | tnattactct | ccttcattga | gaaaattagg | 120 |
| aaactggact | tcgtagaagc | taattgcttt | atccagagcc | acctgcatac | aaacctgcag | 180 |
| cgccacctgc | atacaaacct | gtcagccgac | cccaaagccc | tcagtcgcac | caagcctctg | 240 |
| ctgcacaccc | tcgtgccttc | acactggccg | ttccccaagc | tggggcata | ctncccagct | 300 |
| ctgagaaatg | tattcatcct | tcaaagccct | gctcatgtgt | cctnntcaac | aggaaaatct | 360 |
| cccatgagat | gctctgctat | ccccatctct | cctgccccat | agcttaggca | nacttctgtg | 420 |
| gtggtgagtc | ctgggctgtg | ctgtgatgtg | ttcgcctgcn | atgtntgttc | ttccccacaa | 480 |
| tgatgggccc | ctgaattctc | tatctctagc | acctgtgctc | agtaaaggct | tgggaaacca | 540 |
| ggctcaaagc | ctgcccaga | tgccaccttt | tccagggtgc | ttccgggggc | caccaaccag | 600 |
| agtgcagcct | tctcctccac | caggaactct | tgcagcccca | ccctgagca | cctgcacccc | 660 |
| attacccatc | tttgtttctc | cgtgtgatcg | tattattaca | gaattatata | ctgtattctt | 720 |
| aatacagtat | ataattgtat | aattattctt | aatacagtat | ataattatac | aaatacaaaa | 780 |
| tatgtgttaa | tggaccgttt | atgttactgg | taaagcttta | agtcaacagt | gggacattag | 840 |
| ttaggttttt | ggcgaagtca | aaagttatat | gtgcattttc | aacttcttga | ggggtcggta | 900 |
| cntctnaccc | ccatgttgtt | caanggtcaa | ctgtctacac | atatcatagc | taattcacta | 960 |
| cagaaatgtt | agcttgtgtc | actagtatct | ccccttctca | taagcttaat | acacatacct | 1020 |
| tgagagagct | cttggccatc | tctactaatg | actgaagttt | ttatttatta | tagatgtcat | 1080 |
| aataggcata | aaactacatt | acatcattcg | agtgccaatt | ttgccaccttt | gaccctcttt | 1140 |
| tgcaaaacac | caacgtcagt | acacatatga | agaggaaact | gcccgagaac | tgaagttcct | 1200 |

```
gagaccagga gctgcaggcg ttagatagaa tatggtgacg agagttacga ggatgacgag    1260
agtaaatact tcatactcag tacgtgccaa gcactgctat aagcgctctg tatgtgtgaa    1320
gtcatttaat cctcacagca tcccacggtg taattatttt cattatcccc atgagggaac    1380
agaaactcag aacggttcaa cacatatgcg agaagtcgca gccggtcagt gagagagcag    1440
gttcccgtcc aagcagtcag accccgagtg cacactctcg acccctgtcc agcagactca    1500
ctcgtcataa ggcggggagt gntctgtttc agccagatgc tttatgcatc tcagagtacc    1560
caaaccatga agaatgagg cagtattcan gagcagatgg ngctgggcag taaggctggg    1620
cttcagaata gctggaaagc tcaagtnatg ggacctgcaa gaaaaatcca ttgtttngat    1680
aaatagccaa agtccctagg ctgtaagggg aaggtgtgcc aggtgcaagt ggagctctaa    1740
tgtaaaatcg cacctgagtc tcctggtctt atgagtnctg ggtgtacccc agtgaaaggt    1800
cctgctgcca ccaagtgggc catggttcag ctgtgtaagt gctgagcggc agccggaccg    1860
cttcctctaa cttcacctcc aaaggcacag tgcacctggt tcctccagca tcagctgcg    1920 aggcccctag ccagggtccc ggcccccggc cccggcagc tgctccagct tccttcccca    1980
cagcattcag gatggtctgc gttcatgtag acctttgttt tcagtctgtg ctccgaggtc    2040
actggcagca ctagccccgg ctcctgt                                        2067

<210> SEQ ID NO 61
<211> LENGTH: 1470
<212> TYPE: DNA
<213> ORGANISM: Homo sapiens
<220> FEATURE:
<221> NAME/KEY: misc_feature
<223> OTHER INFORMATION: sequence of STAR61
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (220)..(220)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (976)..(976)
<223> OTHER INFORMATION: n is a, c, g, or t

<400> SEQUENCE: 61
cagcccccac atgcccagcc ctgtgctcag ctctgcagcg gggcatggtg ggcagagaca      60
```

```
cagaggccaa ggccctgctt cggggacggt gggcctggga tgagcatggc cttggccttc    120
gccgagagtn ctcttgtgaa ggaggggtca ggaggggctg ctgcagctgg ggaggagggc    180
gatggcactg tggcangaag tgaantagtg tgggtgcctn gcaccccagg cacggccagc    240
ctggggtatg gacccggggc cntctgttct agagcaggaa ggtatggtga ggacctcaaa    300
aggacagcca ctggagagct ccaggcagag gnacttgaga ggccctgggg ccatcctgtc    360
tcttttctgg gtctgtgtgc tctgggcctg gcccttcct ctgctccccc gggcttggag    420
agggctggcc ttgcctcgtg caaaggacca ctctagactg gtaccaagtc tggcccatgg    480
cctcctgtgg gtgcaggcct gtgcgggtga cctgagagcc agggctggca ggtcagagtc    540
aggagaggga tggcagtgga tgccctgtgc aggatctgcc taatcatggt gaggctggag    600
gaatccaaag tgggcatgca ctctgcactc atttctttat tcatgtgtgc ccatcccaac    660
aagcagggag cctggccagg agggcccctg ggagaaggca ctgatgggct gtgttccatt    720
taggaaggat ggacggttgt gagacgggta agtcagaacg ggctgcccac ctcggccgag    780 agggcccccgt ggtgggttgg caccatctgg gcctggagag ctgctcagga ggctctctag    840
ggctgggtga ccaggnctgg ggtacagtag ccatgggagc aggtgcttac ctggggctgt    900
ccctgagcag gggctgcatt gggtgctctg tgagcacaca cttctctatt cacctgagtc    960
ccnctgagtg atgagnacac ccttgttttg cagatgaatc tgagcatgga gatgttaagt    1020
ggcttgcctg agccacacag cagatggatg gtgtagctgg gacctgaggg caggcagtcc    1080
cagcccgagg acttcccaag gttgtggcaa actctgacag catgaccccca gggaacaccc    1140 atctcagctc tggtcagaca ctgcggagtt gtgttgtaac ccacacagct ggagacagcc    1200
accctagccc cacccttatc ctctcccaaa ggaacctgcc cttcccttc attttcctct    1260 tactgcattg agggaccaca cagtgtggca gaaggaacat gggttcagga cccagatgga    1320
cttgcttcac agtgcagccc tcctgtcctc ttgcagagtg cgtcttccac tgtgaagttg    1380
ggacagtcac accaactcaa tactgctggg cccgtcacac ggtgggcagg caacggatgg    1440
cagtcactgg ctgtgggtct gcagaggtgg                                      1470
```

<210> SEQ ID NO 62
<211> LENGTH: 1011
<212> TYPE: DNA
<213> ORGANISM: Homo sapiens
<220> FEATURE:
<221> NAME/KEY: misc_feature
<223> OTHER INFORMATION: sequence of STAR62

<400> SEQUENCE: 62

```
agtgtcaaat agatctacac aaaacaagat aatgtctgcc cattttttcca aagataatgt     60 ggtgaagtgg gtagagagaa atgcatccat tctccccacc caacctctgc taaattgtcc    120
atgtcacagt actgagacca gggggcttat tcccagcggg cagaatgtgc accaagcacc    180
tcttgtctca atttgcagtc taggccctgc tatttgatgg tgtgaaggct tgcacctggc    240
atggaaggtc cgttttgtac ttcttgcttt agcagttcaa agagcaggga gagctgcgag    300
ggcctctgca gcttcagatg gatgtggtca gcttgttgga ggcgccttct gtggtccatt    360
atctccagcc ccctgcggt gttgctgttt gcttggcttg tctggctctc catgccttgt    420
tggctccaaa atgtcatcat gctgcacccc aggaagaatg tgcaggccca tctctttat    480 gtgctttggg ctatttgat tccccgttgg gtatattccc taggtaagac ccagaagaca    540
caggaggtag ttgctttggg agagtttgga cctatgggta tgaggtaata gacacagtat    600
```

```
cttctctttc atttggtgag actgttagct ctggccgcgg actgaattcc acacagctca        660
cttgggaaaa ctttattcca aaacatagtc acattgaaca ttgtggagaa tgagggacag        720
agaagaggcc ctagatttgt acatctgggt gttatgtcta taaatagaat gctttggtgg        780
tcaactagac ttgttcatgt tgacatttag tcttgccttt tcggtggtga tttaaaaatt        840
atgtatatct tgtttggaat atagtggagc tatggtgtgg cattttcatc tggcttttg         900 tttagctcag cccgtcctgt tatgggcagc cttgaagctc agtagctaat gaagaggtat        960
cctcactccc tccagagagc ggtcccctca cggctcattg agagtttgtc a                1011
```

<210> SEQ ID NO 63
<211> LENGTH: 1410
<212> TYPE: DNA
<213> ORGANISM: Homo sapiens
<220> FEATURE:
<221> NAME/KEY: misc_feature
<223> OTHER INFORMATION: sequence of STAR63

<400> SEQUENCE: 63

```
ccacagcctg atcgtgctgt cgatgagagg aatctgctct aagggtctga gcggagggag         60
atgccgaagc tttgagcttt tgtttctgg cttaaccttg gtggattttc accctctggg         120
cattacctct tgtccagggg aggggctggg ggagtgcctg gagctgtagg gacagagggc        180
tgagtggggg ggactgcttg gctgaccac ataatattct gctgcgtatt aattttttt          240 tgagacagtc tttctctgtt gcccaggctg gagtgtaatg gcttgatagc tcactgccac        300
ctccgcctcc tgggttcaag tgattctcct gcttcagctt ccggagtagc tgggactgca        360
ggtgcccgcc accatggctg gctaattttt gtatttttat tagcaatggg gttttgctat        420
gttgcccagg ccgtcccga actcctgccc tcaagtgata cacctgcctc ggcctcccaa         480
agtgctggga ttagaggctt gagccactgc gcctggccag ctgcatattg ttaattagac        540
ataaaatgca aaataagatg atataaacac aaaggtgtga aataagatgg cacctgctg         600 agcgcgcctg tcctgaagca tcgcccctct gcaaaagcag gggtcagcat gtgttctccg        660
gtccttgctc ttacagagga gtgagctgcc tatgcgtctt ccagccactt cctgggctgc        720
tcagaggcct ctcacggtg ttctgggttg ctgccacttg caggggtgct gaggcggggc         780
tcctcccgtg cggggcatgt ccaggccgcc ctctctgaag gcttggcagg tacaggtggg        840 agtggggtc tctgggctgc tgtgggact gggcaggctc ctggaagacc tccctgtgtt         900
tgggctgaaa gcgcagcccg aggggaggtc cccaggagg ccgctgtcgg gggtgggggc         960
ttggaggagg gaggggccga ggagccggcg acactccgtg acggcccagg aacgtccta       1020 aacaaggcgc cgcgttctcg atgggtggg gtccgctttc tttctcaaa agctgcagtt       1080 actccatgct cggaggactg gcgtccgcgc cctgttccaa tgctgccccg gggccctggc       1140
cttggggaat cggggccttg gactggaccc tgggggcttc gcggagccgg gcctggcggg       1200
gcgagcggag cagaggctgg gcagcccgg ggaagcgctc gccaaagccg ggcgctgctc       1260
ccagagcgcg aggtgcagaa ccagaggctg gtcccgcggc gctaacgaga gaagaggaag      1320
cgcgctgtgt agagggcgcc caccccgtgg ggcgaacccc cttcctcaac tccatggacg      1380
gggctcatgg gttcccagcg gctcagacgc                                        1410
```

<210> SEQ ID NO 64
<211> LENGTH: 1414
<212> TYPE: DNA
<213> ORGANISM: Homo sapiens
<220> FEATURE:
<221> NAME/KEY: misc_feature
<223> OTHER INFORMATION: sequence of STAR64

<400> SEQUENCE: 64

| | | | | | |
|---|---|---|---|---|---|
| tggatcagat | ttgttttata | ccctcccttc | tactgctctg | agagttgtac | atcacagtct | 60 |
| actgtatctg | tttcccatta | ttataatttt | tttgcactgt | gcttgcctga | agggagcctc | 120 |
| aagttcatga | gtctccctac | cctcctccca | aatgagacat | ggacctttga | atgctttcct | 180 |
| gggaccacca | ccccacctttt | catgctgctg | ttatccagga | ttttagttca | acagtgtttt | 240 |
| aaccccccaa | atgagtcatt | tttattgttt | cgtatagtga | atgtgtattt | gggtttgctt | 300 |
| atatggtgac | ctgtttattt | gctcctcatt | gtacctcatg | ctctgctctt | tccttctaga | 360 |
| ttcagtctct | ttcctaatga | ggtgtctcgc | agcaattctt | tacaagacag | ccaagatagg | 420 |
| ccagctctca | gagcacttgt | tgtctgaaaa | agtcttgtct | tatttaattt | cttttttctta | 480 |
| gagatggggt | ctcattatgt | tacccacact | ggtctcaaac | ttctggctta | aagcggtcct | 540 |
| cccaccttgg | cctcccaaag | tgctaggatt | acaggcgtga | gcgacctcgt | ccagcctgtc | 600 |
| tgagaaagcg | tttgttttgc | ccttgctctc | agatgacagt | tgggggatag | aattctaggt | 660 |
| ggacggtttt | tttccttcag | cccttttgaag | agtctgtatt | tcattatct | ccctgcatta | 720 |
| gatgttcttt | tgcaagtaac | gtgtcttttc | tctctgggta | ttcttaaggt | tttctctttg | 780 |
| cctttggtga | gctgcagtgg | atttgctttt | ttcaagaggt | caagagaaag | gaaagtgtga | 840 |
| ggtttctgtt | ttttactgac | aatttgtttg | ttgatttgtt | ttcccaccca | gaggttcctt | 900 |
| gccactttgc | caggctggaa | ggcagacttc | ttctggtgtc | ctgttcacag | acggggcagc | 960 |
| ctgcggaagg | ccctgccaca | tgcagggcct | cggtcctcat | tcccttgcat | gtggacccgg | 1020 |
| gcgtgactcc | tgttcaggct | ggcacttccc | agagctgagc | cccagcctga | ccttcctccc | 1080 |
| atactgtctt | cacacccccct | cctttcttct | gatacctgga | ggttttcctt | tctttcctgt | 1140 |
| cacctccact | tggatttttaa | atcctctgtc | tgtggaattg | tattcggcac | aggaagatgc | 1200 |
| ttgcaagggc | caggctcatc | agccctgtcc | ctgctgctgg | aagcagcaca | gcagagcctc | 1260 |
| atgctcaggc | tgagatggag | cagaggcctg | cagacgagca | cccagctcag | ctgggggttgg | 1320 |
| cgccgatggt | ggagggtcct | cgaaagctct | ggggacgatg | gcagagctat | tggcagggga | 1380 |
| gccgcagggt | cttttgagcc | cttaaaagat | ctct | | | 1414 |

<210> SEQ ID NO 65
<211> LENGTH: 1310
<212> TYPE: DNA
<213> ORGANISM: Homo sapiens
<220> FEATURE:
<221> NAME/KEY: misc_feature
<223> OTHER INFORMATION: sequence of STAR65

<400> SEQUENCE: 65

| | | | | | |
|---|---|---|---|---|---|
| gtgaatgttg | atggatcaaa | tatctttctg | tgttgtttat | caaagttaaa | ataaatgtgg | 60 |
| tcatttaaag | gacaaaagat | gaggggttgg | agtctgttca | agcaaagggt | atattaggag | 120 |
| aaaagcagaa | ttctctccct | gtgaagggac | agtgactcct | attttccacc | tcatttttac | 180 |
| taactctcct | aactatctgc | ttaggtagag | atatatccat | gtacatttat | aaaccacagt | 240 |
| gaatcatttg | attttggaat | aaagatagta | taaaatgtgt | cccagtgttg | atatacatca | 300 |
| tacattaaat | atgtctggca | gtgttctaat | tttacagttg | tccaaagata | atgttagggc | 360 |
| atactggcta | tggatgaagc | tccaatgttc | agattgcaaa | gaaacttaga | attttactaa | 420 |

-continued

| | |
|---|---|
| tgaaaccaaa tacatcccaa gaaattttc agaagaaaaa aagagaaact agtagcaaag | 480 |
| taaagaatca ccacaatatc atcagattt ttttatatgt agaatattta ttcagttctt | 540 |
| ttttcaagta caccttgtct tcattcattg tactttattt tttgtgaagg tttaaattta | 600 |
| tttcttctat gtgtttagtg atatttaaaa tttttattta atcaagttta tcagaaagtt | 660 |
| ctgttagaaa atatgacgag gctttaattc cgccatctat attttccgct attatataaa | 720 |
| gataattgtt ttctcttttt aaaacaactt gaattgggat tttatatcat aattttttaa | 780 |
| tgtcttttt tattatactt taagttctgg gatacatgtg cagaacgtgc aggtgtgtta | 840 |
| catagatata cacgtgccat ggtggtttgc tgcacccact aacctgttat cgacattagg | 900 |
| tatttctcct aatgctatca cccctattt ccccacccc cgagaggccc cagtgtgtga | 960 |
| tgttctcctc cctgtgtcca tgtgttctca ttgttcatct cccacttatg gtatctacca | 1020 |
| taaccttgaa attgtcttat gcattcactt gtttggttgt tatatagcct ccatcaggac | 1080 |
| agggatattt gctgctgctt cttttttttt tcttttgag acagtcttgc tccgtcatcc | 1140 |
| aggctggagt gcttctcggc tcaatgcaac ctccacctcc caggtttaag cgattctcca | 1200 |
| acttcagcct cccaaatggc tgggactgca ggcatgcacc actacacctg gctaattttt | 1260 |
| gtatttgtaa tagagacaat gtttcaccat gttggccagg ctggtctcga | 1310 |

<210> SEQ ID NO 66
<211> LENGTH: 1917
<212> TYPE: DNA
<213> ORGANISM: Homo sapiens
<220> FEATURE:
<221> NAME/KEY: misc_feature
<223> OTHER INFORMATION: sequence of STAR67

<400> SEQUENCE: 66

| | |
|---|---|
| aggatcctaa aattttgtga ccctagagca agtactaact atgaaagtga aatagagaat | 60 |
| gaaggaatta tttaattaag tccagcaaaa cccaaccaaa tcatctgtaa aatatatttg | 120 |
| ttttcaacat ccaggtattt tctgtgtaaa aggttgagtt gtatgctgac ttattgggaa | 180 |
| aaataattga gttttcccct tcactttgcc agtgagagga aatcagtact gtaattgtta | 240 |
| aaggttaccc atacctacct ctactaccgt ctagcatagg taaagtaatg tacactgtga | 300 |
| agtttcctgc ttgactgtaa tgttttcagt ttcatcccat tgattcaaca gctatttatt | 360 |
| cagcacttac tacaaccatg ctggaaaccc aagagtaaat aggctgtgtt actcaacagg | 420 |
| actgaggtac agccgaactg tcaggcaagg ttgctgtcct ttggacttgc ctgctttctc | 480 |
| tctatgtagg aagaagaaat ggacataccg tccaggaaat agatatatgt tacatttcct | 540 |
| tattccataa ttaatattaa taaccctgga cagaaactac caagtttcta gacccttata | 600 |
| gtaccacctt acccttctg gatgaatcct tcacatgttg atacatttta tccaaatgaa | 660 |
| aattttggta ctgtaggtat aacagacaaa gagagaacag aaaactagag atgaagtttg | 720 |
| ggaaaaggtc aagaaagtaa ataatgcttc tagaagacac aaaaagaaaa atgaaatggt | 780 |
| aatgttggga agttttaat acattttgcc ctaaggaaaa aaactacttg ttgaaattct | 840 |
| acttaagact ggacctttc tctaaaaatt gtgcttgatg tgaattaaag caacacaggg | 900 |
| aaatttatgg gctccttcta agttctaccc aactcaccgc aaaactgttc ctagtaggtg | 960 |
| tggtatactc tttcagattc tttgtgtgta tgtatatgtg tgtgtgtgtg tgtgtttgta | 1020 |
| tgtgtacagt ctatatacat atgtgtacct acatgtgtgt atataaat atatatttac | 1080 |
| ctggatgaaa tagcatatta tagaatattc ttttttcttt aaatatatat gtgcatacat | 1140 |

```
atgtatatgc acatatatac ataaatgtag atatagctag gtaggcattc atgtgaaaca    1200
aagaagccta ttacttttta atggttgcat gatattccat cataggagta tagtacaact    1260
tatgtaacac acatttggct tgttgtaaaa ttttggtatt aataaaatag cacatatcat    1320
gcaaagacac ccttgcatag gtctattcat tctttgattt ttaccttagg acaaaattta    1380
aaagtagaat ttctgggtca agcagtatgc tcatttaaaa tgtcattgca tatttccaaa    1440
ttgtcctcca gaaaagtagt aacagtaaca attgatggac tgcgtgtttt ctaaaacttg    1500 cattttttc cttattggtg aggtttggca ttttccatat gtttattggc attttaattt    1560
tttttggttc atgtcttta ttccttcct gcaaatttgt ggtgtgtctc aactttattt      1620
atactctcat tttcataatt ttctaaagga atttgacttt aaaaaaataa gacagccaat    1680
gctttggttt aatttcattg ctgcttttg aagtgactgc tgtgttttta tacttttta      1740 tattttgttg ttttagcaaa ttcttctata ttataattgt gtatgctgga acaaaaagtt    1800
atatttctta atctagataa atatttcaa gatgttgtaa ttacagtccc ctctaaaatc     1860 atataaaatag acgcatagct gtgtgatttg taattagtta tgtccattga tagatcc       1917
```

<210> SEQ ID NO 67
<211> LENGTH: 11
<212> TYPE: DNA
<213> ORGANISM: Artificial
<220> FEATURE:
<223> OTHER INFORMATION: sequence around startcodon of wild-type zeocin resistance gene

<400> SEQUENCE: 67
aaaccatggc c    11

<210> SEQ ID NO 68
<211> LENGTH: 50
<212> TYPE: DNA
<213> ORGANISM: Artificial
<220> FEATURE:
<223> OTHER INFORMATION: primer ZEOforwardMUT

<400> SEQUENCE: 68
gatctcgcga tacaggattt atgttggcca agttgaccag tgccgttccg    50

<210> SEQ ID NO 69
<211> LENGTH: 26
<212> TYPE: DNA
<213> ORGANISM: Artificial
<220> FEATURE:
<223> OTHER INFORMATION: primer ZEO-WTreverse

<400> SEQUENCE: 69
aggcgaattc agtcctgctc ctcggc    26

<210> SEQ ID NO 70
<211> LENGTH: 45
<212> TYPE: DNA
<213> ORGANISM: Artificial
<220> FEATURE:
<223> OTHER INFORMATION: primer ZEO-LEUreverse

<400> SEQUENCE: 70
aggccccgcc cccacggctg ctcgccgatc tcggtcaagg ccggc    45

<210> SEQ ID NO 71
<211> LENGTH: 45
<212> TYPE: DNA

```
<213> ORGANISM: Artificial
<220> FEATURE:
<223> OTHER INFORMATION: primer ZEO-THRreverse

<400> SEQUENCE: 71
aggccccgcc cccacggctg ctcgccgatc tcggtggtgg ccggc            45

<210> SEQ ID NO 72
<211> LENGTH: 44
<212> TYPE: DNA
<213> ORGANISM: Artificial
<220> FEATURE:
<223> OTHER INFORMATION: primer ZEO-VALreverse

<400> SEQUENCE: 72
aggccccgcc cccacggctg ctcgccgatc tcggtccacg ccgg             44

<210> SEQ ID NO 73
<211> LENGTH: 11
<212> TYPE: DNA
<213> ORGANISM: Artificial
<220> FEATURE:
<223> OTHER INFORMATION: sequence around startcodon of wt d2EGFP

<400> SEQUENCE: 73
gaattcatgg g                                                 11

<210> SEQ ID NO 74
<211> LENGTH: 49
<212> TYPE: DNA
<213> ORGANISM: Artificial
<220> FEATURE:
<223> OTHER INFORMATION: primer d2EGFPforwardBamHI

<400> SEQUENCE: 74
gatcggatcc tatgaggaat tcgccaccat ggtgagcaag ggcgaggag        49

<210> SEQ ID NO 75
<211> LENGTH: 41
<212> TYPE: DNA
<213> ORGANISM: Artificial
<220> FEATURE:
<223> OTHER INFORMATION: primer d2EGFPreverseNotI

<400> SEQUENCE: 75
aaggaaaaaa gcggccgcct acacattgat cctagcagaa g                41

<210> SEQ ID NO 76
<211> LENGTH: 57
<212> TYPE: DNA
<213> ORGANISM: Artificial
<220> FEATURE:
<223> OTHER INFORMATION: spacer sequence

<400> SEQUENCE: 76
tcgatccaaa gactgccaaa tctagatccg agattttcag gagctaagga agctaaa    57

<210> SEQ ID NO 77
<211> LENGTH: 99
<212> TYPE: DNA
<213> ORGANISM: Artificial
<220> FEATURE:
<223> OTHER INFORMATION: primer ZEOforwardBamHI-ATGmut/space

<400> SEQUENCE: 77
gatcggatcc ttggtttatg tcgatccaaa gactgccaaa tctagatccg agattttcag    60
```
gagctaagga agctaaagcc aagttgacca gtgaagttc            99

<210> SEQ ID NO 78
<211> LENGTH: 38
<212> TYPE: DNA
<213> ORGANISM: Artificial
<220> FEATURE:
<223> OTHER INFORMATION: primer ZEOforwardBamHI-GTG

<400> SEQUENCE: 78
gatcggatcc accgtggcca agttgaccag tgccgttc              38

<210> SEQ ID NO 79
<211> LENGTH: 38
<212> TYPE: DNA
<213> ORGANISM: Artificial
<220> FEATURE:
<223> OTHER INFORMATION: primer ZEOforwardBamHI-TTG

<400> SEQUENCE: 79
gatcggatcc accttggcca agttgaccag tgccgttc              38

<210> SEQ ID NO 80
<211> LENGTH: 35
<212> TYPE: DNA
<213> ORGANISM: Artificial
<220> FEATURE:
<223> OTHER INFORMATION: primer BSDBamHIforward

<400> SEQUENCE: 80
gatcggatcc accatggcca agcctttgtc tcaag                 35

<210> SEQ ID NO 81
<211> LENGTH: 25
<212> TYPE: DNA
<213> ORGANISM: Artificial
<220> FEATURE:
<223> OTHER INFORMATION: primer BSD150reverse

<400> SEQUENCE: 81
gtaaaatgat atacgttgac accag                            25

<210> SEQ ID NO 82
<211> LENGTH: 25
<212> TYPE: DNA
<213> ORGANISM: Artificial
<220> FEATURE:
<223> OTHER INFORMATION: primer BSD150forward

<400> SEQUENCE: 82
ctggtgtcaa cgtatatcat tttac                            25

<210> SEQ ID NO 83
<211> LENGTH: 24
<212> TYPE: DNA
<213> ORGANISM: Artificial
<220> FEATURE:
<223> OTHER INFORMATION: primer BSD250reverse

<400> SEQUENCE: 83
gccctgttct cgtttccgat cgcg                             24

<210> SEQ ID NO 84
<211> LENGTH: 24
<212> TYPE: DNA

```
<213> ORGANISM: Artificial
<220> FEATURE:
<223> OTHER INFORMATION: primer BSD250forward

<400> SEQUENCE: 84
cgcgatcgga aacgagaaca gggc                                              24

<210> SEQ ID NO 85
<211> LENGTH: 24
<212> TYPE: DNA
<213> ORGANISM: Artificial
<220> FEATURE:
<223> OTHER INFORMATION: primer BSD350reverse

<400> SEQUENCE: 85
gccgtcggct gtccgtcact gtcc                                              24

<210> SEQ ID NO 86
<211> LENGTH: 24
<212> TYPE: DNA
<213> ORGANISM: Artificial
<220> FEATURE:
<223> OTHER INFORMATION: primer BSD350forward

<400> SEQUENCE: 86
ggacagtgac ggacagccga cggc                                              24

<210> SEQ ID NO 87
<211> LENGTH: 38
<212> TYPE: DNA
<213> ORGANISM: Artificial
<220> FEATURE:
<223> OTHER INFORMATION: primer BSD399reverse

<400> SEQUENCE: 87
gatcgaattc ttagccctcc cacacgtaac cagagggc                               38

<210> SEQ ID NO 88
<211> LENGTH: 103
<212> TYPE: DNA
<213> ORGANISM: Artificial
<220> FEATURE:
<223> OTHER INFORMATION: primer BSDforwardBamHIAvrII-ATGmut/space

<400> SEQUENCE: 88
gatcggatcc taggttggtt tatgtcgatc caaagactgc caaatctaga tccgagattt       60
tcaggagcta aggaagctaa agccaagcct ttgtctcaag aag                        103

<210> SEQ ID NO 89
<211> LENGTH: 44
<212> TYPE: DNA
<213> ORGANISM: Artificial
<220> FEATURE:
<223> OTHER INFORMATION: primer BSD399reverseEcoRIAvrII

<400> SEQUENCE: 89
gatcgaattc cctaggttag ccctcccaca cgtaaccaga gggc                        44

<210> SEQ ID NO 90
<211> LENGTH: 42
<212> TYPE: DNA
<213> ORGANISM: Artificial
<220> FEATURE:
<223> OTHER INFORMATION: primer BSDforwardBamHIAvrII-GTG

<400> SEQUENCE: 90
```

-continued gatcggatcc taggaccgtg gccaagcctt tgtctcaaga ag                42

<210> SEQ ID NO 91
<211> LENGTH: 42
<212> TYPE: DNA
<213> ORGANISM: Artificial
<220> FEATURE:
<223> OTHER INFORMATION: primer BSDforwardBamHIAvrII-TTG

<400> SEQUENCE: 91
gatcggatcc taggaccttg gccaagcctt tgtctcaaga ag                42

<210> SEQ ID NO 92
<211> LENGTH: 375
<212> TYPE: DNA
<213> ORGANISM: Artificial
<220> FEATURE:
<223> OTHER INFORMATION: wt zeocin resistance gene
<220> FEATURE:
<221> NAME/KEY: CDS
<222> LOCATION: (1)..(375)

<400> SEQUENCE: 92

```
atg gcc aag ttg acc agt gcc gtt ccg gtg ctc acc gcg cgc gac gtc     48
Met Ala Lys Leu Thr Ser Ala Val Pro Val Leu Thr Ala Arg Asp Val
1               5                   10                  15 gcc gga gcg gtc gag ttc tgg acc gac cgg ctc ggg ttc tcc cgg gac     96
Ala Gly Ala Val Glu Phe Trp Thr Asp Arg Leu Gly Phe Ser Arg Asp
            20                  25                  30 ttc gtg gag gac gac ttc gcc ggt gtg gtc cgg gac gac gtg acc ctg    144
Phe Val Glu Asp Asp Phe Ala Gly Val Val Arg Asp Asp Val Thr Leu
        35                  40                  45 ttc atc agc gcg gtc cag gac cag gtg gtg ccg gac aac acc ctg gcc    192
Phe Ile Ser Ala Val Gln Asp Gln Val Val Pro Asp Asn Thr Leu Ala
    50                  55                  60 tgg gtg tgg gtg cgc ggc ctg gac gag ctg tac gcc gag tgg tcg gag    240
Trp Val Trp Val Arg Gly Leu Asp Glu Leu Tyr Ala Glu Trp Ser Glu
65                  70                  75                  80 gtc gtg tcc acg aac ttc cgg gac gcc tcc ggg ccg gcc atg acc gag    288
Val Val Ser Thr Asn Phe Arg Asp Ala Ser Gly Pro Ala Met Thr Glu
                85                  90                  95 atc ggc gag cag ccg tgg ggg cgg gag ttc gcc ctg cgc gac ccg gcc    336
Ile Gly Glu Gln Pro Trp Gly Arg Glu Phe Ala Leu Arg Asp Pro Ala
            100                 105                 110 ggc aac tgc gtg cac ttc gtg gcc gag gag cag gac tga                375
Gly Asn Cys Val His Phe Val Ala Glu Glu Gln Asp
        115                 120
```

<210> SEQ ID NO 93
<211> LENGTH: 124
<212> TYPE: PRT
<213> ORGANISM: Artificial
<220> FEATURE:
<223> OTHER INFORMATION: Synthetic Construct

<400> SEQUENCE: 93

```
Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45
```

```
Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Gly Phe Ala Leu Arg Asp Pro Ala
                100                 105                 110

Gly Asn Cys Val His Phe Val Ala Glu Glu Gln Asp
            115                 120

<210> SEQ ID NO 94
<211> LENGTH: 399
<212> TYPE: DNA
<213> ORGANISM: Artificial
<220> FEATURE:
<223> OTHER INFORMATION: wt blasticidin resistance gene
<220> FEATURE:
<221> NAME/KEY: CDS
<222> LOCATION: (1)..(399)

<400> SEQUENCE: 94 atg gcc aag cct ttg tct caa gaa gaa tcc acc ctc att gaa aga gca       48
Met Ala Lys Pro Leu Ser Gln Glu Glu Ser Thr Leu Ile Glu Arg Ala
1               5                   10                  15 acg gct aca atc aac agc atc ccc atc tct gaa gac tac agc gtc gcc       96
Thr Ala Thr Ile Asn Ser Ile Pro Ile Ser Glu Asp Tyr Ser Val Ala
                20                  25                  30 agc gca gct ctc tct agc gac ggc cgc atc ttc act ggt gtc aat gta      144
Ser Ala Ala Leu Ser Ser Asp Gly Arg Ile Phe Thr Gly Val Asn Val
            35                  40                  45 tat cat ttt act ggg gga cct tgt gca gaa ctc gtg gtg ctg ggc act      192
Tyr His Phe Thr Gly Gly Pro Cys Ala Glu Leu Val Val Leu Gly Thr
        50                  55                  60 gct gct gct gcg gca gct ggc aac ctg act tgt atc gtc gcg atc gga      240
Ala Ala Ala Ala Ala Ala Gly Asn Leu Thr Cys Ile Val Ala Ile Gly
65                  70                  75                  80 aat gag aac agg ggc atc ttg agc ccc tgc gga cgg tgc cga cag gtg      288
Asn Glu Asn Arg Gly Ile Leu Ser Pro Cys Gly Arg Cys Arg Gln Val
                85                  90                  95 ctt ctc gat ctg cat cct ggg atc aaa gcc ata gtg aag gac agt gat      336
Leu Leu Asp Leu His Pro Gly Ile Lys Ala Ile Val Lys Asp Ser Asp
                100                 105                 110 gga cag ccg acg gca gtt ggg att cgt gaa ttg ctg ccc tct ggt tat      384
Gly Gln Pro Thr Ala Val Gly Ile Arg Glu Leu Leu Pro Ser Gly Tyr
            115                 120                 125 gtg tgg gag ggc taa                                                   399
Val Trp Glu Gly
    130

<210> SEQ ID NO 95
<211> LENGTH: 132
<212> TYPE: PRT
<213> ORGANISM: Artificial
<220> FEATURE:
<223> OTHER INFORMATION: Synthetic Construct

<400> SEQUENCE: 95

Met Ala Lys Pro Leu Ser Gln Glu Glu Ser Thr Leu Ile Glu Arg Ala
1               5                   10                  15

Thr Ala Thr Ile Asn Ser Ile Pro Ile Ser Glu Asp Tyr Ser Val Ala
                20                  25                  30
```

```
Ser Ala Ala Leu Ser Ser Asp Gly Arg Ile Phe Thr Gly Val Asn Val
            35                  40                  45

Tyr His Phe Thr Gly Gly Pro Cys Ala Glu Leu Val Val Leu Gly Thr
    50                  55                  60

Ala Ala Ala Ala Ala Gly Asn Leu Thr Cys Ile Val Ala Ile Gly
65                  70                  75                  80

Asn Glu Asn Arg Gly Ile Leu Ser Pro Cys Gly Arg Cys Arg Gln Val
                85                  90                  95

Leu Leu Asp Leu His Pro Gly Ile Lys Ala Ile Val Lys Asp Ser Asp
                100                 105                 110

Gly Gln Pro Thr Ala Val Gly Ile Arg Glu Leu Leu Pro Ser Gly Tyr
            115                 120                 125

Val Trp Glu Gly
        130

<210> SEQ ID NO 96
<211> LENGTH: 600
<212> TYPE: DNA
<213> ORGANISM: Artificial
<220> FEATURE:
<223> OTHER INFORMATION: wt puromycin resistance gene
<220> FEATURE:
<221> NAME/KEY: CDS
<222> LOCATION: (1)..(600)

<400> SEQUENCE: 96 atg acc gag tac aag ccc acg gtg cgc ctc gcc acc cgc gac gac gtc      48
Met Thr Glu Tyr Lys Pro Thr Val Arg Leu Ala Thr Arg Asp Asp Val
1               5                   10                  15 ccc agg gcc gta cgc acc ctc gcc gcc gcg ttc gcc gac tac ccc gcc      96
Pro Arg Ala Val Arg Thr Leu Ala Ala Ala Phe Ala Asp Tyr Pro Ala
                20                  25                  30 acg cgc cac acc gtc gat ccg gac cgc cac atc gag cgg gtc acc gag     144
Thr Arg His Thr Val Asp Pro Asp Arg His Ile Glu Arg Val Thr Glu
            35                  40                  45 ctg caa gaa ctc ttc ctc acg cgc gtc ggg ctc gac atc ggc aag gtg     192
Leu Gln Glu Leu Phe Leu Thr Arg Val Gly Leu Asp Ile Gly Lys Val
50                  55                  60 tgg gtc gcg gac gac ggc gcc gcg gtg gcg gtc tgg acc acg ccg gag     240
Trp Val Ala Asp Asp Gly Ala Ala Val Ala Val Trp Thr Thr Pro Glu
65                  70                  75                  80 agc gtc gaa gcg ggg gcg gtg ttc gcc gag atc ggc ccg cgc atg gcc     288
Ser Val Glu Ala Gly Ala Val Phe Ala Glu Ile Gly Pro Arg Met Ala
                85                  90                  95 gag ttg agc ggt tcc cgg ctg gcc gcg cag caa cag atg gaa ggc ctc     336
Glu Leu Ser Gly Ser Arg Leu Ala Ala Gln Gln Gln Met Glu Gly Leu
                100                 105                 110 ctg gcg ccg cac cgg ccc aag gag ccc gcg tgg ttc ctg gcc acc gtc     384
Leu Ala Pro His Arg Pro Lys Glu Pro Ala Trp Phe Leu Ala Thr Val
            115                 120                 125 ggc gtc tcg ccc gac cac cag ggc aag ggt ctg ggc agc gcc gtc gtg     432
Gly Val Ser Pro Asp His Gln Gly Lys Gly Leu Gly Ser Ala Val Val
    130                 135                 140 ctc ccc gga gtg gag gcg gcc gag cgc gcc ggg gtg ccc gcc ttc ctg     480
Leu Pro Gly Val Glu Ala Ala Glu Arg Ala Gly Val Pro Ala Phe Leu
145                 150                 155                 160 gag acc tcc gcg ccc cgc aac ctc ccc ttc tac gag cgg ctc ggc ttc     528
Glu Thr Ser Ala Pro Arg Asn Leu Pro Phe Tyr Glu Arg Leu Gly Phe
                165                 170                 175
```

```
acc gtc acc gcc gac gtc gag tgc ccg aag gac cgc gcg acc tgg tgc      576
Thr Val Thr Ala Asp Val Glu Cys Pro Lys Asp Arg Ala Thr Trp Cys
            180                 185                 190 atg acc cgc aag ccc ggt gcc tga                                      600
Met Thr Arg Lys Pro Gly Ala
        195

<210> SEQ ID NO 97
<211> LENGTH: 199
<212> TYPE: PRT
<213> ORGANISM: Artificial
<220> FEATURE:
<223> OTHER INFORMATION: Synthetic Construct

<400> SEQUENCE: 97

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Cys Pro Lys Asp Arg Ala Thr Trp Cys
            180                 185                 190

Met Thr Arg Lys Pro Gly Ala
        195

<210> SEQ ID NO 98
<211> LENGTH: 564
<212> TYPE: DNA
<213> ORGANISM: Artificial
<220> FEATURE:
<223> OTHER INFORMATION: wt DHFR gene (from mouse)
<220> FEATURE:
<221> NAME/KEY: CDS
<222> LOCATION: (1)..(564)

<400> SEQUENCE: 98 atg gtt cga cca ttg aac tgc atc gtc gcc gtg tcc caa aat atg ggg       48
Met Val Arg Pro Leu Asn Cys Ile Val Ala Val Ser Gln Asn Met Gly
1               5                   10                  15 att ggc aag aac gga gac cta ccc tgg cct ccg ctc agg aac gag ttc       96
Ile Gly Lys Asn Gly Asp Leu Pro Trp Pro Pro Leu Arg Asn Glu Phe
            20                  25                  30 aag tac ttc caa aga atg acc aca acc tct tca gtg gaa ggt aaa cag      144
```

| | | | | | | | | | | | | | | |
|---|---|---|---|---|---|---|---|---|---|---|---|---|---|---|
| Lys | Tyr | Phe | Gln | Arg | Met | Thr | Thr | Thr | Ser | Ser | Val | Glu | Gly | Lys | Gln |
| | | | 35 | | | | | 40 | | | | 45 | | | |

```
aat ctg gtg att atg ggt agg aaa acc tgg ttc tcc att cct gag aag    192
Asn Leu Val Ile Met Gly Arg Lys Thr Trp Phe Ser Ile Pro Glu Lys
 50                  55                  60 aat cga cct tta aag gac aga att aat ata gtt ctc agt aga gaa ctc    240
Asn Arg Pro Leu Lys Asp Arg Ile Asn Ile Val Leu Ser Arg Glu Leu
 65                  70                  75                  80 aaa gaa cca cca cga gga gct cat ttt ctt gcc aaa agt ttg gat gat    288
Lys Glu Pro Pro Arg Gly Ala His Phe Leu Ala Lys Ser Leu Asp Asp
                 85                  90                  95 gcc tta aga ctt att gaa caa ccg gaa ttg gca agt aaa gta gac atg    336
Ala Leu Arg Leu Ile Glu Gln Pro Glu Leu Ala Ser Lys Val Asp Met
            100                 105                 110 gtt tgg ata gtc gga ggc agt tct gtt tac cag gaa gcc atg aat caa    384
Val Trp Ile Val Gly Gly Ser Ser Val Tyr Gln Glu Ala Met Asn Gln
        115                 120                 125 cca ggc cac ctc aga ctc ttt gtg aca agg atc atg cag gaa ttt gaa    432
Pro Gly His Leu Arg Leu Phe Val Thr Arg Ile Met Gln Glu Phe Glu
    130                 135                 140 agt gac acg ttt ttc cca gaa att gat ttg ggg aaa tat aaa ctt ctc    480
Ser Asp Thr Phe Phe Pro Glu Ile Asp Leu Gly Lys Tyr Lys Leu Leu
145                 150                 155                 160 cca gaa tac cca ggc gtc ctc tct gag gtc cag gag gaa aaa ggc atc    528
Pro Glu Tyr Pro Gly Val Leu Ser Glu Val Gln Glu Glu Lys Gly Ile
                165                 170                 175 aag tat aag ttt gaa gtc tac gag aag aaa gac taa                    564
Lys Tyr Lys Phe Glu Val Tyr Glu Lys Lys Asp
                180                 185

<210> SEQ ID NO 99
<211> LENGTH: 187
<212> TYPE: PRT
<213> ORGANISM: Artificial
<220> FEATURE:
<223> OTHER INFORMATION: Synthetic Construct

<400> SEQUENCE: 99

Met Val Arg Pro Leu Asn Cys Ile Val Ala Val Ser Gln Asn Met Gly
 1               5                  10                  15

Ile Gly Lys Asn Gly Asp Leu Pro Trp Pro Leu Arg Asn Glu Phe
                20                  25                  30

Lys Tyr Phe Gln Arg Met Thr Thr Thr Ser Ser Val Glu Gly Lys Gln
             35                  40                  45

Asn Leu Val Ile Met Gly Arg Lys Thr Trp Phe Ser Ile Pro Glu Lys
 50                  55                  60

Asn Arg Pro Leu Lys Asp Arg Ile Asn Ile Val Leu Ser Arg Glu Leu
 65                  70                  75                  80

Lys Glu Pro Pro Arg Gly Ala His Phe Leu Ala Lys Ser Leu Asp Asp
                 85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160
```

```
Pro Glu Tyr Pro Gly Val Leu Ser Glu Val Gln Glu Lys Gly Ile
            165                 170                 175
Lys Tyr Lys Phe Glu Val Tyr Glu Lys Lys Asp
            180                 185

<210> SEQ ID NO 100
<211> LENGTH: 1143
<212> TYPE: DNA
<213> ORGANISM: Artificial
<220> FEATURE:
<223> OTHER INFORMATION: wt hygromycin resistance gene
<220> FEATURE:
<221> NAME/KEY: CDS
<222> LOCATION: (1)..(1143)

<400> SEQUENCE: 100 atg aaa aag cct gaa ctc acc gcg acg tct gtc gag aag ttt ctg atc      48
Met Lys Lys Pro Glu Leu Thr Ala Thr Ser Val Glu Lys Phe Leu Ile
1               5                   10                  15 gaa aag ttc gac agc gtc tcc gac ctg atg cag ctc tcg gag ggc gaa      96
Glu Lys Phe Asp Ser Val Ser Asp Leu Met Gln Leu Ser Glu Gly Glu
            20                  25                  30 gaa tct cgt gct ttc agc ttc gat gta gga ggg cgt gga tat gtc ctg     144
Glu Ser Arg Ala Phe Ser Phe Asp Val Gly Gly Arg Gly Tyr Val Leu
        35                  40                  45 cgg gta aat agc tgc gcc gat ggt ttc tac aaa gat cgt tat gtt tat     192
Arg Val Asn Ser Cys Ala Asp Gly Phe Tyr Lys Asp Arg Tyr Val Tyr
    50                  55                  60 cgg cac ttt gca tcg gcc gcg ctc ccg att ccg gaa gtg ctt gac att     240
Arg His Phe Ala Ser Ala Ala Leu Pro Ile Pro Glu Val Leu Asp Ile
65                  70                  75                  80 ggg gaa ttc agc gag agc ctg acc tat tgc atc tcc cgc cgt gca cag     288
Gly Glu Phe Ser Glu Ser Leu Thr Tyr Cys Ile Ser Arg Arg Ala Gln
                85                  90                  95 ggt gtc acg ttg caa gac ctg cct gaa acc gaa ctg ccc gct gtt ctg     336
Gly Val Thr Leu Gln Asp Leu Pro Glu Thr Glu Leu Pro Ala Val Leu
            100                 105                 110 cag ccg gtc gcg gag gcc atg gat gcg atc gct gcg gcc gat ctt agc     384
Gln Pro Val Ala Glu Ala Met Asp Ala Ile Ala Ala Ala Asp Leu Ser
        115                 120                 125 cag acg agc ggg ttc ggc cca ttc gga ccg caa gga atc ggt caa tac     432
Gln Thr Ser Gly Phe Gly Pro Phe Gly Pro Gln Gly Ile Gly Gln Tyr
    130                 135                 140 act aca tgg cgt gat ttc ata tgc gcg att gct gat ccc cat gtg tat     480
Thr Thr Trp Arg Asp Phe Ile Cys Ala Ile Ala Asp Pro His Val Tyr
145                 150                 155                 160 cac tgg caa act gtg atg gac gac acc gtc agt gcg tcc gtc gcg cag     528
His Trp Gln Thr Val Met Asp Asp Thr Val Ser Ala Ser Val Ala Gln
                165                 170                 175 gct ctc gat gag ctg atg ctt tgg gcc gag gac tgc ccc gaa gtc cgg     576
Ala Leu Asp Glu Leu Met Leu Trp Ala Glu Asp Cys Pro Glu Val Arg
            180                 185                 190 cac ctc gtg cac gcg gat ttc ggc tcc aac aat gtc ctg acg gac aat     624
His Leu Val His Ala Asp Phe Gly Ser Asn Asn Val Leu Thr Asp Asn
        195                 200                 205 ggc cgc ata aca gcg gtc att gac tgg agc gag gcg atg ttc ggg gat     672
Gly Arg Ile Thr Ala Val Ile Asp Trp Ser Glu Ala Met Phe Gly Asp
    210                 215                 220 tcc caa tac gag gtc gcc aac atc ttc ttc tgg agg ccg tgg ttg gct     720
Ser Gln Tyr Glu Val Ala Asn Ile Phe Phe Trp Arg Pro Trp Leu Ala
225                 230                 235                 240
```

```
tgt atg gag cag cag acg cgc tac ttc gag cgg agg cat ccg gag ctt      768
Cys Met Glu Gln Gln Thr Arg Tyr Phe Glu Arg Arg His Pro Glu Leu
            245                 250                 255 gca gga tcg ccg cgg ctc cgg gcg tat atg ctc cgc att ggt ctt gac      816
Ala Gly Ser Pro Arg Leu Arg Ala Tyr Met Leu Arg Ile Gly Leu Asp
        260                 265                 270 caa ctc tat cag agc ttg gtt gac ggc aat ttc gat gat gca gct tgg      864
Gln Leu Tyr Gln Ser Leu Val Asp Gly Asn Phe Asp Asp Ala Ala Trp
    275                 280                 285 gcg cag ggt cga tgc gac gca atc gtc cga tcc gga gcc ggg act gtc      912
Ala Gln Gly Arg Cys Asp Ala Ile Val Arg Ser Gly Ala Gly Thr Val
290                 295                 300 ggg cgt aca caa atc gcc cgc aga agc gcg gcc gtc tgg acc gat ggc      960
Gly Arg Thr Gln Ile Ala Arg Arg Ser Ala Ala Val Trp Thr Asp Gly
305                 310                 315                 320 tgt gta gaa gta ctc gcc gat agt gga aac cga cgc ccc agc act cgt     1008
Cys Val Glu Val Leu Ala Asp Ser Gly Asn Arg Arg Pro Ser Thr Arg
                325                 330                 335 ccg gag gca aag gaa ttc ggg aga tgg ggg agg cta act gaa aca cgg     1056
Pro Glu Ala Lys Glu Phe Gly Arg Trp Gly Arg Leu Thr Glu Thr Arg
            340                 345                 350 aag gag aca ata ccg gaa gga acc cgc gct atg acg gca ata aaa aga     1104
Lys Glu Thr Ile Pro Glu Gly Thr Arg Ala Met Thr Ala Ile Lys Arg
        355                 360                 365 cag aat aaa acg cac ggg tgt tgg gtc gtt tgt tca taa                 1143
Gln Asn Lys Thr His Gly Cys Trp Val Val Cys Ser
    370                 375                 380

<210> SEQ ID NO 101
<211> LENGTH: 380
<212> TYPE: PRT
<213> ORGANISM: Artificial
<220> FEATURE:
<223> OTHER INFORMATION: Synthetic Construct

<400> SEQUENCE: 101

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175
```

```
Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
        210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
        290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Glu Ala Lys Glu Phe Gly Arg Trp Gly Arg Leu Thr Glu Thr Arg
                340                 345                 350

Lys Glu Thr Ile Pro Glu Gly Thr Arg Ala Met Thr Ala Ile Lys Arg
                355                 360                 365

Gln Asn Lys Thr His Gly Cys Trp Val Val Cys Ser
        370                 375                 380

<210> SEQ ID NO 102
<211> LENGTH: 804
<212> TYPE: DNA
<213> ORGANISM: Artificial
<220> FEATURE:
<223> OTHER INFORMATION: wt neomycin resistance gene
<220> FEATURE:
<221> NAME/KEY: CDS
<222> LOCATION: (1)..(804)

<400> SEQUENCE: 102 atg gga tcg gcc att gaa caa gat gga ttg cac gca ggt tct ccg gcc      48
Met Gly Ser Ala Ile Glu Gln Asp Gly Leu His Ala Gly Ser Pro Ala
1               5                   10                  15 gct tgg gtg gag agg cta ttc ggc tat gac tgg gca caa cag aca atc      96
Ala Trp Val Glu Arg Leu Phe Gly Tyr Asp Trp Ala Gln Gln Thr Ile
                20                  25                  30 ggc tgc tct gat gcc gcc gtg ttc cgg ctg tca gcg cag ggg cgc ccg     144
Gly Cys Ser Asp Ala Ala Val Phe Arg Leu Ser Ala Gln Gly Arg Pro
            35                  40                  45 gtt ctt ttt gtc aag acc gac ctg tcc ggt gcc ctg aat gaa ctg cag     192
Val Leu Phe Val Lys Thr Asp Leu Ser Gly Ala Leu Asn Glu Leu Gln
        50                  55                  60 gac gag gca gcg cgg cta tcg tgg ctg gcc acg acg ggc gtt cct tgc     240
Asp Glu Ala Ala Arg Leu Ser Trp Leu Ala Thr Thr Gly Val Pro Cys
65                  70                  75                  80 gca gct gtg ctc gac gtt gtc act gaa gcg gga agg gac tgg ctg cta     288
Ala Ala Val Leu Asp Val Val Thr Glu Ala Gly Arg Asp Trp Leu Leu
                85                  90                  95 ttg ggc gaa gtg ccg ggg cag gat ctc ctg tca tct cac ctt gct cct     336
Leu Gly Glu Val Pro Gly Gln Asp Leu Leu Ser Ser His Leu Ala Pro
                100                 105                 110
```

```
gcc gag aaa gta tcc atc atg gct gat gca atg cgg cgg ctg cat acg      384
Ala Glu Lys Val Ser Ile Met Ala Asp Ala Met Arg Arg Leu His Thr
            115                 120                 125 ctt gat ccg gct acc tgc cca ttc gac cac caa gcg aaa cat cgc atc      432
Leu Asp Pro Ala Thr Cys Pro Phe Asp His Gln Ala Lys His Arg Ile
130                 135                 140 gag cga gca cgt act cgg atg gaa gcc ggt ctt gtc gat cag gat gat      480
Glu Arg Ala Arg Thr Arg Met Glu Ala Gly Leu Val Asp Gln Asp Asp
145                 150                 155                 160 ctg gac gaa gag cat cag ggg ctc gcg cca gcc gaa ctg ttc gcc agg      528
Leu Asp Glu Glu His Gln Gly Leu Ala Pro Ala Glu Leu Phe Ala Arg
                165                 170                 175 ctc aag gcg cgc atg ccc gac ggc gat gat ctc gtc gtg acc cat ggc      576
Leu Lys Ala Arg Met Pro Asp Gly Asp Asp Leu Val Val Thr His Gly
            180                 185                 190 gat gcc tgc ttg ccg aat atc atg gtg gaa aat ggc cgc ttt tct gga      624
Asp Ala Cys Leu Pro Asn Ile Met Val Glu Asn Gly Arg Phe Ser Gly
            195                 200                 205 ttc atc gac tgt ggc cgg ctg ggt gtg gcg gac cgc tat cag gac ata      672
Phe Ile Asp Cys Gly Arg Leu Gly Val Ala Asp Arg Tyr Gln Asp Ile
210                 215                 220 gcg ttg gct acc cgt gat att gct gaa gag ctt ggc ggc gaa tgg gct      720
Ala Leu Ala Thr Arg Asp Ile Ala Glu Glu Leu Gly Gly Glu Trp Ala
225                 230                 235                 240 gac cgc ttc ctc gtg ctt tac ggt atc gcc gct ccc gat tcg cag cgc      768
Asp Arg Phe Leu Val Leu Tyr Gly Ile Ala Ala Pro Asp Ser Gln Arg
                245                 250                 255 atc gcc ttc tat cgc ctt ctt gac gag ttc ttc tga                      804
Ile Ala Phe Tyr Arg Leu Leu Asp Glu Phe Phe
            260                 265

<210> SEQ ID NO 103
<211> LENGTH: 267
<212> TYPE: PRT
<213> ORGANISM: Artificial
<220> FEATURE:
<223> OTHER INFORMATION: Synthetic Construct

<400> SEQUENCE: 103

Met Gly Ser Ala Ile Glu Gln Asp Gly Leu His Ala Gly Ser Pro Ala
1               5                   10                  15

Ala Trp Val Glu Arg Leu Phe Gly Tyr Asp Trp Ala Gln Gln Thr Ile
            20                  25                  30

Gly Cys Ser Asp Ala Ala Val Phe Arg Leu Ser Ala Gln Gly Arg Pro
        35                  40                  45

Val Leu Phe Val Lys Thr Asp Leu Ser Gly Ala Leu Asn Glu Leu Gln
    50                  55                  60

Asp Glu Ala Ala Arg Leu Ser Trp Leu Ala Thr Thr Gly Val Pro Cys
65                  70                  75                  80

Ala Ala Val Leu Asp Val Val Thr Glu Ala Gly Arg Asp Trp Leu Leu
                85                  90                  95

Leu Gly Glu Val Pro Gly Gln Asp Leu Leu Ser Ser His Leu Ala Pro
            100                 105                 110

Ala Glu Lys Val Ser Ile Met Ala Asp Ala Met Arg Arg Leu His Thr
        115                 120                 125

Leu Asp Pro Ala Thr Cys Pro Phe Asp His Gln Ala Lys His Arg Ile
    130                 135                 140

Glu Arg Ala Arg Thr Arg Met Glu Ala Gly Leu Val Asp Gln Asp Asp
```

```
                          145                 150                 155
Leu Asp Glu Glu His Gln Gly Leu Ala Pro Ala Glu Leu Phe Ala Arg
                165                 170                 175

Leu Lys Ala Arg Met Pro Asp Gly Asp Asp Leu Val Val Thr His Gly
            180                 185                 190

Asp Ala Cys Leu Pro Asn Ile Met Val Glu Asn Gly Arg Phe Ser Gly
        195                 200                 205

Phe Ile Asp Cys Gly Arg Leu Gly Val Ala Asp Arg Tyr Gln Asp Ile
    210                 215                 220

Ala Leu Ala Thr Arg Asp Ile Ala Glu Glu Leu Gly Gly Glu Trp Ala
225                 230                 235                 240

Asp Arg Phe Leu Val Leu Tyr Gly Ile Ala Ala Pro Asp Ser Gln Arg
                245                 250                 255

Ile Ala Phe Tyr Arg Leu Leu Asp Glu Phe Phe
                260                 265

<210> SEQ ID NO 104
<211> LENGTH: 1121
<212> TYPE: DNA
<213> ORGANISM: Artificial
<220> FEATURE:
<223> OTHER INFORMATION: wt glutamine synthase gene (human)
<220> FEATURE:
<221> NAME/KEY: CDS
<222> LOCATION: (1)..(1119)

<400> SEQUENCE: 104 atg acc acc tca gca agt tcc cac tta aat aaa ggc atc aag cag gtg      48
Met Thr Thr Ser Ala Ser Ser His Leu Asn Lys Gly Ile Lys Gln Val
1               5                   10                  15 tac atg tcc ctg cct cag ggt gag aaa gtc cag gcc atg tat atc tgg      96
Tyr Met Ser Leu Pro Gln Gly Glu Lys Val Gln Ala Met Tyr Ile Trp
            20                  25                  30 atc gat ggt act gga gaa gga ctg cgc tgc aag acc cgg acc ctg gac     144
Ile Asp Gly Thr Gly Glu Gly Leu Arg Cys Lys Thr Arg Thr Leu Asp
        35                  40                  45 agt gag ccc aag tgt gtg gaa gag ttg cct gag tgg aat ttc gat ggc     192
Ser Glu Pro Lys Cys Val Glu Glu Leu Pro Glu Trp Asn Phe Asp Gly
    50                  55                  60 tcc agt act tta cag tct gag ggt tcc aac agt gac atg tat ctc gtg     240
Ser Ser Thr Leu Gln Ser Glu Gly Ser Asn Ser Asp Met Tyr Leu Val
65                  70                  75                  80 cct gct gcc atg ttt cgg gac ccc ttc cgt aag gac cct aac aag ctg     288
Pro Ala Ala Met Phe Arg Asp Pro Phe Arg Lys Asp Pro Asn Lys Leu
                85                  90                  95 gtg tta tgt gaa gtt ttc aag tac aat cga agg cct gca gag acc aat     336
Val Leu Cys Glu Val Phe Lys Tyr Asn Arg Arg Pro Ala Glu Thr Asn
            100                 105                 110 ttg agg cac acc tgt aaa cgg ata atg gac atg gtg agc aac cag cac     384
Leu Arg His Thr Cys Lys Arg Ile Met Asp Met Val Ser Asn Gln His
        115                 120                 125 ccc tgg ttt ggc atg gag cag gag tat acc ctc atg ggg aca gat ggg     432
Pro Trp Phe Gly Met Glu Gln Glu Tyr Thr Leu Met Gly Thr Asp Gly
    130                 135                 140 cac ccc ttt ggt tgg cct tcc aac ggc ttc cca ggg ccc cag ggt cca     480
His Pro Phe Gly Trp Pro Ser Asn Gly Phe Pro Gly Pro Gln Gly Pro
145                 150                 155                 160 tat tac tgt ggt gtg gga gca gac aga gcc tat ggc agg gac atc gtg     528
Tyr Tyr Cys Gly Val Gly Ala Asp Arg Ala Tyr Gly Arg Asp Ile Val
                165                 170                 175
```

```
gag gcc cat tac cgg gcc tgc ttg tat gct gga gtc aag att gcg ggg      576
Glu Ala His Tyr Arg Ala Cys Leu Tyr Ala Gly Val Lys Ile Ala Gly
            180                 185                 190 act aat gcc gag gtc atg cct gcc cag tgg gaa ttt cag att gga cct      624
Thr Asn Ala Glu Val Met Pro Ala Gln Trp Glu Phe Gln Ile Gly Pro
        195                 200                 205 tgt gaa gga atc agc atg gga gat cat ctc tgg gtg gcc cgt ttc atc      672
Cys Glu Gly Ile Ser Met Gly Asp His Leu Trp Val Ala Arg Phe Ile
    210                 215                 220 ttg cat cgt gtg tgt gaa gac ttt gga gtg ata gca acc ttt gat cct      720
Leu His Arg Val Cys Glu Asp Phe Gly Val Ile Ala Thr Phe Asp Pro
225                 230                 235                 240 aag ccc att cct ggg aac tgg aat ggt gca ggc tgc cat acc aac ttc      768
Lys Pro Ile Pro Gly Asn Trp Asn Gly Ala Gly Cys His Thr Asn Phe
                245                 250                 255 agc acc aag gcc atg cgg gag gag aat ggt ctg aag tac atc gag gag      816
Ser Thr Lys Ala Met Arg Glu Glu Asn Gly Leu Lys Tyr Ile Glu Glu
            260                 265                 270 gcc att gag aaa cta agc aag cgg cac cag tac cac atc cgt gcc tat      864
Ala Ile Glu Lys Leu Ser Lys Arg His Gln Tyr His Ile Arg Ala Tyr
        275                 280                 285 gat ccc aag gga ggc ctg gac aat gcc cga cgt cta act gga ttc cat      912
Asp Pro Lys Gly Gly Leu Asp Asn Ala Arg Arg Leu Thr Gly Phe His
    290                 295                 300 gaa acc tcc aac atc aac gac ttt tct ggt ggt gta gcc aat cgt agc      960
Glu Thr Ser Asn Ile Asn Asp Phe Ser Gly Gly Val Ala Asn Arg Ser
305                 310                 315                 320 gcc agc ata cgc att ccc cgg act gtt ggc cag gag aag aag ggt tac     1008
Ala Ser Ile Arg Ile Pro Arg Thr Val Gly Gln Glu Lys Lys Gly Tyr
                325                 330                 335 ttt gaa gat cgt cgc ccc tct gcc aac tgc gac ccc ttt tcg gtg aca     1056
Phe Glu Asp Arg Arg Pro Ser Ala Asn Cys Asp Pro Phe Ser Val Thr
            340                 345                 350 gaa gcc ctc atc cgc acg tgt ctt ctc aat gaa acc ggc gat gag ccc     1104
Glu Ala Leu Ile Arg Thr Cys Leu Leu Asn Glu Thr Gly Asp Glu Pro
        355                 360                 365 ttc cag tac aaa aat ta                                              1121
Phe Gln Tyr Lys Asn
    370

<210> SEQ ID NO 105
<211> LENGTH: 373
<212> TYPE: PRT
<213> ORGANISM: Artificial
<220> FEATURE:
<223> OTHER INFORMATION: Synthetic Construct

<400> SEQUENCE: 105

Met Thr Thr Ser Ala Ser Ser His Leu Asn Lys Gly Ile Lys Gln Val
1               5                   10                  15

Tyr Met Ser Leu Pro Gln Gly Glu Lys Val Gln Ala Met Tyr Ile Trp
            20                  25                  30

Ile Asp Gly Thr Gly Glu Gly Leu Arg Cys Lys Thr Arg Thr Leu Asp
        35                  40                  45

Ser Glu Pro Lys Cys Val Glu Glu Leu Pro Glu Trp Asn Phe Asp Gly
    50                  55                  60

Ser Ser Thr Leu Gln Ser Glu Gly Ser Asn Ser Asp Met Tyr Leu Val
65                  70                  75                  80

Pro Ala Ala Met Phe Arg Asp Pro Phe Arg Lys Asp Pro Asn Lys Leu
```

```
            85                  90                  95
Val Leu Cys Glu Val Phe Lys Tyr Asn Arg Arg Pro Ala Glu Thr Asn
            100                 105                 110

Leu Arg His Thr Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Arg Ala Tyr Gly Arg Asp Ile Val
                165                 170                 175

Glu Ala His Tyr Arg Ala Cys Leu Tyr Ala Gly Val Lys Ile Ala Gly
            180                 185                 190

Thr Asn Ala Glu Val Met Pro Ala Gln Trp Glu Phe Gln Ile Gly Pro
        195                 200                 205

Cys Glu Gly Ile Ser Met Gly Asp His Leu Trp Val Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Gly Asn Gly Leu Lys Tyr Ile Glu Glu
            260                 265                 270

Ala Ile Glu Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Gly Gly Val Ala Asn Arg Ser
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Phe Ser Val Thr
            340                 345                 350

Glu Ala Leu Ile Arg Thr Cys Leu Leu Asn Glu Thr Gly Asp Glu Pro
        355                 360                 365

Phe Gln Tyr Lys Asn
    370

<210> SEQ ID NO 106
<211> LENGTH: 43
<212> TYPE: DNA
<213> ORGANISM: Artificial
<220> FEATURE:
<223> OTHER INFORMATION: primer GTGspaceBamHIF

<400> SEQUENCE: 106
gaattcggat ccaccgtggc gatccaaaga ctgccaaatc tag         43

<210> SEQ ID NO 107
<211> LENGTH: 42
<212> TYPE: DNA
<213> ORGANISM: Artificial
<220> FEATURE:
<223> OTHER INFORMATION: primer ZEOTTTGTGBamHIF

<400> SEQUENCE: 107
gaattcggat cctttgtggc caagttgacc agtgccgttc cg          42
```

<210> SEQ ID NO 108
<211> LENGTH: 46
<212> TYPE: DNA
<213> ORGANISM: Artificial
<220> FEATURE:
<223> OTHER INFORMATION: primer ZEOForwardGTG-Thr9

<400> SEQUENCE: 108
aattggatcc accgtggcca agttgaccag tgccgttacc gtgctc        46

<210> SEQ ID NO 109
<211> LENGTH: 46
<212> TYPE: DNA
<213> ORGANISM: Artificial
<220> FEATURE:
<223> OTHER INFORMATION: pimer ZEOForward GTG-Phe9

<400> SEQUENCE: 109
aattggatcc accgtggcca agttgaccag tgccgtttc gtgctc         46

<210> SEQ ID NO 110
<211> LENGTH: 43
<212> TYPE: DNA
<213> ORGANISM: Artificial
<220> FEATURE:
<223> OTHER INFORMATION: primer TTGspaceBamHIF

<400> SEQUENCE: 110
gaattcggat ccaccttggc gatccaaaga ctgccaaatc tag           43

<210> SEQ ID NO 111
<211> LENGTH: 46
<212> TYPE: DNA
<213> ORGANISM: Artificial
<220> FEATURE:
<223> OTHER INFORMATION: primer ZEOForwardTTG-Thr9

<400> SEQUENCE: 111
aattggatcc accttggcca agttgaccag tgccgttacc gtgctc        46

<210> SEQ ID NO 112
<211> LENGTH: 46
<212> TYPE: DNA
<213> ORGANISM: Artificial
<220> FEATURE:
<223> OTHER INFORMATION: pimer ZEOForwardTTG-Phe9

<400> SEQUENCE: 112
aattggatcc accttggcca agttgaccag tgccgttttc gtgctc        46

<210> SEQ ID NO 113
<211> LENGTH: 37
<212> TYPE: DNA
<213> ORGANISM: Artificial
<220> FEATURE:
<223> OTHER INFORMATION: primer PURO BamHI F

<400> SEQUENCE: 113
gatcggatcc atggttaccg agtacaagcc cacggtg                  37

<210> SEQ ID NO 114
<211> LENGTH: 35
<212> TYPE: DNA
<213> ORGANISM: Artificial
<220> FEATURE:

<223> OTHER INFORMATION: primer PURO300 R LEU

<400> SEQUENCE: 114
cagccgggaa ccgctcaact cggccaggcg cgggc                                 35

<210> SEQ ID NO 115
<211> LENGTH: 49
<212> TYPE: DNA
<213> ORGANISM: Artificial
<220> FEATURE:
<223> OTHER INFORMATION: primer PURO300FLEU

<400> SEQUENCE: 115
cgagttgagc ggttcccggc tgccgcgca gcaacagctg gaaggcctc                   49

<210> SEQ ID NO 116
<211> LENGTH: 44
<212> TYPE: DNA
<213> ORGANISM: Artificial
<220> FEATURE:
<223> OTHER INFORMATION: primer PURO600RLEU

<400> SEQUENCE: 116
aagcttgaat tcaggcaccg ggcttgcggg tcaggcacca ggtc                       44

<210> SEQ ID NO 117
<211> LENGTH: 42
<212> TYPE: DNA
<213> ORGANISM: Artificial
<220> FEATURE:
<223> OTHER INFORMATION: primer PUROBamHI TTG1F

<400> SEQUENCE: 117
gaattcggat ccaccttggt taccgagtac aagcccacgg tg                         42

<210> SEQ ID NO 118
<211> LENGTH: 804
<212> TYPE: DNA
<213> ORGANISM: Artificial
<220> FEATURE:
<223> OTHER INFORMATION: modified neomycin resistance gene lacking
    internal ATG sequences
<220> FEATURE:
<221> NAME/KEY: CDS
<222> LOCATION: (1)..(804)

<400> SEQUENCE: 118

```
atg gga tcg gcc att gaa caa gac gga ttg cac gca ggt tct ccg gcc        48
Met Gly Ser Ala Ile Glu Gln Asp Gly Leu His Ala Gly Ser Pro Ala
1               5                  10                  15 gct tgg gtg gag agg cta ttc ggc tac gac tgg gca caa cag aca atc        96
Ala Trp Val Glu Arg Leu Phe Gly Tyr Asp Trp Ala Gln Gln Thr Ile
            20                  25                  30 ggc tgc tct gac gcc gcc gtg ttc cgg ctg tca gcg cag ggg cgc ccg       144
Gly Cys Ser Asp Ala Ala Val Phe Arg Leu Ser Ala Gln Gly Arg Pro
        35                  40                  45 gtt ctt ttt gtc aag acc gac ctg tcc ggt gcc ctg aac gaa ctg cag       192
Val Leu Phe Val Lys Thr Asp Leu Ser Gly Ala Leu Asn Glu Leu Gln
    50                  55                  60 gac gag gca gcg cgg cta tcg tgg ctg gcc acg acg ggc gtt cct tgc       240
Asp Glu Ala Ala Arg Leu Ser Trp Leu Ala Thr Thr Gly Val Pro Cys
65                  70                  75                  80 gca gct gtg ctc gac gtt gtc act gaa gcg gga agg gac tgg ctg cta       288
Ala Ala Val Leu Asp Val Val Thr Glu Ala Gly Arg Asp Trp Leu Leu
                85                  90                  95
```

| | | |
|---|---|---|
| ttg ggc gaa gtg ccg ggg cag gat ctc ctg tca tct cac ctt gct cct<br>Leu Gly Glu Val Pro Gly Gln Asp Leu Leu Ser Ser His Leu Ala Pro<br>100 105 110 | | 336 |
| gcc gag aaa gta tcc atc ctg gct gac gca ctg cgg cgg ctg cat acg<br>Ala Glu Lys Val Ser Ile Leu Ala Asp Ala Leu Arg Arg Leu His Thr<br>115 120 125 | | 384 |
| ctt gat ccg gct acc tgc cca ttc gac cac caa gcg aaa cat cgc atc<br>Leu Asp Pro Ala Thr Cys Pro Phe Asp His Gln Ala Lys His Arg Ile<br>130 135 140 | | 432 |
| gag cga gca cgt act cgg ctg gaa gcc ggt ctt gtc gat cag gac gat<br>Glu Arg Ala Arg Thr Arg Leu Glu Ala Gly Leu Val Asp Gln Asp Asp<br>145 150 155 160 | | 480 |
| ctg gac gaa gag cat cag ggg ctc gcg cca gcc gaa ctg ttc gcc agg<br>Leu Asp Glu Glu His Gln Gly Leu Ala Pro Ala Glu Leu Phe Ala Arg<br>165 170 175 | | 528 |
| ctc aag gcg cgc ctg ccc gac ggc gac gat ctc gtc gtg acc cac ggc<br>Leu Lys Ala Arg Leu Pro Asp Gly Asp Asp Leu Val Val Thr His Gly<br>180 185 190 | | 576 |
| gac gcc tgc ttg ccg aat atc ctg gtg gaa aac ggc cgc ttt tct gga<br>Asp Ala Cys Leu Pro Asn Ile Leu Val Glu Asn Gly Arg Phe Ser Gly<br>195 200 205 | | 624 |
| ttc atc gac tgt ggc cgg ctg ggt gtg gcg gac cgt tat cag gac ata<br>Phe Ile Asp Cys Gly Arg Leu Gly Val Ala Asp Arg Tyr Gln Asp Ile<br>210 215 220 | | 672 |
| gcg ttg gct acc cgt gat att gct gaa gag ctt ggc ggc gag tgg gct<br>Ala Leu Ala Thr Arg Asp Ile Ala Glu Glu Leu Gly Gly Glu Trp Ala<br>225 230 235 240 | | 720 |
| gac cgc ttc ctc gtg ctt tac ggt atc gcc gct ccc gat tcg cag cgc<br>Asp Arg Phe Leu Val Leu Tyr Gly Ile Ala Ala Pro Asp Ser Gln Arg<br>245 250 255 | | 768 |
| atc gcc ttc tat cgc ctt ctt gac gag ttc ttc tga<br>Ile Ala Phe Tyr Arg Leu Leu Asp Glu Phe Phe<br>260 265 | | 804 |

<210> SEQ ID NO 119
<211> LENGTH: 267
<212> TYPE: PRT
<213> ORGANISM: Artificial
<220> FEATURE:
<223> OTHER INFORMATION: Synthetic Construct

<400> SEQUENCE: 119

Met Gly Ser Ala Ile Glu Gln Asp Gly Leu His Ala Gly Ser Pro Ala
1               5                   10                  15

Ala Trp Val Glu Arg Leu Phe Gly Tyr Asp Trp Ala Gln Gln Thr Ile
            20                  25                  30

Gly Cys Ser Asp Ala Ala Val Phe Arg Leu Ser Ala Gln Gly Arg Pro
        35                  40                  45

Val Leu Phe Val Lys Thr Asp Leu Ser Gly Ala Leu Asn Glu Leu Gln
    50                  55                  60

Asp Glu Ala Ala Arg Leu Ser Trp Leu Ala Thr Thr Gly Val Pro Cys
65                  70                  75                  80

Ala Ala Val Leu Asp Val Val Thr Glu Ala Gly Arg Asp Trp Leu Leu
                85                  90                  95

Leu Gly Glu Val Pro Gly Gln Asp Leu Leu Ser Ser His Leu Ala Pro
            100                 105                 110

Ala Glu Lys Val Ser Ile Leu Ala Asp Ala Leu Arg Arg Leu His Thr
        115                 120                 125

```
Leu Asp Pro Ala Thr Cys Pro Phe Asp His Gln Ala Lys His Arg Ile
    130                 135                 140

Glu Arg Ala Arg Thr Arg Leu Glu Ala Gly Leu Val Asp Gln Asp
145                 150                 155                 160

Leu Asp Glu Glu His Gln Gly Leu Ala Pro Ala Glu Leu Phe Ala Arg
                165                 170                 175

Leu Lys Ala Arg Leu Pro Asp Gly Asp Leu Val Val Thr His Gly
                180                 185                 190

Asp Ala Cys Leu Pro Asn Ile Leu Val Glu Asn Gly Arg Phe Ser Gly
                195                 200                 205

Phe Ile Asp Cys Gly Arg Leu Gly Val Ala Asp Arg Tyr Gln Asp Ile
    210                 215                 220

Ala Leu Ala Thr Arg Asp Ile Ala Glu Glu Leu Gly Gly Glu Trp Ala
225                 230                 235                 240

Asp Arg Phe Leu Val Leu Tyr Gly Ile Ala Ala Pro Asp Ser Gln Arg
                245                 250                 255

Ile Ala Phe Tyr Arg Leu Leu Asp Glu Phe Phe
                260                 265

<210> SEQ ID NO 120
<211> LENGTH: 40
<212> TYPE: DNA
<213> ORGANISM: Artificial
<220> FEATURE:
<223> OTHER INFORMATION: primer NEO-F-HindIII

<400> SEQUENCE: 120
gatcaagctt ttggatcggc cattgaaaca agacggattg                    40

<210> SEQ ID NO 121
<211> LENGTH: 36
<212> TYPE: DNA
<213> ORGANISM: Artificial
<220> FEATURE:
<223> OTHER INFORMATION: primer NEO EcoRI 800R

<400> SEQUENCE: 121
aagcttgaat tctcagaaga actcgtcaag aaggcg                        36

<210> SEQ ID NO 122
<211> LENGTH: 564
<212> TYPE: DNA
<213> ORGANISM: Artificial
<220> FEATURE:
<223> OTHER INFORMATION: modified dhfr gene lacking internal ATG
      sequences
<220> FEATURE:
<221> NAME/KEY: CDS
<222> LOCATION: (1)..(564)

<400> SEQUENCE: 122 atg gtt cga cca ttg aac tgc atc gtc gcc gtg tcc caa aat ctg ggg    48
Met Val Arg Pro Leu Asn Cys Ile Val Ala Val Ser Gln Asn Leu Gly
1               5                   10                  15 att ggc aag aac gga gac cta ccc tgg cct ccg ctc agg aac gag ttc    96
Ile Gly Lys Asn Gly Asp Leu Pro Trp Pro Pro Leu Arg Asn Glu Phe
            20                  25                  30 aag tac ttc caa aga ctg acc aca acc tct tca gtg gaa ggt aaa cag   144
Lys Tyr Phe Gln Arg Leu Thr Thr Thr Ser Ser Val Glu Gly Lys Gln
        35                  40                  45 aat ctg gtg att ctg ggt agg aaa acc tgg ttc tcc att cct gag aag   192
Asn Leu Val Ile Leu Gly Arg Lys Thr Trp Phe Ser Ile Pro Glu Lys
```

```
            50                  55                  60
aat cga cct tta aag gac aga att aat ata gtt ctc agt aga gaa ctc        240
Asn Arg Pro Leu Lys Asp Arg Ile Asn Ile Val Leu Ser Arg Glu Leu
 65                  70                  75                  80 aaa gaa cca cca cga gga gct cat ttt ctt gcc aaa agt ttg gac gac        288
Lys Glu Pro Pro Arg Gly Ala His Phe Leu Ala Lys Ser Leu Asp Asp
                     85                  90                  95 gcc tta aga ctt att gaa caa ccg gaa ttg gca agt aaa gta gac ctg        336
Ala Leu Arg Leu Ile Glu Gln Pro Glu Leu Ala Ser Lys Val Asp Leu
            100                 105                 110 gtt tgg ata gtc gga ggc agt tct gtt tac cag gaa gcc ctg aat caa        384
Val Trp Ile Val Gly Gly Ser Ser Val Tyr Gln Glu Ala Leu Asn Gln
        115                 120                 125 cca ggc cac ctc aga ctc ttt gtg aca agg att ctg cag gaa ttt gaa        432
Pro Gly His Leu Arg Leu Phe Val Thr Arg Ile Leu Gln Glu Phe Glu
    130                 135                 140 agt gac acg ttt ttc cca gaa att gat ttg ggg aaa tat aaa ctt ctc        480
Ser Asp Thr Phe Phe Pro Glu Ile Asp Leu Gly Lys Tyr Lys Leu Leu
145                 150                 155                 160 cca gaa tac cca ggc gtc ctc tct gag gtc cag gag gaa aaa ggc atc        528
Pro Glu Tyr Pro Gly Val Leu Ser Glu Val Gln Glu Glu Lys Gly Ile
                165                 170                 175 aag tat aag ttt gaa gtc tac gag aag aaa gac taa                        564
Lys Tyr Lys Phe Glu Val Tyr Glu Lys Lys Asp
            180                 185

<210> SEQ ID NO 123
<211> LENGTH: 187
<212> TYPE: PRT
<213> ORGANISM: Artificial
<220> FEATURE:
<223> OTHER INFORMATION: Synthetic Construct

<400> SEQUENCE: 123

Met Val Arg Pro Leu Asn Cys Ile Val Ala Val Ser Gln Asn Leu Gly
 1               5                  10                  15

Ile Gly Lys Asn Gly Asp Leu Pro Trp Pro Pro Leu Arg Asn Glu Phe
                20                  25                  30

Lys Tyr Phe Gln Arg Leu Thr Thr Thr Ser Ser Val Glu Gly Lys Gln
            35                  40                  45

Asn Leu Val Ile Leu Gly Arg Lys Thr Trp Phe Ser Ile Pro Glu Lys
 50                  55                  60

Asn Arg Pro Leu Lys Asp Arg Ile Asn Ile Val Leu Ser Arg Glu Leu
 65                  70                  75                  80

Lys Glu Pro Pro Arg Gly Ala His Phe Leu Ala Lys Ser Leu Asp Asp
                 85                  90                  95

Ala Leu Arg Leu Ile Glu Gln Pro Glu Leu Ala Ser Lys Val Asp Leu
            100                 105                 110

Val Trp Ile Val Gly Gly Ser Ser Val Tyr Gln Glu Ala Leu Asn Gln
        115                 120                 125

Pro Gly His Leu Arg Leu Phe Val Thr Arg Ile Leu Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
            180                 185
```

<210> SEQ ID NO 124
<211> LENGTH: 36
<212> TYPE: DNA
<213> ORGANISM: Artificial
<220> FEATURE:
<223> OTHER INFORMATION: primer DHFR-F-HindIII

<400> SEQUENCE: 124
gatcaagctt ttgttcgacc attgaactgc atcgtc                                36

<210> SEQ ID NO 125
<211> LENGTH: 36
<212> TYPE: DNA
<213> ORGANISM: Artificial
<220> FEATURE:
<223> OTHER INFORMATION: primer DHFR-EcoRI-600-R

<400> SEQUENCE: 125
aagcttgaat tcttagtctt tcttctcgta gacttc                                36

<210> SEQ ID NO 126
<211> LENGTH: 154
<212> TYPE: DNA
<213> ORGANISM: Artificial
<220> FEATURE:
<223> OTHER INFORMATION: combined synthetic polyadenylation sequence and
      pausing signal from the human alpha2 globin gene
<220> FEATURE:
<221> NAME/KEY: synthetic polyadenylation sequence
<222> LOCATION: (1)..(49)
<220> FEATURE:
<221> NAME/KEY: cloning site
<222> LOCATION: (50)..(62)
<220> FEATURE:
<221> NAME/KEY: pausing signal from the human alpha2 globin gene
<222> LOCATION: (63)..(154)

<400> SEQUENCE: 126
aataaaatat ctttattttc attacatctg tgtgttggtt ttttgtgtga atcgatagta       60
ctaacatacg ctctccatca aaacaaaacg aaacaaaaca aactagcaaa ataggctgtc      120
cccagtgcaa gtgcaggtgc cagaacattt ctct                                 154

<210> SEQ ID NO 127
<211> LENGTH: 596
<212> TYPE: DNA
<213> ORGANISM: Artificial
<220> FEATURE:
<223> OTHER INFORMATION: IRES sequence

<400> SEQUENCE: 127
gcccctctcc ctcccccccc cctaacgtta ctggccgaag ccgcttggaa taaggccggt       60
gtgcgtttgt ctatatgtga ttttccacca tattgccgtc ttttggcaat gtgagggccc      120
ggaaacctgg ccctgtcttc ttgacgagca ttcctagggg tctttcccct ctcgccaaag      180
gaatgcaagg tctgttgaat gtcgtgaagg aagcagttcc tctggaagct tcttgaagac      240
aaacaacgtc tgtagcgacc ctttgcaggc agcggaaccc cccacctggc gacaggtgcc      300
tctgcggcca aaagccacgt gtataagata cacctgcaaa ggcggcacaa ccccagtgcc      360
acgttgtgag ttggatagtt gtggaaagag tcaaatggct ctcctcaagc gtattcaaca      420 agggctgaa ggatgcccag aaggtacccc attgtatggg atctgatctg gggcctcggt      480
gcacatgctt tacatgtgtt tagtcgaggt taaaaaaacg tctaggcccc ccgaaccacg      540

```
gggacgtggt tttcctttga aaaacacgat gataagcttg ccacaacccc gggata        596
```

<210> SEQ ID NO 128
<211> LENGTH: 804
<212> TYPE: DNA
<213> ORGANISM: Artificial
<220> FEATURE:
<223> OTHER INFORMATION: wild type neomycin (Neo) resistance sequence
<220> FEATURE:
<221> NAME/KEY: CDS
<222> LOCATION: (1)..(804)

<400> SEQUENCE: 128

```
atg gga tcg gcc att gaa caa gat gga ttg cac gca ggt tct ccg gcc        48
Met Gly Ser Ala Ile Glu Gln Asp Gly Leu His Ala Gly Ser Pro Ala
1               5                   10                  15 gct tgg gtg gag agg cta ttc ggc tat gac tgg gca caa cag aca atc        96
Ala Trp Val Glu Arg Leu Phe Gly Tyr Asp Trp Ala Gln Gln Thr Ile
            20                  25                  30 ggc tgc tct gat gcc gcc gtg ttc cgg ctg tca gcg cag ggg cgc ccg       144
Gly Cys Ser Asp Ala Ala Val Phe Arg Leu Ser Ala Gln Gly Arg Pro
        35                  40                  45 gtt ctt ttt gtc aag acc gac ctg tcc ggt gcc ctg aat gaa ctg cag       192
Val Leu Phe Val Lys Thr Asp Leu Ser Gly Ala Leu Asn Glu Leu Gln
    50                  55                  60 gac gag gca gcg cgg cta tcg tgg ctg gcc acg acg ggc gtt cct tgc       240
Asp Glu Ala Ala Arg Leu Ser Trp Leu Ala Thr Thr Gly Val Pro Cys
65                  70                  75                  80 gca gct gtg ctc gac gtt gtc act gaa gcg gga agg gac tgg ctg cta       288
Ala Ala Val Leu Asp Val Val Thr Glu Ala Gly Arg Asp Trp Leu Leu
                85                  90                  95 ttg ggc gaa gtg ccg ggg cag gat ctc ctg tca tct cac ctt gct cct       336
Leu Gly Glu Val Pro Gly Gln Asp Leu Leu Ser Ser His Leu Ala Pro
            100                 105                 110 gcc gag aaa gta tcc atc atg gct gat gca atg cgg cgg ctg cat acg       384
Ala Glu Lys Val Ser Ile Met Ala Asp Ala Met Arg Arg Leu His Thr
        115                 120                 125 ctt gat ccg gct acc tgc cca ttc gac cac caa gcg aaa cat cgc atc       432
Leu Asp Pro Ala Thr Cys Pro Phe Asp His Gln Ala Lys His Arg Ile
    130                 135                 140 gag cga gca cgt act cgg atg gaa gcc ggt ctt gtc gat cag gat gat       480
Glu Arg Ala Arg Thr Arg Met Glu Ala Gly Leu Val Asp Gln Asp Asp
145                 150                 155                 160 ctg gac gaa gag cat cag ggg ctc gcg cca gcc gaa ctg ttc gcc agg       528
Leu Asp Glu Glu His Gln Gly Leu Ala Pro Ala Glu Leu Phe Ala Arg
                165                 170                 175 ctc aag gcg cgc atg ccc gac ggc gag gat ctc gtc gtg acc cat ggc       576
Leu Lys Ala Arg Met Pro Asp Gly Glu Asp Leu Val Val Thr His Gly
            180                 185                 190 gat gcc tgc ttg ccg aat atc atg gtg gaa aat ggc cgc ttt tct gga       624
Asp Ala Cys Leu Pro Asn Ile Met Val Glu Asn Gly Arg Phe Ser Gly
        195                 200                 205 ttc atc gac tgt ggc cgg ctg ggt gtg gcg gac cgc tat cag gac ata       672
Phe Ile Asp Cys Gly Arg Leu Gly Val Ala Asp Arg Tyr Gln Asp Ile
    210                 215                 220 gcg ttg gct acc cgt gat att gct gaa gag ctt ggc ggc gaa tgg gct       720
Ala Leu Ala Thr Arg Asp Ile Ala Glu Glu Leu Gly Gly Glu Trp Ala
225                 230                 235                 240 gac cgc ttc ctc gtg ctt tac ggt atc gcc gct ccc gat tcg cag cgc       768
Asp Arg Phe Leu Val Leu Tyr Gly Ile Ala Ala Pro Asp Ser Gln Arg
                245                 250                 255
```

```
atc gcc ttc tat cgc ctt ctt gac gag ttc ttc tga                          804
Ile Ala Phe Tyr Arg Leu Leu Asp Glu Phe Phe
        260                 265
```

<210> SEQ ID NO 129
<211> LENGTH: 267
<212> TYPE: PRT
<213> ORGANISM: Artificial
<220> FEATURE:
<223> OTHER INFORMATION: Synthetic Construct

<400> SEQUENCE: 129

```
Met Gly Ser Ala Ile Glu Gln Asp Gly Leu His Ala Gly Ser Pro Ala
1               5                   10                  15

Ala Trp Val Glu Arg Leu Phe Gly Tyr Asp Trp Ala Gln Gln Thr Ile
            20                  25                  30

Gly Cys Ser Asp Ala Ala Val Phe Arg Leu Ser Ala Gln Gly Arg Pro
        35                  40                  45

Val Leu Phe Val Lys Thr Asp Leu Ser Gly Ala Leu Asn Glu Leu Gln
    50                  55                  60

Asp Glu Ala Ala Arg Leu Ser Trp Leu Ala Thr Thr Gly Val Pro Cys
65                  70                  75                  80

Ala Ala Val Leu Asp Val Val Thr Glu Ala Gly Arg Asp Trp Leu Leu
                85                  90                  95

Leu Gly Glu Val Pro Gly Gln Asp Leu Leu Ser Ser His Leu Ala Pro
            100                 105                 110

Ala Glu Lys Val Ser Ile Met Ala Asp Ala Met Arg Arg Leu His Thr
        115                 120                 125

Leu Asp Pro Ala Thr Cys Pro Phe Asp His Gln Ala Lys His Arg Ile
    130                 135                 140

Glu Arg Ala Arg Thr Arg Met Glu Ala Gly Leu Val Asp Gln Asp Asp
145                 150                 155                 160

Leu Asp Glu Glu His Gln Gly Leu Ala Pro Ala Glu Leu Phe Ala Arg
                165                 170                 175

Leu Lys Ala Arg Met Pro Asp Gly Glu Asp Leu Val Val Thr His Gly
            180                 185                 190

Asp Ala Cys Leu Pro Asn Ile Met Val Glu Asn Gly Arg Phe Ser Gly
        195                 200                 205

Phe Ile Asp Cys Gly Arg Leu Gly Val Ala Asp Arg Tyr Gln Asp Ile
    210                 215                 220

Ala Leu Ala Thr Arg Asp Ile Ala Glu Glu Leu Gly Gly Glu Trp Ala
225                 230                 235                 240

Asp Arg Phe Leu Val Leu Tyr Gly Ile Ala Ala Pro Asp Ser Gln Arg
                245                 250                 255

Ile Ala Phe Tyr Arg Leu Leu Asp Glu Phe Phe
            260                 265
```

<210> SEQ ID NO 130
<211> LENGTH: 804
<212> TYPE: DNA
<213> ORGANISM: Artificial
<220> FEATURE:
<223> OTHER INFORMATION: CpG poor Neo resistance sequence
<220> FEATURE:
<221> NAME/KEY: CDS
<222> LOCATION: (1)..(804)

<400> SEQUENCE: 130

```
atg gga agt gcc att gaa caa gac gga ttg cac gca ggt tct cct gca           48
```

|  |  |  |  |  |  |  |  |  |  |  |  |  |  |  |  |
|---|---|---|---|---|---|---|---|---|---|---|---|---|---|---|---|
| Met<br>1 | Gly | Ser | Ala | Ile<br>5 | Glu | Gln | Asp | Gly | Leu<br>10 | His | Ala | Gly | Ser | Pro<br>15 | Ala |

```
gct tgg gtg gag agg cta ttt ggc tac gac tgg gca caa cag aca ata     96
Ala Trp Val Glu Arg Leu Phe Gly Tyr Asp Trp Ala Gln Gln Thr Ile
        20                  25                  30 ggc tgc tct gac gca gca gtg ttc aga ctg tca gca cag ggg aga cca    144
Gly Cys Ser Asp Ala Ala Val Phe Arg Leu Ser Ala Gln Gly Arg Pro
 35                  40                  45 gtt ctt ttt gtc aag act gac ctg tca ggt gcc ctg aac gaa ctg cag    192
Val Leu Phe Val Lys Thr Asp Leu Ser Gly Ala Leu Asn Glu Leu Gln
 50                  55                  60 gac gag gca gca aga cta agt tgg ctg gcc act act ggt gtt cct tgt    240
Asp Glu Ala Ala Arg Leu Ser Trp Leu Ala Thr Thr Gly Val Pro Cys
65                  70                  75                  80 gca gct gtg ttg gac gtt gtc act gaa gca gga agg gac tgg ctg cta    288
Ala Ala Val Leu Asp Val Val Thr Glu Ala Gly Arg Asp Trp Leu Leu
                 85                  90                  95 ttg ggt gaa gtg cct ggg cag gat ctc ctg tca tct cac ctt gct cct    336
Leu Gly Glu Val Pro Gly Gln Asp Leu Leu Ser Ser His Leu Ala Pro
            100                 105                 110 gca gag aaa gta tcc atc ctg gct gac gca ctg aga aga ctg cat act    384
Ala Glu Lys Val Ser Ile Leu Ala Asp Ala Leu Arg Arg Leu His Thr
        115                 120                 125 ctt gat cca gct acc tgc cca ttt gac cac caa gca aaa cat aga att    432
Leu Asp Pro Ala Thr Cys Pro Phe Asp His Gln Ala Lys His Arg Ile
130                 135                 140 gag aga gca cga act aga ctg gaa gca ggt ctt gta gat cag gac gat    480
Glu Arg Ala Arg Thr Arg Leu Glu Ala Gly Leu Val Asp Gln Asp Asp
145                 150                 155                 160 ctg gac gaa gag cat cag ggg ttg gca cca gca gaa ctg ttt gcc agg    528
Leu Asp Glu Glu His Gln Gly Leu Ala Pro Ala Glu Leu Phe Ala Arg
                165                 170                 175 ctc aag gca aga ctg cct gac ggt gaa gat ttg gtt gtg acc cac ggt    576
Leu Lys Ala Arg Leu Pro Asp Gly Glu Asp Leu Val Val Thr His Gly
            180                 185                 190 gac gcc tgc ttg cct aat atc ctg gtg gaa aac ggc aga ttt tct gga    624
Asp Ala Cys Leu Pro Asn Ile Leu Val Glu Asn Gly Arg Phe Ser Gly
        195                 200                 205 ttc att gac tgt ggc aga ctg ggt gtg gca gac aga tat cag gac ata    672
Phe Ile Asp Cys Gly Arg Leu Gly Val Ala Asp Arg Tyr Gln Asp Ile
210                 215                 220 gca ttg gct acc aga gat att gct gaa gag ctt ggt ggt gag tgg gct    720
Ala Leu Ala Thr Arg Asp Ile Ala Glu Glu Leu Gly Gly Glu Trp Ala
225                 230                 235                 240 gac aga ttc ttg gtg ctt tac ggt ata gcc gct cct gat tca cag aga    768
Asp Arg Phe Leu Val Leu Tyr Gly Ile Ala Ala Pro Asp Ser Gln Arg
                245                 250                 255 ata gcc ttc tat aga ctt ctt gac gag ttc ttc tga                    804
Ile Ala Phe Tyr Arg Leu Leu Asp Glu Phe Phe
            260                 265
```

<210> SEQ ID NO 131
<211> LENGTH: 267
<212> TYPE: PRT
<213> ORGANISM: Artificial
<220> FEATURE:
<223> OTHER INFORMATION: Synthetic Construct

<400> SEQUENCE: 131

|  |  |  |  |  |  |  |  |  |  |  |  |  |  |  |  |
|---|---|---|---|---|---|---|---|---|---|---|---|---|---|---|---|
| Met<br>1 | Gly | Ser | Ala | Ile<br>5 | Glu | Gln | Asp | Gly | Leu<br>10 | His | Ala | Gly | Ser | Pro<br>15 | Ala |

```
Ala Trp Val Glu Arg Leu Phe Gly Tyr Asp Trp Ala Gln Gln Thr Ile
            20                  25                  30

Gly Cys Ser Asp Ala Ala Val Phe Arg Leu Ser Ala Gln Gly Arg Pro
        35                  40                  45

Val Leu Phe Val Lys Thr Asp Leu Ser Gly Ala Leu Asn Glu Leu Gln
 50                  55                  60

Asp Glu Ala Ala Arg Leu Ser Trp Leu Ala Thr Thr Gly Val Pro Cys
 65                  70                  75                  80

Ala Ala Val Leu Asp Val Val Thr Glu Ala Gly Arg Asp Trp Leu Leu
                 85                  90                  95

Leu Gly Glu Val Pro Gly Gln Asp Leu Leu Ser Ser His Leu Ala Pro
            100                 105                 110

Ala Glu Lys Val Ser Ile Leu Ala Asp Ala Leu Arg Arg Leu His Thr
        115                 120                 125

Leu Asp Pro Ala Thr Cys Pro Phe Asp His Gln Ala Lys His Arg Ile
130                 135                 140

Glu Arg Ala Arg Thr Arg Leu Glu Ala Gly Leu Val Asp Gln Asp Asp
145                 150                 155                 160

Leu Asp Glu Glu His Gln Gly Leu Ala Pro Ala Glu Leu Phe Ala Arg
                165                 170                 175

Leu Lys Ala Arg Leu Pro Asp Gly Glu Asp Leu Val Val Thr His Gly
            180                 185                 190

Asp Ala Cys Leu Pro Asn Ile Leu Val Glu Asn Gly Arg Phe Ser Gly
        195                 200                 205

Phe Ile Asp Cys Gly Arg Leu Gly Val Ala Asp Arg Tyr Gln Asp Ile
210                 215                 220

Ala Leu Ala Thr Arg Asp Ile Ala Glu Glu Leu Gly Gly Glu Trp Ala
225                 230                 235                 240

Asp Arg Phe Leu Val Leu Tyr Gly Ile Ala Pro Asp Ser Gln Arg
                245                 250                 255

Ile Ala Phe Tyr Arg Leu Leu Asp Glu Phe Phe
            260                 265

<210> SEQ ID NO 132
<211> LENGTH: 375
<212> TYPE: DNA
<213> ORGANISM: Artificial
<220> FEATURE:
<223> OTHER INFORMATION: CpG poor and ATG-less zeocin (Zeo) resistance
      sequence
<220> FEATURE:
<221> NAME/KEY: CDS
<222> LOCATION: (1)..(375)

<400> SEQUENCE: 132 ttg gcc aag ttg acc agt gct gtc cca gtg ctc aca gcc agg gac gtg      48
Leu Ala Lys Leu Thr Ser Ala Val Pro Val Leu Thr Ala Arg Asp Val
 1               5                  10                  15 gct gga gct gtt gag ttc tgg act gac agg ttg ggg ttc tcc aga gat      96
Ala Gly Ala Val Glu Phe Trp Thr Asp Arg Leu Gly Phe Ser Arg Asp
             20                  25                  30 ttt gtg gag gac gac ttt gca ggt gtg gtc aga gac gac gtc acc ctg     144
Phe Val Glu Asp Asp Phe Ala Gly Val Val Arg Asp Asp Val Thr Leu
         35                  40                  45 ttc atc tca gca gtc cag gac cag gtg gtg cct gac aac acc ctg gct     192
Phe Ile Ser Ala Val Gln Asp Gln Val Val Pro Asp Asn Thr Leu Ala
 50                  55                  60
```

```
tgg gtg tgg gtg aga gga ctg gac gag ctg tac gct gag tgg agt gag      240
Trp Val Trp Val Arg Gly Leu Asp Glu Leu Tyr Ala Glu Trp Ser Glu
 65              70                  75                  80 gtg gtc tcc acc aac ttc agg gac gcc agt ggc cct gcc ttg aca gag      288
Val Val Ser Thr Asn Phe Arg Asp Ala Ser Gly Pro Ala Leu Thr Glu
                 85                  90                  95 att gga gag cag ccc tgg ggg aga gag ttt gcc ctg aga gac cca gca      336
Ile Gly Glu Gln Pro Trp Gly Arg Glu Phe Ala Leu Arg Asp Pro Ala
                100                 105                 110 ggc aac tgt gtg cac ttt gtg gca gag gag cag gac tga                  375
Gly Asn Cys Val His Phe Val Ala Glu Glu Gln Asp
                115                 120
```

<210> SEQ ID NO 133
<211> LENGTH: 124
<212> TYPE: PRT
<213> ORGANISM: Artificial
<220> FEATURE:
<223> OTHER INFORMATION: Synthetic Construct

<400> SEQUENCE: 133

```
Leu Ala Lys Leu Thr Ser Ala Val Pro Val Leu Thr Ala Arg Asp Val
 1               5                  10                  15

Ala Gly Ala Val Glu Phe Trp Thr Asp Arg Leu Gly Phe Ser Arg Asp
                20                  25                  30

Phe Val Glu Asp Asp Phe Ala Gly Val Val Arg Asp Asp Val Thr Leu
            35                  40                  45

Phe Ile Ser Ala Val Gln Asp Gln Val Val Pro Asp Asn Thr Leu Ala
        50                  55                  60

Trp Val Trp Val Arg Gly Leu Asp Glu Leu Tyr Ala Glu Trp Ser Glu
 65              70                  75                  80

Val Val Ser Thr Asn Phe Arg Asp Ala Ser Gly Pro Ala Leu Thr Glu
                 85                  90                  95

Ile Gly Glu Gln Pro Trp Gly Arg Glu Phe Ala Leu Arg Asp Pro Ala
                100                 105                 110

Gly Asn Cys Val His Phe Val Ala Glu Glu Gln Asp
                115                 120
```

<210> SEQ ID NO 134
<211> LENGTH: 1194
<212> TYPE: DNA
<213> ORGANISM: Escherichia coli
<220> FEATURE:
<221> NAME/KEY: wt trp sequence
<222> LOCATION: (1)..(1194)
<220> FEATURE:
<221> NAME/KEY: CDS
<222> LOCATION: (1)..(1194)

<400> SEQUENCE: 134

```
atg aca aca tta ctt aac ccc tat ttt ggt gag ttt ggc ggc atg tac       48
Met Thr Thr Leu Leu Asn Pro Tyr Phe Gly Glu Phe Gly Gly Met Tyr
 1               5                  10                  15 gtg cca caa atc ctg atg cct gct ctc gcc cag ctg gaa gaa gct ttt       96
Val Pro Gln Ile Leu Met Pro Ala Leu Arg Gln Leu Glu Glu Ala Phe
                20                  25                  30 gtc agt gcg caa aaa gat cct gaa ttt cag gct cag ttc aac gac ctg      144
Val Ser Ala Gln Lys Asp Pro Glu Phe Gln Ala Gln Phe Asn Asp Leu
            35                  40                  45 ctg aaa aac tat gcc ggg cgt cca acc gcg ctg acc aaa tgc cag aac      192
Leu Lys Asn Tyr Ala Gly Arg Pro Thr Ala Leu Thr Lys Cys Gln Asn
        50                  55                  60
```

```
att aca gcc ggg acg aac acc acg ctg tat ctc aag cgt gaa gat ttg      240
Ile Thr Ala Gly Thr Asn Thr Thr Leu Tyr Leu Lys Arg Glu Asp Leu
 65                  70                  75                  80 ctg cac ggc ggc gcg cat aaa act aac cag gtg ctg ggg cag gcg ttg      288
Leu His Gly Gly Ala His Lys Thr Asn Gln Val Leu Gly Gln Ala Leu
                 85                  90                  95 ctg gcg aag cgg atg ggt aaa acc gaa atc atc gcc gaa acc ggt gcc      336
Leu Ala Lys Arg Met Gly Lys Thr Glu Ile Ile Ala Glu Thr Gly Ala
            100                 105                 110 ggt cag cat ggc gtg gcg tcg gcc ctg gcc agc gcc ctg ctc ggc ctg      384
Gly Gln His Gly Val Ala Ser Ala Leu Ala Ser Ala Leu Leu Gly Leu
        115                 120                 125 aaa tgc cgt att tat atg ggt gcc aaa gac gtt gaa cgc cag tcg cct      432
Lys Cys Arg Ile Tyr Met Gly Ala Lys Asp Val Glu Arg Gln Ser Pro
130                 135                 140 aac gtt ttt cgt atg cgc tta atg ggt gcg gaa gtg atc ccg gtg cat      480
Asn Val Phe Arg Met Arg Leu Met Gly Ala Glu Val Ile Pro Val His
145                 150                 155                 160 agc ggt tcc gcg acg ctg aaa gat gcc tgt aac gag gcg ctg cgc gac      528
Ser Gly Ser Ala Thr Leu Lys Asp Ala Cys Asn Glu Ala Leu Arg Asp
                165                 170                 175 tgg tcc ggt agt tac gaa acc gcg cac tat atg ctg ggc acc gca gct      576
Trp Ser Gly Ser Tyr Glu Thr Ala His Tyr Met Leu Gly Thr Ala Ala
            180                 185                 190 ggc ccg cat cct tat ccg acc att gtg cgt gag ttt cag cgg atg att      624
Gly Pro His Pro Tyr Pro Thr Ile Val Arg Glu Phe Gln Arg Met Ile
        195                 200                 205 ggc gaa gaa acc aaa gcg cag att ctg gaa aga gaa ggt cgc ctg ccg      672
Gly Glu Glu Thr Lys Ala Gln Ile Leu Glu Arg Glu Gly Arg Leu Pro
    210                 215                 220 gat gcc gtt atc gcc tgt gtt ggc ggc ggt tcg aat gcc atc ggc atg      720
Asp Ala Val Ile Ala Cys Val Gly Gly Gly Ser Asn Ala Ile Gly Met
225                 230                 235                 240 ttt gct gat ttc atc aat gaa acc aac gtc ggc ctg att ggt gtg gag      768
Phe Ala Asp Phe Ile Asn Glu Thr Asn Val Gly Leu Ile Gly Val Glu
                245                 250                 255 cca ggt ggt cac ggt atc gaa act ggc gag cac ggc gca ccg cta aaa      816
Pro Gly Gly His Gly Ile Glu Thr Gly Glu His Gly Ala Pro Leu Lys
            260                 265                 270 cat ggt cgc gtg ggt atc tat ttc ggt atg aaa gcg ccg atg atg caa      864
His Gly Arg Val Gly Ile Tyr Phe Gly Met Lys Ala Pro Met Met Gln
        275                 280                 285 acc gaa gac ggg cag att gaa gaa tct tac tcc atc tcc gcc gga ctg      912
Thr Glu Asp Gly Gln Ile Glu Glu Ser Tyr Ser Ile Ser Ala Gly Leu
    290                 295                 300 gat ttc ccg tct gtc ggc cca caa cac gcg tat ctt aac agc act gga      960
Asp Phe Pro Ser Val Gly Pro Gln His Ala Tyr Leu Asn Ser Thr Gly
305                 310                 315                 320 cgc gct gat tac gtg tct att acc gat gat gaa gcc ctt gaa gcc ttc     1008
Arg Ala Asp Tyr Val Ser Ile Thr Asp Asp Glu Ala Leu Glu Ala Phe
                325                 330                 335 aaa acg ctg tgc ctg cac gaa ggg atc atc ccg gcg ctg gaa tcc tcc     1056
Lys Thr Leu Cys Leu His Glu Gly Ile Ile Pro Ala Leu Glu Ser Ser
            340                 345                 350 cac gcc ttg gcc cat gcg ttg aaa atg atg cgc gaa aac ccg gat aaa     1104
His Ala Leu Ala His Ala Leu Lys Met Met Arg Glu Asn Pro Asp Lys
        355                 360                 365 gag cag cta ctg gtg gtt aac ctt tcc ggt cgc ggc gat aaa gac atc     1152
Glu Gln Leu Leu Val Val Asn Leu Ser Gly Arg Gly Asp Lys Asp Ile
```

```
                    370                 375                 380
ttc acc gtt cac gat att ttg aaa gca cga ggg gaa atc tga            1194
Phe Thr Val His Asp Ile Leu Lys Ala Arg Gly Glu Ile
385                 390                 395
```

<210> SEQ ID NO 135
<211> LENGTH: 397
<212> TYPE: PRT
<213> ORGANISM: Escherichia coli

<400> SEQUENCE: 135

```
Met Thr Thr Leu Leu Asn Pro Tyr Phe Gly Glu Phe Gly Gly Met Tyr
1               5                   10                  15

Val Pro Gln Ile Leu Met Pro Ala Leu Arg Gln Leu Glu Glu Ala Phe
            20                  25                  30

Val Ser Ala Gln Lys Asp Pro Glu Phe Gln Ala Gln Phe Asn Asp Leu
        35                  40                  45

Leu Lys Asn Tyr Ala Gly Arg Pro Thr Ala Leu Thr Lys Cys Gln Asn
    50                  55                  60

Ile Thr Ala Gly Thr Asn Thr Thr Leu Tyr Leu Lys Arg Glu Asp Leu
65                  70                  75                  80

Leu His Gly Gly Ala His Lys Thr Asn Gln Val Leu Gly Gln Ala Leu
                85                  90                  95

Leu Ala Lys Arg Met Gly Lys Thr Glu Ile Ile Ala Glu Thr Gly Ala
            100                 105                 110

Gly Gln His Gly Val Ala Ser Ala Leu Ala Ser Ala Leu Leu Gly Leu
        115                 120                 125

Lys Cys Arg Ile Tyr Met Gly Ala Lys Asp Val Glu Arg Gln Ser Pro
    130                 135                 140

Asn Val Phe Arg Met Arg Leu Met Gly Ala Glu Val Ile Pro Val His
145                 150                 155                 160

Ser Gly Ser Ala Thr Leu Lys Asp Ala Cys Asn Glu Ala Leu Arg Asp
                165                 170                 175

Trp Ser Gly Ser Tyr Glu Thr Ala His Tyr Met Leu Gly Thr Ala Ala
            180                 185                 190

Gly Pro His Pro Tyr Pro Thr Ile Val Arg Glu Phe Gln Arg Met Ile
        195                 200                 205

Gly Glu Glu Thr Lys Ala Gln Ile Leu Glu Arg Glu Gly Arg Leu Pro
    210                 215                 220

Asp Ala Val Ile Ala Cys Val Gly Gly Gly Ser Asn Ala Ile Gly Met
225                 230                 235                 240

Phe Ala Asp Phe Ile Asn Glu Thr Asn Val Gly Leu Ile Gly Val Glu
                245                 250                 255

Pro Gly Gly His Gly Ile Glu Thr Gly Glu His Gly Ala Pro Leu Lys
            260                 265                 270

His Gly Arg Val Gly Ile Tyr Phe Gly Met Lys Ala Pro Met Met Gln
        275                 280                 285

Thr Glu Asp Gly Gln Ile Glu Glu Ser Tyr Ser Ile Ser Ala Gly Leu
    290                 295                 300

Asp Phe Pro Ser Val Gly Pro Gln His Ala Tyr Leu Asn Ser Thr Gly
305                 310                 315                 320

Arg Ala Asp Tyr Val Ser Ile Thr Asp Asp Glu Ala Leu Glu Ala Phe
                325                 330                 335

Lys Thr Leu Cys Leu His Glu Gly Ile Ile Pro Ala Leu Glu Ser Ser
            340                 345                 350
```

```
His Ala Leu Ala His Ala Leu Lys Met Met Arg Glu Asn Pro Asp Lys
        355                 360                 365

Glu Gln Leu Leu Val Val Asn Leu Ser Gly Arg Gly Asp Lys Asp Ile
    370                 375                 380

Phe Thr Val His Asp Ile Leu Lys Ala Arg Gly Glu Ile
385                 390                 395

<210> SEQ ID NO 136
<211> LENGTH: 1194
<212> TYPE: DNA
<213> ORGANISM: Artificial
<220> FEATURE:
<223> OTHER INFORMATION: ATG-less trp sequence
<220> FEATURE:
<221> NAME/KEY: CDS
<222> LOCATION: (1)..(1194)

<400> SEQUENCE: 136 atg aca aca tta ctt aac ccc tat ttt ggt gag ttt ggc ggc cag tac       48
Met Thr Thr Leu Leu Asn Pro Tyr Phe Gly Glu Phe Gly Gly Gln Tyr
1               5                   10                  15 gtg cca caa atc ctg gtc cct gct ctg cgc cag ctg gaa gag gct ttt       96
Val Pro Gln Ile Leu Val Pro Ala Leu Arg Gln Leu Glu Glu Ala Phe
            20                  25                  30 gtc agt gcc caa aaa gat cct gaa ttt caa gct cag ttc aac gac ctg      144
Val Ser Ala Gln Lys Asp Pro Glu Phe Gln Ala Gln Phe Asn Asp Leu
        35                  40                  45 ctg aaa aac tac gcc ggg cgt cca acc gcg ctg acc aag tgc cag aac      192
Leu Lys Asn Tyr Ala Gly Arg Pro Thr Ala Leu Thr Lys Cys Gln Asn
    50                  55                  60 att acc gcc ggg acg aac acc acg ctg tat ctc aag cgt gaa gat ttg      240
Ile Thr Ala Gly Thr Asn Thr Thr Leu Tyr Leu Lys Arg Glu Asp Leu
65                  70                  75                  80 ctg cac ggc ggc gcg cat aaa act aac cag gtg ctg ggg cag gcg ttg      288
Leu His Gly Gly Ala His Lys Thr Asn Gln Val Leu Gly Gln Ala Leu
                85                  90                  95 ctg gcg aag cgg ctg ggt aaa acc gaa atc atc gcc gaa act ggt gcc      336
Leu Ala Lys Arg Leu Gly Lys Thr Glu Ile Ile Ala Glu Thr Gly Ala
            100                 105                 110 ggt cag cac ggc gtg gcg tcg gcc ctt gcc agc gcc ctg ctc ggc ctg      384
Gly Gln His Gly Val Ala Ser Ala Leu Ala Ser Ala Leu Leu Gly Leu
        115                 120                 125 aag tgc cgt att tat ctg ggt gcc aaa gac gtt gaa cgc cag tcg cct      432
Lys Cys Arg Ile Tyr Leu Gly Ala Lys Asp Val Glu Arg Gln Ser Pro
    130                 135                 140 aac gtt ttt cgt ctg cgc tta ctg ggt gcg gaa gtg atc ccg gtg cat      480
Asn Val Phe Arg Leu Arg Leu Leu Gly Ala Glu Val Ile Pro Val His
145                 150                 155                 160 agc ggt tcc gcg acg ctg aaa gac gcc tgt aac gag gcg ctg cgc gac      528
Ser Gly Ser Ala Thr Leu Lys Asp Ala Cys Asn Glu Ala Leu Arg Asp
                165                 170                 175 tgg tcc ggt agt tac gaa acc gcg cac tat ctg ctg ggc acc gca gct      576
Trp Ser Gly Ser Tyr Glu Thr Ala His Tyr Leu Leu Gly Thr Ala Ala
            180                 185                 190 ggc ccg cat cct tat ccg acc att gtg cgt gag ttt caa cgg atc att      624
Gly Pro His Pro Tyr Pro Thr Ile Val Arg Glu Phe Gln Arg Ile Ile
        195                 200                 205 ggc gaa gaa acc aaa gcg cag att ctg gaa aga gaa ggt cgc ctg ccg      672
Gly Glu Glu Thr Lys Ala Gln Ile Leu Glu Arg Glu Gly Arg Leu Pro
    210                 215                 220
```

```
gac gcc gtt atc gcc tgt gtt ggc ggc ggt tct aac gcc atc ggc atc      720
Asp Ala Val Ile Ala Cys Val Gly Gly Gly Ser Asn Ala Ile Gly Ile
225                 230                 235                 240 ttt gct gat ttc atc aac gaa acc aac gtc ggc ctg att ggt gtg gag      768
Phe Ala Asp Phe Ile Asn Glu Thr Asn Val Gly Leu Ile Gly Val Glu
                245                 250                 255 cca ggt ggt cac ggt atc gaa act ggc gag cac ggc gca ccg cta aaa      816
Pro Gly Gly His Gly Ile Glu Thr Gly Glu His Gly Ala Pro Leu Lys
            260                 265                 270 cac ggt cgc gtg ggt atc tat ttc ggt ctg aaa gcg ccg atc ctg caa      864
His Gly Arg Val Gly Ile Tyr Phe Gly Leu Lys Ala Pro Ile Leu Gln
        275                 280                 285 acc gaa gac ggg cag att gaa gaa tct tac tcc atc tcc gcc gga ctg      912
Thr Glu Asp Gly Gln Ile Glu Glu Ser Tyr Ser Ile Ser Ala Gly Leu
    290                 295                 300 gat ttc ccg tct gtc ggc cca caa cac gcc tat ctt aac agc act gga      960
Asp Phe Pro Ser Val Gly Pro Gln His Ala Tyr Leu Asn Ser Thr Gly
305                 310                 315                 320 cgc gct gat tac gtg tct att acc gac gac gaa gcc ctt gaa gcc ttc     1008
Arg Ala Asp Tyr Val Ser Ile Thr Asp Asp Glu Ala Leu Glu Ala Phe
                325                 330                 335 aaa acg ctg tgc ctg cac gaa ggg atc atc ccg gcg ctg gaa tcc tcc     1056
Lys Thr Leu Cys Leu His Glu Gly Ile Ile Pro Ala Leu Glu Ser Ser
                340                 345                 350 cac gcc ctg gcc cac gcc ttg aaa ctg gct cgc gaa aac ccg gat aaa     1104
His Ala Leu Ala His Ala Leu Lys Leu Ala Arg Glu Asn Pro Asp Lys
            355                 360                 365 gag cag cta ctg gtg gtc aac ctt tcc ggt cgc ggc gat aaa gac atc     1152
Glu Gln Leu Leu Val Val Asn Leu Ser Gly Arg Gly Asp Lys Asp Ile
        370                 375                 380 ttc acc gtt cac gat att ttg aaa gca cga ggg gaa atc tga             1194
Phe Thr Val His Asp Ile Leu Lys Ala Arg Gly Glu Ile
385                 390                 395

<210> SEQ ID NO 137
<211> LENGTH: 397
<212> TYPE: PRT
<213> ORGANISM: Artificial
<220> FEATURE:
<223> OTHER INFORMATION: Synthetic Construct

<400> SEQUENCE: 137

Met Thr Thr Leu Leu Asn Pro Tyr Phe Gly Glu Phe Gly Gly Gln Tyr
1               5                   10                  15

Val Pro Gln Ile Leu Val Pro Ala Leu Arg Gln Leu Glu Glu Ala Phe
            20                  25                  30

Val Ser Ala Gln Lys Asp Pro Glu Phe Gln Ala Gln Phe Asn Asp Leu
        35                  40                  45

Leu Lys Asn Tyr Ala Gly Arg Pro Thr Ala Leu Thr Lys Cys Gln Asn
    50                  55                  60

Ile Thr Ala Gly Thr Asn Thr Thr Leu Tyr Leu Lys Arg Glu Asp Leu
65                  70                  75                  80

Leu His Gly Gly Ala His Lys Thr Asn Gln Val Leu Gly Gln Ala Leu
                85                  90                  95

Leu Ala Lys Arg Leu Gly Lys Thr Glu Ile Ile Ala Glu Thr Gly Ala
            100                 105                 110

Gly Gln His Gly Val Ala Ser Ala Leu Ala Ser Ala Leu Leu Gly Leu
        115                 120                 125

Lys Cys Arg Ile Tyr Leu Gly Ala Lys Asp Val Glu Arg Gln Ser Pro
```

```
            130                 135                 140
Asn Val Phe Arg Leu Arg Leu Leu Gly Ala Glu Val Ile Pro Val His
145                 150                 155                 160

Ser Gly Ser Ala Thr Leu Lys Asp Ala Cys Asn Glu Ala Leu Arg Asp
                165                 170                 175

Trp Ser Gly Ser Tyr Glu Thr Ala His Tyr Leu Leu Gly Thr Ala Ala
                180                 185                 190

Gly Pro His Pro Tyr Pro Thr Ile Val Arg Glu Phe Gln Arg Ile Ile
                195                 200                 205

Gly Glu Glu Thr Lys Ala Gln Ile Leu Glu Arg Glu Gly Arg Leu Pro
210                 215                 220

Asp Ala Val Ile Ala Cys Val Gly Gly Gly Ser Asn Ala Ile Gly Ile
225                 230                 235                 240

Phe Ala Asp Phe Ile Asn Glu Thr Asn Val Gly Leu Ile Gly Val Glu
                245                 250                 255

Pro Gly Gly His Gly Ile Glu Thr Gly Glu His Gly Ala Pro Leu Lys
                260                 265                 270

His Gly Arg Val Gly Ile Tyr Phe Gly Leu Lys Ala Pro Ile Leu Gln
                275                 280                 285

Thr Glu Asp Gly Gln Ile Glu Glu Ser Tyr Ser Ile Ser Ala Gly Leu
290                 295                 300

Asp Phe Pro Ser Val Gly Pro Gln His Ala Tyr Leu Asn Ser Thr Gly
305                 310                 315                 320

Arg Ala Asp Tyr Val Ser Ile Thr Asp Glu Ala Leu Glu Ala Phe
                325                 330                 335

Lys Thr Leu Cys Leu His Glu Gly Ile Ile Pro Ala Leu Glu Ser Ser
                340                 345                 350

His Ala Leu Ala His Ala Leu Lys Leu Ala Arg Glu Asn Pro Asp Lys
                355                 360                 365

Glu Gln Leu Leu Val Val Asn Leu Ser Gly Arg Gly Asp Lys Asp Ile
                370                 375                 380

Phe Thr Val His Asp Ile Leu Lys Ala Arg Gly Glu Ile
385                 390                 395

<210> SEQ ID NO 138
<211> LENGTH: 1305
<212> TYPE: DNA
<213> ORGANISM: Salmonella typhimurium
<220> FEATURE:
<221> NAME/KEY: wt his sequence
<222> LOCATION: (1)..(1305)
<220> FEATURE:
<221> NAME/KEY: CDS
<222> LOCATION: (1)..(1305)

<400> SEQUENCE: 138 atg agc ttc aat acc ctg att gac tgg aac agc tgt agc cct gaa cag    48
Met Ser Phe Asn Thr Leu Ile Asp Trp Asn Ser Cys Ser Pro Glu Gln
1               5                   10                  15 cag cgt gcg ctg ctg acg cgt ccg gcg att tcc gcc tct gac agt att    96
Gln Arg Ala Leu Leu Thr Arg Pro Ala Ile Ser Ala Ser Asp Ser Ile
            20                  25                  30 acc cgg acg gtc agc gat att ctg gat aat gta aaa acg cgc ggt gac    144
Thr Arg Thr Val Ser Asp Ile Leu Asp Asn Val Lys Thr Arg Gly Asp
        35                  40                  45 gat gcc ctg cgt gaa tac agc gct aaa ttt gat aaa aca gaa gtg aca    192
Asp Ala Leu Arg Glu Tyr Ser Ala Lys Phe Asp Lys Thr Glu Val Thr
    50                  55                  60
```

-continued

| | | |
|---|---|---|
| gcg cta cgc gtc acc cct gaa gag atc gcc gcc gcc ggc gcg cgt ctg<br>Ala Leu Arg Val Thr Pro Glu Glu Ile Ala Ala Ala Gly Ala Arg Leu<br>65                            70                      75                      80 | | 240 |
| agc gac gaa tta aaa cag gcg atg acc gct gcc gtc aaa aat att gaa<br>Ser Asp Glu Leu Lys Gln Ala Met Thr Ala Ala Val Lys Asn Ile Glu<br>                 85                      90                      95 | | 288 |
| acg ttc cat tcc gcg cag acg cta ccg cct gta gat gtg gaa acc cag<br>Thr Phe His Ser Ala Gln Thr Leu Pro Pro Val Asp Val Glu Thr Gln<br>                100                   105                  110 | | 336 |
| cca ggc gtg cgt tgc cag cag gtt acg cgt ccc gtc tcg tct gtc ggt<br>Pro Gly Val Arg Cys Gln Gln Val Thr Arg Pro Val Ser Ser Val Gly<br>                115                   120                  125 | | 384 |
| ctg tat att ccc ggc ggc tcg gct ccg ctc ttc tca acg gtg ctg atg<br>Leu Tyr Ile Pro Gly Gly Ser Ala Pro Leu Phe Ser Thr Val Leu Met<br>130                            135                      140 | | 432 |
| ctg gcg acg ccg gcg cgc att gcg gga tgc cag aag gtg gtt ctg tgc<br>Leu Ala Thr Pro Ala Arg Ile Ala Gly Cys Gln Lys Val Val Leu Cys<br>145                            150                      155                      160 | | 480 |
| tcg ccg ccg ccc atc gct gat gaa atc ctc tat gcg gcg caa ctg tgt<br>Ser Pro Pro Pro Ile Ala Asp Glu Ile Leu Tyr Ala Ala Gln Leu Cys<br>                            165                   170                  175 | | 528 |
| ggc gtg cag gaa atc ttt aac gtc ggc ggc gcg cag gcg att gcc gct<br>Gly Val Gln Glu Ile Phe Asn Val Gly Gly Ala Gln Ala Ile Ala Ala<br>                180                   185                  190 | | 576 |
| ctg gcc ttc ggc agc gag tcc gta ccg aaa gtg gat aaa att ttt ggc<br>Leu Ala Phe Gly Ser Glu Ser Val Pro Lys Val Asp Lys Ile Phe Gly<br>                   195                   200                  205 | | 624 |
| ccc ggc aac gcc ttt gta acc gaa gcc aaa cgt cag gtc agc cag cgt<br>Pro Gly Asn Ala Phe Val Thr Glu Ala Lys Arg Gln Val Ser Gln Arg<br>210                            215                      220 | | 672 |
| ctc gac ggc gcg gct atc gat atg cca gcc ggg ccg tct gaa gta ctg<br>Leu Asp Gly Ala Ala Ile Asp Met Pro Ala Gly Pro Ser Glu Val Leu<br>225                            230                      235                      240 | | 720 |
| gtg atc gca gac agc ggc gca aca ccg gat ttc gtc gct tct gac ctg<br>Val Ile Ala Asp Ser Gly Ala Thr Pro Asp Phe Val Ala Ser Asp Leu<br>                          245                   250                  255 | | 768 |
| ctc tcc cag gct gag cac ggc ccg gat tcc cag gtg atc ctg ctg acg<br>Leu Ser Gln Ala Glu His Gly Pro Asp Ser Gln Val Ile Leu Leu Thr<br>                260                   265                  270 | | 816 |
| cct gat gct gac att gcc cgc aag gtg gcg gag gcg gta gaa cgt caa<br>Pro Asp Ala Asp Ile Ala Arg Lys Val Ala Glu Ala Val Glu Arg Gln<br>                   275                   280                  285 | | 864 |
| ctg gcg gaa ctg ccg cgc gcg gac acc gcc cgg cag gcc ctg agc gcc<br>Leu Ala Glu Leu Pro Arg Ala Asp Thr Ala Arg Gln Ala Leu Ser Ala<br>290                            295                      300 | | 912 |
| agt cgt ctg att gtg acc aaa gat tta gcg cag tgc gtc gcc atc tct<br>Ser Arg Leu Ile Val Thr Lys Asp Leu Ala Gln Cys Val Ala Ile Ser<br>305                            310                      315                      320 | | 960 |
| aat cag tat ggg ccg gaa cac tta atc atc cag acg cgc aat gcg cgc<br>Asn Gln Tyr Gly Pro Glu His Leu Ile Ile Gln Thr Arg Asn Ala Arg<br>                   325                   330                  335 | | 1008 |
| gat ttg gtg gat gcg att acc agc gca ggc tcg gta ttt ctc ggc gac<br>Asp Leu Val Asp Ala Ile Thr Ser Ala Gly Ser Val Phe Leu Gly Asp<br>                340                   345                  350 | | 1056 |
| tgg tcg ccg gaa tcc gcc ggt gat tac gct tcc gga acc aac cat gtt<br>Trp Ser Pro Glu Ser Ala Gly Asp Tyr Ala Ser Gly Thr Asn His Val<br>                   355                   360                  365 | | 1104 |
| tta ccg acc tat ggc tat act gct acc tgt tcc agc ctt ggg tta gcg<br>Leu Pro Thr Tyr Gly Tyr Thr Ala Thr Cys Ser Ser Leu Gly Leu Ala | | 1152 |

```
                    370                 375                 380
gat ttc cag aaa cgg atg acc gtt cag gaa ctg tcg aaa gcg ggc ttt        1200
Asp Phe Gln Lys Arg Met Thr Val Gln Glu Leu Ser Lys Ala Gly Phe
385                 390                 395                 400 tcc gct ctg gca tca acc att gaa aca ttg gcg gcg gca gaa cgt ctg        1248
Ser Ala Leu Ala Ser Thr Ile Glu Thr Leu Ala Ala Ala Glu Arg Leu
                405                 410                 415 acc gcc cat aaa aat gcc gtg acc ctg cgc gta aac gcc ctc aag gag        1296
Thr Ala His Lys Asn Ala Val Thr Leu Arg Val Asn Ala Leu Lys Glu
            420                 425                 430 caa gca tga                                                            1305
Gln Ala <210> SEQ ID NO 139
<211> LENGTH: 434
<212> TYPE: PRT
<213> ORGANISM: Salmonella typhimurium

<400> SEQUENCE: 139

Met Ser Phe Asn Thr Leu Ile Asp Trp Asn Ser Cys Ser Pro Glu Gln
1               5                   10                  15

Gln Arg Ala Leu Leu Thr Arg Pro Ala Ile Ser Ala Ser Asp Ser Ile
            20                  25                  30

Thr Arg Thr Val Ser Asp Ile Leu Asp Asn Val Lys Thr Arg Gly Asp
        35                  40                  45

Asp Ala Leu Arg Glu Tyr Ser Ala Lys Phe Asp Lys Thr Glu Val Thr
    50                  55                  60

Ala Leu Arg Val Thr Pro Glu Glu Ile Ala Ala Gly Ala Arg Leu
65                  70                  75                  80

Ser Asp Glu Leu Lys Gln Ala Met Thr Ala Ala Val Lys Asn Ile Glu
                85                  90                  95

Thr Phe His Ser Ala Gln Thr Leu Pro Pro Val Asp Val Glu Thr Gln
            100                 105                 110

Pro Gly Val Arg Cys Gln Gln Val Thr Arg Pro Val Ser Ser Val Gly
        115                 120                 125

Leu Tyr Ile Pro Gly Gly Ser Ala Pro Leu Phe Ser Thr Val Leu Met
    130                 135                 140

Leu Ala Thr Pro Ala Arg Ile Ala Gly Cys Gln Lys Val Val Leu Cys
145                 150                 155                 160

Ser Pro Pro Pro Ile Ala Asp Glu Ile Leu Tyr Ala Ala Gln Leu Cys
                165                 170                 175

Gly Val Gln Glu Ile Phe Asn Val Gly Gly Ala Gln Ala Ile Ala Ala
            180                 185                 190

Leu Ala Phe Gly Ser Glu Ser Val Pro Lys Val Asp Lys Ile Phe Gly
        195                 200                 205

Pro Gly Asn Ala Phe Val Thr Glu Ala Lys Arg Gln Val Ser Gln Arg
    210                 215                 220

Leu Asp Gly Ala Ala Ile Asp Met Pro Ala Gly Pro Ser Glu Val Leu
225                 230                 235                 240

Val Ile Ala Asp Ser Gly Ala Thr Pro Asp Phe Val Ala Ser Asp Leu
                245                 250                 255

Leu Ser Gln Ala Glu His Gly Pro Asp Ser Gln Val Ile Leu Leu Thr
            260                 265                 270

Pro Asp Ala Asp Ile Ala Arg Lys Val Ala Glu Ala Val Glu Arg Gln
        275                 280                 285
```

-continued

```
Leu Ala Glu Leu Pro Arg Ala Asp Thr Ala Arg Gln Ala Leu Ser Ala
    290                 295                 300

Ser Arg Leu Ile Val Thr Lys Asp Leu Ala Gln Cys Val Ala Ile Ser
305                 310                 315                 320

Asn Gln Tyr Gly Pro Glu His Leu Ile Ile Gln Thr Arg Asn Ala Arg
                325                 330                 335

Asp Leu Val Asp Ala Ile Thr Ser Ala Gly Ser Val Phe Leu Gly Asp
            340                 345                 350

Trp Ser Pro Glu Ser Ala Gly Asp Tyr Ala Ser Gly Thr Asn His Val
        355                 360                 365

Leu Pro Thr Tyr Gly Tyr Thr Ala Thr Cys Ser Ser Leu Gly Leu Ala
    370                 375                 380

Asp Phe Gln Lys Arg Met Thr Val Gln Glu Leu Ser Lys Ala Gly Phe
385                 390                 395                 400

Ser Ala Leu Ala Ser Thr Ile Glu Thr Leu Ala Ala Ala Glu Arg Leu
                405                 410                 415

Thr Ala His Lys Asn Ala Val Thr Leu Arg Val Asn Ala Leu Lys Glu
            420                 425                 430

Gln Ala
```

<210> SEQ ID NO 140
<211> LENGTH: 1305
<212> TYPE: DNA
<213> ORGANISM: Artificial
<220> FEATURE:
<223> OTHER INFORMATION: ATG-less his sequence
<220> FEATURE:
<221> NAME/KEY: CDS
<222> LOCATION: (1)..(1305)

<400> SEQUENCE: 140

```
atg agc ttc aat acc ctg att gac tgg aac agc tgt agc cct gaa cag      48
Met Ser Phe Asn Thr Leu Ile Asp Trp Asn Ser Cys Ser Pro Glu Gln
1               5                  10                  15 cag cgt gcg ctg ctg acg cgt ccg gcg att tcc gcc tct gac agt att      96
Gln Arg Ala Leu Leu Thr Arg Pro Ala Ile Ser Ala Ser Asp Ser Ile
                20                  25                  30 acc cgg acg gtc agc gat att ctg gat aac gta aaa acg cgc ggt gac     144
Thr Arg Thr Val Ser Asp Ile Leu Asp Asn Val Lys Thr Arg Gly Asp
            35                  40                  45 gac gcc ctg cgt gaa tac agc gct aaa ttt gat aaa aca gaa gtg aca     192
Asp Ala Leu Arg Glu Tyr Ser Ala Lys Phe Asp Lys Thr Glu Val Thr
        50                  55                  60 gcg cta cgc gtc acc cct gaa gag atc gcc gcc gcc ggc gcg cgt ctg     240
Ala Leu Arg Val Thr Pro Glu Glu Ile Ala Ala Ala Gly Ala Arg Leu
65                  70                  75                  80 agc gac gaa tta aaa cag gcg att acc gct gcc gtc aaa aat att gaa     288
Ser Asp Glu Leu Lys Gln Ala Ile Thr Ala Ala Val Lys Asn Ile Glu
                85                  90                  95 acg ttc cat tcc gcg cag acg cta ccg cct gta gac gtg gaa acc cag     336
Thr Phe His Ser Ala Gln Thr Leu Pro Pro Val Asp Val Glu Thr Gln
                100                 105                 110 cca ggc gtg cgt tgc cag cag gtt acg cgt ccc gtc tcg tct gtc ggt     384
Pro Gly Val Arg Cys Gln Gln Val Thr Arg Pro Val Ser Ser Val Gly
            115                 120                 125 ctg tat att ccc ggc ggc tcg gct ccg ctc ttc tca acg gtg ctg ctg     432
Leu Tyr Ile Pro Gly Gly Ser Ala Pro Leu Phe Ser Thr Val Leu Leu
        130                 135                 140 ctg gcg acg ccg gcg cgc att gcg ggt tgc cag aag gtg gtt ctg tgc     480
```

```
Leu Ala Thr Pro Ala Arg Ile Ala Gly Cys Gln Lys Val Val Leu Cys
145                 150                 155                 160 tcg ccg ccg ccc atc gct gac gaa atc ctc tac gcg gcg caa ctg tgt       528
Ser Pro Pro Pro Ile Ala Asp Glu Ile Leu Tyr Ala Ala Gln Leu Cys
                165                 170                 175 ggc gtg cag gaa atc ttt aac gtc ggc ggc gcg cag gcg att gcc gct       576
Gly Val Gln Glu Ile Phe Asn Val Gly Gly Ala Gln Ala Ile Ala Ala
            180                 185                 190 ctg gcc ttc ggc agc gag tcc gta ccg aaa gtg gat aaa att ttt ggc       624
Leu Ala Phe Gly Ser Glu Ser Val Pro Lys Val Asp Lys Ile Phe Gly
        195                 200                 205 ccc ggc aac gcc ttt gta acc gaa gcc aaa cgt cag gtc agc cag cgt       672
Pro Gly Asn Ala Phe Val Thr Glu Ala Lys Arg Gln Val Ser Gln Arg
    210                 215                 220 ctc gac ggc gcg gct atc gat att cca gcc ggg ccg tct gaa gta ctg       720
Leu Asp Gly Ala Ala Ile Asp Ile Pro Ala Gly Pro Ser Glu Val Leu
225                 230                 235                 240 gtg atc gca gac agc ggc gca aca ccg gat ttc gtc gct tct gac ctg       768
Val Ile Ala Asp Ser Gly Ala Thr Pro Asp Phe Val Ala Ser Asp Leu
                245                 250                 255 ctc tcc cag gct gag cac ggc ccg gat tcc cag gtg atc ctg ctg acg       816
Leu Ser Gln Ala Glu His Gly Pro Asp Ser Gln Val Ile Leu Leu Thr
            260                 265                 270 cct gac gct gac att gcc cgc aag gtg gcg gag gcg gta gaa cgt caa       864
Pro Asp Ala Asp Ile Ala Arg Lys Val Ala Glu Ala Val Glu Arg Gln
        275                 280                 285 ctg gcg gaa ctg ccg cgc gcg gac acc gcc cgg cag gcc ctg agc gcc       912
Leu Ala Glu Leu Pro Arg Ala Asp Thr Ala Arg Gln Ala Leu Ser Ala
    290                 295                 300 agt cgt ctg att gtg acc aaa gat tta gcg cag tgc gtc gcc atc tct       960
Ser Arg Leu Ile Val Thr Lys Asp Leu Ala Gln Cys Val Ala Ile Ser
305                 310                 315                 320 aat cag tac ggg ccg gaa cac tta atc atc cag acg cgc aac gcg cgc      1008
Asn Gln Tyr Gly Pro Glu His Leu Ile Ile Gln Thr Arg Asn Ala Arg
                325                 330                 335 gat ttg gtg gac gcg att acc agc gca ggc tcg gta ttt ctc ggc gac      1056
Asp Leu Val Asp Ala Ile Thr Ser Ala Gly Ser Val Phe Leu Gly Asp
            340                 345                 350 tgg tcg ccg gaa tcc gcc ggt gat tac gct tcc gga acc aac cac gtt      1104
Trp Ser Pro Glu Ser Ala Gly Asp Tyr Ala Ser Gly Thr Asn His Val
        355                 360                 365 tta ccg acc tac ggc tat act gct acc tgt tcc agc ctt ggg tta gcg      1152
Leu Pro Thr Tyr Gly Tyr Thr Ala Thr Cys Ser Ser Leu Gly Leu Ala
    370                 375                 380 gat ttc cag aaa cgg att acc gtt cag gaa ctg tca aaa gcg ggc ttt      1200
Asp Phe Gln Lys Arg Ile Thr Val Gln Glu Leu Ser Lys Ala Gly Phe
385                 390                 395                 400 tcc gct ctg gca tca acc att gaa aca ttg gcg gcg gca gaa cgt ctg      1248
Ser Ala Leu Ala Ser Thr Ile Glu Thr Leu Ala Ala Ala Glu Arg Leu
                405                 410                 415 acc gcc cat aaa aac gcc gtg acc ctg cgc gta aac gcc ctc aag gag      1296
Thr Ala His Lys Asn Ala Val Thr Leu Arg Val Asn Ala Leu Lys Glu
            420                 425                 430 caa gca taa                                                          1305
Gln Ala <210> SEQ ID NO 141
<211> LENGTH: 434
<212> TYPE: PRT
<213> ORGANISM: Artificial
```

<220> FEATURE:
<223> OTHER INFORMATION: Synthetic Construct

<400> SEQUENCE: 141

```
Met Ser Phe Asn Thr Leu Ile Asp Trp Asn Ser Cys Ser Pro Glu Gln
1               5                   10                  15

Gln Arg Ala Leu Leu Thr Arg Pro Ala Ile Ser Ala Ser Asp Ser Ile
            20                  25                  30

Thr Arg Thr Val Ser Asp Ile Leu Asp Asn Val Lys Thr Arg Gly Asp
        35                  40                  45

Asp Ala Leu Arg Glu Tyr Ser Ala Lys Phe Asp Lys Thr Glu Val Thr
    50                  55                  60

Ala Leu Arg Val Thr Pro Glu Glu Ile Ala Ala Ala Gly Ala Arg Leu
65                  70                  75                  80

Ser Asp Glu Leu Lys Gln Ala Ile Thr Ala Ala Val Lys Asn Ile Glu
                85                  90                  95

Thr Phe His Ser Ala Gln Thr Leu Pro Pro Val Asp Val Glu Thr Gln
            100                 105                 110

Pro Gly Val Arg Cys Gln Gln Val Thr Arg Pro Val Ser Ser Val Gly
        115                 120                 125

Leu Tyr Ile Pro Gly Gly Ser Ala Pro Leu Phe Ser Thr Val Leu Leu
    130                 135                 140

Leu Ala Thr Pro Ala Arg Ile Ala Gly Cys Gln Lys Val Val Leu Cys
145                 150                 155                 160

Ser Pro Pro Pro Ile Ala Asp Glu Ile Leu Tyr Ala Ala Gln Leu Cys
                165                 170                 175

Gly Val Gln Glu Ile Phe Asn Val Gly Gly Ala Gln Ala Ile Ala Ala
            180                 185                 190

Leu Ala Phe Gly Ser Glu Ser Val Pro Lys Val Asp Lys Ile Phe Gly
        195                 200                 205

Pro Gly Asn Ala Phe Val Thr Glu Ala Lys Arg Gln Val Ser Gln Arg
    210                 215                 220

Leu Asp Gly Ala Ala Ile Asp Ile Pro Ala Gly Pro Ser Glu Val Leu
225                 230                 235                 240

Val Ile Ala Asp Ser Gly Ala Thr Pro Asp Phe Val Ala Ser Asp Leu
                245                 250                 255

Leu Ser Gln Ala Glu His Gly Pro Asp Ser Gln Val Ile Leu Leu Thr
            260                 265                 270

Pro Asp Ala Asp Ile Ala Arg Lys Val Ala Glu Ala Val Glu Arg Gln
        275                 280                 285

Leu Ala Glu Leu Pro Arg Ala Asp Thr Ala Arg Gln Ala Leu Ser Ala
    290                 295                 300

Ser Arg Leu Ile Val Thr Lys Asp Leu Ala Gln Cys Val Ala Ile Ser
305                 310                 315                 320

Asn Gln Tyr Gly Pro Glu His Leu Ile Ile Gln Thr Arg Asn Ala Arg
                325                 330                 335

Asp Leu Val Asp Ala Ile Thr Ser Ala Gly Ser Val Phe Leu Gly Asp
            340                 345                 350

Trp Ser Pro Glu Ser Ala Gly Asp Tyr Ala Ser Gly Thr Asn His Val
        355                 360                 365

Leu Pro Thr Tyr Gly Tyr Thr Ala Thr Cys Ser Ser Leu Gly Leu Ala
    370                 375                 380

Asp Phe Gln Lys Arg Ile Thr Val Gln Glu Leu Ser Lys Ala Gly Phe
385                 390                 395                 400
```

-continued

```
Ser Ala Leu Ala Ser Thr Ile Glu Thr Leu Ala Ala Ala Glu Arg Leu
                405                 410                 415

Thr Ala His Lys Asn Ala Val Thr Leu Arg Val Asn Ala Leu Lys Glu
            420                 425                 430

Gln Ala
```